US006187533B1

(12) United States Patent
Bell et al.

(10) Patent No.: US 6,187,533 B1
(45) Date of Patent: Feb. 13, 2001

(54) MUTATIONS IN THE DIABETES SUSCEPTIBILITY GENES HEPATOCYTE NUCLEAR FACTOR (HNF) 1 ALPHA (α), HNF1β AND HNF4α

(75) Inventors: Graeme I. Bell, Chicago, IL (US); Kazuya Yamagata, Kaizuka (JP); Naohisha Oda, Chicago, IL (US); Pamela J. Kaisaki, Headington (GB); Hiroto Furuta, Wakayama (JP); Yukio Horikawa, Chicago, IL (US); Stephan Menzel, Headington (GB)

(73) Assignee: Arch Development Corporation, Chicago, IL (US)

( * ) Notice: Under 35 U.S.C. 154(b), the term of this patent shall be extended for 0 days.

(21) Appl. No.: 08/927,219

(22) Filed: Sep. 9, 1997

Related U.S. Application Data

(60) Provisional application No. 60/029,679, filed on Oct. 30, 1996, provisional application No. 60/028,056, filed on Oct. 2, 1996, and provisional application No. 60/025,719, filed on Sep. 10, 1996.

(51) Int. Cl.[7] .............................. C12Q 1/68; C12P 19/34
(52) U.S. Cl. ............................................... 435/6; 435/91.2
(58) Field of Search .............................. 435/6; 536/91.2, 536/23.1

(56) References Cited

U.S. PATENT DOCUMENTS

| 5,403,712 | 4/1995 | Crabtree et al. .......................... 435/6 |
| 5,541,060 | 7/1996 | Bell et al. ................................. 435/6 |
| 5,795,726 | 8/1998 | Gucksmann . |
| 5,800,998 | 9/1998 | Gucksmann . |

FOREIGN PATENT DOCUMENTS

| WO 98/21239 | 5/1998 | (WO) . |
| WO 98/21363 | 5/1998 | (WO) . |

OTHER PUBLICATIONS

Yamagata et al. (I) "Mutations in the hepatocyte nuclear factor –1alpha gene in maturity onset diabetes of the young (MODY3)", Nature; vol. 384, pp. 455–458, Dec. 5, 1996.*

Kaisaki et al, "Mutations in the Hepatocyte Nuclear Factor –1alpha Gene in MODY and Early–Onset NIDDM", Diabetes; vol. 46, pp. 528–535, Mar. 1997.*

Yamada et al, "Mutations in the Hepatocyte Nuclear Factor–1alpha Gene (MODY3) Are Not a Major Cause of Late–Onset NIDDM in Japanese Subjects", Diabetes; vol. 46, pp. 1512–1513, Sep. 1997.*

Bulman et al, "A missense mutation in the hepatocyte nuclear factor 4 alpha gene in a UK pedigree with maturity–onset diabetes of the young", Diabetologia 1997; vol. 40, pp. 859–862.*

Urhammer et al, Genetic variation in the heptatocyte nuclear factor–1alpha gene in Danish Caucasians with late–onset NIDDM, Diabetologia 1997; vol. 40, pp. 473–475.*

Yamagata et al. (II) "Mutations in the heptatocyte nuclear factor –4alpha gene in maturity onset diabetes of the young (MODY1)", Nature; vol. 384, pp. 458–460, Dec. 5, 1996.*

Bach et al., "Cloning of human hepatic nuclear factor 1 (HNF1) and chromosomal localization of its gene in man and mouse," *Genomics*, 8:155–164, 1990.

Bach and Yaniv, "More potent transcriptional activators or a transdominant inhibitor of the HNF1 homeprotein family are generated by alternative RNA processing," *EMBO J.*, 12(11):4229–4242, 1993.

Barrera–Hernandez et al., "Effects of diabetes mellitus on hepatocyte nuclear factor 1 decrease albumin gene transcription," *J. Biol. Chem.*, 271(17):9969–9975, 1996.

Baumheuter et al., "A variant nuclear protein in dedifferentiated hepatoma cells binds to the same functional sequences in the β fibrinogen gene promoter as HNF–1," *EMBO J.*, 7(8):2485–2493, 1988.

Baumheuter et al., "HNF–1 shares three sequence motifs with the POU domain proteins and is identical to LF–B1 and APF," *Genes and Development*, 4:372–379 1990.

Bell et al., "Gene for non–insulin–dependent diabetes mellitus (maturity–onset diabetes of the young subtype) is linked to DNA polymorphism on human chromosome 20q," *Proc. Natl. Acad. Sci. USA*, 88:1484–1488, 1991.

Blumenfeld et al., "Hepatic nuclear factor 1 (HNF1) shows a wider distribution than products of its known target genes in developing mouse," *Development*, 113:58–599, 1991.

Bourguet et al., "Crystal structure of the ligand–binding domain of the human nuclear receptor RXR–α,"*Nature*, 375:377–382, 1995.

Bowden et al., "Identification of genetic markers flanking the locus for maturity–onset diabetes of the young on human chromosome 20," *Diabetes*, 41:88–92, 1992.

Bowden et al., "Linkage analysis of maturity–onset diabetes of the young (MODY): genetic heterogeneity and nonpenetrance," *Am. J. Hum. Genet.* 50:607–618, 1992.

Bulman et al., "A missense mutation in the hepatocyte nuclear factor 4 alpha gene in a UK pedigree with maturity–onset diabetes of the young," *Diabetologia*, 40:859–862, 1997.

(List continued on next page.)

*Primary Examiner*—W. Gary Jones
*Assistant Examiner*—Jehanne Souaya
(74) *Attorney, Agent, or Firm*—Fulbright & Jaworski

(57) ABSTRACT

The present invention relates generally to the fields diabetes. More particularly, it concerns the identification of genes responsible for NIDDM for use in diagnostics and therapeutics. The present invention demonstrates that the MODY3 locus is, in fact, the HNF1α gene, MODY4 locus is the HNF1β and the MODY1 locus is the HNF4α gene. The invention further relates to the discovery that analysis of mutations in the HNF1α, HNF1β and HNF4α genes can be diagnostic for diabetes. The invention also contemplates methods of treating diabetes in view of the fact that HNF1α, HNF1β and HNF4α mutations can cause diabetes.

16 Claims, 147 Drawing Sheets

OTHER PUBLICATIONS

Byrne et al., "Altered insulin secretory responses to glucose in subjects with a mutation in the MODY1 gene on chromosome 20," *Diabetes*, 44(6):699–704, 1995b.

Byrne et al., "Insulin secretion and clearance during low-dose graded glucose infusion," *Am. J. Physiol.*, 268:E21–27, 1995a.

Byrne et al., "Insulin secretory abnormalities in subjects with hyperglycemia due to glucokinase mutations," *J. Clin. Invest.*, 93:1120–1130, 1994.

Carter et al., "A pleiotropic element in the medium–chain acyl coenzyme A dehydrogenase gene promoter mediates transcriptional regulation by multiple nuclear receptor transcription factors and defines novel receptor–DNA binding motifs," *Mol. Cell Biol.*, 14(7):4360–4372, 1994.

Carter et al., "Hepatocyte nuclear factor–4 activates medium chain acyl–CoA dehydrogenase gene transcription by interacting with a complex regulatory element," *J. Biol. Chem., J. Biol. Chem.*, 268(19):13805–13810, 1993.

Cereghini et al., "Liver–enriched transcription factors and hepatocyte differentiation," *FASEB J.*, 10:267–282, 1996.

Chartier et al., "Cloning and sequencing of cDNAs encoding the human hepatocyte nuclear factor 4 indicate the presence of two isoforms in human liver," *Gene*, 147:269–272, 1994.

Chen et al., "Disruption of the HNF–4 gene, expressed visceral endoderm, leads to cell death in embryonic ectoderm and impaired gastrulation of mouse embryos," *Genes and Dev.*, 8:2466–2477, 1994.

Chouard et al., "A distal dimerization domain is essential for DNA–binding by the atypical HNF1 homeodomain," *Nucl. Acids Res.*, 18(19):5853–5863, 1990.

Citron et al., "Identity of 4a–carbinolamine dehydratase, a component of the phenylalanine hydroxylation system, and DCOH, a transregulator of homeodomain proteins," *Proc. Natl. Acad. Sci. USA*, 89:11891–11894, 1992.

Courtois et al; "Interaction of a liver–specific nuclear factor with the fibrinogen and $a_1$–antitrypsin promoters," *Science* 238:688–692, 1987.

Courtois et al., "Purified hepatocyte nuclear factor 1 interacts with a family of hepatocyte–specific promoters," *Proc. Natl. Acad. Sci. USA*, 85:7937–7941, 1988.

Cox et al., "Perspectives in diabetes; mapping diabetes–susceptibility genes; lessons learned from search for DNA marker for maturity–onset diabetes of the young," *Diabetes*, 41:401–407, 1992.

De Simone et al., "LFB3, a heterodimer–forming homeoprotein of the LFB1 family, is expressed inspecialized epithelia," *EMBO J.*, 10:1435–1443 1991.

Drewes et al., "Human hepatocyte nuclear factor 4 isoforms are encoded by distinct and differentially expressed genes," *Mol. Cell. Biol.*, 16(3):925–931, 1996.

Duncan et al., "Expression of transcription factor HNF–4 in the extraembryonic endoderm, gut, and nephrogenic tissue of the developing mouse embryo: HNF–4 is a marker for primary endoderm in the implanting blastocyst," *Proc. Natl. Acad. Sci. USA*, 91:7598–7602, 1994.

Emens et al., "Hepatocyte nuclear factor 1 α 1 is expressed in a hamster insulinoma line and transactivates the rate insulin I gene," *Proc. Natl. Acad. Sci. USA*, 89:7300–7304, 1992.

Erdmann and Heim, "Orphan nuclear receptor HNF–4 binds to the human coagulation factor VII promoter," *J. Biol. Chem.*, 270:22988–22996, 1995.

Fajans et al., "Maturity–onset diabetes of the young," *Life Sci.*, 55(6):413–422, 1994.

Figueiredo and Brownlee, "cis–Acting elements and transcription factors involved in the promoter activity of the human factor VIII gene," *J. Biol. Chem.*, 270:11828–11838, 1995.

Forman and Samuels, "Dimerization among nuclear hormone receptors," 2(7):587–594, 1990.

Forman and Samuels, "Interactions among a subfamily of nuclear hormone receptors: the regulatory zipper model," *Mol. Endocrinol.*, 4(9):1293–1301, 1990.

Frain et al., "The liver–specific transcription factor LF–B1 contains a highly diverged homeobox DNA binding domain," *Cell*, 59:145–157, 1989.

Frayling et al., "Mutations in the hepatocyte nuclear factor–1α gene are a common cause of maturity–onset diabetes of the young in the U.K.," *Diabetes*, 46:720–725, 1997.

Freedman and Luisi, "On the mechanism of DNA Binding by nuclear hormone receptors: a structural and functional perspective," *J. Cell Biochem.*, 51:140–150, 1993.

Furuta et al., "Organization and partial sequence of the Hepatocyte Nuclear Factor–4α/MODY1 gene and identification of a missense mutation , R127W, in a Japanese family with MODY," *Diabetes*, 46(10):1652–1657, 1997.

Galson et al., "The orphan receptor hepatic nuclear factor 4 functions as a transcriptional activator for tissue–specific and hypoxia–specific erythropoietin gene expression and is antagonized by EAR3/COUP–TF1," *Mol. Cell Biol.*, 15(4):2135–2144, 1995.

Garcia et al., "Functional interaction of nuclear factors EF–C, HNF–4, and RXRα with Hepatitis B Virus Enhancer 1," *J. Virol.*, 67(7):3940–3950, 1993.

German et al., "Regulation of insulin gene expression by glucose and calcium in transfected primary islet cultures," *J. Biol. Chem.*, 265:22063–22066, 1990.

Glucksmann et al., "Novel mutations and a mutational hotspot in the MODY3 gene," *Diabetes*, 46:1081–1086, 1997.

Gronemeyer and Moras, "How to Finger DNA," *Nature*, 375:190–191, 1995.

Hanis et al., "A genome–wide search for human non–insulin–dependent (type 2) diabetes genes reveals a major susceptibility locus on chromosome 2," *Nature Genet.*, 13:161–166, 1996.

Hansen et al., "Novel MODY3 mutations in the hepatocyte nuclear factor–1α gene," *Diabetes*, 46:726–730, 1997.

Hansen and Crabtree, "Regulation of the HNF–1 homeodomain proteins by DCoH," *Current Opinion in Genetics and Development*, 3:246–253, 1993.

Hata et al., "Identification of two splice isoforms of mRNA for mouse hepatocyte nuclear factor 4 (HNF–4)," *Biochim. Biophy. Acta*, 1260:55–61, 1995.

Herman et al. "Abnormal insulin secretion, not insulin resistance, is the genetic or primary defect of MODY in the RW pedigree," *Diabetes* 43:40–46, 1994.

Hung and High, "Liver–enriched transcription factor HNF–4 and ubiquitous factor NF–Y are critical for expression of blood coagulation factor X," *J. Biol. Chem.*, 271:2323–2331, 1996.

International Search Report dated Feb. 26, 1998. (PCT/US97/16037) (ARCD:272P).

Irwin et al., "Sequential imputation for multilocus linkage analysis," *Proc. Natl. Acad. Sci. U.S.A.*, 91:11684–11688, 1994.

Iwasaki et al., "Characterization of Japanese families with early–onset type 2 (non–insulin dependent) diabetes mellitus and screening for mutations in the glucokinase and mitochondrial tRNA $^{Leu(UUR)}$ genes," *Acta. Diabetol.*, 32:17–22, 1995.

Iwasaki et al., "Mutations in the hepatocyte nuclear factor–1α/MODY3 gene in Japanese subjects with early– and late–onset NIDDM," *Diabetes*, 46:1504–1508, 1997.

Iwasaki et al., "One Japanese MODY family with severe and progressive microangiopathies," *Diab. Res. and Clin. Pract.*, 4:237–240, 1988.

Jiang et al., "Exclusive homodimerization of the orphan receptor hepatocyte nuclear factor 4 defines a new subclass of nuclear receptors," *Mol. Cell Biol.*, 15(9):5131–5143, 1995.

Jiang and Sladek, "The DNA binding domain of hepatocyte nuclear factor 4 mediates cooperative, specific binding to DNA and heterodimerization with the retinoid X receptor α," *J. Biol. Chem.*, 272:1218–1225, 1997.

Kaisaki et al., "Mutations in the hepatocyte nuclear factor–1α gene in MODY and early–onset NIDDM," *Diabetes*, 46:528–535, 1997; with published Errata, *Diabetes*, 46:1239, 1997.

Kritis et al., "Isolation and characterization of a third isoform of human hepatocyte nuclear factor 4," *Gene*, 173:275–280, 1996.

Ktistaki et al., "Recruitment of hepatocyte nuclear factor 4 into specific intranuclear compartments depends on tyrosine phosphorylation that affects its DNA–binding and transactivation potential," *Proc. Natl. Acad. Sci. USA*, 92:9876–9880, 1995.

Kuo et al., "A transcriptional hierarchy involved in mammalian cell–type specification," *Nature* 355:457–461, 1992.

Kuo et al., "Molecular cloning, functional expression, and chromosomal localization of mouse hepatocyte nuclear factor 1," *Nature*, 355:457–461, 1990.

Ladias, "Convergence of multiple nuclear receptor signaling pathways onto the long terminal repeat of human immunodeficiency virus–1," *J. Biol. Chem.*, 269(8):5944–5951, 1994.

Lai et al., "Hepatocyte nuclear factor 3/fork head or "winged helix" proteins: a family of transcription factors of diverse biologic function," *Proc. Natl. Acad. Sci. USA*, 90:10421–10423, 1993.

Lazzaro et al., "LFB1 and LFB3 homeoproteins are sequentially expressed during kidney development," *Development*, 114:469–479, 1992.

Lee et al., "Structure of the retenoid X receptor α DNA binding domain: a helix required for homodimeric DNA binding," *Science*, 260:1117–1121, 1993.

Lehto et al., "Characterization of the MODY 3 phenotype," *J. Clin. Invest.*, 99(4):582–591, 1997.

Lemaigre et al. "Hepatocyte nuclear factor 6, a transcriptase factor that contains a novel type of homeodomain and a single cut domain," *Proc. Natl. Acad. Sci. USA*, 93:9460–9464, 1996.

Lesage et al., "Linkage analyses of the MODY3 locus on chromosome 12q with late–onset NIDDM," *Diabetes*, 44:1243–1247, 1995.

Mangelsdorf et al., "The nuclear receptor superfamily: the second decade," *Cell*, 83:835–839, 1995.

Mendel et al., "Characterization of a cofactor that regulates dimerization of a mammalian homeodomain protein," *Science* 254:1762–1767, 1991.

Mendel and Crabtree, "HNF–1, a member of a novel class of dimerizing homeodomain proteins," *JBC*, 266:677–680, 1991.

Mendel et al., "HNF–1α and HNF–1β (vHNF–1) share dimerization and homeo domains, but not activation domains, and form heterodimers in vitro," *Genes and Dev.*, 5:1042–1056, 1991a.

Menzel et al., "Localization of MODY3 to a 5–cM region of human chromosome 12," *Diabetes*, 44:1408–1413, 1995.

Metzger et al., "Orphan receptor HNF–4 and bZip protein C/EBPα bind to overlapping regions of the apolipoprotein B gene promoter and synergistically activate transcription," *J. Biol. Chem.*, 268(22):16831–16838.

Milatovich et al., "Genes for the dimerization cofactor of hepatocyte nuclear factor–1α (DCOH) are on human and murine chromosomes 10," *Genomics*, 16:292–295, 1993.

Miquerol et al. "Expression of the L–type pyruvate kinase gene and the hepatocyte nuclear factor 4 transcription factor in exocrine and endocrine pancreas," *J. Biol. Chem.*, 269:8944–8951, 1994.

Miura and Tanaka, "Analysis of the rat hepatocyte nuclear factor (HNF) 1 gene promotor: synergistic activation by HNF4 and HNF1 proteins," *Nucleic Acids Research*, 21(16):3731–3736, 1993.

Nagy et al., "Expression of hepatic transcription factors during liver development and oval cell differentiation," *J. Cell Biol.*, 126(1):223–233, 1994.

Naka and Brownlee, "Transcriptional regulation of the human factor IX promoter by the orphan receptor superfamily factors, HNF4, ARP1 and COUP/Ear3," *Brit. J. Haematol.*, 92:231–240, 1996.

Nakshatri and Chambon, "The directly repeated RG(G/T) motifs of the rat and mouse cellular retinol–binding protein II genes are promiscuous binding sites for RAR, RXR, HNF–4, and ARP–1 homo– and heterodimers," *J. Biol. Chem.*, 269(2):890–902, 1994.

O'Hare et al., "Transformation of mouse fibroblasts to methotrexate resistance by a recombinant plasmid expressing a prokaryotic dihydrofolate reductase," *Proc. Natl. Acad. Sci USA*, 78(3):1527–1531, 1981.

Polonsky et al., "Non–insulin–dependent diabetes mellitus–a genetically programmed failure of the beta cell to compensate for insulin resistance," Seminars in Medicine of the Beth Israel Hospital, Boston, *N. Engl. J. Med.* 334:777–783, 1996.

Pontoglio et al., "Hepatocyte nuclear factor 1 inactivation results in hepatic dysfunction, phenylketonuria, and renal fanconi syndrome," *Cell*, 84:575–585, 1996.

Rastinejad et al., "Structural determinants of nuclear receptor assembly on DNA direct repeats," *Nature*, 375:203–211, 1995.

Reijnen et al., "Disruption of a binding site for hepatocyte nuclear factor 4 results in hemophilia B leyden," *Proc. Natl. Acad. Sci. USA*, 89:6300–6303, 1992.

Renaud et al. "Crystal structure of the RAR–γ ligand–binding domain bound to all–trans retinoic acid," *Nature*, 378:681–689, 1995.

Rey–Campos et al., "vHNF–1 is a homeoprotein that activates transcription and forms heterodimers with HNF–1," *EMBO J.*, 10:1445–1457, 1991.

Ringeisen et al., "The transactivation potential of variant Hepatocyte Nuclear Factor 1 is modified by alternative splicing," *J. Biol. Chem.*, 268:25706–25711, 1993.

Rothschild et al., "A genetic map of chromosome 20q12–q13.1: multiple highly polymorphic microsatellite and RFLP markers linked to the maturity–onset diabetes of the young (MODY) locus," *Am. J. Hum. Genet.*, 52:110–23, 1993.

Schuler et al., "A gene map of the human genome," *Science*, 274:540–546, 1996.

Sladek et al., "Liver–enriched transcription factor HNF–4 is a novel member of the steroid hormone receptor superfamily," *Genes and Dev.*, 4:2353–2365, 1990.

Sladek, "Orphan receptor HNF–4 and liver–specific gene expression," *Receptor*, 3(3)223–232, 1993.

Sladek, "Orphan receptor HNF–4 and liver–specific gene expression," *Receptor*, 4(1)64, 1994.

Stoffel, M. et al., "A yeast artificial chromosome–based map of the region of chromosome 20 containing the diabetes–susceptibility gene, MODY1, and a myeloid leukemia related gene," *Proc. Natl. Acad. USA*, 93:3937–3941, 1996.

Tavaviras et al., "Characterization of the mouse HNF–4 gene and its expression during mouse embryogenesis," *Mech. Dev.*, 48:67–79, 1994.

Thöny et al., "Characterization of the human PCBD gene encoding the bifunctional protein pterin–4α–carbinolamine dehydratase/dimerization cofactor for the transcription factor HNF–1α," *Biochem. Biophys. Res. Comm.*, 210(3):966–973, 1995.

Tian and Schibler, "Tissue–specific expression of the gene encoding hepatocyte nuclear factor 1 may involve hepatocyte nuclear factor 4," *Genes Dev* 5:2225–2234, 1991.

Tokuyama et al., "Evolution of β–cell dysfunction in the male zucker diabetic fatty rat," *Diabetes*, 44:1447–1457, 1995.

Tronche and Yaniv, "HNF1, a homeoprotein member of the hepatic transcription regulatory network," *BioEssays*, 14(9):579–587, 1992.

Urhammer et al., "A prevalent amino acid polymorphism at codon 98 in the hepatocyte nuclear factor–1α gene is associated with reduced serum c–peptide and insulin responses to an oral glucose challenge," *Diabetes*, 46:912–916, 1997.

Vaxillaire et al., "A gene for maturity onset diabetes of the young (MODY) maps to chromosome 12q," *Nature Genetics*, 9:418–423, 1995.

Vaxillaire et al., "Identification of nine novel mutations in the hepatocyte nuclear factor 1 alpha gene associated with maturity–onset diabetes of the young (MODY3)," *Human Mol. Gen.*, 6(4):583–586, 1997.

Wade et al., "Apolipoprotien(a) gene transcription is regulated by liver–enriched trans–acting factor hepatocyte nuclear factor 1α," *J. Biol. Chem.*, 269:19757–19765, 1994.

Wagner et al. "A structural role for hormone in the thyroid hormone receptor," *Nature*, 378:690–697, 1995.

Weinstein et al., The winged–helix transcription factor HNF–3β is required for notochord development in the mouse embryo, *Cell*, 78–575–588, 1994.

Xanthopoulos et al., "The different tissue transcription patterns of genes for HNF–1, C/EBP, HNF–3, and HNF–4, protein factors that govern liver–specific transcription," *Proc. Natl. Acad. Sci. USA*, 88:3807–3811, 1991.

Yamagata et al., "Mutations in the hepatocyte nuclear factor–1α gene in maturity–onset diabetes of the young (MODY3)," *Nature*, 384:455–458, 1996b.

Yamagata et al., "Mutations in the hepatocyte nuclear factor–1α gene in maturity–onset diabetes of the young (MODY1)," *Nature*, 384:458–460, 1996a.

Zhang et al., "Mutations that alter ligand–induced switches and dimerization activities in the retinoid X receptor," *Mol. Cell. Biol.*, 14:4311–4323, 1994.

Zhong et al., "The expression pattern of a Drosophila homolog to the mouse transcription factor HNF–4 suggests a determinative role in gut formation," *EMBO J.*, 12(2):537–544, 1993.

Zhong et al., "Tissue–specific regulation of mouse hepatocyte nuclear factor 4 expression," *Mol. Cell. Biol.*, 14:7276–7284, 1994.

* cited by examiner

FIG. 7A

```
          M-------D-DMADYSAALDPA TLEFENVQVLTMGNDL------L---------------G------G-         Majority
                                    10         20         30         40         50         60         70
  1    MRLSKTLVDMDMADYSAALDPAYTTLEFENVQVLTMGNDLLPLRIARLRHPLRHHWSI-SGGVDSSPQGD              hHNF4-a-protein
  1    M-------DMADYSAALDPAYTTLEFENVQVLTMGND--------------------------------              mHNF4-protein
  1    M-------DMADYTEALDPAYTTLEFENMQVLSIGTD--------------------------------              X.LavesHNF4-protein
  1    MH------ADALASAYPAASQHSPI----GLALSPMGGGL----GLSNSSNQSSENFALCNGNGNAGSAGG            Drosophila HNF4

TSPSEGTN--------------------------------LNASNSLGVSALCAICGDRATGKHYGASSCDGCKGFF      Majority
                   80         90        100        110        120        130        140
  70   TSPSEGTN--------------------------------LNAPNSLGVSALCAICGDRATGKHYGASSCDGCKGFF      hHNF4-a-protein
  31   TSPSEGAN--------------------------------LNSSNSLSVSALCAICGDRATGKHYGASSCDGCKGFF      mHNF4-protein
  31   TSTSDVTS--------------------------------LSASNSIGINSLCAICGDRATGKHYGASSCDGCKGFF      X.LavesHNF4-protein
  59   GSASSGSNNNNSMFSPYNNLNGSSGTNSSQQQLQQQQQQSPTVCAICGDRATGKHYGASSCDGCKGFF                Drosophila HNF4

RRSVRKNHMYSCRFSRQCVVDKDKRNQCRYCRLKKCFRAGMKKEAVQNERDRISTRRSSYEDSSLP----S            Majority
                  150        160        170        180        190        200        210
  115  RRSVRKNHMYSCRFSRQCVVDKDKRNQCRYCRLKKCFRAGMKKEAVQNERDRISTRRSSYEDSSLP----S            hHNF4-a-protein
  76   RRSVRKNHMYSCRFSRQCVVDKDKRNQCRYCRLKKCFRAGMKKEAVQNERDRISTRRSSYEDSSLP----S            mHNF4-protein
  76   RRSVRKNHMYSCRFSRQCVVDKDKRNQCRYCRLKKCFRAGMKKEAVQNERDRISTRRSSYEDSSLP----S            X.LavesHNF4-protein
  129  RRSVRKNHQYTCREANCVVDKDKRNQCRYCRLRKCFRAGMKKEAVQNERDRISCRRTSNDDPDPGNGLS              Drosophila HNF4
```

FIG. 7B-1

Partial Sequence of Human HNF4 Gene
(Exon 1, SEQ ID NO:34)

```
GCAGAGAGGG CACTGGGAGG AGGCAGTGGG AGGGCGGAGG
GCGGGGGCCT TCGGGGTGGG CGCCCAGGGT AGGGCAGGTG
GCCGCGGCGT GGAGGCAGGG AGAATGCGAC TCTCCAAAAC
CCTCGTCGAC ATGGACATGG CCGACTACAG TGCTGCACTG
GACCCAGCCT ACACCACCCT GGAATTTGAG AATGTGCAGG

TGTTGACGAT GGGCAATGGT AGGTGGGGGC AGATGTGCCC
AGGTGTGCCA GTGGGGGCAG GTGTGCCTGG GTCCAGGAGC
AGATCTTTGG CACTCAACTT TGGGGTGGGA GGAGAATGAT
ACAAAATGGT AGGTTGGTCC TACAGGCCAG CACAGGTGTT
GCCAAGTGAA GCCCATGTGC CCAGGCACAG TGATCACAGG

CATTCTGGGT GAAGGGAGGC CTGCAAGGGC CAATTTCCAG
CAAAAGTCGA TCCCGGCTAT TCCTCCCAGG CCCTTCCAGT
CCTCACTGCC TCACAGTGGC TCTGCTTGGC GCTTGGCACA
GTGACATGAT GGTGAGCTCC CCCTTGGTGC CCAGCTCCAG
CGATTCAGCC CAGCACGGCC CCTTCGTGAA CCCCTTGGGC

CTAGGTTCAG AGAGACGGCA AGGGATGTTG TATCCCTGGA
GATGGTGGTT GGAGACATAA CCGCATTTCT C
```

FIG. 8A

Partial Sequence of Human HNF4 Gene
(Exon 1b, SEQ ID NO:36)

```
TGGATGTTTG TACATGTGTG CTGTGTGTGC GGGTCATAGA
GCACATGTGT TTGTGCATGC GGACCTGTTG GAGTGCCCTG
TTCTTCCTGC ATCTTTATCC TGTATGGGCG TTTTGTCGTG
TGCCCATATT TGTACCTGCT GTGTATATAT GCAGTTCCCT
GTGCTGCGGG CGGGGGTCAG CGGTCTCTGG TGTGCACGAC

TGCACAGACC CAAATGCAGG ACTCTGTTGT TGCCACTCAC
CAAGTGAGAT TCATATCAGC AACATGTCCG TTTGTCTCTG
AGCAGATTTG TTGCCGCTGC GTCTCGCCAG ATTGAGGCAT
CCCCTCCGAC ATCACTGGAG CATATCTGGA GGGGTGGACA
GTTCTCCACA GGGAGGTAGG GGAAAGAGG  AGGCCCGGAA

ACCCCTCCTG GAGGGAAGAG CCCCATCGGT CCCAGGCCAG
CCTCAGAGGA GAGGGGGCAG GCAGCTGGCT GAGGTCAGCC
TYGCCACCTG CTTCCTTCTG TGTCTTGGAG CCACTCAGCC
AGTATGAGGC TGCAGCTCCA GCTGAGGTCT GGAATCTTGT
GGTCAGCTCA GCTAGGGTGA GGAGGCAGCT GCTGGGCACT

GCTTGTTGTC AGCTCAGCAG GTGCTCACCT GCCCCTGCCG
TCCAGTCACG TGTCACCTTG GGCATGTCAC CTCCCCTATC
CTGGCTTCTG TATCTTCTAC AAAACAGGCT TCATTCCCCC
AGGCCTGCTG GCTGGACGGC TTTTAGGCCT GTCTGAGGAC
CACGCCAGGA GCGCAAGGCA AAACACACC  AGAGAT
```

FIG. 8B

Partial Sequence of Human HNF4 Gene
(Exon 2, SEQ ID NO:38)

```
CCCCTTGCGA GTTAGGAGGC CGGCTCCCAC CCCAGAAGGT
GGCCAGGTTT TCATGCCTTC CTAGAGAAAG CTGGGGCTGG
TGGCCTCCAC CACAGGGAGA CGCAGACCCT CAGAAACAAG
TCTGTGAAGT CACAACCAGC CCCAGTTTAC AGATGTGAAA
CTGAAGCTCC AAAAGTCAG GAGGTCACTG AGTGGGGAGG

TGATGGAGTG GAACAGCCCC CAGATCTGGC TGAGGCCGAA
GCCCTGGAGA GATCCCCGCA AGGCTCCTT AGATGCCTGA
CATTCTGTTC TTCCTGAAGC CTCACTCCCT TCTCTCCTGG
CGCAGACACG TCCCCATCAG AAGGCACCAA CCTCAACGCG
CCCAACAGCC TGGGTGTCAG CGCCCTGTGT GCCATCTGCG

GGGACCGGGC CACGGGCAAA CACTACGGTG CCTCGAGCTG
TGACGGCTGC AAGGGCTTCT TCCGGAGGAG CGTGCGGAAG
AACCACATGT ACTCCTGCAG GTGAGGAGCC TCAATTTCTT
CAGCTGGGAA ATGGGCACAC TTGGGCTCAT GGCCCCAAGG
TCTGTCTTCT CCCTGAGTGG GTAGGTCCCA GAGACAGCTG

CCCTTCAGGG CCTTCAAGGC TCCTTCTGGTT TTGT
```

FIG. 8C

Partial Sequence of Human HNF4 Gene
(Exon 3, SEQ ID NO:40)

```
AGAGAGTTCA TAGCACCTTT CCAGCTCCTG GTGGGTTCAA
GAGAGAACTC CCGGGATGAA GAGATGAGAG CACTGAGGTT
GGGGGGTCAA CTGGATAGCC AGGGCCCTAG TTCTGTCCTA
AGAGGAGGAA GTTGTGTCTT CTCCATCCAA CCATCCAAAAG
ACCTCCCCAG ATTTAGCCGG CAGTGCGTGG TGGACAAAGA

CAAGAGGAAC CAGTGCCGCT ACTGCAGGCT CAAGAAATGC
TTCCGGGCTG GCATGAAGAA GGAAGGTGAG CCTCGGCCCT
CCCCGCCCCA CCACCACTGC ACCACCTGCA CCCACAGCTC
CCCGACAGTC ATTTACAACT GTAGCCACAC TTTATGACTC
AGTGGCAGGC CCCAGGGTGA CTGGCTAATG GCTGAGAAGA

GGGAGGGCCT GGAAATCTGA CCATAGGGAG CGGCTGGGCT
TGGTCTTGAG AAAGATTC
```

FIG. 8D

Partial Sequence of Human HNF4 Gene
(Exon 4, SEQ ID NO:42)

tcccactcct catcagtcac agacaccccc accccctact
ccatccctgt tctccctcct cacctctctg tgcctcctca
cagCCGTCCA GAATGAGCGG GACCGGATCA GCACTCGAAG
GTCAAGCTAT GAGGACAGCA GCCTGCCCTC CATCAATGCG
CTCCTGCAGG CGGAGGTCCT GTCCCGACAG GTACCGGGGT GATCCTGCCA CCCACCCAGG GGATCCCCCA CACTACAGAG
GAGCTCACCT CCTCCACCTC CATTCTCCCC AGCCAGGCCC
TGGAGCAGCT GACGGGAGGG GCCTCAGATA TTACAGAAGG
GACACTGAGT GCGGTTTCAC ATGGCCCAGT TTGCAGCAAG
GGCAGGAATC GAACCTGGCG CCCTGGGGCA CTTTCTAATT CATCCTACTG CCTGCATCCC ACAGGCCAAG CAGAGTCTTC
ACCTTCACTG AGGGCCTGCG ATCAGCTCAG CTCCGAGAGA
ACAGAGCAGT GGCTCAGTGG AGAGAGGTGG CAAAGTGGGG
CCCAGCCCTT CCCTTGCTGA GTGACCTTGG GCAAGTCACA
GCACCTCTCT GAGCCATGGT TGCCTCATTG TCAGAAAGG

ATGATGATTT TTTGCCTGC TTCTCCTCTA AGGCTGACAG
ACTCCTTGGG GCTCTAAAGC TG

*FIG. 8E*

Partial Sequence of Human HNF4 Gene
(Exon 5, SEQ ID NO:44)

TTCTCCTCA TCCCTGCCTC CTCCCTCCCT CCGTTTTTAC
CCTGAGCTTC CTTCAGAGCT GGAGGGCACC CACTATCCAG
CCCCCTCCCC ACATCTGATT CCAGGGAGGG GGCTCTGTGC
AGGGGACAGA GAATGCGGGA GGGCCCGGAC ATCTCCAGCA
TTTTCTTCCC TGTATCTCTC GAAGATCACC TCCCCCGTCT

CCGGGATCAA CGGCGACATT CGGGCGAAGA AGATTGCCAG
CATCGCAGAT GTGTGTGAGT CCATGAAGGA GCAGCTGCTG
GTTCTCGTTG AGTGGGCCAA GTACATCCCA GCTTTCTGCG
AGCTCCCCCT GGACGACCAG GTGAGGATGG GCGTGGATGG
TGGGCAGTAG TGGGCAGTGG GCGGGGCAGC CAGGGGGCTG

CTGGCCCACC TGGGATATAG CCGTGGACTG GCTTGATTTT
ATTTTATTTA ACAAAATATG TAGTGCACAC ACGTGTCTGA
AACTTTAAAT CACCTTACAA ATATTAACTC AGTTAGCTCC
TCCAACAACT CTATGAGGTA GGTACTAAGG TACTATTATT
ACTGCCATCT CATAGGTGAG AGATTGGGGC ACAGAGAGGT

TAAGTAACCT GCTCAAGGTC ACATAGCTAC TATCCAGCAT
AGCTGGG

*FIG. 8F*

Partial Sequence of Human HNF4 Gene
(Exon 6, SEQ ID NO:46)

```
ATTTTTACAA AGCACCCTTC ATAATTCTCC ATAGCTGGTC
CATGGGTGGG AATTTGGGAC CCACAGTTTT GGAACTTTTT
GGGATCATAG ACCTTTTTGA GAATCTCAAA AAAGAAAAAA
AAGCACACAG AATGTTGCTT ACAGTTTCAT CAGGCACACA
GAAGAGGCCC AGCACGAAGC AGTTTCTTGC CCAAGGACAC

AGCAGTTCAA GGACAGAGTC AGCGCGAGGT CTCTCAGCTC
TGAGCACATG TTCTTTCCCC TTCCAGGTTT CTAGTTTTAT
GGGTAGTAGT TTTATGATGC CCATTTCACA GTTCAGGCAG
GTAGAGGCAG AGGGGAGCAT TAAGCTGACT TGCCCAGCGT
CACTGAGTTG GCTACGGGCA GCCTTCCCAA GGGTACAGAT

GGCAAACACT GTTCCTTATC TCTTTCAGGT GGCCCTGCTC
AGAGCCCATG CTGGCGAGCA CCTGCTGCTC GGAGCCACCA
AGAGATCCAT GGTGGTCAAG GACGTGCTGC TCCTAGGTGA
GGCGGCTGCC TGCCCTGGCC AGGGCTCCAG GGAGGGTATG
CCTAGCATGG CACTCACCCA GGCAAGGAGA TTCACATGGT

GGCATGCAAG GGTGAGGGAG ACTAGTCAGG AGTGGCCCTG
TCCTCAGGCT TGCATTGGAG GGCTCCAGGA CTCAGTTTTC
AACTGGGTAC CCCACTCAGA TGCAAGGAAA TGTGGATGCA
AGTCACCAAA TTCCCAGCAT AGAAGTCAGA GCACGATCAG
GGTTATCCCT GGAATTACCT GTGCATCCTT TTTTCTTTTG

ACAGAGTCTT GCTCTGTCAC TCAGGCTGGA GTGCAATGAT
GTGA
```

FIG. 8G

Partial Sequence of Human HNF4 Gene
(Exon 7, SEQ ID NO:48)

```
GCAACACTAG TATTTTAATA TAACAATGCT ATGAGGGAGC
TCGATTATTT ATCCTCATCT TATAGATAAG AAAACTGAGG
CACAGAGAGG TTAAGTAACT TATCCAACTA TAACCAGCTA
TCAGGGGCAG AGCCATTTAA GCAGGGCAGT GCAGTTCCAG
AATCTGGTCC TTTAACCTTG ATGCTTTGGT GCCTATCAGG

TGACCTTTGA ATGTCATCGA TCTTGTGAGT CATGTTGGTA
AATGGAGCTT GGGTCATGTG AAAGAGGTCC TAGAAAGCCA
AGTTCCAAGC TCAGCCGGAT GACTCAAGGC AGCTTATCTT
CTGAATCTGG GCCTCAGCTT CCTTACCTGT GAAATGGGAG
TCACCATCCC TGCAGGTCCT CCTCCCACAG GCACCAGCTA

TCTTGCCAAC TTAAAAGCCA AAACTAGAGG AGAGGGGTCA
ACCCAAAGTG ACTTCCCATC CTCCCTCCCT CCCAACCCTT
CCAGGCAATG ACTACATTGT CCCTCGGCAC TGCCCGGAGC
TGGCGGAGAT GAGCCGGGTG TCCATACGCA TCCTTGACGA
GCTGGTGCTG CCCTTCCAGG AGCTGCAGAT CGATGACAAT

GAGTATGCCT ACCTCAAAGC CATCATCTTC TTTGACCCAG
GTACAGTGCA CACCTCCTAA GCCATCCTG ACTCTCTCTC
CAGAACGCTC TGCCAGACTT CTCCTATTGG GTTCTGTACA
CTGAGTTCAC AGCCTCATCT CATGTTAACG ACAGCCAGGA
GAGGCCGTTT TCATTTAACA GATGAGGCAA GTCAAGATTT

GAAGAGACAA TATGGCCGGG CGCAGTGGCT CACACCTGTA
ATCCCATCAC TTTGGGAGGC TGAGGCGGGC GGATCACCTG
AGGTCAGGGG TCAAGATGAG CCTGGCTAAC ATGGAGAAAC
CCCATCTCTA CTTAAAA
```

FIG. 8H

Partial Sequence of Human HNF4 Gene
(Exon 8, SEQ ID NO:50)

```
GTGGCTCTGC CAACAACTGG CTGTGCGACC CAGGACAAGT
CCTATCTTTG CACTGTGTCT GGGTTTCCCC GTGTGTAAGA
TGAGGCGGTT GCTAGGTGCT TATTGGATGC ATTCCTCAAG
TCCCGCCCTC CATCTCCTAT TCCCCTCTCT TCTGGTTTAG
TGCTTTAGGA AATGTGGCAG AAATCTTTTT CTGCCTGTGT

CTAGGAAATC ATAATTCATG CTGGCGTACC CTGGTTGTTG
AGGTCCCTGA ATCCTTGTGC CCACACTGCT GAAGACTCCT
TGTGTGACAC AAGTCAGGGG ACATCTGGGT CTTGACTCCC
CAGATGCTCC AGGTGGACCC TGCTGCCCTC CCTTGCCCAC
CCTCTTCCAT TGTAGATGCC AAGGGGCTGA GCGATCCAGG

GAAGATCAAG CGGCTGCGTT CCCAGGTGCA GGTGAGCTTG
GAGGACTACA TCAACGACCG CCAGTATGAC TCGCGTGGCC
GCTTTGGAGA GCTGCTGCTG CTGCTGCCCA CCTTGCAGAG
CATCACGTGG CAGATGATCG AGCAGATCCA GTTCATCAAG
CTCTTCGGCA TGGCCAAGAT TGACAACCTG TTGGAGGAGA

TGCTGCTGGG AGGTCCGTGC CAAGCCCAGG AGGGGCGGGG
TTGGATTGGG GACTCCCCAG GAGACAGGCC TCACACAGTG
AGCTCACCCC TCAGCTCCTT GGCTTCCCCA CTGTGCCGCT
TTGGGCAAGT TGCTTAACCT GTCTGTGCCT CAGTTTCCTC
ACCAGAAAAA TGGGAACAAG GCAATGGTCT ATTTGTTCAG

GCACCGAGAA CCTAGCACGT GCCAGTCACT GTTCTAAGTG
CTGGCAATTC AGCAAAGAAC AAGATCTTTG CCCTCGGGGA
GGCTGTGTGT GTGTGATAT GTATGGATGC GTGGATATCT
GTGTATATGC CCGTATGTGC GTGCATGTGT ATATAAAGCC
TCACATTTTA TGATTTTGA
```

FIG. 8I

Partial Sequence of Human HNF4 Gene
(Exon 9, SEQ ID NO:52)

```
GGGACACATA GATGCTATAA GTAGGTCAGT TGGCTGCAGC
AGAGATGTGG GGGATGAGGC TGAAAGGTGA GGCGGGACCA
AATGGTTGAA GGACTTGCAC TCCAAGGAGC TTTGAGAGCC
ATTGATTACA TCCATTATGT TACTATGTGA CCAATACATT
ACTCATTAGA ACATTTACGT GATCTCAGAG CTTCCTTATA

TGCACCTTGT TCCTTTCAAC TCACTTTTGT TCTCTTGGTT
TTTTGGGGTC CTCTTAACAC CCTCATGAAG TCTATAGATG
GGAATGGTAC ACCCTAGTTT ACTAACCCAG GAATAGGTAC
CCAACAGGCA CTGCCAATAT TGGATGGGCT GGTTGATTGG
CCACGCCTGA GGAAGATGGC GTCCAAGGC CTGAGGTCTG

CATCCCAGAC TCTCCATCCT GATCGACCTT CTCTACCTGC
AGGGTCCCCC AGCGATGCAC CCCATGCCCA CCACCCCCTG
CACCCTCACC TGATGCAGGA ACATATGGGA ACCAACGTCA
TCGTTGCCAA CACAATGCCC ACTCACCTCA GCAACGGACA
GATGTGTGAG TGGCCCCGAC CCAGGGGACA GGCAGGTGGG

CAAACTCTGG GATTTTACCT TGCAAAGGGT GAGGATGGGG
CTTAAGACAG GAGGCAGGAG AAAGTGGAGT CTAGAAGGTA
GAACCAGGAT GCAACAGTTT TCTGGGTTCC AGGGTAGGGA
ATAAAGGGCA AGATTGTCCA TTTGTTGAGG CTGTTTATTC
AGTAAGGTGA CTGACAGCCT TTACTGAATG AAGCCATTGT

TGGGATGAGG CAATCCACTG GATGAGGTAA CCCATTGGGT
GAAGATGTCT TGGGTGAGAA TTCCATTAGT TGACATTGTC
CATTAAGTAA AAGTGGTCAT TGAAGTAAGG CTGCACAGTT
GGGTAAGGCT ATCCATTAGA CATTAGATGA GACTACCCAT
TGGGTCAGGA TGTCTGCTGG GCTA
```

FIG. 8J

Partial Sequence of Human HNF4 Gene
(Exon 10, SEQ ID NO:54)

```
TTTGGGAGAA GCAGTCCAAG TCTGCATATC AAATAAATGA
TGGAGGAGAT GGGTGGTAGG ACCTTCCAGA CCTCATAAAA
CTTAGGCTTT ATGATCTGGG ACTCACAGAA GGTTGAGCAA
TAAAAGACCT TAGGGATTAT CTGGCTTAAT TAATTCTCTC
ATTTTATAGA GGAAGAAATT AAGTCAAGGT GGGGCAGGGT

GGGAGGGGAG AACTTTCCCG GGCTCTTCA TTTACTCCCA
CAAAGGCTGG AATTTTGAGC AGCCCCTGTC TGTCTGTTTG
TCCTTCCAGC CACCCCTGAG ACCCACAGC CCTCACCGCG
AGGTGGCTCA GGGTCTGAGC CCTATAAGCT CCTGCCGGGA
GCCGTCGCCA CAATCGTCAA GCCCCTCTCT GCCATCCCCC

AGCCGACCAT CACCAAGCAG GAAGTTATCT AGCAAGCCGC
TGGGGCTTGG GGGCTCCACT GGCTCCCCCC AGCCCCCTAA
GAGAGCACCT GGTGATCACG TGGTCACGGC AAAGGAAGAC
GTGATGCCAG GACCAGTCCC AGAGCAGGAA TGGGAAGGAT
GAAGGGCCCG AGAACATGGC CTAAGGCACA TCCCACTGCA
```

FIG. 8K-1

Partial Sequence of Human HNF4 Gene
(Exon 10, SEQ ID NO:54)

```
CCCTGACGCC CTGCTCTGAT AACAAGACTT TGACTTGGGG
AGACCCTCTA CTGCCTTGGA CAACTTTCTC ATGTTGAAGC
CACTGCCTTC ACCTTCACCT TCATCCATGT CCAACCCCCG
ACTTCATCCC AAAGGACAGC CGCCTGGAGA TGACTTGAGC
CTTACTTAAA CCCAGCTCCC TTCTTCCCTA GCCTGGTGCT

TCTCCTCTCC TAGCCCCGGT CATGGTGTCC AGACAGAGCC
CTCTGAGGCT GGGTCCAATT GTGGCACTTG GGGCACCTTG
CTCCTCCTTC TGCTGCTGCC CCCACCTCTG CTGCCTCCCT
CTGCTGTCAC CTTGCTCAGC CATCCCGTCT TCTCCAACAC
CACCTCTACA GAGGCCAAGG AGGCCTTGGA AACGATTCCC

CCAGTCATTC TGGGAACATG TTGTAAGCAC TGACTGGGAC
CAGGCACCAG GCAGGGTCTA GAAGGCTGTG GTGAGGGAAG
ACGCCTTTCT CCTCCAACCC AAC
```

FIG. 8K-2

Translation of human HNF1a Sequence(cDNA=SEQ ID NO:1 and protein=SEQ ID NO:2)

```
                                          1
                                          Met Val Ser Lys Leu Ser Gln Leu Gln
GGCCCTGTGGCAGCCGAGCC ATG GTT TCT AAA CTG AGC CAG CTG CAG
                     20                              30

Ala Leu Ile Gln Ala Leu Gly Glu Pro Gly Tyr Leu Leu Al
GCA CTG ATC CAG GCA CTG GGT GAG CCG GGG CCC TAC CTC CTG GC
                              50                              60

Gly Glu Leu Ala Glu Leu Pro Asn Gly Leu Gly Glu Thr Arg Gl
--- GAG CTG GCT GAG CTG CCC AAT GGG CTG GGG GAG ACT CGG GG
            80                              90

Exon 1 | 110  Exon 2
Ile Leu Lys Glu Leu Asn Leu Glu Ser Pro Glu Glu Ala Ala Hi
ATC CTC AAA GAG CTC AAC CTC GAG AGC CCT GAG GAG GCG GCC CA
                              120
```

FIG. 11A-1

```
         Thr Glu Leu Leu Ala Ala Leu Leu Glu Ser Gly Leu Ser Lys Glu
         ACG GAG CTC CTG GCG GCC CTG CTC GAG TCA GGG CTG AGC AAA GAG
10                                  40

Gly Gly Gly Pro Leu Asp Lys Gly Glu Ser Cys Gly Gly Gly Arg
         GGA GAA GGC CCC CTG GAC AAG GGG GAG TCC TGC GGC GGT CGA
                            70

Ser Glu Asp Glu Thr Asp Asp Gly Glu Asp Phe Thr Pro Pro
         TCC GAG GAC GAG ACG GAC GAC GAT GGG GAA GAC TTC ACG CCA CCC
                                                100

Gln Lys Ala Val Val Glu Thr Leu Leu Gl|n Glu Asp Pro Trp Arg
         CAG AAA GCC GTG GTG GAG ACC CTT CTG CA|G GAG GAC CCG TGG CGT
                                                              140
130 Gln(Hinek-missense)
```

*FIG. 11A-2*

```
        Val Ala Lys Met Val Lys Ser Tyr Leu Gln Gln His Asn Ile Pro
        GTG GCG AAG ATG GTC AAG TCC TAC CTG CAG CAG CAC AAC ATC CCA
                                    150
                    Exon 2
        170
        Ser Gln His Leu Asn Lys Gly Thr Pro Met Lys Thr Gln Lys Arg
        TCC CAA CAC CTC AAC AAG GGC ACT CCC ATG AAG ACG CAG AAG CGG
        Exon 3                      180
        200
        G|ln Gln Phe Thr His Ala Gly Gln Gly Gly Leu Ile Glu Glu Pro
        C|AG CAG TTC ACC CAT GCA GGG CAG GGA GGG CTG ATT GAA GAG CCC
                                    210
        230
        Lys Trp Gly Pro Ala Ser Gln Gln Ile Leu Phe Gln Ala Tyr Glu
        AAG TGG GGC CCA GCA TCC CAG CAG ATC CTG TTC CAG GCC TAT GAG
```

FIG. 11B-1

```
                    140
Gln Arg Glu Val Val Asp Thr Thr Gly Leu Asn Gln Ser His Leu
CAG CGG GAG GTG GTC GAT ACC ACT GGC CTC AAC CAG TCC CAC CTG
                                    A
      160
Ala Ala Leu Tyr Thr Trp Tyr Val Arg Lys Gln Arg Glu Val Ala
GCC GCC CTG TAC ACC TGG TAC GTC CGC AAG CAG CGA GAG GTG GCG

190
Thr Gly Asp Glu Leu Pro Thr Lys Lys Gly Arg Arg Asn Arg Phe
ACA GGT GAT GAG CTA CCA ACC AAG AAG GGG CGG AGG AAC CGT TTC

220
Arg Gln Lys Asn Pro Ser Lys Glu Glu Arg Glu Thr Leu Val Glu
AGG CAG AAG AAC CCT AGC AAG GAG GAG CGA GAG ACG CTA GTG GAG
```

*FIG. 11B-2*

```
          Exon 3 |       240 Exon 4
260
Glu Cys Asn Ar|g Ala Glu Cys Ile Gln Arg Gly Val Ser Pro Ser
GAG TGC AAT AG|G GCG GAA TGC ATC CAG AGA GGG GTG TCC CCA TCA 270
Tyr Asn Trp Phe Ala Asn Arg Arg Lys Glu Glu Ala Phe Arg His
TAC AAC TGG TTT GCC AAC CGG CGC AAA GAA GAA GCC TTC CGG CAC CCCC (Donoghue - C insertion)

Pro Gly Pro Ala Leu Pro Ala His Ser Ser Pro Gly Leu Pro Pro
CCG GGA CCT GCG CTG CCC GCT CAC AGC TCC CCT GGC CTG CCT CCA

330
Pro Ala Thr Ser Glu Thr Ala Glu Val Pro Ser Ser Ser Gly Gly
CCT GCG ACC AGT GAG ACT GCA GAA GTA CCC TCA AGC AGC GGC GGT
350
```

Gln Ala Gln Gly Leu Gly Ser Asn Leu Val Thr Glu Val Arg Val
CAG GCA CAG GGG CTG GGC TCC AAC CTC GTC ACG GAG GTG CGT GTC

280

Lys Leu Ala Met Asp Thr Tyr Ser Gly Pro Pro Gly Pro Gly
AAG CTG GCC ATG GAC ACG TAC AGC GGG CCC CCA GGG CCA GGC

Exon 4 |      320 Exon 5
Pro Ala Leu Ser Pro Ser Lys Val His G|ly Val Arg   Gly Gln
CCT GCC CTC TCC CCC AGT AAG GTC CAC G|GT GTG CGC TNT GGA CAG

340

Pro Leu Val Thr Val Ser Thr Pro Leu His Gln Val Ser Pro Thr
CCC TTA GTG ACA GTG TCT ACA CCC CTC CAC CAA GTG TCC CCC ACG

FIG. 11C-2

(Pratt - mutation splice acceptor site Exon 6, AG--> GG)
                                                    360                                                        Exon 5
Gly Leu Glu Pro Ser His Ser Leu Leu Ser Thr Glu Ala Lys Leu
GGC CTG GAG CCC AGC CAC AGC CTG CTG AGT ACA GAA GCC AAG CTG C-- (Newton - CT deletion)

Ala Leu His Ser Leu Glu Gln Thr Ser Pro Gly Leu Asn Gln Gln
GCA CTG CAC AGC TTG GAG CAG ACA TCC CCA GGC CTC AAC CAG CAG
                                        420
Exon 6 | Exon 7     440
Gly Pro Gly Glu Pro Ala Ser Leu Gly Pro Thr Phe Thr Asn Thr
GGG CCT GGT GAG CCT GCC TCC CTG GGT CCT ACG TTC ACC AAC ACA
                                        450
470
Ser Val Pro Val Ile Asn Ser Met Gly Ser Ser Leu Thr Thr Leu
AGT GTG CCG GTC ATC AAC AGC ATG GGC AGC AGC CTG ACC ACC CTG

*FIG. 11D-1*

370 Exon 6

| Val | Ser | Ala | Ala | Gly | Gly | Pro | Leu | Pro | Pro | Val | Ser | Thr | Leu | Thr |
|-----|-----|-----|-----|-----|-----|-----|-----|-----|-----|-----|-----|-----|-----|-----|
| GTC | TCA | GCA | GCT | GGG | GGC | CCC | CTC | CCC | CCT | GTC | AGC | ACC | CTG | ACA |

| Pro | Gln | Asn | Leu | Ile | Met | Ala | Ser | Leu | Pro | Gly | Val | Met | Thr | Ile |
|-----|-----|-----|-----|-----|-----|-----|-----|-----|-----|-----|-----|-----|-----|-----|
| CCC | CAG | AAC | CTC | ATC | ATG | GCC | TCA | CTT | CCT | GGG | GTC | ATG | ACC | ATC |

430

| Gly | Ala | Ser | Thr | Leu | Val | Ile | Gly | Leu | Ala | Ser | Thr | Gln | Ala | Gln |
|-----|-----|-----|-----|-----|-----|-----|-----|-----|-----|-----|-----|-----|-----|-----|
| GGT | GCC | TCC | ACC | CTG | GTC | ATC | G\|GC | CTG | GCC | TCC | ACG | CAG | GCA | CAG |

460

| Gln | Pro | Val | Gln | Phe | Ser | Gln | Pro | Leu | His | Pro | Ser | Tyr | Gln | Gln |
|-----|-----|-----|-----|-----|-----|-----|-----|-----|-----|-----|-----|-----|-----|-----|
| CAG | CCC | GTC | CAG | TTC | TCC | CAG | CCG | CTG | CAC | CCC | TCC | TAC | CAG | CAG |

FIG. 11D-2

```
                      480
Exon 7  500  | Exon 8
Pro Leu Met Pro Pro Val Gln Ser His Val Thr Gln Ser Pro Phe
CCG CTC ATG CCA CCT GTG CAG AGC CAT GTG ACC CAG AGC CCC TTC 510
His Lys Pro Glu Val Ala Gln Tyr Thr His Thr Gly Leu Leu Pro
CAC AAG CCC GAG GTG GCC CAG TAC ACC CAC ACG GGC CTG CTC CCG 530
        Exon 8  540  | Exon 9
Ser Leu Thr Pro Thr Lys Gln| Val Phe Thr Ser Asp Thr Glu Ala
AGC CTC ACG CCC ACC AAG CAG| GTC TTC ACC TCA GAC ACT GAG GCC 560
Exon 9  | 590 Exon 10
Leu His Val Pro Ser Gln Asp Pro Ala Gly Ile Gln His Leu Gln
CTC CAC GTC CCC AGC CAG GAC CCT GCC GGC ATC CAG CAC CTG CAG

| Met | Ala | Thr | Met | Ala | Gln | Leu | Gln | Ser | Pro | His | Ala | Leu | Tyr | Ser |
|---|---|---|---|---|---|---|---|---|---|---|---|---|---|---|
| ATG | GCC | ACC | ATG | GCT | CAG | CTG | CAG | AGC | CCC | CAC | G\|CC | CTC | TAC | AGC |
|  | A |  |  |  |  |  |  |  |  |  |  |  |  |  |

520

| Gln | Thr | Met | Leu | Ile | Thr | Asp | Thr | Thr | Asn | Leu | Ser | Ala | Leu | Ala |
|---|---|---|---|---|---|---|---|---|---|---|---|---|---|---|
| CAG | ACT | ATG | CTC | ATC | ACC | GAC | ACC | ACC | AAC | CTG | AGC | GCC | CTG | GCC |

550

| Ser | Ser | Glu | Ser | Gly | Leu | His | Thr | Pro | Ala | Ser | Gln | Ala | Thr | Thr |
|---|---|---|---|---|---|---|---|---|---|---|---|---|---|---|
| TCC | AGT | GAG | TCC | GGG | CTT | CAC | ACG | CCG | GCA | TCT | CAG | GCC | ACC | ACC |

580

| Pro | Ala | His | Arg | Leu | Ser | Ala | Ser | Pro | Thr\| | Val | Ser | Ser | Ser | Ser |
|---|---|---|---|---|---|---|---|---|---|---|---|---|---|---|
| CCG | GCC | CAC | CGG | CTC | AGC | GCC | AGC | CCC | ACA\| | GTG | TCC | TCC | AGC | AGC |

*FIG. 11E-2*

| 620 | | | | | 600 | | | | | | | | 630 | 631 | |
|---|---|---|---|---|---|---|---|---|---|---|---|---|---|---|---|
| Leu | Val | Leu | Tyr | Gln | Ser | Ser | Asp | Ser | Ser | Asn | Gly | Gln | Ser | His | |
| CTG | GTG | CTG | TAC | CAG | AGC | TCA | GAC | AGC | TCC | AGC | AAT | GGC | CAG | AGC | CAC |

```
CAG ATG GCC TCT TCC TCC CAG TAACCAGGCACCTGGGCCTGGGGCCTGTAC
AGCAACCGGTGGCCCTTCCTGGACAGCTGTGCCTCGCTCCCCACTCTGCTCTGATGCATCA
GTCGTGGAGAGCTAGGAGCAAAGCCTGTGTTCATGGCAGATGTAGGAGGACTGTCGCTGCT
CAGCCTGGGCCTATGGGAGAGCCCTGGGACCGCTACACCACTCTGGCCAGCCACACTTCTCA
CTTGTTCTGTCACCAATGTACCCGGGCCCTCCCTTCCTGCCCCAACTCCCTTCCAGCT
GGCTACTCTGTGCCAGAGCCTGGGGCTCTAACTGCCTGAGCCCAGGGAGGCCGAAGCTAA
CCCATGACCTCCAGCTTCCTGCTTCCTGTATTTCTTCCCAAGAGCATGATGCCTCTGAGGCCAGCC
```

FIG. 11F-1

610
Leu Leu Pro Ser Asn His Ser Val Ile Glu Thr Phe Ile Ser Thr
CTG CTG CCA TCC AAC CAC AGC GTC ATC GAG ACC TTC ATC TCC ACC

CTGCCTGCTCTTGGGGGTGATGAGGGCAGCAGCCCTGCCTGGAGGACCTGAGCCTGCCG
AGAAAGGGAGGGCTCTGAGGCGCCCCAACCCGTGTGCTGCGAGGGTGCACAGGAGGGG
TTCGTGGGATACAGTCTTCTTACTTGGAACTGAAGGGGCCTATGACTTGGGCACCCC
AGGACACAGGCCTGTGTAGCTGTGACCTGCTGAGCTCTGAGAGGCCCTGGATCAGCGTGGC
TAGTGACCCCACATGCCATTTGTACTGACCCCATCACCTACTCACACAGGCATTTCCTGGGT
ACAGGGAAGGCCAGGGGCTCCCTGGTCTTCCTCCCCAGCGATTCCCCTCTCCCAGGC
CTGGCCCTCCTGCCCTCTACTGGGAAGGCTACTTCGGGGCTGGGAAGTGTCCTTACTCCCTGT

FIG. 11F-2

GGGAGCCCTCGCCAACCCGTGCCCAAGTCCCAGGTCCCTGGTGGGGCAGCTCCTCTGTCTCGAGC

CCGAGCAGCTGAGGCAGGGCCGGGGAACTGGCCAAGCTGAGGTGCCCAGGAGAAGAAAGAG

CCTGGCTGGCTGAGGGCCAGTTCGCAGCCCACCCTGAGGAGTCTGAGGTCCTGAGCACTGCC

TGCTGAGAACCTGGCCCTTCAGTGTACCGGTCTTACCCTGGGATTCAGGAAAAGGCCTGGG

TTTAGTAAAGTCAAGGAGAAATGCGGGTGG

FIG. 11G-1

GCCCTGCAGACCCTGCCCTTGTTTGGGGCAGGAGTAGCTGAGCTCACAAGGCAGCAAGGC

GTGACCCCAGGGCACAGGAGCTACCTGTGTGGACAGGACTAACACTCAGAAGCCTGGGTG

AGGAGGGACAAAGGAGCCCTGTGAACCCAGGACAAGCATGGTCCCACATCCCTGGGCCTGC

GTGACCCGGCACCCCCTGCAGCTTGTAGCCCAGCCCGGGGCGAGTGGCACGTTTATTTAACT

FIG. 11G-2

```
human  TGGGGCCTGGGATTTAGGTTTCTAAATCGTGGGCCATGGGGCAGCCTTAT       618
mouse  TGGG-CTTGGGTGTTAGGTTTCCAGTTGAAGGACCCAGGACAGCTTTAT HNF-6
human  CTCTGCAAAAGCATTGAGGGTAGAAGTCAATGATTTGGGAAGTTATTGAA       668
mouse  CTC----AAA---TTGAGGATAGAAGTCAATGATCTGGACGTGATTGGC human  TTAGGGGATCTCGGAGGTAGGCT-GTCAGTGCCTGATAGTATCAGTTAGA       717
mouse  TTAGGCTTCATTAGTGGTAGGCTTGCCAGTGTCTAAACATGTCAGCTGGG human  ATGCCTGACTTGGGGGTGACAATGGCTTGGAGGGGTGGTGAGTCAAGGG-       766
mouse  TTGTCCACCTTG--GTGA----GACTTGG--GGGCTGCTGAGGCAAGGGG
```

*FIG. 13A*

```
human  TGAAATGAGTGCCCGTGAGTCATGATGCCTGCCTTGTACAATTGATAACT  816
mouse  TCCAACCAATGCCAGTCCCTGTTGGGTGCCTTGCCTTGGAAGATTGGTAAGT human  GAACATCGGTGAGTTAGGGCCC-------CAGCAGTTGTAATTAGCAC     857
mouse  GACTATTAATGAGCGGGAGGTGGGGCAACAGTTGTAATTAGCAC
                          AP-1 human  CCCGGGTGTCAGCCAGAAACCAAACAGCCAAATCCCTGCAGCCCGC      907
mouse  CCCAGGTGTCAGTCAGAAACCAAACAGCCAAATCCTGTGGCTCCAC
                          HNF-3 human  CCAGCCTATCCACGGCGGGGACCGATTAACCATTAAAGCCACCCCTC     957
mouse  CCAGCCTACCCAGCAACGGGGG--TGATTAACCATTAACTCCTACCCCTC
                          HNF-1α human  CCCGGCAGAGCCTCCACCCCTTCAGAGAGGCTAGGCCAAGACTCCCAGCA  1007
mouse  CCCA-CAGAGCCTCCACCC-TCTGCAGAGGCTAGGCCAGGAGGCCAGGCT
                          NF-1
```

FIG. 13B

```
human  GATCTTCCCAGAGGACGGTTTGAAAG----GAAGGCAGAGAGGGCAC-TG  1052
mouse  GAGTCTCCCAGAGGACAGTTTGAAAGAGAGGCAGAGAGGCAGAGAAGGACCTG human  GGAGGAGGCAGTGGGAGGGGAGAG--GGCGGGGGCC--------TTCGG    1091
mouse  GGAGGAGGCAGGCAGGAGGGGACGGGGGGGGGGGGCTGGGCTCAGCCCAG human  GG---TGGGCG-----CCCAGG----GTAGGGCAGGTGGCGGGCGTGGA    1130
mouse  GGGCTTGGGTGGCATCCTGGGCCGGGCAGGGGCTAAGGCGTGGG human  GGCAGGGAGAATGCGACTCTCCAAAACCCTCGTCGACATGGACATG    1176
mouse  TA-GGGGAGAATGCGACTCTCTAAAACCCTTGCCGGAATGGATATG
```

*FIG. 13C*

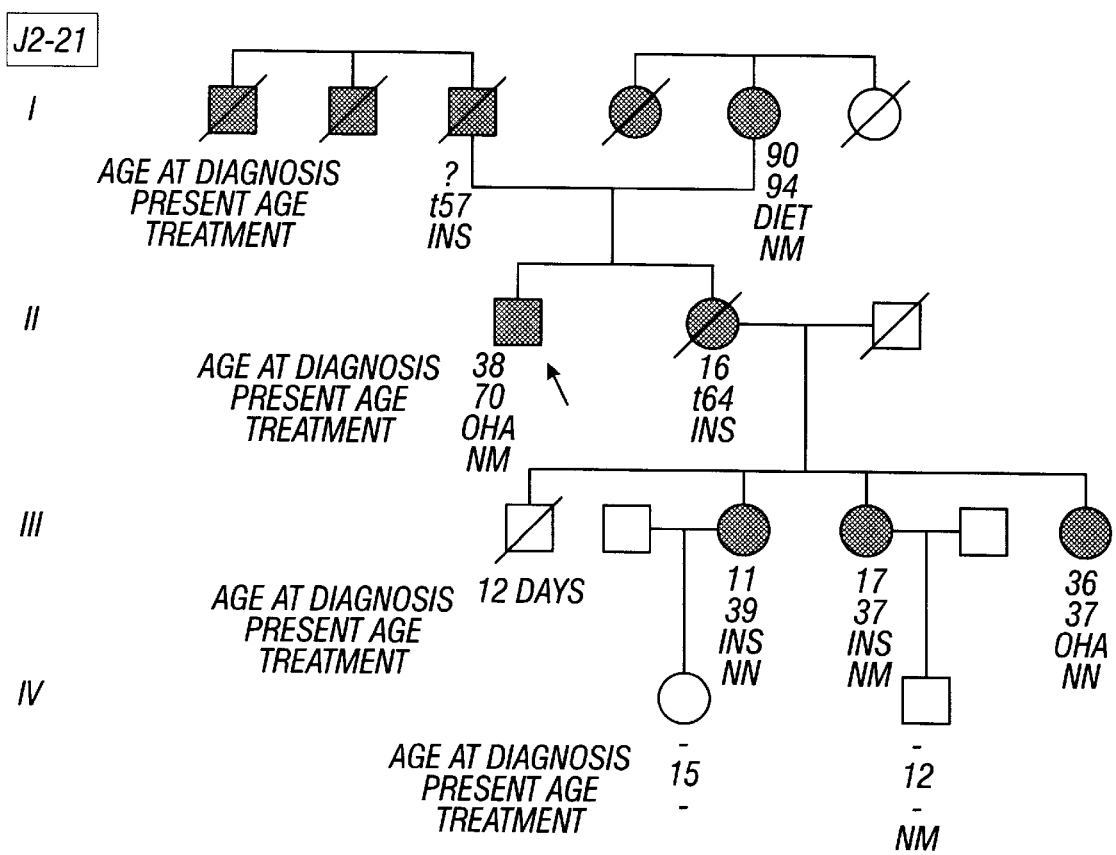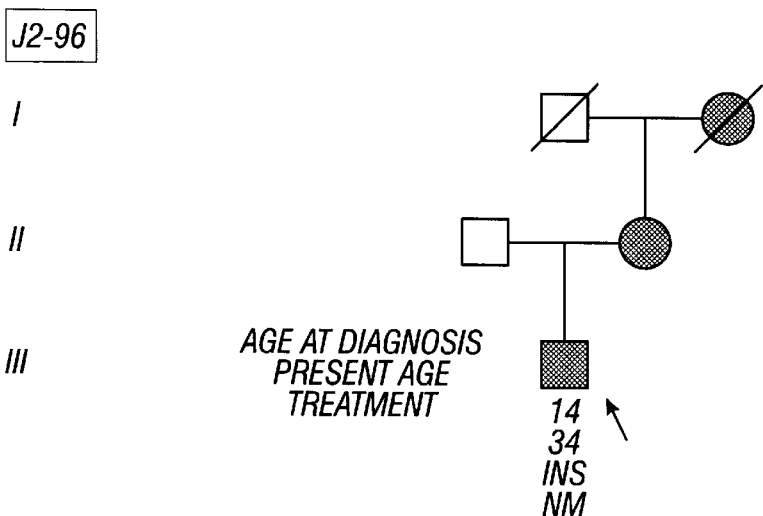
FIG. 15

```
                                                             NF1                           HNF-3
  1   AGCCAGCACTGTTCTTGGCACATGGTAATCTTAACATATTTTCCTACAGG
                                         NF1
 91   CCAAAATGGATGGAAGGGCCCCAAAATGGCCGTGAGCATCCTCTGCCCTTGA
                                HNF-3
181   CCGCTCTCGTAAGCAGCAAGCATTTTTGGCTCTCCTGTCTCAGCATGATGCC
                          NF1                AP4
271   CTCCTGATGGCCCTGGCCCCCCAGCACCTTCCATCCCAGCTGCTCAGGGC
                           AP4
361   TCCCATCGCAGGCCATAGCTCCCCTGTCCCTCTCCGCTGCCATGAGGCCTGCA
                HNF-3                                  C/EBP   * Exon 1
451   AAGCACACGGATAAATATGAACCTTGGAGAATTCCCAGCTCCAATGTAAA
541   CCAGGGGTTGGGGGTGCCCACAGGGCTTGGCTAGTGGGGTTTTGGG
```

*FIG. 26A-1*

```
AP1
GAGGCCTGGTGTCAGGCCCGGGAGTGGGTGGAAGGGTC
                      AP4
GAAGAGCTAGCCCCAGCTGTCTAGAGCTCCCTGCTG

CCTACAAGGTTCTTTCGGGGGTGGGACCCAACGCTGCT
                          HNF-4α
CCCTCACCTGGCGCCCACCCTCCCCCTCTGCCCAC

CTTTGCAGGGCTGAAGTCCAAAGTTCAGTCCCTTCGCT
HNF-3                              AP1
CAGAACAGGCAGGGCCCTGATTCACGGGCCGCTGGGG

GGGGCAGTGGGTGCAAGGAGTTTGGTTTGTGTCTGCCG
```

FIG. 26A-2

```
631  GCCGGGCAGGCAAACGCAACCCACGCGGTGGGGAGGCTAGCGGCTGGTGGACCCGG
     SerLysSerGlnLeuGlnThrGluLeuLeuAlaAlaAlaLeuLeuGluSerGlyLeu
721  TCTAAACTGAGCCAGCTGCAGACGGAGCTCCTGGCGGCCCTGCTCGAGTCAGGGCTG
                                                    G
     ProGlyProTyrLeuLeuAlaGlyGluGlyProLeuAspLysGlyGluSerCysGly
811  CCGGGCCCCTACCTCCTGGCTGGGGAAGGCCCCCTGGACAAGGGGGAGTCCTGCGGC
     GlyLeuGlyGluThrArgGlySerGluAspAspAspGlyGluAspPhe
901  GGGCTGGGGGAGACTCGGGGCTCCGAGGACGACGACGGGGATGGGGAAGACTTC
                                         Val
                                         T
     SerProGluAlaAlaHisGlnLysAlaValValValGluThrLeuLeuGl(n) 109
991  AGCCCTGAGGAGGCGGCCCACCAGAAAGCCGTGGTGGTGGAGACCCTTCTGCA gtaagg
```

FIG. 26B-1

```
                                                      1MetVal
GCCGCGTGGCCCTGTGGCCAGCCGAGCCATGGTT
                        Leu
SerLysGluAlaLeuIleGlnAlaLeuGlyGlu
AGCAAAGAGGCACTGATCCAGGCACTGGGTGAG
                    C

GlyGlyArgGlyGluAlaGluLeuProAsn
GGGGGTCGAGGGGAGCTGGCTGAGCTGCCCAAT

ThrProProIleLeuLysGluLeuAsnLeu
ACGCCACCCATCCTCAAAGAGCTGGAGAACCTC agccctgccccgtccccgctcccaggagagccta
```

FIG. 26B-2

```
1081  gaggggcccccctcagtctcctaacgagcccccttctgagttgagtcc
1171  agggcccatgagagcccaggggtcctgcttggagtttgagcctcca
1261  ccaggcctttagcccagtcctggcnagggggacatttcccagggg
1351  c::::::: 9 kb ::::::::cacccaccatccatccgtccat
1441  acatatcttcatctgtgtgtgtcgtcnacaagtctctgtttctaaacc
1531  tttgtcatgtgtgtgcgtgtaggcttccataactgcttcatgca
1621  ccctgagtctatgtgtaggccctggctcctgtcctcatgaccatgtgt
1711  ccgcagccccacctatgggggagagacagcccttgctgagcagatcccg
              a
```

FIG. 26C-1 ccatgacctttcagccttagcctagttgctgggaaggggggac
gccctgaactgctcctctgcagagtcccaaatcccatgagc
tccaagatggggagaaaagcagtgaattcacaactcaaatgc
ccaccattcattcattcattcattcattccatcc
tttatctgttccagtgtctgtatccataggcctgtgtccacg
ctgtgtccctgtgtcctggcataaatgaccatacctcaccgt
cagtccccaccctcagagttgacaaggttccagcacccagga
                      g
Exon 2   109 (Gl)  nGluAspProTrpArgValAlaLys
tccttgccctctcccag GGAGGACCCGTGGCGTGTGGCGAAG

*FIG. 26C-2*

```
                MetValLysSerTyrLeuGlnGlnHisAsnIleProGlnArgGluValVal
1801  ATGGTCAAGTCCTACCTGCAGCAGCACAACATCCCACAGCGGGAGGTGGTC
                                                A(R131Q)

LeuAsnLysGlyThrGlnLysThrProMetLysArgAlaAlaLeuTyrThr
1891  CTCAACAAGGGCACTCAAAAGACGCCCATGAAGCGAGCAGCCCTGTACACC 1981  taatgaccctaccccgcatctttcctgggagggcccaggactctccctaa 2071  acagacaggtagatggaaggaagtcagtgggattcaacctgcattatta 2161  ttggtccctgaacatccaaagatgaatgggtccctgctttcttttc 2251  ctggaaaatatgtaagctcctgagcctcagcttcttcatctgtacaatg 2341  ttacctgcagtcttgtactgagaaggatggtgagatcatatcttgggttgg
```

FIG. 26D-1

```
AspThrThrGlyLeuAsnGlnSerHisLeuSerGlnHis
GATACCACTGGCCTCAACCAGTCCCACCTGTCCCAACAC

176
TrpTyrValArgLysGlnArgGluValAlaGlnG(1n)
TGGTACGTCCGCAAGCAGCGAGAGGTGGCGCAGC gtaag ctcataggtgggggctggaagcttcaccatccccattac cctattctgcgccaggcactctgtgggacggggagtanac tttttttagata::::::: 3.8 Kb ::::::cgtgact gggatagtaaatgtgccaaatcagaacaaatgctaatgc taggaaagcattcagggattgattagtgatgtttgcctt
```

FIG. 26D-2

```
2431  gaacacaggttaagaaagtgatggcatgtgtgtgctgtgtgtttgtcatcagt
2521  ggttcagcgccatggcaatgagaaagaatcaagggcaaggtcaggggaatg
             Exon 3      176(G)lnPheThrHisAlaGlyGlnGlyGlyLeuIleGl
2611  ctttctgtgcctgcag AGTTCACCCATGCAGGGCAGGGGAGGGCTGATTGA
      ArgAsnArgPheLysTrpGlyProAlaSerGlnGlnIleLeuPheGlnAla
2701  AGGAACCGTTTCAAGTGGGGCCCCAGCATCCCCAGCAGATCCTGTTCCAGGCC
      ThrLeuValGluGluCysAsnAr(g)238
2791  ACGCTAGTGGAGGAGTGCAATAG gtacaacggcgggcgggaaacagtgct
```

*FIG. 26E-1* agattagatgattctagtttctagtctgtaagctccct gacgagggaaggtgagagtggccagtaccccactcacgg
   t                           t GluProThrGlyAspGluLeuProThrLysLysGlyArg
AGAGCCCACAGGTGATGAGCTACCAAGAAGGGGCGG TyrGluArgGlnLysAsnProSerLysGluArgGlu      TA(R229x,
TATGAGAGGCAGAAGAACCCTAGCAAGGAGGAGGAGAG     R229Q)

ggtttggtctgggctgcgcggcaaggccaggggaaggggaag

FIG. 26E-2

```
2881  gtgactcctaggtcctgtaaaggctgtgtccagttgccgagaactcctgatat
                                                           c
2971  taagcccattcctcgcagccccctgaccntggacaccaagcaaccccctt
3061  atggctctttgctcacttatgaatggagagactgaggtcagacagactg
3151  cccagatctgccagcctcaaaccctccggcagagntcagctcctcagaacc
              Exon 4    238 (Ar)gAlaGluCysIleGlnAr
3241  cctggaggctcatgggtggctatttctgcag GGCGGAATGCATCCAGAG
                                           G(C241G)
      euValThrGluValArgValTyrAsnTrpPheAlaAsnArgArgLysGlu
3331  TCGTCACGGAGGTGCGTGTCTACAACTGGTTTGCCAACCGGCGCAAAGAA
                                                       A(R272H)
```

*FIG. 26F-1* tggcttagcctggcccagaaaattgagaatacttgaacc ccatgatgctcacccaattcgattctctacaatcct tcaattgccaaggtcacacagcagacctggcattggaa ctcccctcatgccccaggacagggttcctctgagcctgg GlyValSerProSerGlnAlaGlnGlyLeuGlySerAsnL
AGGGTGTCCCCATCACAGGCACAGGGCTGGGCTCCAACC GluAlaPheArgHisLysLeuAlaMetAspThrTyrSerG
GAAGCCTTCCGGCACAAGCTGGCCATGGACACGTACAGCG

*FIG. 26F-2*

```
          lyProProGlyProGlyProAlaLeuProAlaHisSerSer
3421 GGCCCCCCCAGGCCCGGGACCTGCTGCCCCGCTGCCCGCTCACAGCTCC
      C  Ĉ(P291fsinsC)
                319
3511 isG(ly)
     ACG gtaagtggtatgtggggacacaagggacacgtgggaaggtgggagggt 3601 ttgcacgtcagtttggttccattc::::::: 2 kb ::::::gcagct 3691 gctggctgcataaaggcaggacaggcaggatggcctaagcaaccaatggag Exon 5   319
3781 aagtggggtgctgaggcaggcacactgcttccctctccag (G)lyValArgTy GTGTGGCTA erSerGlyProLeuValThrValSerThrProLeuHisGlnValSer
3871 GCAGGCGGTCCCTTAGTGACAGTGTCTACACCCTCCACCAAGTGTCC
```

*FIG. 26G-1*

ProGlyLeuProProProAlaLeuSerProSerLysValH
CCTGGCCCTGCCCTCCACCTGCCCCTCTCCCCAGTAAGGTCC tggggaggactgtcccattgacagcagtcacctaacctct gaccagggattggcaaaaggtagaacaaaggcagatt tttgaagtgctgagggctgtggaggcaggggaggggcaggg GlyGlnProAlaThrSerGluThrAlaGluValProSerS
TGGACAGCCCTGCCCAGCCAGTGAGACTGCAGAAGTACCCTCAA ProThrGlyLeuGluProSerHisSerLeuLeuSerThrG
CCCACGGGCCTGGAGCCCAGCCACAGCCTGCTGAGTACAG

FIG. 26G-2

```
           luAlaLysLeu369
     3961  AAGCCAAGCTG gtgagtgtccttgcttgtaaggaaa 4051  cctgtggggacccccggacccccggacacagcttggct ThrAlaLeuHisSerLeuGluGlnThrSerProGly
     4141  ACAGCACTGCACAGCTTGGAGCAGACATCCCCAGGC
```

FIG. 26H-1 acccaacctcatcttcctggcaggggagattctggagcagtccctagggaggc

Exon 6 ³⁷⁰ValSerAlaAlaGlyGlyProLeuProProValSerThrLeu
tcccctcgtag GTCTCAGCAGCTGGGGCCCCCCTGTCAGCACCCTG
g(IVSnt-2A→G)                                  (P379fsdelCT)

LeuAsnGlnGlnProGlnAsnLeuIleMetAlaSerLeuProGlyValMetThr
CTCAACCAGCAGCCCCAGAACCTCATCATGGCCCTCACTTCCTGGGTCATGACC
(Q401fsdelC)

*FIG. 26H-2*

```
         IleGlyProGlyGluProAlaSerLeuGlyProThrPheThrAsnThrGly
4231     ATCGGGCCTGGTGAGCCTGCCCTGGTCCCTACGTTCACCAACACAGGT 4321     gggcacctggggtgggaggctcatggggcaaccgcanaatccaggagctgga 4411     caacatgt::::::  0.8 kb  ::::::taggagaggggagcagagaactg 4501     cagggaaccgcagtttgacaactttgaacaagtcaccgcttgctttccc
```

*FIG. 26I-1*

AlaSerThrLeuValIleG(ly)⁴³⁷
GCCTCCACCCTGGTCATCG gtaagctggtggggatgggt aaagccactgggactcattcattcattcata acccatggcctttgcactgctgtgtacccagggctc attagcttagacaaagagctaaaggctcagagaggggga

FIG. 26I-2

```
4591       atgacttgccagagccacttaaattagtgtggcaggtcccagtggagggctg 4681       tgggaaggagaggtggtgccctttgggaggtcttgggcaggggtgggatat Exon 7
437(G)     lyLeuAlaSerThrGlnAlaGlnSerValProValIleAsnSerMetGly
4771       GCCTGGCCTCCACGGCCAGGCAGAGTGTGCCGGTCATCAACAGCATGGGC
                                            T(P447L)

roLeuHisProSerTyrGlnGlnProLeuMetProProValGlnSerHis
4861       CGCTGCACCCCTCCTACCCAGCAGCCGCTCATGCCACCTGTGCAGAGCCAT
```

FIG. 26J-1 tttcctgaccaccttgcccctcttccaaccacgggctc aactgggggcccagctgattccctccccttccactccag

SerSerLeuThrThrLeuGlnProValGlnPheSerGlnP
AGCAGCCTGACCACCCTGCAGCCCGTCCAGTTCTCCCAGC
                   T
                  Ser

ValThrGlnAsnProPheMetAlaThrMetAlaGlnLeuG
GTGACCCAGAACCCCTTCATGGCCACCATGGCTCAGCTGC
         AA                              
          G

*FIG. 26J-2*

```
      lnSerProHisA(1a) 501
4951  AGAGCCCCCACG gtgagcacccctgtgccccacacagcaggagatgatgata
                                g
5041  ggcaggcattgcagtctgcatgtgtctctgggacaagtgtgttccgtgatt
5131  acgtatctgtgtgtgcacgactgcttgtgtgagcagatccctagtgcgtg
5221  gcctgtgtttctctgaaactcttagggccatatgaatttctaaaatctattc
5311  agccttggatctccaactgctgcccagtctgccctggctgttcagcaggccccatgc
```

FIG. 26K-1

```
gaggttggctgtgtcaatggatgcaggggaaggggtgcct
gagggtgtctgcaggccagtgtgttcccatgtgaatgc
tctgggtgtgtatcggttgtgcatgcatttgtgtgcat
aga::::: 1.5 kb ::::::ccagttttgaaaatc
cccccttcccccagtcttgaggcctgggactagggctg
```

*FIG. 26K-2*

Exon 8

```
5401  tcaggcacgtttgccacgtctgccctctcccctg
           yLeuLeuProGlnThrMetLeuIleThrAspThrThr
5491  CCTGCTCCCCGCAGACTATGCTCATCACCGACACCACC
5581  tgctggccctccctcggcctgtgacagagcccctcac
           rAspThrGluAlaSerSerGluSerGlyLeuHisThr
5671  AGACACTGAGGCCTCCAGTGAGTCCGGGCTTCACACG
           (T547E548fsdelTG)
```

FIG. 26L-1

```
501 (A) laLeuTyrSerHisLysProGluValAlaAlaGlnTyrThrHisGl
         CCCTCTACAGCCACAAGCCCGAGGTGGCCCAGTACACCCACGGG
cggccag                                                  A AsnLeuSerAlaLeuAlaSerLeuThrProThrLysGln 541
         AACCTGAGCGCCCTGGCCAGCCTCACGCCCACCAAGCAG  gtaaggtccaggcc Exon 9            542 ValPheThrSe
         ccccacatcccccgggctcaggaggctgctgtctgctccccccag  GTCTTCACCTC ProAlaSerGlnAlaThrThrLeuHisValProSerGlnAspProAlaGlyIl
         CCGGCATCTCCAGGCCACCACCCTCCACGTCCCCAGCCAGGACCCCTGCCGGCAT
```

FIG. 26L-2

```
          eGlnHisLeuGlnProAlaHisArgLeuSerAlaSerProThrV
5761      CCAGCACCTGCAGCCGGCCCACCCGGCTCAGCGCCAGCCCCACAG 5851      tccatgtgttggtcccacccctctgttgctgtccgtcactgtgggg 5941      ggcgtggaagggtggggtggcttccatgaa::::: 1.5 kb 6031      gcggccgtggaccctggctgggaggctcccttgttaagaaccg 6121      ggaggtgtggccctgcctccccatcctgagtaccccctagggaca Exon 10    590 (V) alSerSerSerLeuValLeuTyrGl
6211      gtttgcctctgcag TGTCCTCCAGCAGCCTGGTGCTGTACCA sSerValIleGluThrPheIleSerThrGlnMetAlaSerSer
6301      CAGCGTCATCGAGACCTTCATCTCCACCCAGATGGCCTCTTCC

6391      GGGGGT
```

*FIG. 26M-1*

(a1) 590
gtgagaggccctggctccacccctccctactgtccctgccccct
a(IVS9nt1G-A)                              t ctgtgcatgcagcaggcctagggctgctgtgaggaagcactggca ::::::tccagtgttcacagtaagatgtactcaggccagtccatgg agggtagaggtgtgactttggggttcctgtgttatgtgctgtgatcca ggcaggtggggtgtgggtgcctggtgggtggctagcagcctt
                                        c SerSerAspSerSerAsnGlyGlnSerHisLeuLeuProSerAsnHi
GAGCTCAGACTCCAGCAATGGCCAGCCACCTGCTGCCATCCAACCA SerGlnOC$^{631}$
TCCCAGTAACCACACGGGCACCTGGGCCCTGTACTGCTT

*FIG. 26M-2*

PrF
CATGAACCCCGAAGAGTAGTGTCTTCTCTGGACTAAAGCGGAACTGAGAACCGGTGGA

GGCTGATAAGCAGAACCAGTAAAAGAGAAGGTCTCTAGCCCCCCAGCGTGAGTACAATGGAC

CCCTCTCTCCGGGTTCCCCCTCCCCACCATCATTTGCATCCAGCCGAAAGCTGGGCCCT
                                                    PrR

TTTCTGACTCCCTTTCGGAGGAGCCCTCCCGGGACCCCGGGAGTAACAGGTGTCTGGAGGC
                                                             1
                                                           Met Val
TCTCGCACCACCCCACCCCCCCTCACCCCTTCTTTTTCCGTCCCTTGGAAA       ATG GTG
                                                         Ex1-1R

Ser Ser Gly Val Thr Lys Glu Val Leu Val Gln Ala Leu Glu Glu
AGC TCC GGG GTC ACC AAG GAG GTG CTG GTT CAG GCC TTG GAG GAG

Leu Ser Pro Gly Ser Gly Ala Glu Pro Asp Thr Lys Pro Val Phe
CTG TCC CCT GGC TCC GGC AGC CGG GCC GAG CCC GAC ACC AAG CCG GTC TTC

FIG. 27A-1

AAAGCCCCGCGCCTAGGCTTGCAAGGCACTGGCTTAACAAGTCCAAAGGTTAGGTGAAGTTT

CCTGGCAAAGCCCCGCTCCCCGGCCCCAGGTCTCTGCTCTCCAGGTCTGCCCCTCCGGCTCT    Ex1-1F    Exon 1

TCCCACTAATTTGCATATCTTATATGGCCTAATGGTGGCGATCATGCAAGTT AGAAG
                                        Ex1-2F

TGAAGGGTGGAGGGGTTCCTGGATTTGGGGTTTGCTTGTGAAACTCCCTCCACCCTCCTC

```
Ser Lys Leu Thr Ser Leu Gln Gln Glu Leu Leu Ser Ala Leu Leu
TCC AAG CTC ACG TCG CTC CAG CAA GAA CTC CTG AGC GCC CTG CTG

Leu Leu Pro Ser Pro Asn Phe Gly Val Lys Leu Glu Thr Leu Pro
TTG CTG CCA TCC CCG AAC TTC GGG GTG AAG CTG GAG ACG CTG CCC

His Thr Leu Thr Asn Gly His Ala Lys Gly Arg Leu Ser Gly Asp
CAT ACT CTC ACC AAC GGC CAC GCC AAG GGC CGC TTG TCC GGC GAC
```

*FIG. 27A-2*

```
Glu Gly Ser Glu Asp Gly Asp Tyr Asp Thr Pro Pro Ile Leu
GAG GGC TCC GAG GAC GGC GAC TAT GAC ACA CCT CCC ATC CTC
                                    115

Ala Glu Val Asp Arg Met Leu Se(r)
GCG GAG GTG GAC CGG ATG CTC AG GTAGGCGCAGAGCCAGGTGGAGGGACCC
Ex1-2R
AAGCCCGTTTCCCACCAAAAAATTCCCCGGGGGCGCTCTTCTCTCCCAACACCCG

CCAGGCCATCGTCC:::::: 9 kb ::::::TCAGAAGAAAGGGATGAGGTGTACCG

GTTGTAGCTTAGATGGGGGAAAATTCAGAATTTGCATAGACCATAGTAGCACCCCCT
                                  115
2 (Se)r Glu Asp Pro Trp Arg Ala Ala Lys Met Ile Lys Gly Tyr
CTAG   T GAG GAC CCT TGG AGG GCT GCT AAA ATG ATC AAG GGT TAC

Gly Leu Asn Gln Ser His Leu Ser Gln His Leu Asn Lys Gly Thr
GGC CTG AAC CAG TCG CAC CTC TCC CAG CAT CTC AAC AAG GGC ACC
                                    182

Arg Lys Gln Arg Glu Ile Leu Arg G(ln)
AGA AAG CAA CGA GAG ATC CTC CGA C GTAAGTGTTTTCATCCTGCCTCTGCC
```

*FIG. 27B-1*

```
Lys Glu Leu Gln Ala Leu Asn Thr Glu Glu Ala Ala Glu Gln Arg
AAG GAG CTG CAG GCG CTC AAC ACC GAG GAG GCG GCG GAG CAG CGG

ACCCGAACCCCTGGAGCCCCCGGCCCTGAGTGACACTGCGCCCGACCACACTCGCC

GACCCTTCCCAATCCCCTTAGCGGGACAACCCTGCGCCCACCGGGCTTCTTCTCCCAGGC

TACAGGGGCAGTCACCTTCCTCTGTGTTTAGCTTCCATTTTGGCCTACATGTCTACCCCAAA
                                                        Exon
AGAAAAGAATGTTTCTCCCCAGATGTCTCCCACTAGTACCCTAACCATCTGCTTGTCTGT
                       Ex2F Met Gln Gln His Asn Ile Pro Gln Arg Glu Val Val Asp Val Thr
ATG CAG CAA CAC AAC ATC CCC CAG AGG GAG GTG GTC GAT GTC ACC Pro Met Lys Thr Gln Lys Arg Ala Ala Leu Tyr Thr Trp Tyr Val
CCT ATG AAG ACC CAG AAG CGT GCC GCT CTG TAC ACC TGG TAC GTC
Ex2R
TCAACCTGAAGTGACCTTTGCCCTCTCACCCCATTGGCTGCCTCAGTTTCCCTTTCATCGAC
```

*FIG. 27B-2*

```
AAGGCCTTGTGAGCACTTGGCAGATATGAGGAAGGTGGCAAGTAGATTGGCCTTGGTG

CAGTTGCTCTGAGGAGCCTGTCAGTGT::::::  5 kb  ::::::GATTGAGCTCAC

GAGCCAAAGGGGAAAAATAATTTTCTTAAAACTATAGCTGGCTATGTTTGAGCTC

CTGAGGGCTCCCCATCTCCAGCTCCACATGCAGTGAGAGAAGGTTGCAAAGCTTAGTTA
                                                        182
EX3F                  Exon 3   (G)ln Phe Asn Gln
GAAGGCTACAGACCCTATCAAATCTACTCCTTTCTCTTTTCAG AA TTC AAC CAG
          (G)ln
Gln Leu Leu Phe Leu Phe Pro Glu Phe Ser Gln Gln Ser His Gly
CAG CTG CTG TTC CTC TTT CCA GAG TTC AGT CAA CAG AGC CAT GGG
```

*FIG. 27C-1*

```
GTTGCTGTGTACAATGGATTGGCTTCTGTCATGTTCTTCAGTCACAGCCCCCTTGCTACCCAGC
CCACTTGACATCAAATACAGGAGTTCAGGATGCAGAGTGTTGCTTCATCTCTGAAGGCCAGT
CTTCAAAGAAAAGGAAAAAGGGTGGCTTTGCTGGAGCAACTGAGGTGGGCAGTAAGGCCTGTG
GACGAGGGGAATAAACCTGTCTCTTCGTCCGTTGTCTGTCTCTGTCTGTCTCTGCTGAGT
```

| Thr | Val | Gln | Ser | Ser | Gly | Asn | Met | Thr | Asp | Lys | Ser | Ser | Gln | Asp |
|---|---|---|---|---|---|---|---|---|---|---|---|---|---|---|
| ACA | GTC | CAG | AGT | TCT | GGA | AAT | ATG | ACA | GAC | AAA | AGC | AGT | CAG | GAT |

| Pro | Gly | Gln | Ser | Asp | Asp | Ala | Cys | Ser | Glu | Pro | Thr | Asn | Lys | Lys |
|---|---|---|---|---|---|---|---|---|---|---|---|---|---|---|
| CCT | GGG | CAG | TCC | GAT | GAT | GCC | TGC | TCT | GAG | CCC | ACC | AAC | AAG | AAG |

*FIG. 27C-2*

```
Met Arg Arg Asn Arg Phe Lys Trp Gly Pro Ala Ser Gln Gln Ile
ATG CGC CGC AAC CGG TTC AAA TGG GGG CCC GCG TCC CAG CAA ATC
                                            270

Arg Glu Ala Leu Val Glu Glu Cys Asn Ar(g)
AGA GAG GCC TTA GTG GAG GAA TGC AAC AG GTAACACCACCAGAAGCTCAGG

CACTAGTTATACAGATAAGTGTGGCTAAATCAGAGCTTCTCAAAGTATGTTCCACA::::::
                                  270
          Exon 4 (Ar)g Ala Glu Cys Leu Gln Arg
CCTTCACTCACCATCTCCCCTCCATTCCCCAG G GCA GAA TGT TTG CAG CGA Thr Glu Val Arg Val Tyr Asn Trp Phe Ala Asn Arg Arg Lys Glu
ACT GAG GTC CGT GTC TAC AAC TGG TTT GCA AAC CGC AGG AAG GAG Gln Thr His Ser Leu Asn Pro Leu Leu Ser His Gly Ser Pro His
CAG ACT CAC AGC CTG AAC CCT CTG CTC TCC CAC GGC TCC CCC CAC
```

*FIG. 27D-1*

```
Leu Tyr Gln Ala Tyr Asp Arg Gln Lys Asn Pro Ser Lys Glu Glu
TTG TAC CAG GCC TAC GAT CGG CAA AAG AAC CCC AGC AAG GAA GAG
                              EX3R
TGGGCAGGTGGGCAAGTACACAGACCCCAGGAACCCCTCCCCTCGGTCCTGGATATTGAGA
                                      EX4-1F
2 kb ::::::GTGATTGTGTGTTTTGGGCCAAGCACCAACAAGTCCCCCCGCCCC

Gly Val Ser Pro Ser Lys Ala His Gly Leu Gly Ser Asn Leu Val
GGG GTG TCC CCC TCC AAA GCC CAC GGC CTG GGC TCC AAC TTG GTC
                                                        EX4-2F
Glu Ala Phe Arg Gln Lys Leu Ala Met Asp Ala Tyr Ser Ser Asn
GAG GCA TTC CGG CAA AAG CTG GCC ATG GAC GCC TAT AGC TCC AAC
                                                         349
His Gln Pro Ser Ser Ser Pro Pro Asn Lys Leu Ser G(ly)
CAC CAG CCC AGC TCC TCT CCT CCA AAC AAG CTG TCA G GTAAGCAAAGGT
                                                 G   K   Q   R
```

FIG. 27D-2

```
                                          EX4-1R
TGGGCCTCACTGCCTCGGCAACCCAACCCATCCCTGGTTCTTGCCACGGATCTTATCTGT
 L  G  L  T  A  S  A  T  Q  P  S  W  F  L  P  R  I  L  S  G

GAATATACTCCCCTGGAAATAATGTGTGGCTCTGATCAGTT::::::: 3 kb ::::::
 N  I  L  P  W  K  OC
                399

GCGCTTACATTCTAGAATTAAATAGAGAACATGCCATATTTACCCTGGAGAAAAGCAGC
              EX5F
TGAAAACAAGAGGTGCCGAGTCATTGTTCCAGGACCCTGGTGGCACTAATGTTCCCTAC
Glu Ile Thr Ser Ser Ser Thr Ile Ser His His Gly Asn Ser Ala
GAG ATC ACT TCC TCC TCA ACA ATC AGT CAC CAT GGC AAC AGC GCC
                                                        402
Leu Asp Pro Gly His His Asn Leu Leu Ser Pro Asp Gly Lys Met
CTG GAC CCA GGC CAC CAC AAT CTC CTC TCA CCT GAT GGT AAA ATG GTG

CTCACAAGGCCCTGCCTCAAACAATGAACCATTGTAGCCCCCATAGGGAAAATGAGGGCT

::::: 5 kb :::::CCCAAAGTGATGGGATTACAGGGGGTGAAGCACCATGCCCCAGCCA
```

FIG. 27E-1

TTAAGGGTTTTCAGAGGAGCAAACGCTTTTGAGATGATCCTAGGGCCGCTCTCATTGCCA
L  R  V  F  R  G  A  N  A  F  E  M  I  L  G  P  L  S  H  C  Q

CCAAGGCACTGGGGATACATCAGTGAACAAAACAAACGAGATAAAAATTCCTGCCCTCGTG

CGATATTTCTTGTGGGTGGACAGGGGGAGGAGAAAGCAACTTTATTTCTTATTACCCACCCT
                                                349
                            Exon 5 (G)ly Val Arg Tyr Ser Gln Gln Gly Asn Asn
TGGGTTTGTGTTGTTTTGCAG        GA GTG CGC TAC AGC CAG CAG GGA AAC AAT Met Val Thr Ser Gln Ser Val Leu Gln Gln Val Ser Pro Ala Ser
ATG GTG ACC AGC AGC CAG TCG GTT TTA CAG CAA GTC TCC CCA GCC AGC
                                                            EX5R
AGTACACCTGGGCCATTGTCGCTCTCTGGAGCTGATAAGAGATAAGAGGCAAAACAAACACAACTT

GTCCAGAGTCGGGAAGGAGAGGTAGTGCTGGTGACCCACCCTTTGGCGGGTAGAAAA::::::

ATAATTGTTATTGAGTGAATGAAGGAATGAATTTGAGAACTAGTCATGCCAAGGAATCGCTA

*FIG. 27E-2*

```
                    EX6F
AGTCACATCGTGTTGGAAACTGCTCTCTTGTGGTCCAAGTCCACCCATGTTTCTCTTGTT
Ser Thr Leu Thr Asn Ile His Ser Leu Ser His His Asn Pro Gln
AGC ACC TTG ACG AAT ATC CAC AGC CTC TCC CAC CAT AAT CCC CAG
                                     447
Ile Ala Gln S(er)
ATT GCA CAA A GTAAGTTCTATTCTTGGTTGGAAAACCTGGGGCAGGGAGAAGAA

TAGTAAATTGGTTAACTTCTTTAGTTTCTCATCTGTCTCCTTAAATCCAATATTTGG

AGCTGTGCATCCCTGGGTCAAATCATTGAACCT::::::::4 kb ::::::::ATGACTC
```

*FIG. 27F-1*

```
         403
Exon 6  Ile Ser Val Ser Gly Gly Gly Leu Pro Pro Val
TTTTCTCTCCATCAG ATC TCA GTC TCA GGA GGA GGT TTG CCC CCA GTC Gln Ser Gln Asn Leu Ile Met Thr Pro Leu Ser Gly Val Met Ala
CAA TCT CAA AAC CTC ATC ATG ACA CCC CTC TCT GGA GTC ATG GCA

EX6R
GAATGGGAAGCAAATTAATGTGGTGAAAAATAACTGTAGGTCTCCTTCAAACTCACCCACAAC

ATTGTTTAGCCCTAAAACAAGAAAAAATTGTGGAATGGGATTTGGATCCTGGTCACAGTTTAGC

TGGGAGACTCTCAGGCTTTAATCAGATCTGTTTAATGCCCATCTCCAACCCACAACTCATTG
```

FIG. 27F-2

```
TGGAACTTGAGCAAGTAAATTAATATCTCTCCAAGTCTCCGTTTCTTTACACTTGCCTCCCATGG
       EX7F                              Exon 7
ATGGCATCCATCCACCTCTCCTTATCCCAGGAGCTGTCTGTGTCTTTCCTCTTGCTCCCACA
Ser Val Ala Gly Ser Leu Ala Ala Leu Gln Pro Val Gln Phe Ser Gln
AGT GTG GCC GGC AGC CTG GCA GCC CTG CAG CCC GTC CAG TTC TCC CAG Pro Gly Ser His Met Ala Gln Gln Pro Phe Met Ala Ala Val Thr Gln
CCA GGC AGC CAC ATG GCC CAG CAG CCC TTC ATG GCA GCT GTG ACT CAG
                                            EX7R
GGACCCCTCAGTGGCCAACCACTTTCCCCTCTCTGGGTCTGAACTTTCTCGGAAGTTTATTGGCT

TGAGTGTGCTGTACCTTTTCTAGTCCTCTTCTCTACCCCTGAGATTCCCAGGGAAGGGTTTG

GGTAGGGAAATGTGTTCTGAGAGCAGGTGGTTTCTCCCTCACAGCCAAGCATCCACATGCTTTC

ATCCCCACTATAACCACCAGCCCCTTTATCTACCTGAGGAGAGATGGGAGCTATGGTGTGGGATG
```

FIG. 27G-1

```
AATCTCCTATGTAACAGGCTCAGCCCGGTGACTGGGACATTGAGCGGGGGCTCAAATG
447
(S)er Leu Asn Thr Ser Gln Ala Gln Ser Val Pro Val Ile Asn
  G   GC  CTC AAC ACC TCC CAA GCA CAG AGT GTC CCT GTC ATC AAC

Gln Leu His Ser Pro His Gln Gln Pro Leu Met Gln Gln Ser
CAG CTG CAC AGC CCT CAC CAG CAG CCC CTC ATG CAG CAG AGC
                                       512
Leu Gln Asn Ser His M(et)
CTG CAG AAC TCA CAC A GTAAGGACACGGGCATGTGGAGGGAGGGAGCACTCA

ACCGACTAAGACAATTTCTCAAGCATAACTCT

TGGTCACTTTCCCTGCCTATGATCAACCGACTAAGACAATTTCTCAAGCATAACTCT

AA::::::: 2 kb :::::::TGACCCTTTGCTCTCCCCGTTCCGTACCGGAGGCCTCCCT
                                                           EX8F

GGGAGTTGGTTATGTGACTTGGAATTTACATGAATCTTATGGATAACTAATATGAGAA

GGGGCTCTGTACCTGTGTCTTTGCCTGTATGCACCTTGATTCTGTCTTCACTCTGT
```

FIG. 27G-2

```
                                                          512
Exon 8  (M)et Tyr Ala His Lys Gln Glu Pro Pro Gln Tyr Ser His
CTCTCCAG TG TAC GCA CAC AAG CAG GAA CCC CCC CAG TAT TCC CAC
                                                          551
Ile Ser Thr Leu Thr Asn Met Ser Ser Ser Lys Gln
ATC AGT ACA CTC ACC AAC ATG TCT TCA AGT AAA CAG GTAATGCCAGCAG
                                                         EX9F
GGCAAGCATGGACTCGGCCAGAAATTATATCCT:::::: 10 kb ::::::CTTTGCTG
                                                          552
                     Exon 9  Cys Pro Leu Gln Ala
TGACACAGCTGAGCACCTCTCTCCTCTCTCTGCAG  TGT CCT CTA CAA GCC
        EX9R
CCATCACCCTCTGGGCAGCTGTCATGGAAAAGCCCAGTGACCTGACCCAGCACCCTGCCGAGAG
```

FIG. 27H-1

```
Thr Ser Arg Phe Pro Ser Ala Met Val Val Thr Asp Thr Ser Ser
ACC TCC CGG TTT CCA TCT GCA ATG GTG GTC ACA GAT ACC AGC AGC
                                                              EX8R
GATATGCGGGGTGTGTGGGCAGGGTGTGTGATAAGGCCATGGATGTGCAAAGGTTGT

GTTGAGTTGGGCATCATCCCTTAGAGAAGCCAAACTAATGCCCATGACCCTGCCAAA
557
Trp OP
TGG TGA TGCCCCACACCACTTACTTCGTGCCAACAACAAGGACCCTGTTTTCCACA

GTCCCTGCTACCTGAGGGACGTCCTGCTGGCACCTCAGACAATCCACTCTCAGGAGGCGCA
```

*FIG. 27H-2*

```
GCCCGAAGCCCCAGTTTCCCTTCTATGCAGTATTGCCCACAATGCCCTCTCCCACGATGTCAA
GTACTGTCTATGTTGTGATCCTTCATCGAACAAACTGATGCGAAAACTTGAATCTGTTAC
AGACTCCCCCCCCATCCCCACATGATCTTGAGATTTCTTTAAAGAAGTAAATT
TCCCCTCTGCCCTGTATATAATACTAAAGTGTCTATTAGTTTCTTTGTAAAGGTCAGAG
TGAAGCCCCTTGTCCTCTCCCGCGGCCCTGGACACTTATGGGACAGCATACCTTGGACT
TGAATGTGTAGTGTGTCAGAGTAACATGCCAGCTTCCTGTGGGCCAGGAGCTCAGCCTGCAC
CTCAAAAGCCCTTCCATTAAAAACAATTTATTTTATCACTAAAAAAAA
```

FIG. 271-1

GGACTCCTGTCTGTCCTGGAGGTGGGAGACAAGGAACCACCGAAGAGGAAGCAAGAAAGCC

TGAAATGAGGAGAGAAGGACATGTGCTATTGAACTGAGCCAAACACACTGTAAATATCCAC

TGTCCAATGGCTGTAAACTATAAACTACTGTAATTAAGTGCAATTTCCCCTCTGTGTCCTC

TCAAAATTTCAAAAAGTGATCTGTCCCCTCTCCCCTCATGGAGAAACATCCTAAGTGGGAAG

GACTACCAGCTAACTCCAGTCTCCCTGACATTAAGACACACCTCTGGATCCCCTGGAGGGGC

TCCCTAAGAAACCCCAGGGCCAGGGAAACTGGCTGTGTTTGATAGCAGAAGAAAAGTTGCAGT

FIG. 271-2

1    TGGGTTGCCCTGTGACTGCACTGGCGATACCCCACAAAGCCCACTCT
91   GGATACGAAACAGGGAGGGGAAGAGAGGATGGACGTCTA
181  CTCAAACCACCCCTTTGAAGTTGATTGTACATTTTACAGAAAAGGAAA
271  GTAGACGGGTAGGTGCCCTGAATGTAAATCCAGGTCTCTGCCTCCG
361  ATCCGAGATGGAGCCCAGCCTGGGCCAGAAACACTGGGAGCTGTGGGA
451  AATTGGAGGTGAATCTGGCCCCTCCCAAACTTCCAGTCCATTCTGCTC

FIG. 28A-1

GAAGGTAGGAGAGACGGGTGGAGAGAAACAGGGGATGGCAAGGG

CCAGGCCCCACTTGGCTGCTTGATTTATGCCATCTCATTTCCTT

CTGAGGCTCGGAGAGGAGAATCATTTACCCAAGTCCCAGTTA

GGGAGGGGGTGAGGGTGAGGGAAACAGGAGAATGTGATGGGAAA

GACGGAGAGGGCAGGGCTGGGATCACAGGGAGCAGGAGCGGGG

CCAGGGGGAACCGGGGGAACTGGAAGGGAGCTCC

FIG. 28A-2

541  CAGAACAAGGATCCAGAAGATTGGCATCTGGGGCCTGGGGATTAGGTTTC
         P1F →
631  ATTGAGGGTAGAAGTCAATGATTTGGGAAGTTATTGAATTAGGGGATCTC
               HNF-6
721  CCTGACTTGGGGTGACAATGGCTTGGAGGGGTGGGTGAGTCAAGGGTCAA
811  ATAACTGAAACATCGGTGAGTTAGGCCCCAGCCAGTTGTAATTAGCACCCC
901  GCCCCGCCCCAGCCCTATCCACCGGCGGGGGACCGATTAACCATTAACCCCC
                          A                HNF-1α
991  GGCCAAGACTCCCAGCAGATCTTCCCAGAGGACGGTTTGAAAGGAAGGCA
                    ←  P1R
                    *

FIG. 28B-1

```
TAAATCGTGGGCCATGGGGGCCAGCCCTTATCTCTGCAAAAGC
GGAGGTAGGCTGTCAGTGCCCTGATAGTATCAGTTAGAATG
                    ──P2F──▶
ATGAGTGCCCGTGAGTCATGATGCCCTTGTACAATTG
                                  ──HNF-3──
GGGTGTCAGCCAGAAACCAAACAGCCAAATCCCTGCA
ACCCCTCCCCGGCAGCCCTCCACCCCTTCACAGAGGCTA
                          ──E1F──▶
GAGAGGGCACTGGGAGGAGGCAGTGGGAGGGCGGAGGGGCG
```

FIG. 28B-2

```
                                                               1
      M   R   L   S   K   T   L   V   D  Met
GCAGGGAGAATGCGACTCTCCAAAACCCTCGTCGACATG

PheGluAsnValGlnValLeuThrMetGlyAsnG(ly)  30
TTTGAGAATGTGCAGGTGTTGACGAATGGGCAATG GTAGG

AGGAGCAGATCTTTGGGCACTCAACTTTGGGTGGAGGA

AGTGAAGCCCATGTGCCCAGGCACAGTGATCACAGGCAT

Exon 1C  (G)lyProSerSerProHisCysLeuT
GGCTATTCCTCCCCAG GCCCTTCCAGTCCTCACTGCCTCA
```

FIG. 28C-2

```
      hrValAlaLeuLeuGlyAlaTrpHisSerAspMetMet
1531  CAGTGGCTCTGCTTGGCGCTTGGCACAGTGACATGATG GTGAG

1621  TCGTGAACCCCCTTGGGCCCTAGGTTCAGAGAGACGGGCAAGGGATG

1711  TGTCTTTGGGACTTTCCCTAGGGAAATGAAATTGGCACTTAGGGA

1801  CACTGTGTGTGTTGTGTGTGCGTTCGTGTGTGATAGTGAGTTTC

1891  ATATGTGTGTTCATTTGTCTCTGTGAGTTCTCGGTCTATT

1981  GCCCGTGTTGATCTTGCTTATGTAAGTGTATGTGTGTG
```

FIG. 28D-1

CTCCCCCCTTGGTGCCCCAGCTCCCAGCGGATTCAGCCCAGCCACGGCCCCT
          →E1CR

TTGTATCCCTGGAGATGGTGGTTGGGAGACATAACCGCATTTCTCGG

AAATGGAGCTCTCAGGGAAGTTTGCTAACTACGAAGCCAACTCAG

CATGTAGGTTGTATGGGGTGATGCCCTTCAGGAACCCCATTTGC

TTCCTTTGTATTCATTGAGTGGGTCTGTGTTTGTGTCTTAGGAGTT

TACTTGTGTCTGTGTGGATGTTTGTACATGTGTGCTGTGTGCGGGT

*FIG. 28D-2*

```
                              E1BF ─────▶
2071   CATAGAGCACACATGCGTTTGTGCATGCGGACCTGTTGGAGTGCCC
2161   CATATTTGTACCTGCTGTGTATATGCAGTTCCCTGTGCTGCG
2251   TGCAGGACTCTGTTGTTGCCACTCACCAAGTGAGATTCATATCA
2341   euAlaArgLeuArgHisProLeuArgHisHisTrpSerIleSer
       TCGCCAGATTGAGGCATCCCCTCCGACATCACTGGAGCATATCT
```

FIG. 28E-1

TGTTCTTCCTGCATCTTTATCCTGTGTATGGGCGTTTGTCGTGCC

GGCGGGGGGTCAGCGTCTCTGGTGTGCACGACTGCACAGACCCAAA
         A     Exon 1B    IleLeuLeuProLeuArgL

GCAACATGTCCGTTTGTCTCTGAGCAG ATTTTGTTGCCGCTGCGTC

GlyGlyValAspSerSerProGlnGlyA(sp)
GGAGGGGTGGACAGTTCTCCACAGGGAG GTAGGGGAAAAGAGGAGG
                                   G

*FIG. 28E-2*

| | |
|---|---|
| 2431 | CCCGGAAACCCCTCCTGGAGGGAAGAGCCCCATCGGTCCCAGG |
| 2521 | CACCCTGCTTCCTTCTGTCTTGGAGCCACTCAGCCAGTATG |
| 2611 | AGGGTGAGGAGGCAGCTGCTGGGCACTGCTTGTTGTCAGCTCA |
| 2701 | ATGTCACCTCCCCTATCCCTGGCTTCTGTATCTTCTACAAAACA |
| 2791 | TGAGGACCACGCCAGGAGCGCCAAGGCAAAAACACACCAGAGAT |
| 2881 | CACCCCAGAAGGTGGCCAGGTTTTCATGCCTTCCCTAGAGAAAG |
| 2971 | AAGTCTGTGAAGTCACAACCAGCCCCCAGTTTACAGATGTGAAA |

FIG. 28F-1

```
CCAGCCTCAGAGGAGAGGGGCAGGCAGCTGGCTGAGGTCAGCCTGC
AGGCTGCAGCTCCAGCTGAGCTGGAATCTTGTGGTCAGCTCAGCT
GCAGGTGCTCACCTGCCCCCTGCCCGTCCAGTCACGTGTGACCCTGGGC
GGCTTCATTCCCCCAGGCCCTGCTGGCTTTTAGGAGCCTGTC
:::::: 4.4 kb  :::::: CCCCTTGCCGAGTTAGGAGGCCGGCTCC
CTGGGGCTGGCCCTCCACCAGGAGACGCAGACCCTCAGAAAC
CTGAAGCTCCAAAAAGTCAGGAGGTCACTGAGTGGGAGGTGATGGA
```
                    → E1BR

*FIG. 28F-2*

```
3061  GTGGGAACAGCCCCCAGATCTGGCTGAGGCCGAAGCCCTGGAGA
                                          30°(A)  spThrSerProSer
                               Exon 2
3151  AAGCCTCACTCCCCTTCTCTCCTGGCCAG ACACGTCCCCATGA
                                 T
      uCysAlaIleCysGlyAspArgAlaThrGlyLysHisTyrGly
3241  GTGTGCCATCTGCGGGACCGGCCACGGGCAAACACTACGGT
                                              88
      gLysAsnHisMetTyrSerCysAr(g)
3331  GAAGAACCACATGTACTCCTGCAG GTGAGGAGCCCTCAATTTCT
         ——E2R
3421  TTCTCCCTGAGTGGGTAGGTCCCAGAGACAGCTGCCCTTCAGGG
```

FIG. 28G-1

E2F →
GAGATCCCCGCCAAGGCTCCCCTTAGAGATGCCCTGACATTCTGCTCTTCCTG
                                          T
erGluGlyThrAsnLeuAsnSerLeuGlyValSerAlaLeu
GAGAAGGCACCAACCTCAACGCCCCAACAGCCTGGTGTCAGCGCCCT
AlaSerSerCysAspGlyCysLysGlyPhePheArgArgSerValAr
GCCTCGAGCTGTGACGGCTGCAAGGGCTTCTTCCGGAGGAGCGTGCG
CTTCAGCTGTGGGAAATGGGCACACACTTGGGCTCATGGCCCCAAGGTCTGTC
GGCCTTCAAGGCTCTCTTCTGGTTTTGTAAAAGACTTTGTGAATCCAAGA

*FIG. 28G-2*

3511 AGAGCATCTATTCTAGGAACCACATTTACTGATCATCAAGCTA

3601 AGTCTTTGTGTGTATTTAC::::::1.6 kb ::::::GTAC

3691 CGACCCAGGACCACATGTTGCCCTCTCTGAGCCTCAGTTTTCCC

3781 TCCAGCTCCCTGGTGGGTTCAAGAGAGAACTCCCGGGATGAAGA

E3F ⟶
3871 GTTCTGTCCTAAGAGGAGGAAGTTGTGTCTTCTCCATCCAACC

FIG. 28H-1

```
CTGGCTGCCGTTTATTGAGCTCTTTATCATATGCCAGGCACAATACTA
TCCAGAGGTCAAGGTTCCCAACTCAGCTCTAACCACCAGCAGAG
ATGTTTAGCAGGACACAGGACTGGGCTCTTAGAGAGTTCATAGCACCTT
GATGAGAGCACTGAGGTTGGGGGTCAACTGGATAGCCAGGCCCTA
                                        88
Exon 3    (Ar)gPheSerArgGlnCysValValAlaAspLysA
          ATTTAGCCGGGCAGTGCCGTGGTGGACAAAG
ATCCAAAGCCCCTCCCCAG
```

FIG. 28H-2

```
                spLysArgAsnGlnCysArgTyrCysArgLeuLys
3691            ACAAGAGGAACCAGTGCCGCTACTGCAGGCTCAAG

4051            ACCACCACTGCCCCACCCTGCCACCCAGTCTCCCGAC

4141            ACTGGCTAATGGCTGAGAAGAGGGAGGGCCTGGAAAT 4231            5.9 kb ::TCCCCACTCCCTCATCAGTCACAGACACCC
```

*FIG. 28I-1*

```
                            LysCysPheArgAlaGlyMetLysLysGluA(1a) 120
        AAATGCTTCCGGGCTGGCATGAAGAAGGAAG GTGAGCCTCGGCCCTCCCCGCCCC
        CGACAGTCATTTACAACTGTAGCCACACTTTATGACTCAGTGGCAGGCCCCAGGGTG
                                    ————E3R———>

AAATCTGACCATAGGGAGCGGGCTTGGTCTTGAGAAAGATTC:::::::::  Exon 4
                      E4F——>
        ACCCCCACCCTACTCCATCCCTGTTCCCTCCCTCACCTCTCTGTGCCTCCTCAC
```

*FIG. 28I-2*

```
120  (A)laValGlnAsnGluArgArgAspArgIleSerThrArgArgSer
4321 AG CCGTCCAGAATGAGCGGGACCGGATCAGCACTCGAAGGTCA
                                    155
            T(R127W)        (T/I130)
     aGluValLeuSerArgGln
4411 GGAGGTCCTGTCCCGACAG GTACCGGGGGTGATCCTGCCACCCA
4501 TTCTCCCCAGCCAGGCCCTGGAGCAGCTGACGGGAGGGCCCTCA
                                    ←——— E4R
4591 GCAGCAAGGGCAGGAATCGAACCTGGCCCTGGGGCACTTTCT
4681 CTTCACTGAGGGCCTGCGATCAGCTCAGCTCCGAGAGAACAGAG
```

FIG. 28J-1

```
SerTyrGluAspSerSerLeuPheSerIleAsnAlaLeuLeuGlnAla
AGCTATGAGGAGACAGCAGCCTGCCCTTCCATCAATGCGCTCCTGCAGGC

CCCAGGGATCCCCCACACTACAGAGGAGCTCACCTCTCCACCTCCA

GATATTACAGAAGGACACTGAGTGCGGTTTCACATGGCCCAGTTT

AATTCATCCCTACTGCCATCCCACAGCCAAGCAGCAGAGTCTTCAC

CAGTGGCCTCAGTGGAGAGAGGTGGCAAAGTGGGGCCCCAGCCCTTCC
```

FIG. 28J-2

```
4771  CTTGCTGAGTGACCCTTGGGCAAGTCACAGCACCTCTCTGA
4861  CTCCTCTAAGGCTGACAGACTCCCTTGGGCTCTAAAGCTG
4951  CCGTTTTTACCCTGAGCTTCCCTTCAGAGCTGGAGGCACC
                E5F →
5041  AGGGACAGAGAATGCGGAGGGCCCCGACATCTCCAGCA
      nGlyAspIleArgAlaLysLysIleAlaSerIleAlaAsp
5131  CGGCGACATTCGGGCGAAGAAGATTGCCAGCATCGCAGAT
```

*FIG. 28K-1*

GCCATGGTTGCCCTCATTGTCAGAAAAGGATGATGATTTTTGCCCTGCTT

::::::: 1.0 kb :::::::TTCTCCCCTCATCCCCTGCCTCCTCCCTCCCT

CACTATCCAGCCCCCACATCTGATTCCAGGGAGGGGCTCTGTGC

Exon 5  ¹⁵⁶IleThrSerProValSerGlyIleAs
TTTCTTCCCTGTATCTCTCGAAG ATCACCTCCCCGTCTCCGGATCAA ValCysGluSerMetLysGluGlnLeuLeuValLeuValGluTrpAlaLy
GTGTGTGAGTCCATGAAGGAGCAGCTGCTGGTTCTCGTTGAGTGGGCCAA

FIG. 28K-2

```
                sTyrIleProAlaPheCysGluLeuProLeuAspAspGln
                                                       197
5221  GTACATCCCAGCTTTCTGCGAGCTTCCCCTGGACGACCAG GTGAGGA

5311  CAGGGGGCTGGCCCACCTGGGATATAGCCGTGGACTGGCTTGATT
                                        ──────E5R──────▶

5401  AACTTTAAATCACCTTACAAATATTAACTCAGTTAGCTCCTCCAACAA

5491  CATAGGTGAGGAGATTGGGGCACAGAGAGGTTAAGTAACCTGCTCAAG

5581  ::::::::ATTTTTACAAAGCACCCTTCATAATTCTCCATAGCTGGTC

5671  GATCATAGACCTTTTTGAGAATCTCAAAAAGAAAAAAAGCACACA

5761  GCACGAAGCAGTTTCTTGCCCAAGGACAGCAGTTCAAGGACAGAGT
```

*FIG. 28L-1*

```
TGGGCGTGGATGGTGGGCAGTAGTGGGCAGTGGGCGGGGCAGC
TTATTTTATTTAACAAAATATGTAGTGCACACGTGTCTGA
CTCTATGAGGTAGGTACTAAGGTACTATTATTACTGCCATCT
GTCACATAGCTACTATCCAGCATAGCTGGG::::: 4.3 kb
CATGGGTGGGAATTTGGGACCCACAGTTTTGGAACTTTTTGG
GAATGTTGCTTACAGTTTCATCAGGCACACAGAAGAGGCCCA
CAGCGCGAGGTCTCTCAGCTCCTGAGCACATGTTCTTCCCCT
```

FIG. 28L-2

5851  TCCAGGTTTCTAGTTTTATGGGTAGTAGTTTATG

E6F
              ⎯⎯⎯⎯⎯→
5941  GCCCAGCGTCACTGAGTTGGCTACGGGCAGCCCTTC
      rgAlaHisAlaAlaGlyGluHisLeuLeuLeuGlyAla
6031  GAGCCCATGCTGGGAGCACCTGCTCTCGGAGCC
6121  GCCCTGGCCAGGGCTCCCAGGGAGGGTATGCCTAG
6211  CTAGTCAGGAGTGCCCTGTCCCTCAGGCTTGCAT
6301  GTGGATGCAAGTCACCAAATTCCCAGCATTGAAG

*FIG. 28M-1*

```
ATGCCCATTTCACAGTTCAGGCAGGTAGAGGCAGAGGGGAGCATTAAGCTGACTT
                           198      ValAlaLeuLeuA
              Exon 6
CCAAGGGTACAGATGGCAAACACTGTTCCTCTCTCTTTCAG GTGGCCCTGCTCA
ThrLysArgSerMetValPheLysAspValLeuLeuLeuG(ly)²³⁷
ACCAAGAGATCCATGGTGTTCAAGGACGTGCTCCTGCTCCCTAG GTGAGGCGGCTGCCT
CATGGCACTCACCCCAGGCAAGGAGATTCACATGGTGGCATGCAAGGGTGAGGGAGA
    → E6R
TGGAGGGCTCCAGGACTCAGTTTTTCAACTGGGTACCCCCACTCAGATGCAAGGAAAAT
TCAGAGCACGATCAGGGTTATCCCCTGGAATTACCTGTGCATCCTTTTTCTTTTGA
```

*FIG. 28M-2*

| | |
|---|---|
| 6391 | CAGAGTCTTGCTCTGTCACTCAGGCTGGAGTGCAATGATGTGA |
| 6481 | ATGCTATGAGGGAGCTCGATTATTTATCCTCATCTTATAGATA |
| 6571 | AGCTATCAGGGGCAGAGCCATTTAAGCAGGGCAGTGCAGTTCC |
| 6661 | TTTGAAATGTCATCGATCTTGTGAGTCATGTTGGTAAATGGAGC |
| 6751 | CGGATGACTCAAGGCAGCTTATCTTCTGAATCTGGGCCTCAGC |
| 6841 | CACAGGCACCAGCTATCTTGCCAACTTAAAAGCCAAAACTAGA |

...... 1.4 kb ...... :GCAAACACTACCTATTTTAATATAACA
AGAAAACTGAGGCACAGAGAGGTTAAGTAACTTATCCAACTATAACC
AGAATCTCGGTCCTTAACCTTGATGCTTTGGTGCCTATCAGGTGACC
TTGGGTCATGTGAAAGAGGTCCTAGAAAGCCAAGTTCCAAGCTCAGC
TTCCTTACCTGTGAAATGGGAGTCACCATCCCTGCAGGTCCTCCTCC
GGAGAGGGTCAACCCAAGGTGACTTCCCATCCCTCCCTCCCCAA

*FIG. 28N-2*

```
                                                                    237
       Exon 7  (G)lyAsnAspTyrIleValProArgHisCysProGluLeuAla
6931          GCAATGACTACATTGTCCCTCGGCACTGCCCGGAGCTGGCG
              CCCTTCCAG
              alaLeuProPheGlnGluLeuGlnIleAspAspAsnGluTyrAlaTyrLeuL
7021          TGCTGCCCTTCCAGGAGCTGCAGATCGATGACAATGAGTATGCCTACCTCA
                                        T(Q268X)         C
7111   CCTAAGCCATCCCCTGACTCTCTCTCCAGAACGTCTGCCAGACTTCTCCT
                                                        ←—— E7R
7201   TAACGACAGCCAGGAGGCCGTTTTCATTTAACAGATGAGGCAAGTCAA
7291   CTGTAATCCCCATCACTTTGGGAGGCTGAGGCGGGCGGATCACCTGAGGTC
```

FIG. 280-1

```
GluMetSerArgValSerIleArgIleLeuAspGluLeuV
GAGATGAGCCGGGTGTCCATACGCATCCTTGACGAGCTGG ysAlaIleIlePhePhePheAspProA(sp)289
AAGCCATCATCTTCTTCTTTGACCCCAG GTACAGTGCACACCT

ATTGGGTTCTGTACACTGAGTTCACAGCCCTCATCTCATGT

GATTTGAAGAGACAATATGGCCCGGGGCGCAGTGGCTCACAC

AGGGGTCAAGATGAGCCTGGCTAACATGGAGAAACCCCAT
```

FIG. 280-2

```
7381  CTCTACTTAAAA::::::1.5 kb ::::::GT
7471  CTGGGTTTCCCCGTGTGTAAGATGAGGCGGTTGC
7561  CTTCTGGTTTAGTGCTTTAGGAAATGTGGCAGAA
7651  TGAGGTCCCCTGAATCCTTGTGCCCACACTGCTGA
7741  CCAGCTGGACCCTGCCTGCTGCCCCTCCCTTGCCCACCC
```

FIG. 28P-1

```
GGCTCTGCCAACAACTGGTGTGCCGACCCAGGACAAGTCCTATCTTTGCACTGTGT
TAGGTGCTTATTGGATGCATTCCCTCAAGTCCCGCCCTCCATTCCTATTCCCCTCT
ATCTTTTCTGCCCTGTGTCTAGGAAATCATAATTCATGGCCGTACCCTGGTTGT
                                    E8F
AGACTCCTTGTGTGACACAAGTCAGGGGACATCTGGTCTTGACTCCCAGATGCT
Exon 8  ²⁸⁹(A)  spAlaLysGlyLeuSerAspProGlyLysIleLysArgLeuAr
        ATGCCAAGGGGCTGAGCCTGATCCAGGGAAGATCAAGGCGG
TCTTCCATTGTAG
```

FIG. 28P-2

```
        gSerGlnValGlnValSerLeuGluAspTyrIleAsnAspArgGln
7831    TTCCCAGGTGCAGGTGAGCTTGGAGGACTACATCAACGACCGCCAG oThrLeuGluSerIleThrTrpGlnMetIleGluGlnIleGlnPhe
7921    CACCTTGCAGAGCATCACCTGGCAGATGATCGAGCAGATCCAGTTC uMetLeuLeuGlyG(ly)³⁶⁸
8011    GATGCTGCTGGGAG  GTCCGTGCCAAGCCCAGGAGGGGGGGTTG
                        G  P  C  Q  A  Q  E  G  R  G  W

8101    CCTCAGCTCCTTGGCTTCCCCACTGTGCCGCTTTGGGCAAGTTGCT
         L  S  S  L  A  S  P  L  C  R  F  G  Q  V  A
```

FIG. 28Q-1

TyrAspSerArgGlyArgPheGlyGluLeuLeuLeuLeuPr
TATGACTCGCGTGGCCGCTTTGGAGAGCTGCTGCTGCTGCC

IleLysLeuPheGlyMetAlaAlaLysIleAspAsnLeuLeuGlnGl
ATCAAGCTCTTCGGCATGGCCAAGATTGACAACCTGTTGCAGGA

GAGTGGGGACTCCCCAGGAGACAGGCCTCACACAGTGAGCTCACC
 S  G  D  S  P  G  D  R  P  H  T  V  S  S  P

TAACCTGTCTGTGCCTCAGTTTCCTCACCAGAAAAATGGGAACA

FIG. 28Q-2

```
8191  AGGCAATGGTCTATTTGTTCAGGCACCGAGAACCTAGCACGTGCCAGTC
                                         ⟵ E8R
8281  TGCCCTCGGGGAGGCTGTGTGTGTGAGTATGTGATGCGTGGATA
8371  CCTCACATTTATGATTTGAAATAAACAGGTAATATGA::::: 4.4
8461  GGCTGCAGCAGAGATGTGGGGATGAGGCTGAAAGGTGAGGCGGGACCA
8551  TTGATTACATCCATTATGTTACTATGTGACCAATACATTACTCATTAGA
```

FIG. 28R-1

```
ACTGTTCTAAGTGCTGGCAATTCAGCAAAGAACAAGATCTT
TCTGTGTATATGCCCGTATGTGCCATGTGTATATAAAG
kb ::::::GGGACACATAGATGCTATAAGTAGGTCAGTT
AATGGTTGAAGGACTTGCACTCCAAGGAGCTTTGAGAGCCA
ACATTTACGTGATCTCAGAGCTTCCTTATATGCCACCTTGTT
```

FIG. 28R-2

```
8641  CCTTTCAACTCACTTTTGTTCTCTTGGTTTTTGGGT
8731  CTAACCCAGGAATAGGTACCCAACACAGGCACTGCCAATA
8821  TGAGGTCTGCATCCCCAGACTCTCCATCCTGATCGACCT
               isProHisLeuMetGlnGluHisMetGlyThrAsnVal
8911  ACCCTCACCTGCATGCAGGAACATATGGGAACCAACGTC
               rpProProArgGlyGlnAlaA(1a) 419
9001  GGCCCCGACCCAGGGGACAGGCAG GTGGGCAAACTCT
```

FIG. 28S-1

CCTCTTAACACCCTCTCATGAAGTCTATAGATGGGAATGGTACACCCTAGTTTA

E9F→
TTGGATGGGCTGGTTGATTGGCCACGCCCTGAGGAAGATGGCGTCCCAAGGCC

Exon 9    368  (G)lySerProSerAspAlaProHisAlaHisHisProLeuH
TCTCTACCTGCAG  GGTCCCCCAGCCACCCATGCCCCACCACCCCCTGC IleValAlaAsnThrMetProThrHisLeuSerAsnGlyGlnMetCysGluT
ATCGTTGCCAACATGCCAACACAATGCCCACTCACCTCAGCAACGACAGATGTGTGAGT

GGGATTTTACCTTGCAAAGGGTGAGGATGGGGCTTAAGACAGGAGGCAGGAGA

*FIG. 28S-2*

```
9091  AAGTGGAGTCTAGAAGGTAGAACCAGGATGCAACAGTTTTC
                      ←——— E9R
9181  TGTTTATTCAGTAAGGTGACTGACAGCCTTTACTGAATGAA
9271  AAGATGTCTTGGGTGAGAATTCCATTAGTTGACATTGTCCA
9361  TCCATTAGACATTAGAGATGAGACTACCCATTGGGTCAGGATG
9451  AAGTCTGCATATCAAATAAATGATGGAGGAGATGGGTGGTA
```

FIG. 28T-1

TGGGTTCCAGGGTAGGGAATAAAGGGCAAGATTGTCCATTTGTTGAGGC

GCCATTGTGGGATGAGGCAATCCACTGGATGAGGTAACCCATTGGGTG

TTAAGTAAAAGTGGTCATTGAAGTAAGGCTGCACAGTTGGGTAAGGCTA

TCTGCTGGGCTA::::::1.4 kb ::::::TTTGGGAGAAGCAGTCC

GGACCTTCCAGACCTCATAAAACTTAGGCTTTATGATCTGGGACTCACA

FIG. 28T-2

9541 GAAGGTTGAGCAATAAAAAGACCCTTAGGGATTATCTGGCTTAATTAATTCTC

E10F ———▶
9631 GGTGGGAGGGGAGAACTTTCCCCGGGCTCTTCATTTACTCCCACAAAGGCT 419 (A) laThrProGluThrProGlnProSerProProGlyGlySerGlySer
9721 AG  CCACCCCTGAGACCCTGAGACCCCACAGCCCTCACCGCCAGGTGGCTCAGGGTCT lLysProLeuSerAlaIleProGlnProThrIleThrLysGlnGluVal
9811 CAAGCCCCTCTCTGCCATCCCCAGCCGACCATCACCAAGCAGGAAGTT

*FIG. 28U-1*

```
TCATTTTATAGAGGAAGAAATTAAGTCAAGGTGGGGCAG

Exon 10
GGAATTTTGAGCCAGCCCCCTGTCTGTCTGTTTGTCCTTCC

GluProTyrLysLeuLeuProGlyAlaValAlaThrIleVa
GAGCCCTATAAGCTCCTGCCCGGGAGCCGTCGCCACAATCGT

IleOP⁴⁶⁵
ATCTAGCAAGCCGGCTTGGGGCTCCACTGGCTCCC
```

FIG. 28U-2

9901 CCCAGCCCCCCTAAGAGAGCACCTGGTGATCACGTGGTCACGGC
                                    ⎯⎯⎯→ E10R
9991 GATGAAGGGCCCGAGAACATGGCCTAAGGCACATCCCACTGCA
10081 CTACTGCCTTGGACAACTTTCTCATGTTGAAGCCACTGCCTTC
10171 AGCCGCCTGGAGATGACTTGAGCCCTTAC

FIG. 28V-1

AAAGGAAGACGTGATGCCAGGACCCAGTCCCAGAGCAGGAATGGGAAG

CCCTGAGCGCCCTGCTCTGATAACAAGACTTTGACTTGGGGAGACCT

ACCTTCACCTTCATCCATGTCCAACCCCGACTTCATCCCAAAGGAC

FIG. 28V-2

MUTATIONS IN THE DIABETES SUSCEPTIBILITY GENES HEPATOCYTE NUCLEAR FACTOR (HNF) 1 ALPHA (α), HNF1β AND HNF4α

The present application is a continuation-in-part of now abandoned U.S. patent application Ser. No. 60/029,679 filed Oct. 30, 1996, which was a continuation-in-part of U.S. patent application Ser. No. 60/028,056 filed Oct. 2, 1996, which was a continuation-in-part of U.S. patent application Ser. No. 60/025,719 filed Sep. 10, 1996. The entire text of each of the above-referenced disclosures is specifically incorporated by reference herein without disclaimer.

The government owns rights in the present invention pursuant to grant number DK-20595 and DK-44840 from the National Institutes of Health.

BACKGROUND OF THE INVENTION

1. Field of the Invention

The present invention relates generally to the fields diabetes. More particularly, it concerns the identification of genes responsible for diabetes for use in diagnostics and therapeutics.

2. Description of Related Art

Diabetes is a major cause of health difficulties in the United States. Non-insulin-dependent diabetes mellitus (NIDDM also referred to as Type 2 diabetes) is a major public health disorder of glucose homeostasis affecting about 5% of the general population in the United States. The causes of the fasting hyperglycemia and/or glucose intolerance associated with this form of diabetes are not well understood.

Clinically, NIDDM is a heterogeneous disorder characterized by chronic hyperglycemia leading to progressive micro- and macrovascular lesions in the cardiovascular, renal and visual systems as well as diabetic neuropathy. For these reasons, the disease may be associated with early morbidity and mortality.

Subtypes of the NIDDM can be identified based at least to some degree on the time of onset of the symptoms. The principal type of NIDDM has on-set in mid-life or later. Early-onset NIDDM or maturity-onset diabetes of the young (MODY) shares many features with the more common form(s) of NIDDM whose onset occurs in mid-life. Maturity-onset diabetes of the young (MODY) is a form of non-insulin dependent (Type 2) diabetes mellitus (NIDDM) that is characterized by an early age at onset, usually before 25 years of age, and an autosomal dominant mode of inheritance (Fajans 1989). Except for these features, the clinical characteristics of patients with MODY are similar to those with the more common late-onset form(s) of NIDDM.

Although most forms of NIDDM do not exhibit simple Mendelian inheritance, the contribution of heredity to the development of NIDDM has been recognized for many years (Cammidge 1928) and the high degree of concordance of NIDDM in monozygotic twin pairs (Barnett et al. 1981) indicates that genetic factors play an important role in its development.

MODY is characterized by its early age of onset which is during childhood, adolescence or young adulthood and usually before the age of 25 years. It has a clear mode of inheritance being autosomal dominant. Further characteristics include high penetrance (of the symptomology), and availability of multigenerational pedigrees for genetic studies of NIDDM. MODY occurs worldwide and has been found to be a phenotypically and genetically heterogeneous disorder.

A number of genetically distinct forms of MODY have been identified. Genetic studies have shown tight linkage between MODY and DNA markers on chromosome 20, this being the location of the MODY1 gene (Bell et al., 1991; Cox et al., 1992). MODY2 is associated with mutations in the glucokinase gene (GCK) located on chromosome 7 (Froguel et al. 1992 and 1993). Recent linkage studies have shown the existence of a further form of MODY which has been termed MODY3 (Vaxillaire et al., 1995). MODY3 has been shown to be linked to chromosome 12 and is localized to a 5 cM region between markers D12S86 and D12S807/D12S820 of the chromosome (Menzel et al., 1995).

Although it is well established that MODY2 is associated with mutations in GCK there is still no information as to the identity of other MODY genes. There is a clear need to identify these genes and the mutations that result in diseased states. The identification of these genes and their products will facilitate a better understanding of the diseased states associated with mutations in these genes and has important implications in the diagnosis and therapy of MODY.

Since an understanding of the molecular basis of diabetes in general and MODY specifically may facilitate the development of new therapeutic strategies for the treatment of these disorders, studies are needed to identify diabetes-susceptibility genes associated with MODY. Moreover, methods of detecting individuals with a propensity to develop such diseases are needed. Where possible, the molecular mechanism underpinning the genetic lesion should be determined in order to allow diagnosis and specifically-directed therapy.

SUMMARY OF THE INVENTION

The present invention relates to the inventors discovery that the MODY3 locus is the HNF1α gene, the MODY1 locus is the HNF4α gene and the MODY4 locus is the HNF1β gene. The invention further relates to the discovery that analysis of mutations in the HNF1α, HNF1β and HNF4α genes can be diagnostic for diabetes. The invention also contemplates methods of treating diabetes in view of the fact that mutations in HNF1α, HNF1,β and HNF4α can cause diabetes.

In one embodiment, the invention contemplates methods for screening for diabetes mellitus. These methods comprise: obtaining sample nucleic acid from an animal; and analyzing the nucleic acids to detect a mutation in an HNF-encoding nucleic acid segment; wherein a mutation in the HNF-encoding nucleic acid segment is indicative of a propensity for non-insulin dependent diabetes.

In certain embodiments the HNF-encoding nucleic acid is an HNF1α-encoding nucleic acid. In view of the inventor's discovery that the MODY3 locus is HNF1α, a mutation in the HNF1α-encoding nucleic acid is indicative of a propensity for diabetes. In some presently preferred embodiments, the HNF1α-encoding nucleic acid is located on human chromosome 12q, which is the location site of the MODY3 locus. In other embodiments, the HNF-encoding nucleic acid is an HNF4α-encoding nucleic acid. In view of the inventor's discovery that the MODY1 locus is HNF4α, a mutation in the HNF4α-encoding nucleic acid is indicative of a propensity for diabetes. In some presently preferred embodiments, the HNF4α-encoding nucleic acid is located on human chromosome 20, which is the location of the MODY1 locus.

It is important to note that the terms NIDDM, MODY, MODY1, MODY3, and MODY4 are used to designate diabetes disease states, and the use of a particular such name may not always represent the same causation of that disease state. The inventors have discovered that mutations in HNF4α can lead to a MODY1 disease state; however, not all mutations in HNF4α that lead to diabetes might cause a "MODY1" disease state. Conversely, not all diabetes disease states brought about by a mutation in HNF4α might be considered a MODY1 disease state. Therefore, Applicants prefer to use, in some cases, "HNF4α-diabetes" to note any diabetic disease state brought on by a mutation or malfunction of HNF4α, even those that do not exhibit all, or any, MODY1 disease states. Likewise, Applicants may use "HNF1α-diabetes" and "HNF1β-diabetes" rather than "MODY3" and "MODY4", respectively.

The nucleic acid to be analyzed can be either RNA or DNA. The nucleic acid can be analyzed in a whole tissue mount, a homogenate, or, preferably, isolated from tissue to be analyzed. In some preferred embodiments, the step of analyzing the HNF-encoding nucleic acid comprises sequencing of the HNF-encoding nucleic acid to obtain a sequence, the sequence may then be compared to a native nucleic acid sequence of HNF to determine a mutation. Such a native nucleic acid sequence of HNF1α may have the sequence set forth in SEQ ID NO: 1. Such a native nucleic acid sequence of HNF4α has a sequence set forth in SEQ ID NO:78.

The method allows for the diagnosis of almost any mutation, including, for example, point mutations, translocation mutations, deletion mutations, and insertion mutations. The method of analysis may comprise PCR, an RNase protection assay, an RFLP procedure, etc. Using this method, the inventors have diagnosed a variety of HNF1α mutations, including those set forth in Table 8. In preferred embodiments mutations occur at codons 17, 7, 27, 55/56, 98, 131, 122, 142, 129, 131, 159, 171, 229, 241, 272, 288, 289, 291, 292, 273, 379, 401, 443, 447, 459, 487, 515, 519, 547, 548 or 620 of an HNF1α-encoding nucleic acid, for example, having the sequence of SEQ ID NO:1. In other preferred embodiments a mutation occurs at the splice acceptor region of intron 5 and exon 6 of an HNF1α-encoding nucleic acid. In other embodiments a mutation occurs at the splice acceptor region of intron 9 of an HNF1α-encoding nucleic acid. In other embodiments, the mutation occurs independently, in intron 1, intron 2, intron 5, intron 7 or intron 9 of the HNF1α gene. The inventors have also found a variety of HNF4α mutations, including those found in Table 10. In some preferred embodiments, the HNF-encoding nucleic acid is an HNF4α-encoding nucleic acid and a mutation occurs in exon 7 of the HNF4α-encoding nucleic acid. In other preferred embodiments, a mutation occurs at codon 268, 127, 130 or 154 of an HNF4α-encoding nucleic acid having the sequence of SEQ ID NO:78.

The invention also contemplates methods of treating diabetes in an animal comprising: diagnosing an animal that has diabetes and modulating HNF function in the animal.

The step of diagnosing an animal with diabetes frequently comprises analysis of an HNF1α-encoding nucleic acid sequence or an HNF4α-encoding nucleic acid sequence for a mutation.

The step of modulating HNF function may comprise providing an HNF1α or HNF4α polypeptide to the animal. In cases where normal HNF1α or HNF4α function is sought to be revived, the HNF1α or HNF4α polypeptide may be a native HNF1α or HNF4α polypeptide. For example, a native HNF1α polypeptide may have the sequence of SEQ ID NO: 2. A native HNF4α polypeptide may have the sequence of SEQ ID NO: 79. The provision of an HNF1α or HNF4α polypeptide is accomplished by any of a number of ways. For example, expression of an HNF1α or HNF4α polypeptide may be induced, with the expression being of an HNF1α or HNF4α polypeptide encoded in the animal's genome or of an HNF1α or HNF4α polypeptide encoded by a nucleic acid provided to the animal. The provision of an HNF1α or HNF4α polypeptide may be accomplished by a method comprising introduction of an HNF1α or HNF4α-encoding nucleic acid to the animal, for example, by injecting the HNF1α or HNF4α-encoding nucleic acid into the animal.

Modulating HNF function in the animal can comprise providing a modulator of HNF1α or HNF4α function to the animal. Such modulators are in the nature of drugs and can be, for example HNF4, HNF6, HNF3 or any other peptide or molecule that regulates HNF1α. These modulators may be formulated into a pharmaceutical compound for delivery to the animal. The modulator of HNF1α, HNF1β or HNF4α function may be an agonist or antagonist of HNF1α, HNF1β or HNF4α. The modulator may modulate transcription of an HNF1α, HNF1β or HNF4α-encoding nucleic acid, translation of an HNF1α, HNF1β, or HNF4α-encoding nucleic acid, or the functioning of the HNF1α, HNF1β or HNF4α polypeptide.

The invention also contemplates methods of screening for modulators of HNF function comprising: obtaining an HNF polypeptide, for example an HNF1α, HNF1β or HNF4α polypeptide; determining a standard activity of the HNF; contacting the polypeptide with a putative modulator; and assaying for a change in the standard activity of the polypeptide. In some preferred methods, the standard activity profile of a HNF1α polypeptide is determined by measuring the binding of the HNF1α polypeptide to a nucleic acid segment comprising the sequence of SEQ ID NO: 9. To facilitate measuring the HNF1α activity, the nucleic acid segment comprising the sequence of SEQ ID NO: 9 or the HNF1α polypeptide may comprise a detectable label. In some preferred methods, the standard activity profile of a HNF4α polypeptide is determined by measuring the binding of the HNF4α polypeptide to a nucleic acid segment comprising the sequence of SEQ ID NO: 85. To facilitate measuring the HNF4α activity, the nucleic acid segment comprising the sequence of SEQ ID NO: 85 or the HNF4α polypeptide may comprise a detectable label. In other embodiments, the standard activity profile of an HNF polypeptide is determined by determining the ability of an HNF1α polypeptide to stimulate transcription of a reporter gene, the reporter gene operatively positioned under control of a nucleic acid segment comprising the sequence of SEQ ID NO: 1. In other embodiments, the standard activity profile of an HNF polypeptide is determined by determining the ability of an HNF4α polypeptide to stimulate transcription of a reporter gene, the reporter gene operatively positioned under control of a nucleic acid segment comprising the sequence of SEQ ID NO: 78. Similar assays are contemplated for HNF1β polypeptide.

The invention also contemplates methods of screening for modulators of HNF polypeptide function comprising: obtaining an HNF1α, HNF1β or HNF4α-encoding nucleic acid segment; determining a standard transcription and translation activity of the HNF1α, HNF1β or HNF4α-encoding nucleic acid sequence; contacting the HNF1α or HNF4α-encoding nucleic acid segment with a putative modulator; maintaining the nucleic acid segment and putative modulator under conditions that normally allow for HNF1α or HNF4α transcription and translation; and assaying for a change in the transcription and translation activity.

The inventors discovery allows for the preparation of a host of HNF modulators such as MODY3/HNF1α-modulators, MODY4/HNF1β-modulators and MODY1/HNF4α modulators. Such modulators themselves are within the scope of the invention. Such an HNF modulator may be prepared or preparable by a process comprising screening for modulators of HNF function comprising: obtaining an HNF polypeptide; determining a standard activity profile of the HNF polypeptide; contacting the HNF polypeptide with a putative modulator; and assaying for a change in the standard activity profile. An HNF modulator prepared by a process comprising screening for modulators of HNF function comprising: obtaining an HNF-encoding nucleic acid segment; determining a standard transcription and translation activity of the HNF-nucleic acid sequence; contacting the HNF-encoding nucleic acid segment with a putative modulator; maintaining the nucleic acid segment and putative modulator under conditions that normally allow for HNF transcription and translation; and assaying for a change in the transcription and translation activity.

Some aspects of the invention relate to isolated and purified polynucleotides encoding an HNF polypeptide. Such polynucleotides can be: an HNF1α-encoding nucleic acid sequence, or an HNF4α-encoding nucleic acid sequence. In some particular embodiments, the polynucleotide encodes an HNF1α having an amino acid sequence as set forth in SEQ ID NO: 127. In preferred embodiments, the polynucleotide may be an HNF1α-encoding nucleic acid sequence have a sequence of SEQ ID NO: 126. In additional particular embodiments, the polynucleotide encodes an HNF1β having an amino acid sequence as set forth in SEQ ID NO:139. In preferred embodiments, the polynucleotide may be an HNF1β-encoding nucleic acid sequence having a sequence of SEQ ID NO:128. The polynucleotide may encode an HNF4α having an amino acid sequence as set forth in SEQ ID NO: 140. In preferred embodiments, the polynucleotide may be an HNF4α-encoding nucleic acid sequence having a sequence of SEQ ID NO: 130.

Other embodiments comprise isolated and purified nucleic acid segments comprising 10, 14, 15, 25, 30, 35, 40, 45, 50, 55, 60, 70, 80, 90, 100, 125, 150, 175, 200, 250, 300, 350, 400, 450, or 500 contiguous nucleic acids identical to the sequence of SEQ ID NO: 128 or SEQ ID NO: 126 or the complement of these sequences. These nucleic acid segments can be used by those of skill in the art as hybridization probes, PCR primers, for the expression of HNF polypeptides, for the expression of other polypeptides, etc. In some embodiments, the segment encodes a full-length HNF polypeptide. Of particular interest are the promoters for HNF1α and HNF 1β, which are disclosed in SEQ ID NOS: 126 and 128 respectively and in FIGS. 26 and 27, respectively and discussed elsewhere in this application. These promoters may be used by those of skill in the art in many varying applications.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The individual ID is noted at the top right corner of each symbol and the HNF1α genotype, if determined, noted below: N, normal allele; M, mutant allele. The arrow indicates the individual from each pedigree who was screened for mutations. Note that some individuals have inherited the mutant allele but do not yet have NIDDM, usually because of their young age (e.g. P pedigree, individual IV-6; and Ber pedigree, individual V-2). Also, some individuals have NIDDM even though they did not inherit the mutant HNF1α allele segregating in that family (e.g. Ber pedigree, individual II-2). Such heterogeneity has been noted previously (Bell et al, 1991) and is a reflection of the high prevalence of NIDDM.

Figure 6:
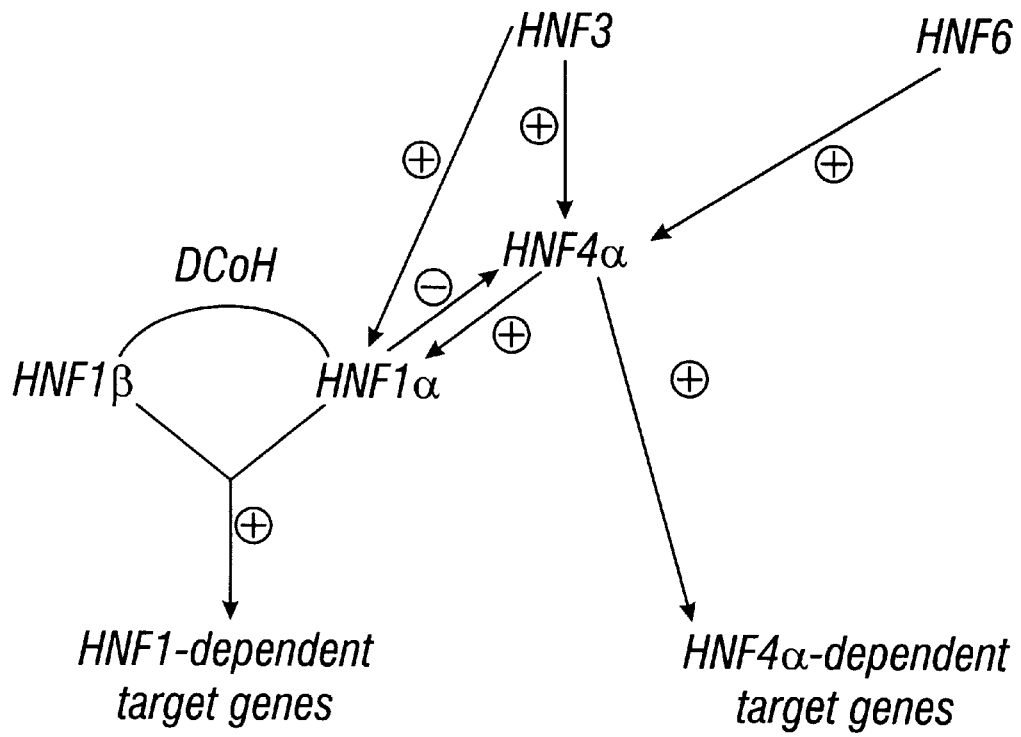

FIG. 6. The involvement of hepatocyte nuclear factors in diabetes.

Figures 2, 7B:
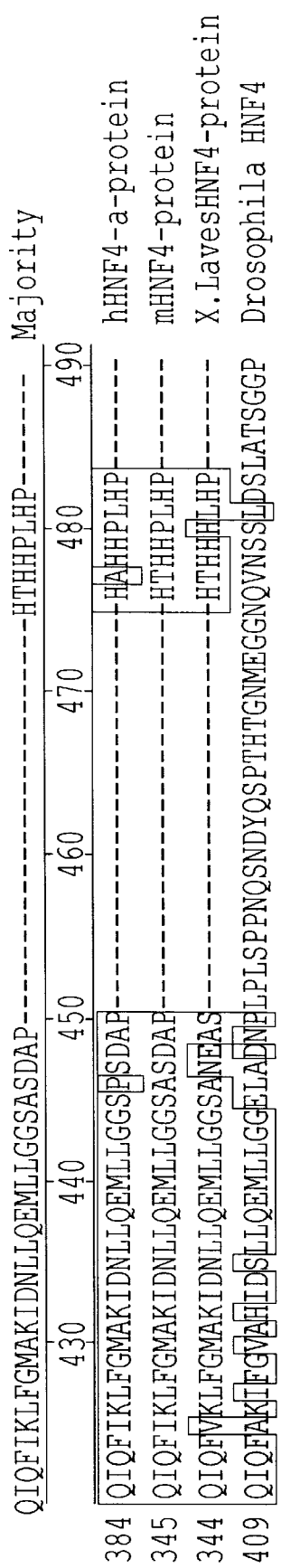
Figure 7C:
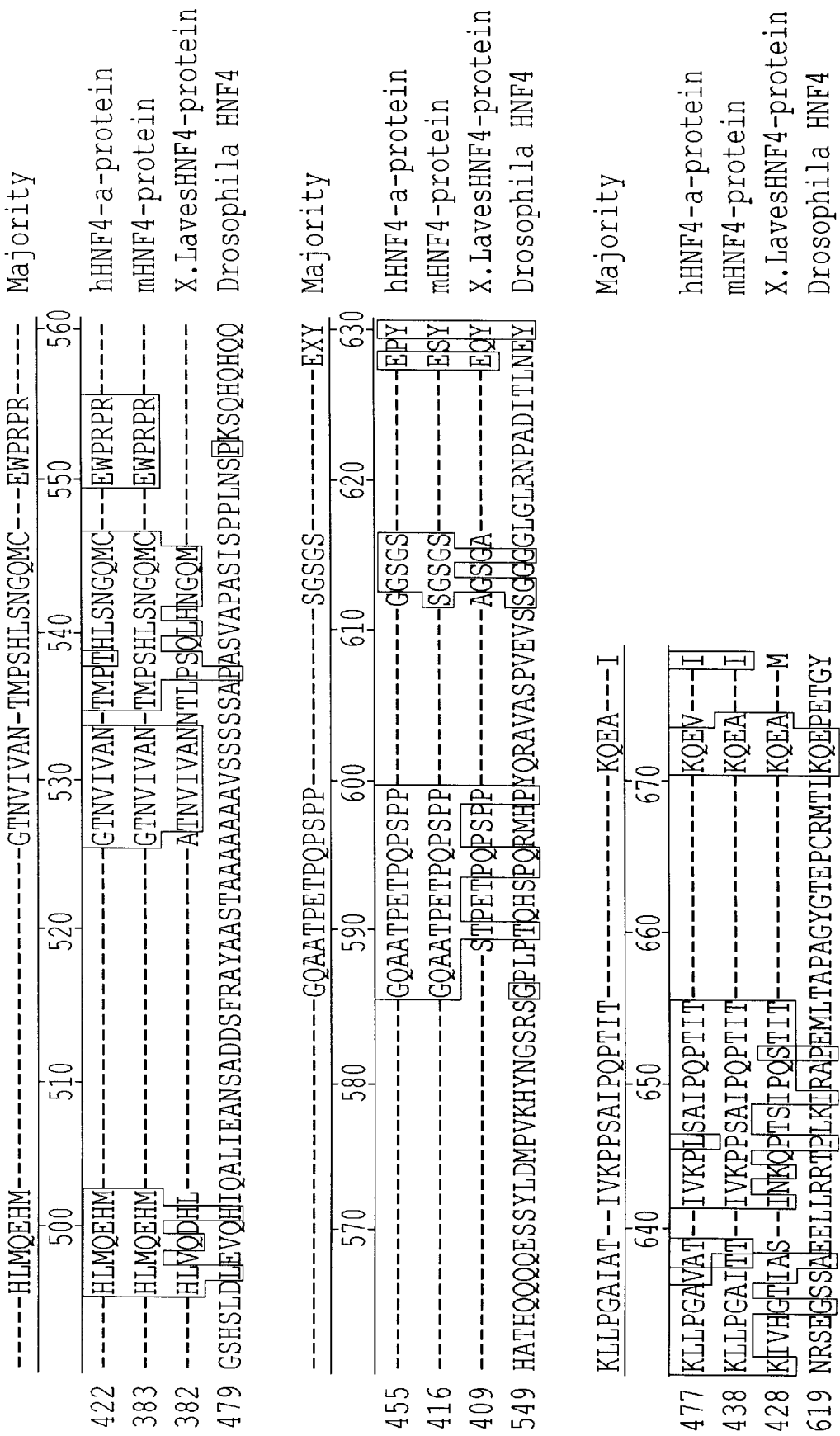

FIGS. 7A–7C show an alignment of the HNF4α protein sequence from humans (h) with sequences from human, mouse (m), Xenopus (x) and Drosophila (d) species. The putative DNA binding sites are underlined and the putative ligand binding sites are in bold.

FIGS. 8A–K. The DNA sequences for exon 1 (FIG. 8A), exon 1b (FIG. 8B), exon 2 (FIG. 8C), exon 3 (FIG. 8D), exon 4 (FIG. 8E), exon 5 (FIG. 8F), exon 6 (FIG. 8G), exon 7 (FIG. 8H), exon 8 (FIG. 8I), exon 9 (FIG. 8J), and exon 10 (FIG. 8K) of HNF4α.

Figure 9:
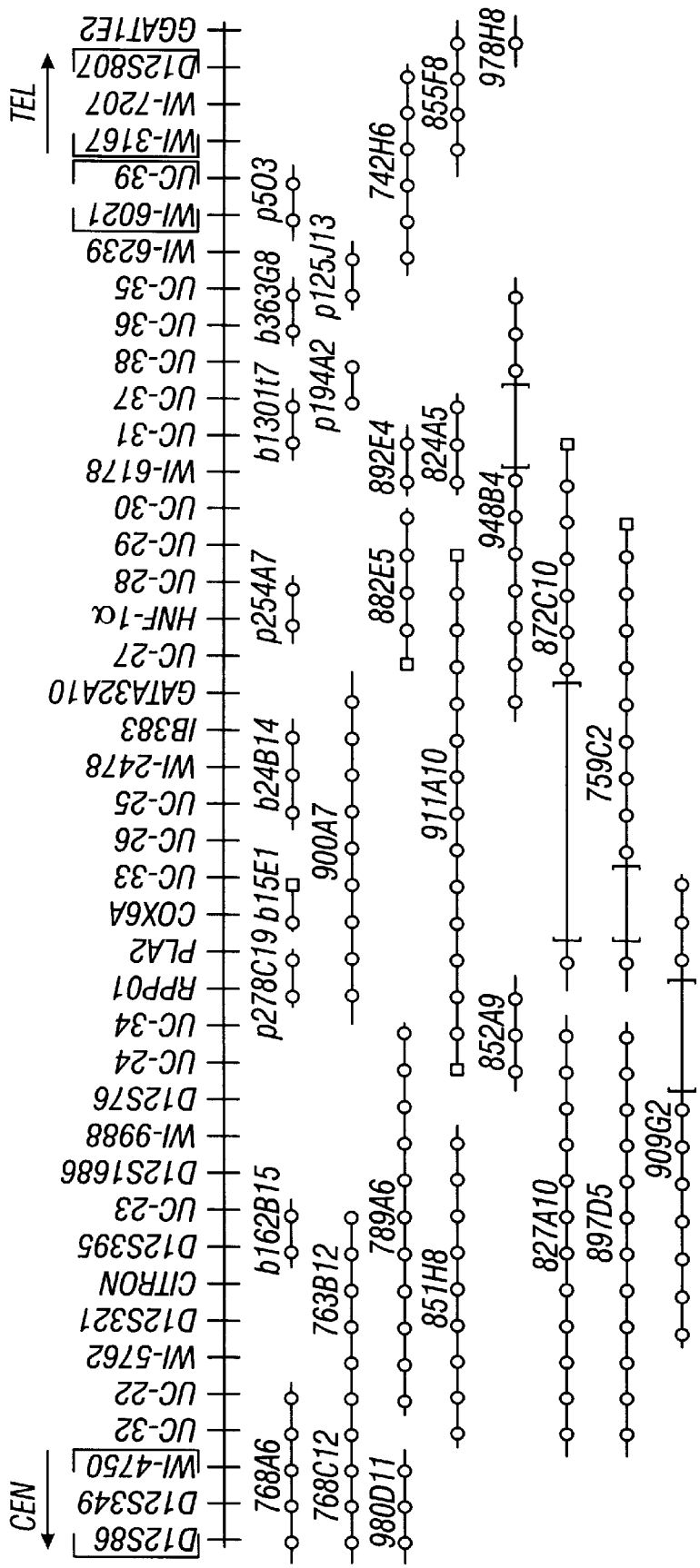

FIG. 9. Physical map of the MODY3 region of chromosome 12. YAC, BAC (b) and PAC (p) clones are represented as lines, the length of which reflects the number of included STSs and not the actual size. The physical distance between adjacent STSs has not been determined directly and STSs for which the order has not been unambiguous determined are indicated in brackets. A circle indicates that the clone was positive for the indicated STS and a square indicates a STS derived from the end of that specific clone. Several YACs contain large internal deletions which are noted by brackets. The STSs are from GDB™ and the GenBank STS databases.

Figure 10A:
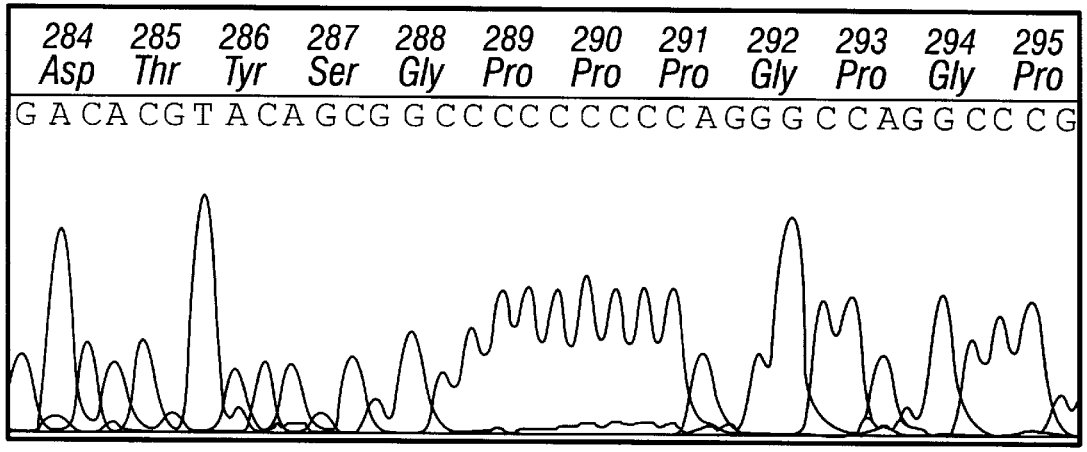
Figure 10B:
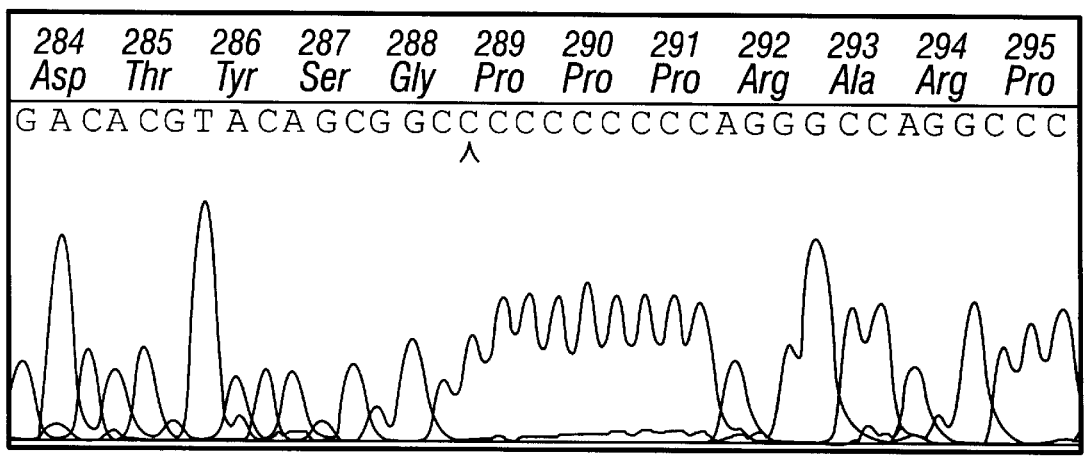

FIG. 10A and FIG. 10B. Partial sequence of exon 4 of the HNF-1α gene of individual EA1 (Edinburgh pedigree). The sequences of the normal (FIG. 10A) and mutant (FIG. 10B) alleles are shown. There is an insertion of a C in codon 291 (noted by the arrowhead) in the mutant allele resulting in a frameshift and premature termination.

FIG. 11A, FIG. 11B, FIG. 11C, FIG. 11D, FIG. 11E, FIG. 11F, and FIG. 11G. The cDNA sequence of HNF1α denoting position of the exons.

Figure 12:
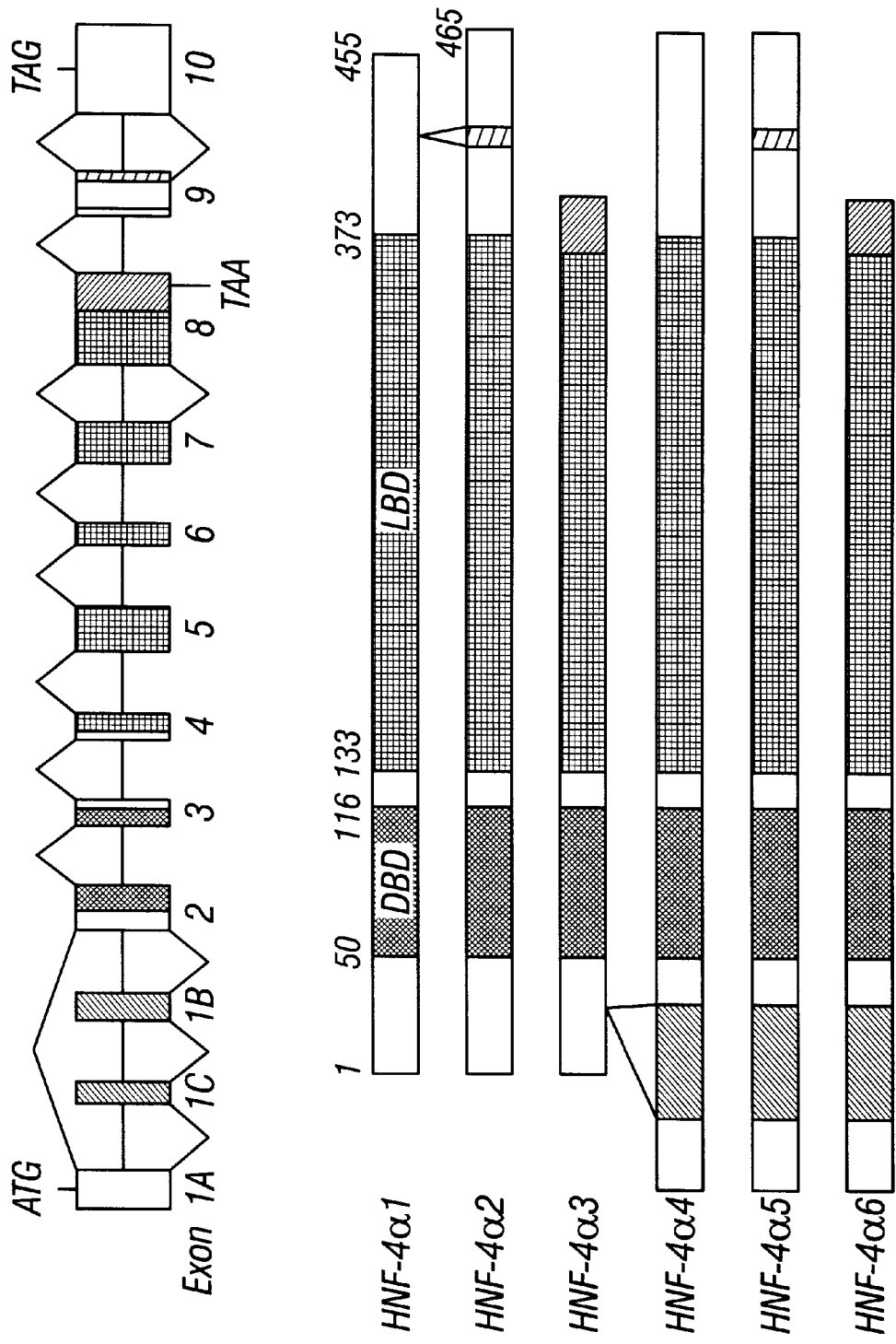

FIG. 12. Model of the human HNF-4α showing the different patterns of alternative splicing and structures of the different forms of HNF-4α that can be generated by alternative splicing. The amino acids that define the boundaries of some of the regions of the protein are shown. DBD and LBD co rrespond to the DNA and ligand-binding domains of HNF4α, respectively.

FIG. 13A, FIG. 13B, and FIG. 13C. FIGS. 13A–C show a comparison of the sequences of the promoter regions of the human and mouse HNF4 α genes (SEQ ID NO: 135 and SEQ ID NO: 137, respectively). Identical residues are shown in boxes. The binding sites for transcription factors that may regulate the expression of HNF-4α are overlined. The asterisk notes the predicted transcriptional start site based on the study of the mouse HNF-4α gene (Zhong et al., 1994). The minimal promoter region required for high-level expression of the mouse gene in hepatoma cells is shown by shading. The ATG codon which defines the start of translation is noted. The arrowhead s hows the DNA polymorphism found in the promoter region of the proband of family J2-96. The GenBank accession nos. for the mouse promoter sequence are S74519 and S77762.

Figure 14A:
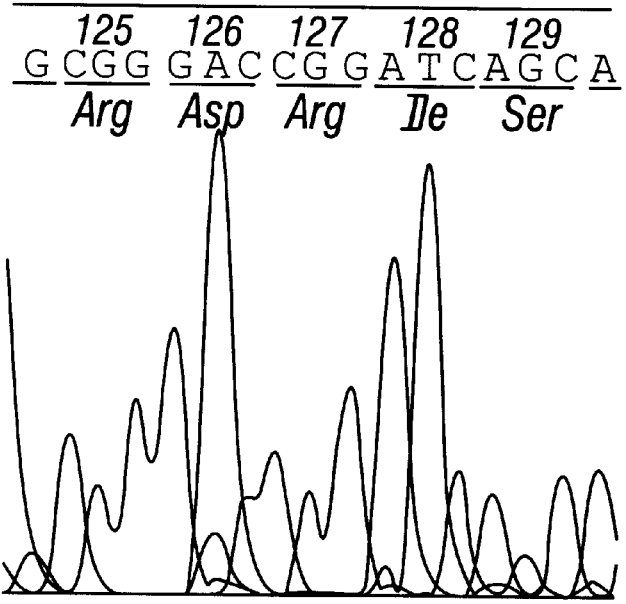
Figure 14B:
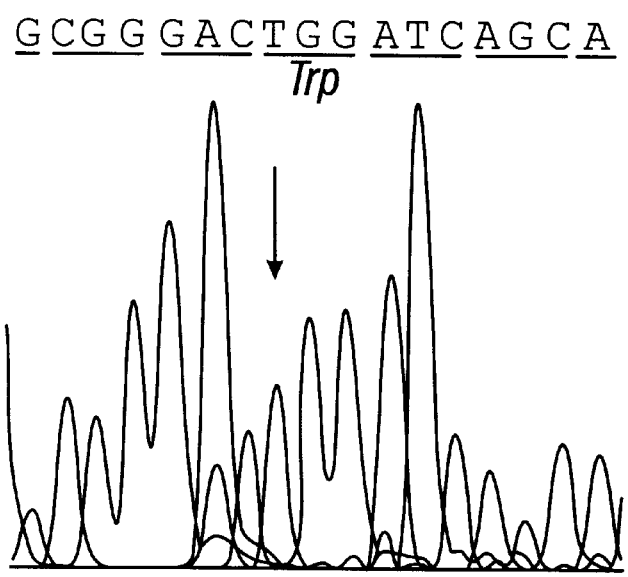

FIG. 14A and FIG. 14B. Partial sequence of exon 4 of HNF4α gene of patient J2-2 1. The sequences of the normal (FIG. 14A SEQ ID NO: 141 and corresponding amino acids SEQ ID NO: 142) and mutant (FIG. 14B; SEQ ID NO: 143) alleles are shown and the arrow indicates the C→T sub substitution at codon 127.

FIG. 15. Pedigrees of Japanese families with mutations/polymorphisms in the HNF-4α gene. Individuals with diabetes are noted by filled symbols and nondiabetic (or not tested) individuals are indicated by open symbols. The arrow indicates the proband. The clinical features of each subject are shown including age at diagnosis, present age and present treatment. The HNF4α genotype of tested individuals is noted: N-normal and M-mutation/polymorphism.

Figures 1, 16:
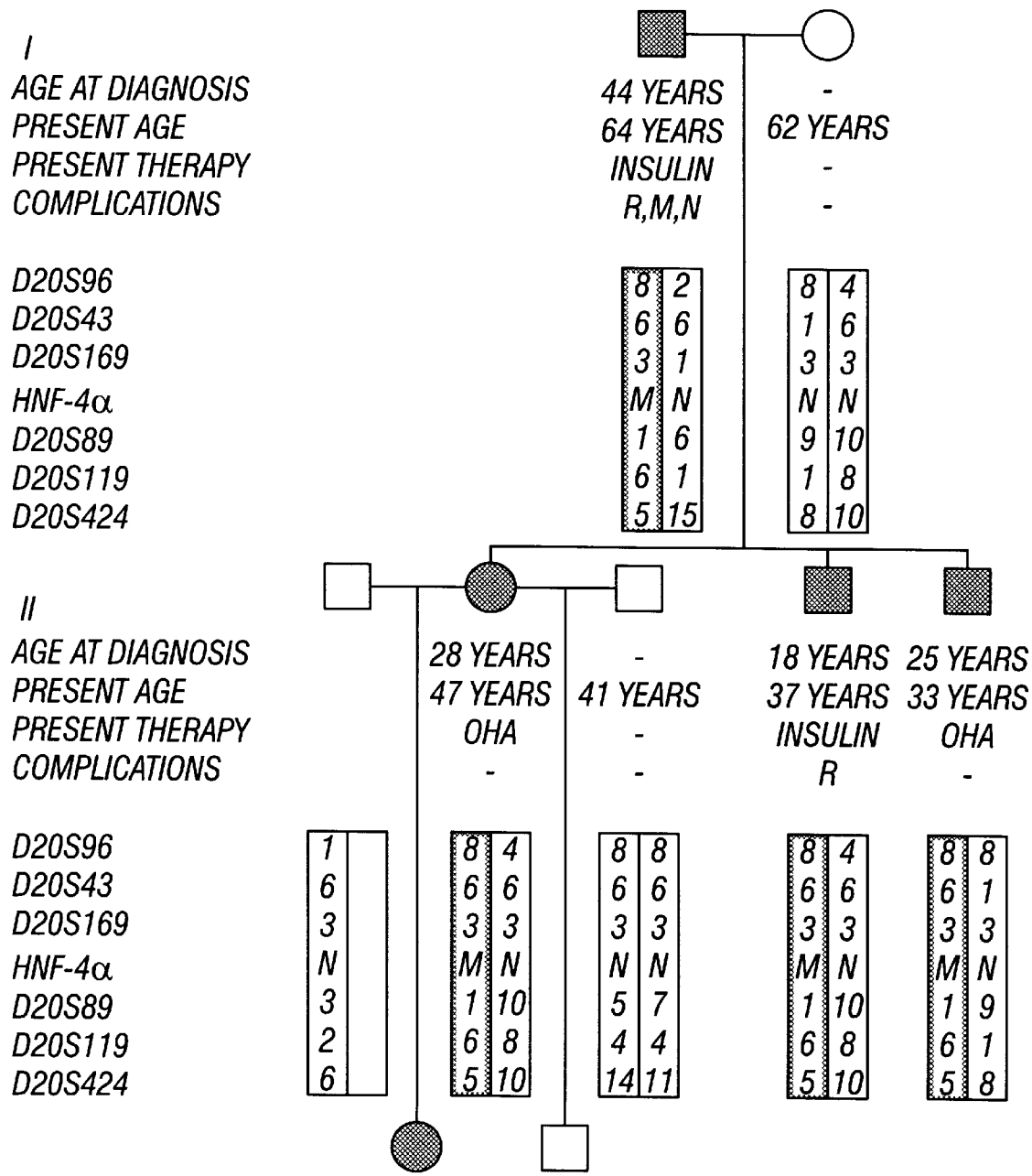

FIG. 16. Identification of a nonsense mutation in the HNF4α gene in a german family, the Dresden-a 11 pedigree. The members of this family with MODY and impaired glucose tolerance are indicated with black and shaded symbols, respectively. The age at diagnosis of diabetes mellitus, present age and therapy (OHA, oral hypoglycemic agents), and nature of complications (M, macrovascular disease; R, retinopathy; and N, peripheral polyneuropathy) are indicated. The haplotype associated with MODY in this family is shown.

Figures 2, 16, 17:
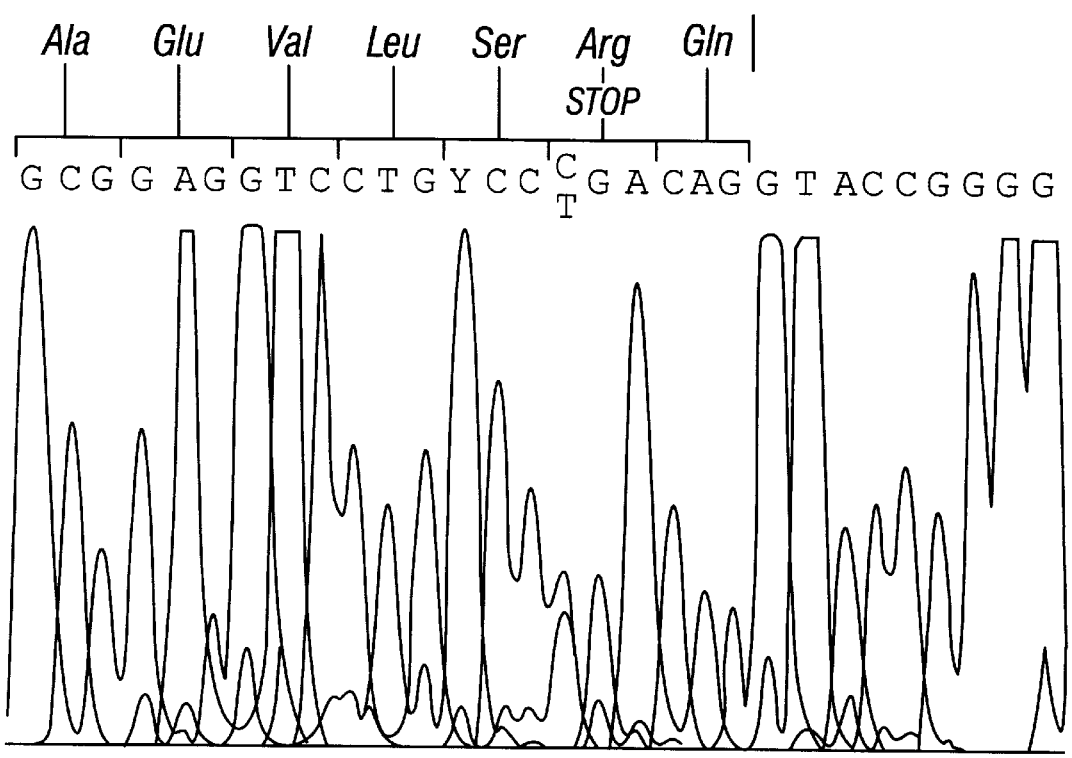
Figure 18A:
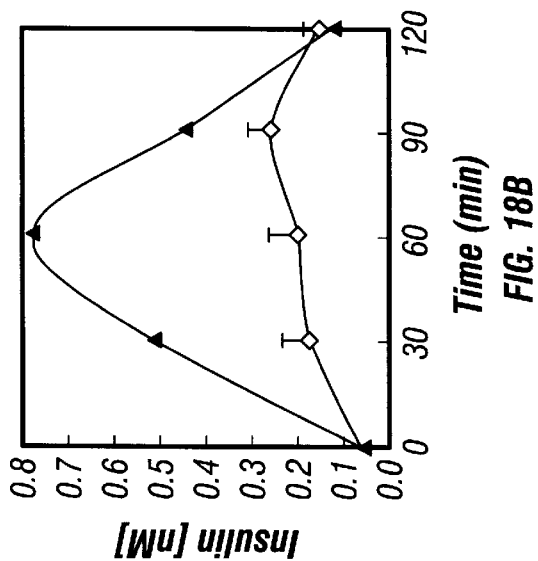
Figure 18B:
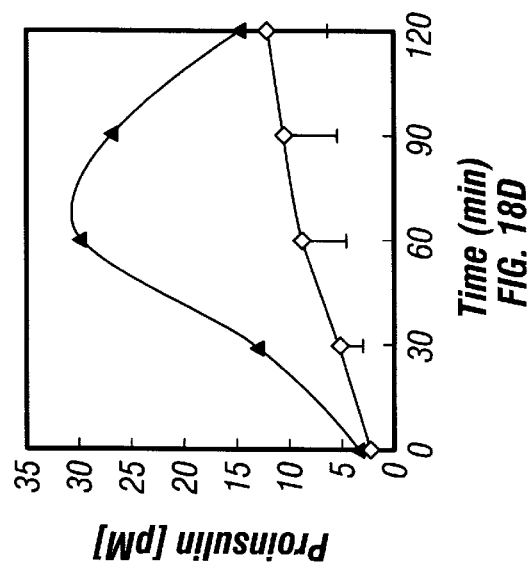
Figure 18C:
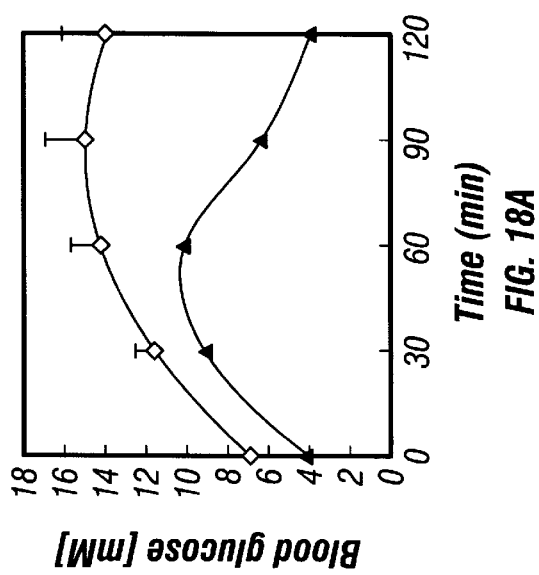
Figure 18D:
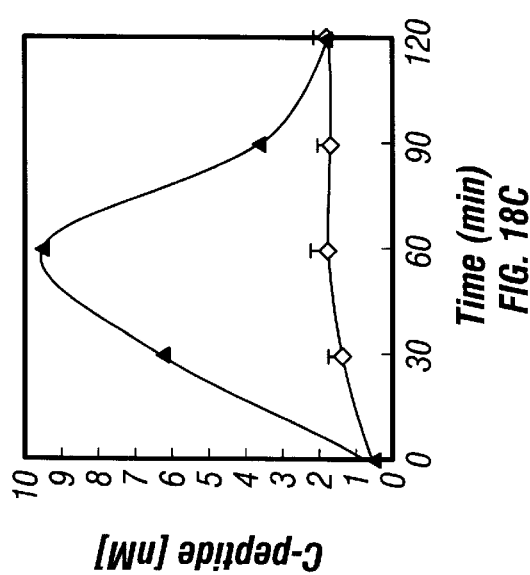
Figure 19A:
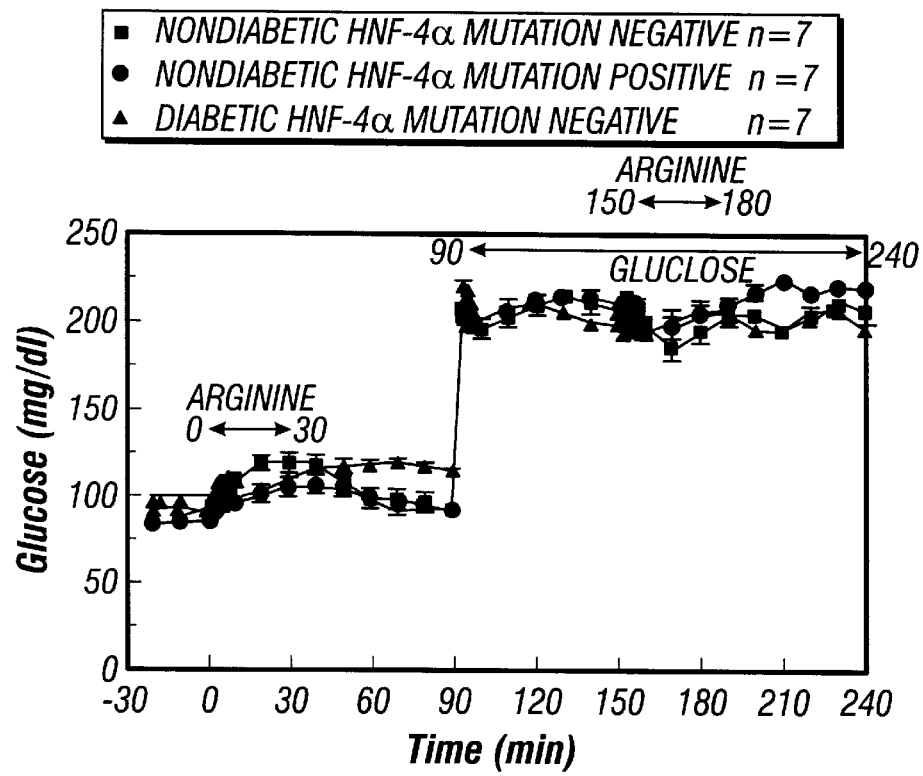
Figure 19B:
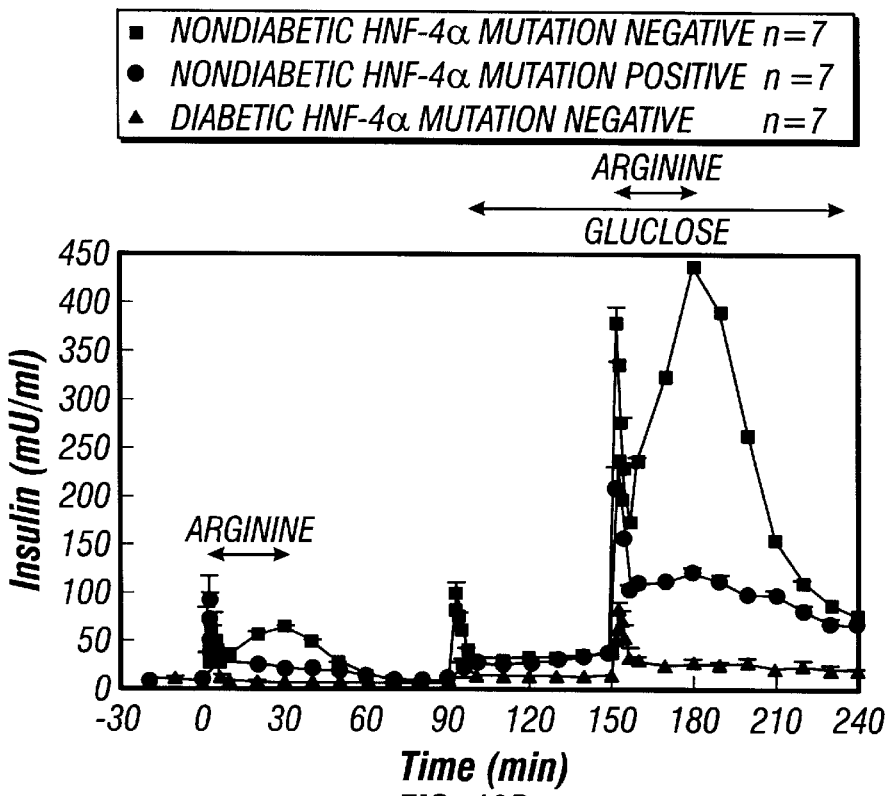
Figure 19C:
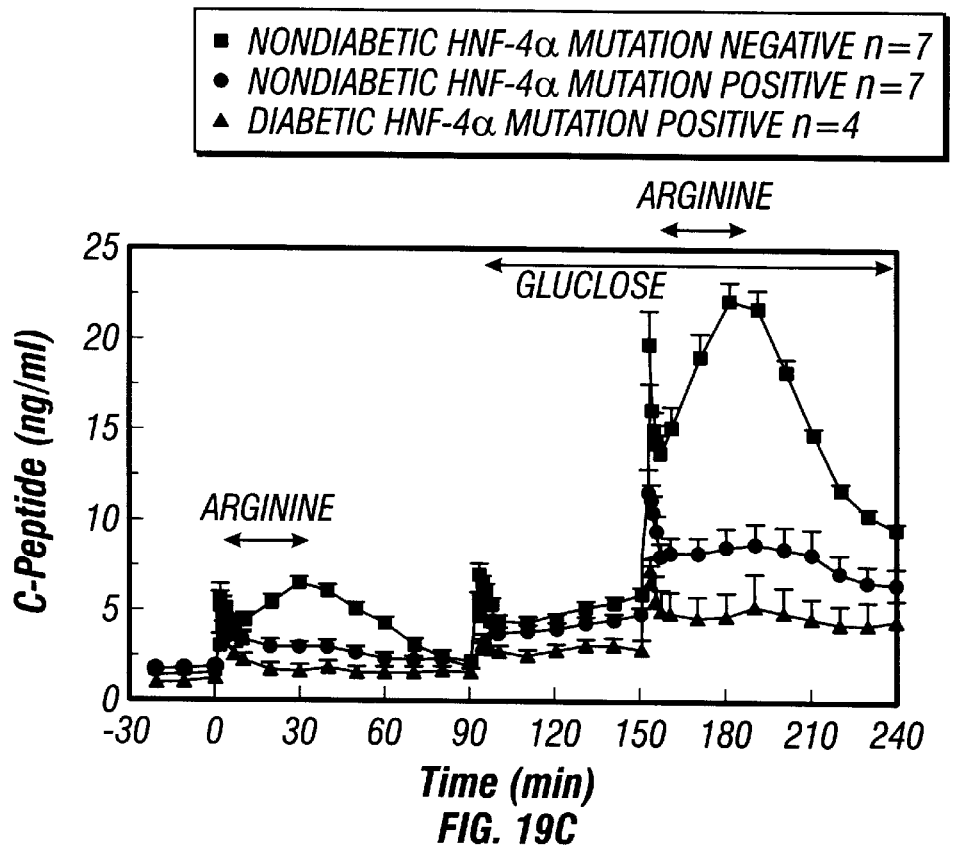
Figure 19D:
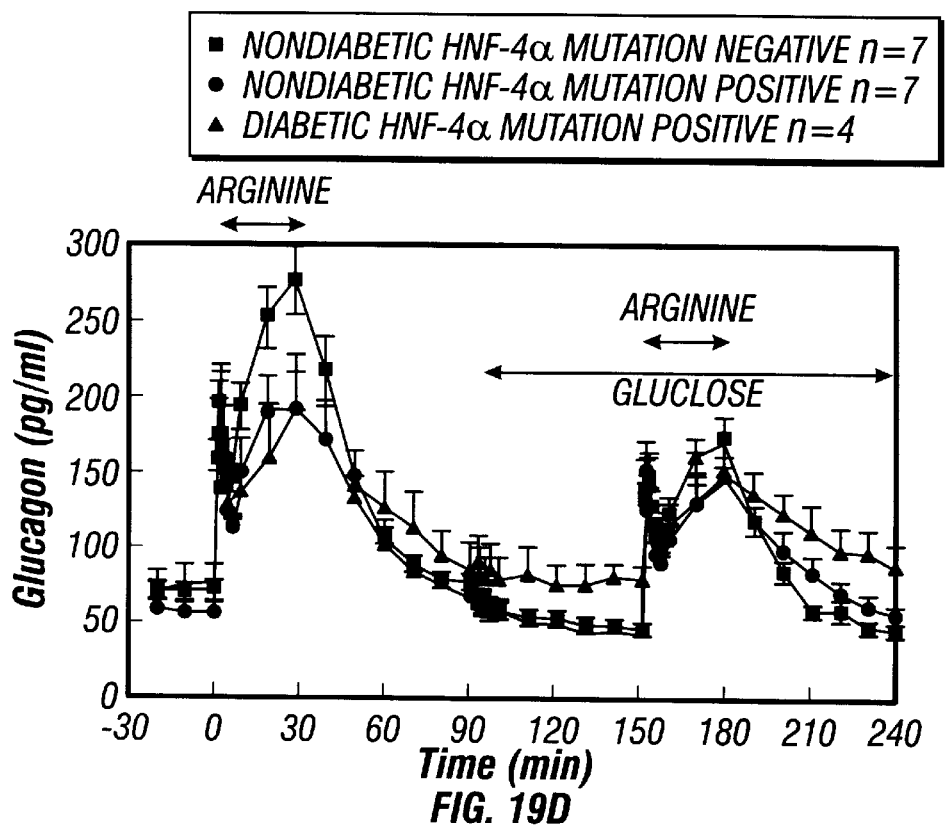

FIG. 17. Partial sequence of exon 4 of the HNF4α gene of subject II-4 of the Dresden-11 pedigree. The R154X mutation is indicated (SEQ ID NO: 144 and SEQ ID NO: 145). Intron 4 follows the Gln codon, CAG.

FIG. 18A, FIG. 18B, FIG. 18C and FIG. 18D. Oral glucose tolerance testing in the Dresden-11 family. The blood glucose (FIG. 18A), insulin (FIG. 18B), C-peptide (FIG. 18C) and proinsulin (FIG. 18D) levels during the course of the glucose tolerance test are shown. The open symbols are the means±SEM for subject s with the R154X mutation, including those with diabetes and impaired glucose tolerance, and the filled symbols are the means for the two normal subjects.

FIG. 19A, FIG. 19B, FIG. 19C and FIG. 19D. Effect of bolus and infusion of arginine, of glucose, and of arginine during hyperglycemic clamp on plasma concentration of glucose (FIG. 19A), insulin (FIG. 19B), C-peptide (FIG. 19C), and glucagon (FIG. 19D) in 3 groups of subjects of the RW pedigree.

Figure 20A:
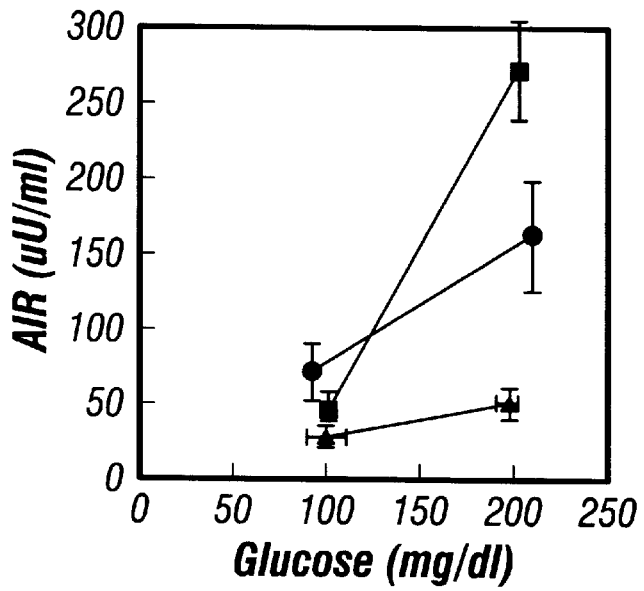
Figure 20B:
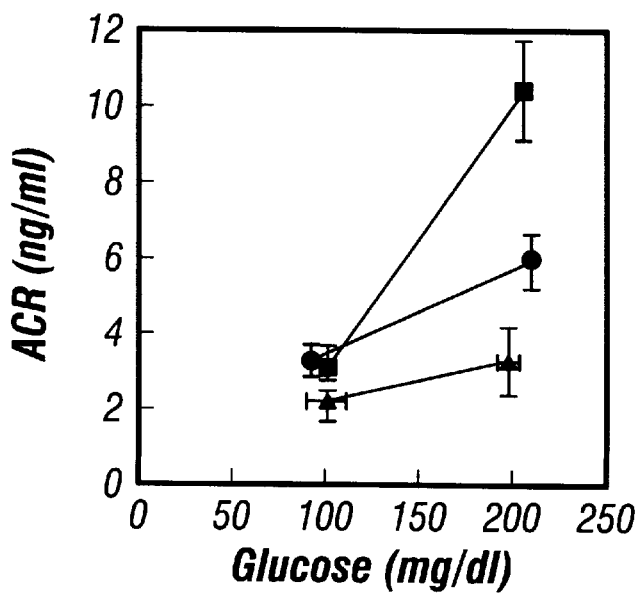

FIG. 20A and FIG. 20B. Acute insulin (FIG. 20A) and C-peptide (FIG. 20B) response to bolus administration of arginine in 3 groups of subjects of the RW pedigree at baseline and during the hyperglycemic clamp procedure. The slope of the line connecting these insulin responses (slope of potentiation) was lower in ND[+] vs. ND [−], $p<0.001$. The slope for [+] was lowest.

Figure 21:
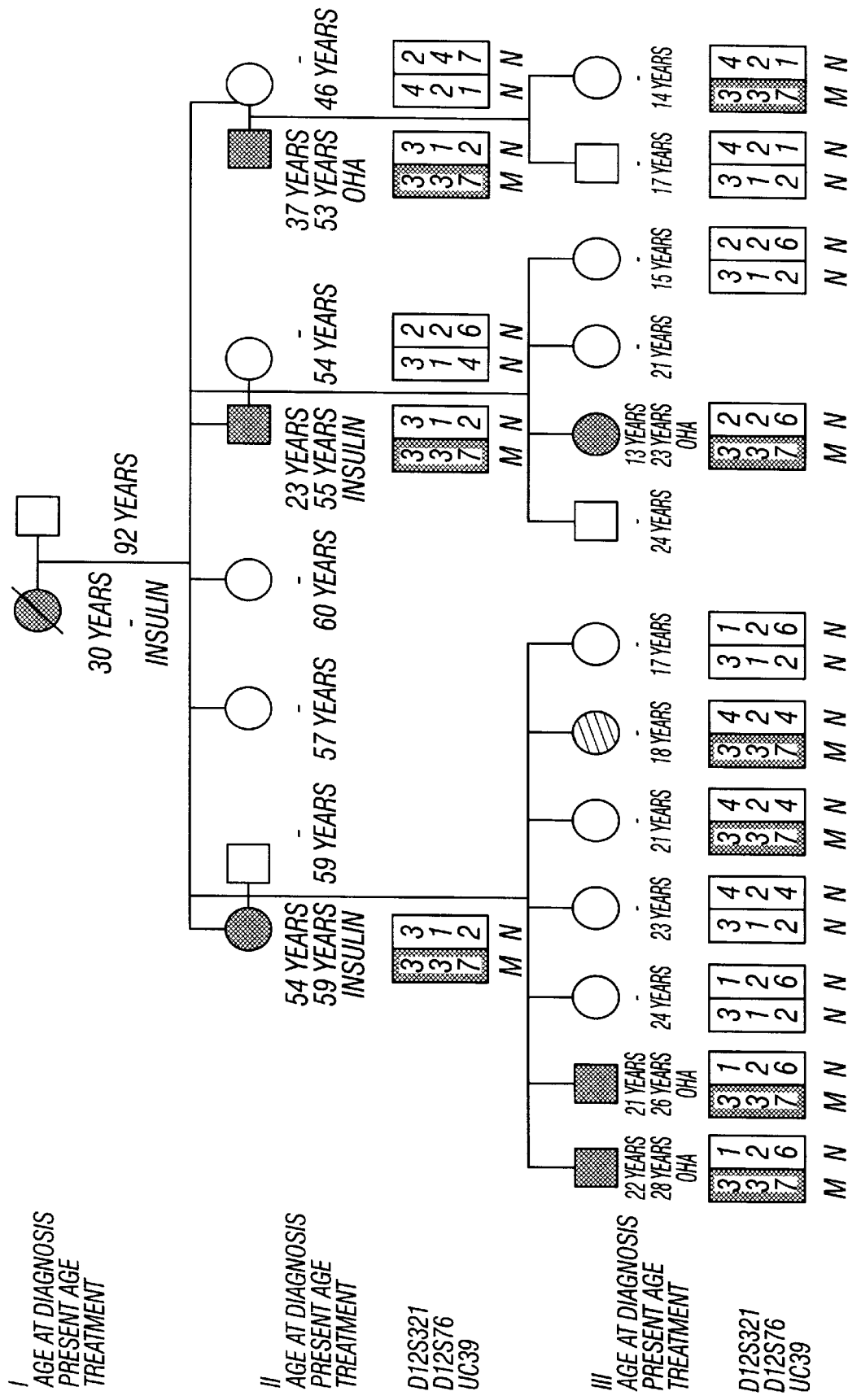

FIG. 21. MODY pedigree, Italy-1. Subjects with MODY and impaired glucose tolerance are indicated by filled and cross-hatched symbols, respectively. Nondiabetic subjects (by testing or history) are indicated by open symbols. The clinical features of the subjects are noted below the symbol including current treatment: insulin or oral hypoglycemic agent (OHA). The haplotype at the markers D12S321-D12S76-UC-39 is shown and the at-risk haplotype is noted by shading. The HNF-1α genotype is shown: N, normal; M, mutant (A→C substitution at nucleotide -58). Although treated with insulin, subject III-9 exhibited a fasting C-peptide value of 1.2 ng/ml indicating that she has MODY rather than insulin-dependent diabetes mellitus.

FIG. 22A, FIG. 22B, and FIG. 22C. FIGS. 22A–C show a comparison of the sequence of the promoter region of the human, rat, mouse, chicken and frog HNF-1α genes (SEQ ID NO: 134; SEQ ID NO:138; SEQ ID NO:136; SEQ ID NO:132; SEQ ID NO:133 respectively). The A→C substitution at nucleotide -58 and HNF-4α binding site are shown. Residues identical to the human sequence are boxed. Nucleotides are numbered relative to the transcriptional start site of the human gene (indicated by an asterisk). The boxed ATG triplet is the initiating methionine. The dashes indicate gaps introduced in the sequences to generate this alignment.

Figure 23:
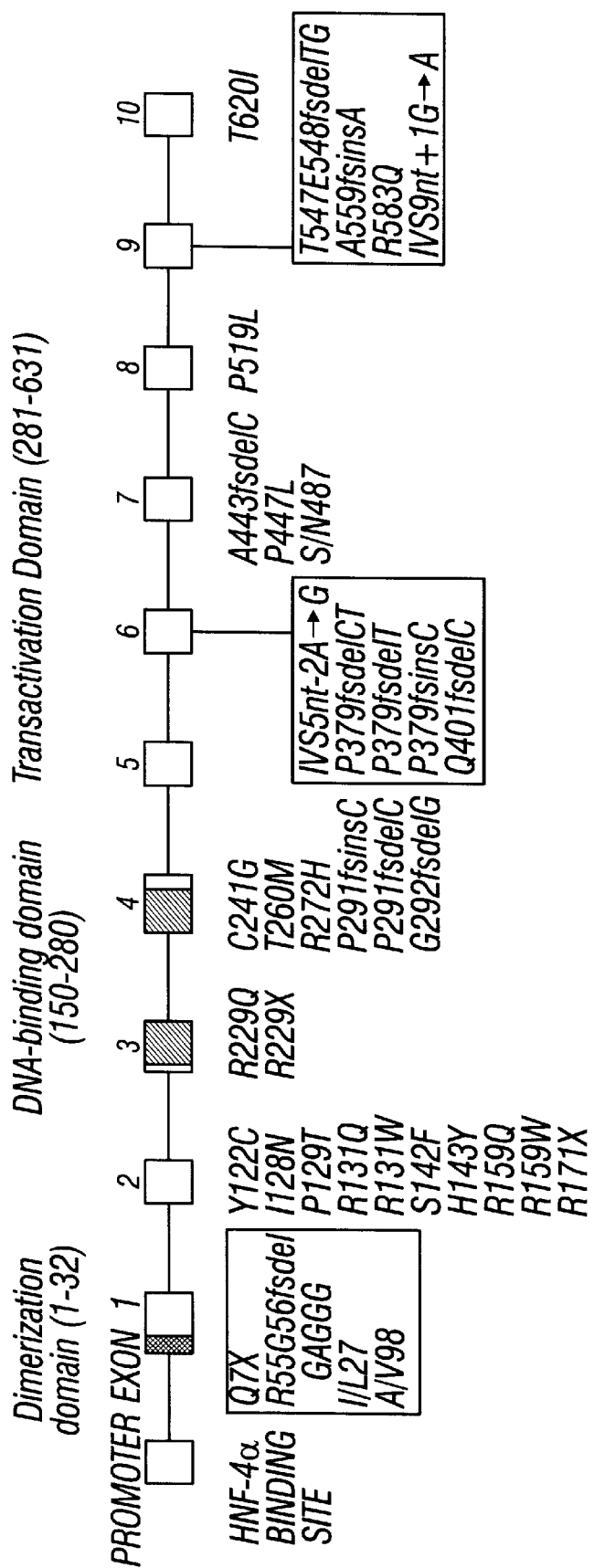

FIG. 23. Summary of mutations in the human HNF-1α gene. This cartoon shows the exons and promoter region as boxes. The mutations and amino acid polymorphisms are from Yamagata et al., 1996; Lehto M, et al., 1997; Kaisaki P. J, et al., 1997; Vaxillaire et al., 1997; Frayling et al., 1997; Hansen T, et al., 1997; Urhammer et al., 1997; Glucksmann et al., 1997. The amino acid polymorphisms are I/L27, ANV98 and S/N487. The single-letter abbreviations for the amino acids are used.

Figure 24:
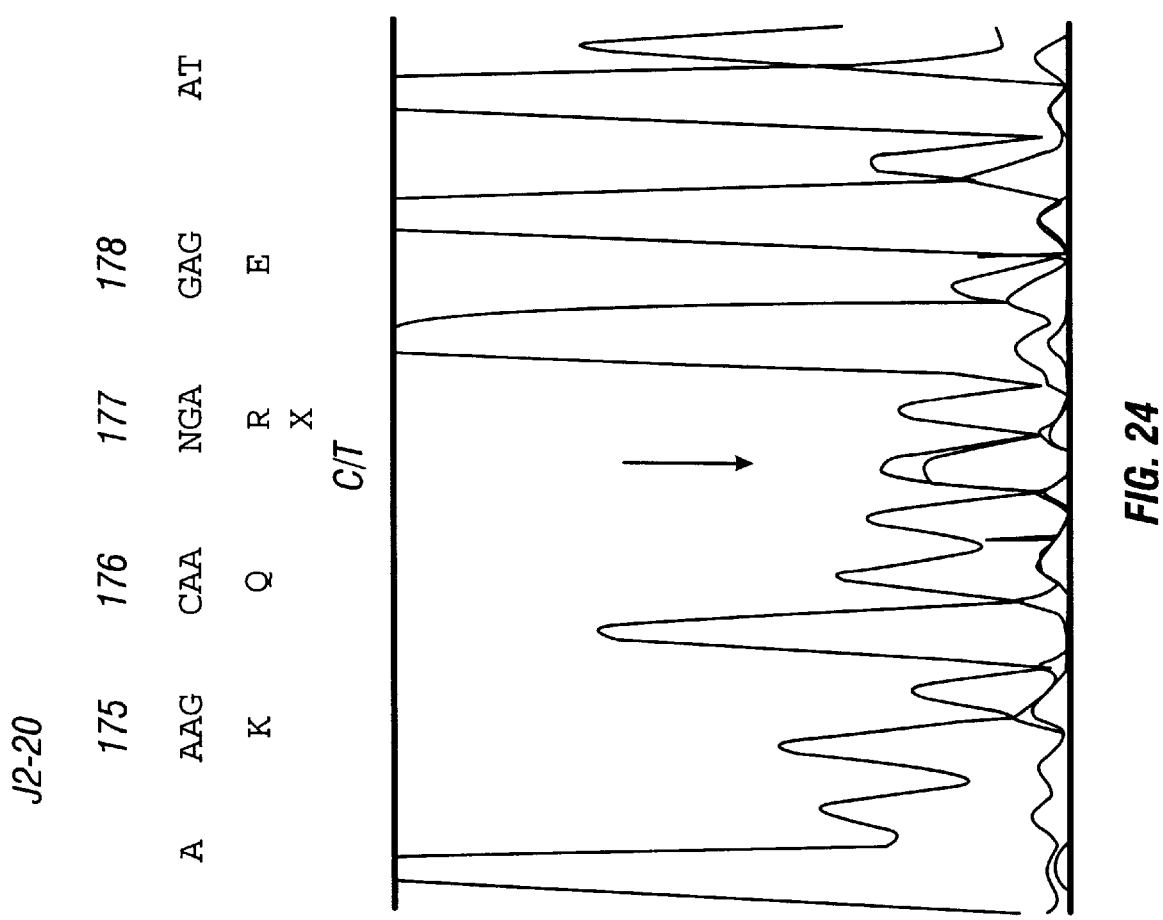

FIG. 24 Partial sequence of exon 2 of HNF-1β gene of subject J2-20 (SEQ ID NO: 146 and SEQ ID NO: 147). The C→T mutation in codon 177 is indicated.

Figure 25:
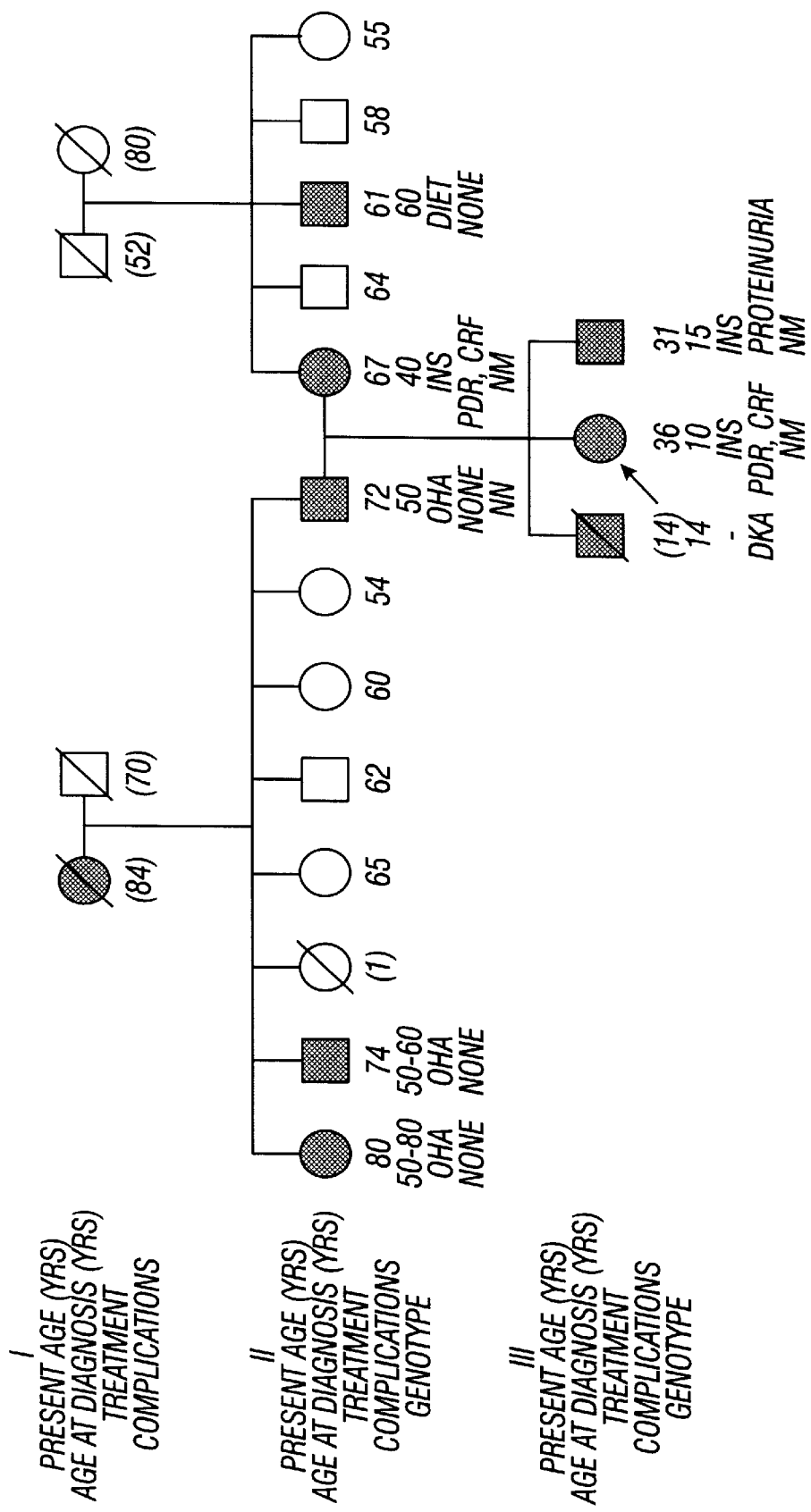

FIG. 25. J2-20 pedigree. Individuals with diabetes mellitus are noted by filled symbols. The arrow indicates the proband. The present age, age at diagnosis, current treatment and complications are shown. The HNF-1β genotype is noted: N, normal; M, mutant. OHA, oral hypoglycemic agent; PDR, proliferative diabetic retinopathy; CRF, chronic renal failure; and DKA, diabetic ketoacidosis.

FIG. 26A–FIG. 26M Partial sequence of human HNF1α gene. These figures depict a contiguous sequence and have been split into panels due to the size of the sequence. The nucleotide and predicted amino acid sequences are shown. Exon and intron sequences are in uppercase and lower cases respectively. The approximate size of the gaps in the introns, the complete sequence of which was not determined are noted. In the promoter region, potential binding sites for transcription factors that may regulate expression of this gene are indicated, with sites identified by DNase footprinting in italics, those identified by sequence homology in normal type. The minimal promoters region is shown in boldface type. The polymorphisms and mutations in the HNF1α gene identified to date are shown in boldface type with the designation of the mutation noted. The asterisk notes the predicted transcriptional start site based on studies of rat HNF1α gene. The letter n indicates that the sequence was ambiguous at this site FIG. 27A–FIG. 27I Partial sequence of human HNF1β gene. These figures depict a contiguous sequence and have been split into panels due to the size of the sequence. The nucleotide and predicted amino acid sequences are shown. Exon and intron sequences are in uppercase and lower cases respectively. The approximate size of the gaps in the introns, the complete sequence of which was not determined are noted. In the promoter region, potential binding sites for transcription factors that may regulate expression of this gene are indicated, with sites identified by DNase footprinting in italics, those identified by sequence homology in normal type.

Figures 1, 28C:
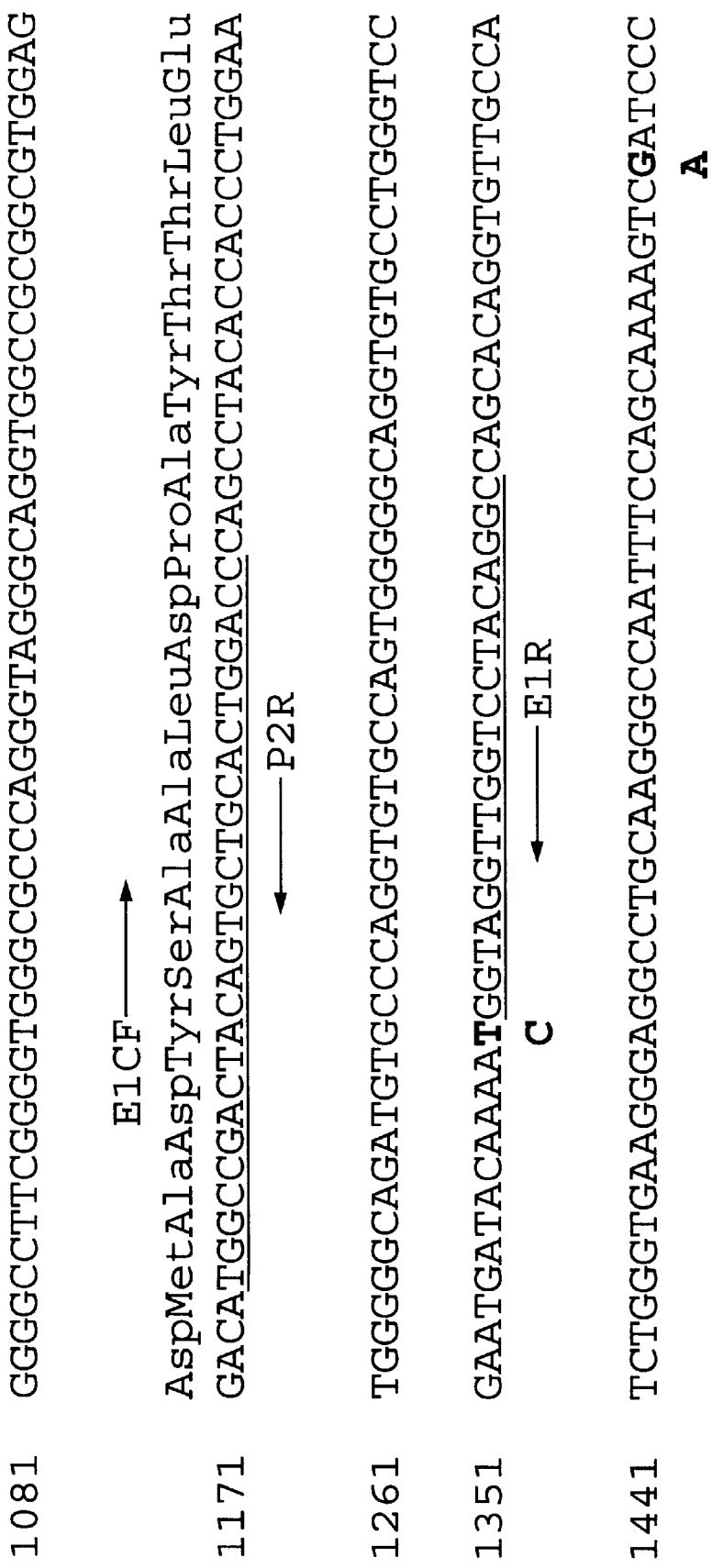

FIG. 28A–FIG. 28V Partial sequence of human HNF4α gene. These depict a contiguous sequence and have been split into panels due to the size of the sequence. The nucleotide and predicted amino acid sequences are shown. Exon and intron sequences are in uppercase and lower cases respectively.

DESCRIPTION OF ILLUSTRATIVE EMBODIMENTS

The present invention concerns the early detection, diagnosis, prognosis and treatment of diabetes. The present invention describes for the first time mutations responsible for HNF1α, HNF1β and HNF4α-related diabetes. The specific mutation and identity of the corresponding wild-type genes from diabetic subjects, are disclosed. These mutations are indicators of HNF1α, HNF1β and HNF4α related diabetes and are diagnostic of the potential for the development of diabetes. It is envisioned that the techniques disclosed herein will also be used to identify other gene mutations responsible for other forms of diabetes.

Those skilled in the art will realize that the nucleic acid sequences disclosed will find utility in a variety of applications in diabetes detection, diagnosis, prognosis and treatment. Examples of such applications within the scope of the present invention include amplification of markers of MODY using specific primers; detection of markers of HNF1α, HNF1β and HNF4α by hybridization with oligonucleotide probes; incorporation of isolated nucleic acids into vectors and expression of vector-incorporated nucleic acids as RNA and protein; development of immunologic reagents corresponding to gene encoded products; and therapeutic treatment for the identified MODY using these reagents as well as, anti-sense nucleic acids, or other inhibitors specific for the identified MODY. The present invention further discloses screening assays for compounds to upregulate gene expression or to combat the effects of the mutant HNF1α, HNF1β and HNF4α genes.

A. Diabetes and Mody

Diabetes mellitus affects approximately 5% of the population of the United States and over 100 million people worldwide (King et al., 1988, Harris et al., 1992). A better way of identifying the populace who are at risk of developing diabetes is needed as a subject may have normal plasma glucose compositions but may be at risk of developing overt diabetes. These issues could be resolved if it were possible to diagnose susceptible people before the onset of overt diabetes. This is presently not possible with subjects having classical diabetes due to its multifactorial nature.

MODY is a monogenic form of diabetes and thus the genes responsible can be more easily studied than those whose mutation contributes to the development of polygenic form(s) of this disorder such as type 1 and type 2 diabetes mellitus. Recent studies have shown that subjects with maturity onset diabetes of the young (MODY), a subset of diabetes characterized by diabetes in the first or second decade of life and autosomal dominant inheritance have shown that MODY may result from mutations in genes on chromosome 20 (HNF4α/MODY1), chromosome 7 (glucokinase/MODY2) chromosome 12 (HNF 1α/MODY3) and chromosome 17 (HNF1β/MODY4).

The clinical characteristics that manifest in HNF4α, HNF1α and HNF1β type diabetes resemble those seen in patients with type 2 diabetes. These characteristics include frequent severe fasting hyperglycemia, the need for oral hypoglycemic agents, eventual insulin requirements, and vascular and neuropathic complications (Fajans et al., 1994; Menzel et al., 1995).

The inventors have shown that prediabetic subjects with mutations in the HNF1α and HNF4α genes have subtle but important alterations in the normal pattern of glucose-stimulated insulin secretion. Compared to control subjects with no family history of diabetes, they had normal insulin secretion rates at lower glucose concentrations. However the increase in insulin secretion rate resulting from an increase in the plasma glucose concentration above 8 mM was less in prediabetic HNF1α-mutation subjects than controls (see FIG. 2–FIG. 4).

Exposure of the normal β-cell to increased plasma glucose concentrations for 42-hours results in an increase in 0-cell responsiveness to a subsequent glucose stimulus. Following a 42-hr glucose infusion which raised the plasma glucose concentration to an average value of 7.1±1.4 mM, the insulin secretion rate of prediabetic HNF1α-mutation subjects increased by 35% between 5–9 mM glucose with a resultant shift in the dose-response curve to the left. Five out of six prediabetic HNFIC-mutation subjects showed this increase in insulin secretion rate, and only one subject MD13 failed to demonstrate this effect. The magnitude of this priming effect of glucose was similar to that seen in the controls.

Diabetic HNF1α-mutation subjects demonstrated diminished insulin secretion across the entire range of glucose concentrations studied. Thus, over the concentration range between 5 and 9 mM glucose, the diabetic subjects secreted 50% less insulin than the controls and 51% less than the prediabetic HNF1α-mutation subjects. Furthermore, the priming effect of glucose was lost in the subjects with overt diabetes.

Evaluation of insulin resistance indicated that HNF1α-mutation subjects were no more resistant than the controls. In fact, there was a tendency towards a lesser degree of insulin resistance in the HNF1α-mutation subjects, making it highly unlikely that insulin resistance plays a primary role in the pathophysiology of diabetes in these subjects.

The inventors have recently characterized insulin secretory responses in prediabetic HNF4α and HNF1α-mutation subjects. Prediabetic HNF4α and HNF1α-mutation subjects both have reduced insulin secretory responses to glucose which are evident only as the plasma glucose rises above a threshold of 7 or 8 mM, respectively. Whereas in HNF1α-mutation subjects the priming effect of glucose on insulin secretion is retained, a low-dose glucose infusion did not have any significant effects on insulin secretion in prediabetic HNF4α-mutation subjects (Byrne et al., 1995b). In subjects with mutations in the glucokinase gene, the dose-response curve is shifted to the right and ISR is markedly decreased at glucose concentrations below 7 mM, but insulin secretion continues to increase with increasing plasma glucose concentrations even above levels of 8 mM. The priming effect of glucose on insulin secretion also is preserved (Byrne et al., 1994). The inventors have recently performed similar studies in subjects with classical Type 2 and impaired glucose tolerance. In subjects with IGT, although the dose-response curve relating glucose and insulin secretion was shifted to the right, the priming effect of glucose on insulin secretion was retained. In subjects with overt Type 2 diabetes, the increase in insulin secretion in response to an increase in glucose was markedly reduced and the priming effect of glucose on insulin secretion was lost.

It thus appears that β-cell dysfunction plays an important, pathophysiologic role in the development of the three forms of MODY which have been characterized to date. A clear prediabetic phase has not been identified in subjects with glucokinase mutations. However, profound defects in the ability of the β-cell to respond to a glucose stimulus is present even in the face of the mild elevations in glucose which characterizes the majority of these subjects. By contrast, a prediabetic phase is a feature of the HNF4α and HNF1α forms of diabetes. These prediabetic subjects have reduced insulin secretory responses to elevated concentrations of glucose induced by the step-wise glucose infusion prior to onset of diabetes. Prediabetic HNF4α and HNF1α subjects can be distinguished based on the effects of a low dose glucose infusion on insulin secretion. The priming effect of glucose on insulin secretion is retained in HNF1α subjects in the prediabetic phase but is lost after the onset of overt hyperglycemia whereas this priming effect is absent in HNF4α diabetes even in the prediabetic phase of the disease. The severe reductions in insulin secretory responses to glucose seen in the overtly diabetic HNF1α subjects are likely to be due in part to the effects of high glucose, in view of the well documented adverse effects of hyperglycemia on insulin secretion. A full understanding of the reasons for these changes in the dose-response relationships between glucose and insulin secretion requires a better understanding of the roles of HNF4α and HNF1α in regulating normal pancreatic β-cell function.

Further studies by the inventors have shown that elevations in the 2-hr post-challenge blood glucose levels predict alterations in insulin secretory responses to glucose. However, in that case, subjects with impaired glucose tolerance demonstrated reduced insulin secretory responses over a range of glucose concentrations and not just in response to increases in glucose above 8 mM as was seen in the prediabetic HNF1α-mutation subjects. Thus, the inventors do not believe that the alterations in insulin secretion seen in the prediabetic HNF1α subjects resulted from the modest elevations in glucose. Rather, the inventors' results suggest that the percent priming and overall insulin secretion rates deteriorate as glucose tolerance deteriorates, and the lack of ability to increase insulin secretion at high glucose levels is a feature of the mutation in the HNF1α gene.

From the studies described above and in the Examples that follow it is clear that the identification and characterization of the gene(s) associated with MODY diabetes is important. Mutations in such genes lead to diabetes and it would be diagnostically and therapeutically advantageous to identify the mutations in subjects predisposed to such mutations.

Studies attempting to find the location of the MODY3 gene showed that the putative gene linked to MODY3 type diabetes was localized to a 5 cM interval between the markers D12S86 and D12S807/D12S820 (Menzel et al., 1995). However the identity of the gene has not been elucidated. The present invention for the first time shows that the gene linked to MODY3 expresses a factor previously identified from hepatocyte known as hepatocyte nuclear factor 1α herein referred to as HNF1α.

Similarly studies attempting to find the location of the MODY1 gene showed that the putative gene linked to MODY1 type diabetes was localized to a 13 cM interval between the markers D20S169 and D20S176 (Stoffel et al., 1996). Likewise, as with MODY3, the identity of the gene in MODY1 has not been elucidated. The present invention for the first time shows that the gene linked to MODY1 expresses a factor previously identified from hepatocytes known as hepatocyte nuclear factor 4α herein referred to as HNF4α.

Subsequently, the inventors performed studies to elucidate the genetic defects responsible for other forms of MODY. The present invention for the first time shows that MODY is likely a consequence of mutations in hepatocyte nuclear factor 1β herein referred to as HNF1β.

The association of mutation in HNF1α, HNF1β and HNF4α with diabetes indicates the importance of the HNF network in controlling pancreatic β-cell function and glucose homeostasis. Hence the studies presented here have categorized exemplary mutations in the HNF1α, HNF1β and HNF4α genes as identified by PCR techniques. These landmark results form the basis of many therapeutic and diagnostic techniques as measures to alleviate diabetes, particularly HNF1α-diabetes, HNF 1β-diabetes and HNF 4α-diabetes.

B. Hepatocyte Nuclear Factors are the Genes Linked to Mody Type Diabetes.

Hepatocyte Nuclear Factor 1α

Hepatic nuclear factor 1α (also known as APF, LFB1 or HP1) has been described as a sequence specific DNA binding protein from rat liver. It is thought to interact with promoter elements present in many genes including albumin, α- and β-fibrinogen, α-1-antitrypsin, α-fetoprotein pyruvate kinase, transthyretin and aldose B among others. HNF1α has been purified from rat liver extracts by DNA affinity chromatography using fibrinogen promoter element (Courtoise, 1987) and was characterized as a single 88 kDa protein. It is now known that HNF1α is a transcription factor.

Mendel and Crabtree (1993) suggested that HNF1α interacted with "hepatocyte-specific" genes in which it plays a prominent role in regulation of both in vitro and in vivo transcription. However, it was later shown that HNF1α mRNA can also be found in several non-hepatocyte tissues including the kidney stomach, intestines, thymus and spleen and pancreas (Baumhueter et al., 1990; Kuo et al., 1990). This suggests that HNF1α expression may participate in the differentiation of non-hepatic organs as well as hepatogenesis.

Transcription factors are proteins that control transcription by binding to cis-acting regulatory DNA sequences in a gene. As such, these factors play a crucial role in development and differentiation by dictating the pattern of expression of genes within specific cells and tissues.

The homeodomain proteins are a class of transcription factors. These proteins all possess the unusual characteristic of having very similar DNA-binding domains even though they mediate diverse effects. HNF1α is an example of a homeodomain protein. HNF1α has been shown to dimerize with itself in solution. It appears that maximal transcriptional activation by HNF1α requires a novel dimerization cofactor. This cofactor, known as the dimerization cofactor of HNF1α (DCoH), does not in itself bind DNA, rather, it binds HNF1α.

HNF1α binds to DNA as a dimer; this was confirmed from studies on the purification and cloning of HNF1α. Other studies showed that there was a DNA binding protein that binds to the HNF1α binding site in cells that lacks the HNF1α mRNA. This second protein HNF1β is a homolog of HNF1α but is the product of a separate gene.

Regulation studies of the HNF1α promoter showed that binding sites for transcription factors HNF3, AP1 and HNF4α are essential for the expression of HNF1α (Hansen and Crabtree, 1993). It has been demonstrated that HNF4α is located on chromosome 20 of the human genome. The present inventors suggest that MODY1, which is known to be linked to chromosome 20, may act as a regulator of MODY3 gene expression as such mutations in HNF4α may be responsible for the MODY1 form of diabetes.

HNF1α proteins possess three functional regions, namely, the dimerization, activation and DNA-binding domains. The dimerization domain is localized to the first 32 amino acids of the HNF1α proteins. The DNA-binding domain is a POU-like homeodomain which binds to a 13 bp palindromic DNA sequence in the promoters of HNF1α binding proteins (Courtois et al., 1988; Frain et al., 1989). The consensus sequence for this HNF1α binding site on these genes is:

GTTAATNATTACC (SEQ ID NO:9)

Diabetes mellitus alters the transcription of numerous genes in many different tissues. The mechanisms underlying these alterations in transcription are largely unknown. One example of altered transcription is seen in the reduced transcription of the albumin gene in diabetes (Wanke et al., 1991). Recently, it has been demonstrated that HNF1α protein levels are reduced in diabetes, leading to the theory that decreased gene transcription in diabetes is due to decreased levels of HNF1α factor critical for the regulation of hepatic albumin gene expression. This is thought to be the case in other genes that posses an HNF1α binding site and are affected by diabetes. Therefore changes in the abundance of HNF1α in diabetes appears to affect the expression of genes whose expression is predominantly regulated by this factor.

The expression of the insulin gene in adult mammals is localized to the β cells in the pancreatic islets. Studies of this gene have defined a small region in the promoter, the FF-minienhancer, capable of conferring tissue-specific and glucose responsive transcriptional activity on a heterologous promoter (German et al., 1990). This minienhancer region is composed of two primary regulatory elements, for the Far box and the FLAT element, which interact to upregulate transcription.

Further analysis of the FLAT element showed it to be a cluster of several cis loci that mediate discrete positive and negative effects. The positive locus is characterized as FLAT-F and its activity is only revealed when there is a mutation in the negative locus FLAT-E. This FLAT-F region is able to specifically bind a number of DNA-binding proteins. The sequence of FLAT-F has significant similarity to the consensus sequence of HNF1α. This led to studies to determine whether HNF1α itself may play a role in the transcriptional regulation of the rat insulin gene. Subsequently, it was shown that HNF1α expression is present in the pancreatic β-cell derived insulinoma cell line HIT. HNF1α has been shown to bind with and transactivate rat insulin gene enhancers that contain an HNF1α site.

Hepatocyte Nuclear Factor 4α

Hepatocyte nuclear factor 4α (HNF4α) is another transcription factor first associated with the liver and having limited tissue distribution (Xanthopoulos et al., 1991; Zhong et al., 1994). HNF4α can activate transcription in several non-hepatic cell lines, indicating that no liver-specific modification is required for its function (Sladek et al., 1990).

It has been observed that there is an apparent contradiction between the molecular mass of HNF4α predicted from the primary sequence (50.6 kDa) (Sladek et al., 1990) and that determined by gel electrophoresis (54 kDa) suggesting that this difference may be due to post-translational modification(s). Of the many types of post-translational modifications that might regulate gene expression, most attention has been focused on phosphorylation, which can influence transcription factor activity in many ways (Hunter and Karin, 1992).

Three main levels of regulation have been described: phosphorylation can affect the DNA-binding activity (Boyle et al., 1991; Segil et al., 1991; Shuai et al., 1994), the transcriptional activation potential (Yamamoto et al., 1988; Trautwein et al., 1993), or the translocation of a transcription factor from the cytoplasm into the nucleus (Metz and Ziff, 1991; Kerr et al., 1991; Schindler et al., 1992; Shuai et al., 1992). These possibilities are by no means mutually exclusive, and in principle phosphorylation can be responsible for simultaneous regulation at several distinct levels. With the exception of certain signal transduction proteins (Darnell et al., 1994), all examples of this type of regulation have involved phosphorylation at serine or threonine residues.

It has been demonstrated that the activity of HNF4α is post-translationally regulated by tyrosine phosphorylation, providing an example of a non-signal-transduction factor modulated by this modification. The HNF4α polypeptide (SEQ ID NO:79) contains 12 tyrosine residues scattered throughout the DNA-binding, dimerization, and putative ligand-binding domains (Sladek et al., 1990) which could be potential phosphorylation sites. It seems that the tyrosine phosphorylation of HNF4α is required for its DNA-binding activity. It has been shown that the transcriptionally active form of HNF4α is localized in specific subnuclear domains. This intranuclear distribution depends directly or indirectly on tyrosine phosphorylation, suggesting the existence of an additional control mechanism at the level of subnuclear targeting playing a role in transcription regulation.

Hepatocyte nuclear factor 4α (HNF-4α) is a positive-acting transcription factor which is expressed very early in embryo development and is essential to liver development and function (reviewed in Sladek, 1993 and Sladek, 1994). Mouse HNF4α mRNA appears in the primary endoderm of implanting blastocysts at embryonic day 4.5 and in the liver and gut primordia at day 8.5 (Duncan et al., 1994), while mice deficient in HNF4α do not survive past day 9 post-coitus (Chen et al., 1994).

HNF4α has also been proposed to be responsible for the final commitment for cells to differentiate into hepatocytes (Nagy et al., 1994). In adult rodents, HNF4α is located primarily in the liver, kidney, and intestine, and in insects HNF4α is found in the equivalent tissues (Sladek et al., 1990; Zhong et al., 1993). HNF4α is known to activate a wide variety of essential genes, including those involved in cholesterol, fatty acid, and glucose metabolism; blood coagulation; detoxification mechanisms; hepatitis B virus infections; and liver differentiation (reviewed in Sladek, 1993 and Sladek, 1994).

HNF4α is a member of the superfamily of ligand-dependent transcription factors, which includes the steroid hormone receptors, thyroid hormone receptor (TR), vitamin A receptor, and vitamin D receptor (VDR), as well as a large number of receptors for which ligands have not yet been identified, the so-called orphan receptors (reviewed in Landers and Spelsberg, 1992; O'Malley and Conneely, 1992; Parker, 1993; and Tsai and O'Malley, 1994). All receptors are characterized by two conserved domains: the zinc finger region, which mediates DNA binding, and a large hydrophobic domain which mediates protein dimerization, transactivation, and ligand binding.

Whether HNF4α responds to a ligand is not known, but it has been shown to activate transcription in the absence of an exogenously added ligand (Hall et al., 1994; Kuo et al., 1992; Metzger et al., 1993; Mietus et al., 1992; Reijnen et al., 1992; Sladek et al., 1990). HNF4α is also highly conserved with the Drosophila HNF-4, containing 91% amino acid sequence identity to the rat HNF4α in the DNA binding domain and 68% identity in the large hydrophobic domain (Zhong et al., 1993).

The members of the receptor superfamily have been classified in a variety of ways, one of which is by their ability to dimerize with themselves and with other members of the superfamily. For example, the steroid hormone receptors, glucocorticoid, mineralocorticoid, and progesterone receptors (GR, MR, and PR, respectively), all bind DNA and activate transcription as homodimers. They are present in the cytoplasm complexed with heat shock proteins (HSP) until the presence of the appropriate ligand disrupts the complex, allowing the receptors to translocate to the nucleus (reviewed in Freedman and Luisi, 1993; O'Malley and Tsai, 1993; and Tsai and O'Malley, 1994). On the other hand, the retinoid acid receptor (RAR) and retinoid X receptor (RXR) as well as the VDR, peroxisome proliferator-activated receptor (PPAR), and TR, which do not bind HSP and reside primarily in the nucleus, all bind DNA and activate transcription not only as homodimers but also as heterodimers (reviewed in Giguére, 1994; Parker, 1993; and Stunnenberg, 1993). Several of the nuclear receptors bind DNA very inefficiently, if at all, as homodimers (RXRα, RAR, VDR, TR, and PPAR) but bind DNA well as heterodimers (reviewed in Giguere, 1994 and Stunnenberg, 1993). At least two of the receptors (RAR and TR) form heterodimers in solution with RXRα (Hermann et al., 1992; Kurokawa et al., 1993; Zhang et al., 1992).

The most common dimerization partner for all of these receptors is RXRα. The third class of receptors identified to date reside in both the nucleus and the cytoplasm and bind DNA preferentially as monomers (NGFI-B, FTZ-F1, steroidogenic factor 1 [SF-1], and RORα1) (Giguére et al., 1995; Kurachi et al., 1994; Ohno et al., 1994).

HNF4α is very similar to the retinoid receptors, in particular to RXRα, in both amino acid sequence and DNA binding specificity. Mouse RXRα is 60% identical to rat HNF4α in the DNA binding domain and 44% identical in the large hydrophobic domain. In comparison, RARE, which readily heterodimerizes with RXRα, is 61% identical to RXRα in the DNA binding domain and only 27% identical in the large hydrophobic domain (Mangelsdorf et al., 1992). HNF4α and RXRα have also been shown to share response elements from at least six different genes as well as a consensus site of a direct repeat of AGGTCA separated by one nucleotide (referred to as DR+1) (Carter et al., 1994; Carter et al., 1993; Garcia et al., 1993; Ge et al., 1994; Hall et al., 1994; Hall et al., 1992; Kekule et al., 1993; Ladias, 1994; Lucas et al., 1991; Nakshatri and Chambon, 1994; Widom et al., 1992). The structural and functional similarities of HNF4α and RXRα suggest that HNF4α might heterodimerize with RXRα and/or other receptors.

Electrophoretic mobility shift analyses (EMSA) of HNF4α and RXRα proteins expressed in vivo and in vitro showed that HNF4α in fact does not heterodimerize with RXRα on any one of a number of response elements and that while HNF4α forms homodimers in solution in the absence the DNA, it does not form heterodimers with RXRα. It has also been shown that HNF4α does not heterodimerize with a number of other receptors on DNA, suggesting that the lack of heterodimerization is a general property of HNF4α.

These studies led to the proposal that HNF4α defines a new subfamily of nuclear receptors which are presently exclusively in the nucleus, exist in solution, bind DNA as homodimers, and do not form heterodimers with RXRα or other receptors.

HNF4α is a member of the steroid hormone receptor family. The members of this family have been classified according to the amino acid sequence in the knuckle of the first zinc finger (referred to as the P box) a region important for recognizing the sequence of the half site of the palindrome in hormone response elements (Forman and Samuels, 1990). For examples members of the thyroid hormone receptor subfamily contain amino acid sequence EGCKG (SEQ ID NO:83) and bind to the thyroid response element (TRE). Members of the estrogen receptor subfamily contain the amino acids EGCKA (SEQ ID NO:84) and bind to estrogen response elements (ERE). The sequence of HNF4α is DGCKG (SEQ ID NO:85) and is most similar to that of the thyroid response element. Despite this similarity it appears that HNF4α does not bind TRE nor does it bind ERE, and the true ligand for HNF4α is as yet undetermined. The screening methods of the present invention will lead one of ordinary skill in the art to elucidate such a ligand or ligands.

The present invention describes the exon-intron organization and partial sequence of the human HNF4α gene. In addition, the inventors have screened the exons, flanking introns and minimal promoter region for mutations in a group of 57 unrelated Japanese subjects with early-onset diabetes/MODY of unknown cause. The results of these screens suggest that mutations in the HNF4α gene may cause early-onset diabetes/MODY in Japanese but they are less common than mutations in the HNF1α/MODY3 gene. The information presented herein on the sequence of the HNF4α gene and its promoter region will facilitate the search for mutations in other populations and studies of the role of this gene in determining normal pancreatic β-cell function.

Furthermore, current understanding of the MODY1 form of diabetes is based on studies of only a single family, the R-W pedigree. Here the inventors report the identification of a second family with MODY1 and the first in which there has been a detailed characterization of hepatic function. The present inventors demonstrate that MODY1 is primarily a disorder of β-cell function, however, the inventors have ascertained that mutations in HNF4α may lead to β-cell as well as 0β-cell secretory defects or to a reduction in pancreatic islet mass.

Hepatic Nuclear Factor 1β and DCoH

Human HNF1β is a homeodomain-containing transcription factor of 557 amino acids (type A) with alternative splicing generating two other forms of 531 (type B) and 399 amino acids (type C) (Mendel et al., 1991a; De Simone et al., 1991; Rey-Campos et al., 1991; Bach and Yaniv, 1993). The nucleic and amino acid sequences for human HNF1β are given in SEQ ID NO:128 and SEQ ID NO:129, respectively. HNF1β is structurally related to HNF1α and functions as a homodimer or a heterodimer with HNF1α. These dimers are stabilized by the bifunctional protein, DCoH/PCBD (Mendel et al., 1991b; Citron et al., 1992), which binds to the dimerization domain of HNF1forming a heterotetrameric complex and enhancing transcriptional activity. As a homotetramer, PCBD is involved in the regeneration of tetrahydrobiopterin, an essential cofactor of phenylalanine hydroxylase and other mono-oxygenases, catalyzing the conversion of 4-hydroxytetrahydrobiopterin to quinonoid-dihydrobiopterin (Citron et al.1993; Johnen et al., 1995). Loss of rare autosomal recessive form of mild hyperphenylalaninemia. HNF1β and DCoH mRNA are expressed in mouse pancreatic islets implying that they may function together with HNF-1α to regulate gene expression in this tissue. Human DCoH is a protein of 104 amino acids (including the initiating methionine) (Thöny et al., 1995) and functions as described herein below.

MODY-type Diabetes is a Manifestation of Defects in Hepatocyte Nuclear Factors

It is established that all forms of Type 2 diabetes are associated with profound insulin secretory defects which include loss of the first phase response to intravenous glucose, delayed and blunted responses to ingestion of a mixed meal, loss of the normal oscillatory patterns of insulin secretion, and increased secretion of proinsulin and proinsulin-like products. The molecular basis of these secretory defects in humans is unknown, although in rats it has been shown that there are global changes in gene expression in the islets of diabetic and prediabetic animals. One such global alteration is the reduction in the levels of mRNAs encoding many pancreatic islet specific proteins. This defect in gene expression would be compatible with decreased levels of a master transcription factor whose levels affect the expression of a whole array of downstream genes.

The present invention predicts that the β-cell dysfunction and insulin secretory defects associated with MODY3 are as a result of mutations in HNF1α, furthermore it demonstrates that β-cell dysfunction associated with MODY1 are a result of mutations in HNF4α.

The features of MODY-type diabetes are very similar to those of late onset Type 2 diabetes. Hence, acquired defects in the expression of HNF1α, HNF4α, and HNF1β respectively, may well occur in late onset diabetes and lead to β-cell dysfunction and insulin secretory defects in this form of diabetes. The identification of agents that activate transcription of HNF1α, HNF1β and HNF4α will be therapeutic for the treatment of MODY, as well as late onset Type 2 diabetes. The present invention details methods for the identification of such agents which will then be used to increase the expression of HNF1α, HNF1β and HNF4α which in turn will lead to the increased transcription/expression or activation of β-cell genes such as insulin.

It is clear from the present invention that hepatocyte nuclear factors, their expression, regulation and modification have far reaching implications in diabetes. To date three of the four types of MODY diabetes identified, are predicted to affect gene expression. Other forms of MODY can not be ruled out, for example genetic linkage studies predict the presence of additional MODY genes, the chromosomal localization of which are presently unknown.

The absolute HNF4α dependence of the HNF1α promoter coupled with evidence of the ability of HNF4α to rescue endogenous HNF1α expression is indicative of HNF4α being an essential regulator of HNF1α (FIG. 6). Thus activation or repression of HNF4α will result in an indirect activation or repression of HNF1α. The present invention elucidates methods for identifying factors responsible for modulating HNF4α expression and/or activity.

HNF1β, also known as vHNF1, is closely related to HNF1α and is able to form heterodimers with HNF 1α. Dimerization between members of classes of transcription factors appears to solve the problem of controlling expression of a very large number genes. An obvious advantage of the dimerization ability of a transcription factor is that it provides an opportunity to diversify the number of regulatory mechanisms that can be associated with a single regulatory DNA binding site. Another advantage lies in the possibility of translating subtle alterations in the relative levels of expression of members of a dimerization pair into a substantial quantitative effect on transcription.

FIG. 6 summarizes the different factors involved in the regulation of expression and activity of the HNF transcription factors described above. From the inventors investigations it is conceivable that aberrations at any points along this pathway or any factors affecting this pathway directly or indirectly will result in β-cell dysfunction and diabetes mellitus, either as MODY or late-onset diabetes.

The present invention has shown that mutations in HNF1α are clearly responsible for MODY3 type diabetes. As discussed earlier HNF1α binds to DNA as a dimer. This can either be a homodimer or a heterodimer with HNF1β (SEQ ID NO: 80). The two forms of HNF1 are expressed in comparable amounts in the liver but there is a three-fold higher expression of HNF 1β in the kidney as compared to HNF 1α.

HNF1β lacks the transcriptional activity attributable to HNF1α. One potential consequence of this observation in combination with its ability to dimerize with HNF1α is that HNF1β is likely to be a negative regulator of HNF1α transcriptional activity. This observation is suggested by the presence of vHNF1 in systems that do not express the majority of hepatocyte-specific gene products (Baumhueter et al., 1988). However, studies by Mendel et al., (1991) were unable to confirm this observation.

Studies by Mendel et al., (1991) indicated that a dimerization cofactor of HNF1(DCoH) may increase the stability of HNF1α dimers. Thus, it is suggested that DCoH has the potential to restrict the activity of HNF1α and/or HNF1β. There are a number of hypotheses as to how DCoH affects HNF1 activation of transcription. HNF1α is a monomer in solution and can only bind DNA as a dimer, the presence of DCoH favors the formation of the dimeric HNF1α. Alternatively it is plausible that DCoH induces a conformational change in HNF1α to create a more potent transcriptional activator either directly or by allowing interaction with other proteins, for example HNF1β. Yet another alternative is that DCoH decreases the rate of HNF1α degradation thereby stabilizing HNF1α and potentiating the effects of HNF1α.

The present invention demonstrates that MODY4, which was previously uncharacterized, is a manifestation of defects in HNF 1β. The present invention describes specific mutations in HNF1β that have led to MODY4 in certain individuals. In light of these observations, there are described herein methods for the identification and isolation of factors involved in the activity of HNF1β and DCOH with a view to obtaining insights into therapeutic intervention in diabetes.

C. In vitro Screening Assays for Candidate Substances

Certain aspects of this invention concern methods for conveniently evaluating candidate substances to identify compounds capable of stimulating HNF1α-, HNF1β-or HNF4α-mediated transcription. Such compounds will be capable of promoting gene expression, and thus can be said to have up-regulating activity. In as much as increased gene expression of, for example, the insulin gene in the body functions to alleviate the symptoms of diabetes, any positive substances identified by the assays of the present invention will be anti-diabetic drugs. Before human administration, such compounds would be rigorously tested using conventional animal models known to those of skill in the art.

Successful candidate substances may function in the absence of mutations in HNF1α, HNF1β or HNF4α in which case the candidate compound may be termed a "positive stimulator" of HNF1α, HNF1β or HNF4α, respectively. Alternatively, such compounds may stimulate transcription in the presence of mutated HNF1α, HNF1β or HNF4α overcoming the effects of the mutations, i.e., function to oppose HNF1α-mutant, and/or HNF1β, and/or HNF4α-mediated diabetes, and thus may be termed "an HNF1α mutant agonist" "HNF1β mutant agonist" or "HNF4α mutant agonist" respectively. Compounds may even be discovered which combine all three of these actions. Although the agonist class of compounds may ultimately seem to be the most desirable, compounds of either class will likely be useful therapeutic agents for use in stimulating gene expression and combating MODY1, MODY3, MODY4, and late-onset Type 2 diabetes in human subjects.

Candidates for HNF1α

As HNF1α is herein shown to be linked to MODY3 type, one method by which to identify a candidate substance capable of stimulating HNF1α-mediated transcription in diabetes is based upon specific protein:DNA binding. Accordingly, to conduct such an assay, one may prepare an HNF1α binding protein composition, such as recombinant HNF1α, and determine the ability of a candidate substance to increase HNF1α protein binding to a DNA segment including a complementary HNF1α binding sequence, i.e., to increase the amount or the binding affinity of a protein:DNA complex.

This generally would be achieved using two parallel assays, one of which contains HNF1α and the specific DNA alone and one of which contains HNF1α, DNA and the candidate substance composition. One would perform each assay under conditions, and for a period of time, effective to allow the formation of protein:DNA complexes, and one would then separate the bound protein:DNA complexes from any unbound protein or DNA and measure the amount of the protein:DNA complexes. An increase in the amount of the bound protein:DNA complex formed in the presence of the candidate substance would be indicative of a candidate substance capable of promoting HNF1α binding, and thus, capable of stimulating HNF 1α-mediated transcription.

In such binding assays, the amount of the protein:DNA complex may be measured, after the removal of unbound species, by detecting a label, such as a radioactive or enzymatic label, which has been incorporated into the original HNF1α protein composition or recombinant protein or HNF1α-containing DNA segment. Alternatively, one could detect the protein portion of the complex by means of an antibody directed against the protein, such as those disclosed herein.

Preferred binding assays are those in which either the HNF1α protein, recombinant protein or purified composition or the HNF1α-containing DNA segment is bound to a solid support and contacted with the other component to allow complex formation. Unbound protein or DNA components are then separated from the protein:DNA complexes by washing and the amount of the remaining bound complex quantitated by detecting the label or with antibodies. Such DNA binding assays form the basis of filter-binding and microtiter plate-type assays and can be performed in a semi-automated manner to enable analysis of a large number of candidate substances in a short period of time. Electrophoretic methods, such as the gel-shift assay disclosed herein, could also be employed to separate unbound protein or DNA from bound protein:DNA complexes, but such labor-intensive methods are not preferred.

Assays such as those described above are initially directed to identifying positive stimulator candidate substances and do not, by themselves, address the activity of the substance in the presence of HNF1α mutants. However, such positive regulators may also prove to act as HNF1α mutant agonists, and in any event, would likely have utility in transcriptional promotion, either in vitro or in vivo. Positive regulators would likely be further evaluated to assess the effects of HNF1α mutants on their action, for example, by employing a cellular reporter gene assay such as those described herein below.

Virtually any candidate substance may be analyzed by these methods, including compounds which may interact with HNF1α binding protein(s), HNF1α or protein:DNA complexes, and also substances such as enzymes which may act by physically altering one of the structures present. Of course, any compound isolated from natural sources such as plants, animals or even marine, forest or soil samples, may be assayed, as may any synthetic chemical or recombinant protein.

Another potential method for stimulating HNF1α-mediated transcription is to prepare a HNF1α protein composition and to modify the protein composition in a manner effective to increase HNF1α protein binding to a DNA segment including the HNF1α protein binding sequence. The binding assays would be performed in parallel, similar to those described above, allowing the native and modified HNF1α binding protein to be compared. In addition to phosphatases and kinases, other agents, including proteases and chemical agents, could be employed to modify HNF1α binding protein. The present invention, with the cloning of mutant HNF1α cDNA, also opens the way for genetically engineering HNF1α protein to promote gene transcription in diabetes. In this regard, the mutation of potential phosphorylation sites and/or the modification or deletion of other domains is contemplated.

Candidates for HNF4α binding

The criteria shown above for screening of modulators of HNF1α are also true of HNF4α. HNF4α is a member of the steroid hormone receptor superfamily however, the ligand for HNF4α is unknown. The identification of the endogenous ligand for HNF4α binding would be an important step towards elucidating the mechanisms of eucaryotic gene control, and would also provide biomedical science with a powerful tool by which to regulate specific gene expression. Such a development would lead to numerous useful applications in the pharmaceutical and biotechnological industries. Although many applications are envisioned, one particularly useful application would be as the central component in screening assays to identify new classes of pharmacologically active substances which may be employed to manipulate, and particularly, to promote, the transcription of genes whose expression is altered in diabetes.

Hence HNF4α would be of great use in identifying agents to combat MODY and Type 2 diabetes. An anti-diabetic agent isolated by the screening methods of the present invention would act to promote the cellular transcription or function of HNF4α, which would in turn serve to increase transcription of genes whose activity is regulated by HNF4α (for example HNF1α) thereby increasing the transcription of genes involved in diabetes and alleviating the symptoms of diabetes.

Candidates for HNF1β binding

The criteria shown above for screening of modulators of HNF1α and HNF4α are also true of HNF1β. HNF1β is a 557 amino acid that is structurally related to HNF1α and functions as a homodimer and heterodimer with HNF1α. These dimers are stabilized by DCoH. The identification of factors that affect this dimerization, or any of the factors involved in the heterotetrameric complex, will provide useful compounds for the modulation of transcriptional activity. Such a development would lead to numerous useful applications in the pharmaceutical and biotechnological industries. Although many applications are envisioned, one particularly useful application would be as the central component in screening assays to identify new classes of pharmacologically active substances which may be employed to manipulate, and particularly, to promote, the transcription of genes whose expression is altered in diabetes.

Hence HNF1β would be of great use in identifying agents to combat MODY and Type 2 diabetes. An anti-diabetic agent isolated by the screening methods of the present invention would act to promote the cellular transcription or function of HNF1β, which would in turn serve to increase transcription of genes whose activity is regulated by HNF1β (for example HNF1α) thereby increasing the transcription of genes involved in diabetes and alleviating the symptoms of diabetes.

D. Reporter Genes and Cell-Based Screening Assays

Cellular assays also are available for screening candidate substances to identify those capable of stimulating HNF1α- HNF 13β- and HNF4α-mediated transcription and gene expression. In these assays, the increased expression of any natural or heterologous gene under the control of a functional HNF1α, HNF1β or HNF4α protein may be employed as a measure of stimulatory activity, although the use of reporter genes is preferred. A reporter gene is a gene that confers on its recombinant host cell a readily detectable phenotype that emerges only under specific conditions. In the present case, the reporter gene, being under the control of a functional HNF1α, HNF1β or HNF4α protein, will generally be repressed under conditions of MODY3, MODY4 or MODY1 diabetes respectively and will generally be expressed in the MODY3, MODY4 or MODY1 non diabetic conditions respectively.

Reporter genes are genes which encode a polypeptide not otherwise produced by the host cell which is detectable by analysis of the cell culture, e.g., by fluorometric, radioisotopic or spectrophotometric analysis of the cell culture. Exemplary enzymes include luciferases, transferases, esterases, phosphatases, proteases (tissue plasminogen activator or urokinase), and other enzymes capable of being detected by their physical presence or functional activity. A reporter gene often used is chloramphenicol acetyltransferase (CAT) which may be employed with a radiolabeled substrate, or luciferase, which is measured fluorometrically.

Another class of reporter genes which confer detectable characteristics on a host cell are those which encode polypeptides, generally enzymes, which render their transformants resistant against toxins, e.g., the neo gene which protects host cells against toxic levels of the antibiotic G418, and genes encoding dihydrofolate reductase, which confers resistance to methotrexate. Genes of this class are not generally preferred since the phenotype (resistance) does not provide a convenient or rapid quantitative output. Resistance to antibiotic or toxin requires days of culture to confirm, or complex assay procedures if other than a biological determination is to be made.

Other genes of potential for use in screening assays are those capable of transforming hosts to express unique cell surface antigens, e.g., viral env proteins such as HIV gp120β or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstances the signal is modified in order to remove sequences that interdict secretion. For example, the herpes gD coat protein has been modified by site directed deletion of its transmembrane binding domain, thereby facilitating its secretion (EP 139,417A). This truncated form of the herpes gD protein is detectable in the culture medium by conventional immunoassays. Preferably, however, the products of the reporter gene are lodged in the intracellular or membrane compartments. Then they can be fixed to the culture container, e.g., microtiter wells, in which they are grown, followed by addition of a detectable signal generating substance such as a chromogenic substrate for reporter enzymes.

The transcriptional promotion process which, in its entirety, leads to enhanced transcription is termed "activation." The mechanism by which a successful candidate substance acts is not material since the objective is to promote HNF1α, HNF1β or HNF4α mediated gene expression, or even, to promote gene expression in the presence of mutant HNF1α, HNF1β, or HNF4α gene products, by whatever means.

To create an appropriate vector or plasmid for use in such assays one would ligate the HNF1α-containing promoter, whether a hybrid or the native HNF1α promoter, to a DNA segment encoding the reporter gene by conventional methods. Similar assays are also contemplated using HNF1β and HNF4α promoters. The HNF1α, HNF1β or HNF4α promoter sequences may be obtained by in vitro synthesis or recovered from genomic DNA and should be ligated upstream of the start codon of the reporter gene. The present invention provides the promoter region for human HNF1α, a comparison of the sequence of the promoter region of the human, rat, mouse, chicken and frog HNF1α genes is given in FIG. 22. There is also provided herein a comparison of the sequences of the promoter regions of the human and mouse HNF4α genes (FIG. 13). The partial sequence of the human HNF 1β gene including promoter has also been identified by the present inventors and deposited in the GenBank database under accession numbers U90279-90287 and U96079. Any of these promoters may be particularly preferred in the present invention. An AT-rich TATA box region should also be employed and should be located between the HNF sequence and the reporter gene start codon. The region 3' to the coding sequence for the reporter gene will ideally contain a transcription termination and polyadenylation site. The promoter and reporter gene may be inserted into a replicable vector and transfected into a cloning host such as E. coli, the host cultured and the replicated vector recovered in order to prepare sufficient quantities of the construction for later transfection into a suitable eukaryotic host.

Host cells for use in the screening assays of the present invention will generally be mammalian cells, and are preferably cell lines which may be used in connection with transient transfection studies. Cell lines should be relatively easy to grow in large scale culture. Also, they should contain as little native background as possible considering the nature of the reporter polypeptide. Examples include the Hep G2, VERO, HeLa, human embryonic kidney (HEK)- 293, CHO, WI38, BHK, COS-7, and MDCK cell lines, with monkey CV-1 cells being particularly preferred.

The screening assay typically is conducted by growing recombinant host cells in the presence and absence of candidate substances and determining the amount or the activity of the reporter gene. To assay for candidate substances capable of exerting their effects in the presence of mutated HNF1α, HNF1β and/or HNF4α gene products, one would make serial molar proportions of such gene products that alter HNF1α-, HNF1β-and HNF4α-mediated expression. One would ideally measure the reporter signal level after an incubation period that is sufficient to demonstrate mutant-mediated repression of signal expression in controls incubated solely with mutants. Cells containing varying proportions of candidate substances would then be evaluated for signal activation in comparison to the suppressed levels.

Candidates that demonstrate dose related enhancement of reporter gene transcription or expression are then selected for further evaluation as clinical therapeutic agents. The stimulation of transcription may be observed in the absence of mutant HNF1α, HNF1β or HNF4α, in which case the candidate compound might be a positive stimulator of HNF1α HNF1β or HNF4α transcription, respectively. Alternatively, the candidate compound might only give a stimulation in the presence of mutated HNF1α, mutated HNF1β or mutated HNF4α protein, which would indicate that it functions to oppose the mutation-mediated suppression of the gene expression. Candidate compounds of either class might be useful therapeutic agents that would stimulate gene expression and thereby combating MODY and Type 2 diabetes.

E. Nucleic Acids

As described the Examples, the present invention discloses the gene at the MODY3 locus of chromosome 12, MODY4 locus as being associated with HNF 1β and the gene at the MODY1 locus of chromosome 20. Mutations in these genes are responsible for diabetes. The present invention discloses mutations in the HNF1α, HNF1β, and HNF4α genes identified by PCR techniques. The gene for the MODY3 locus has for the first time been identified as hepatocyte nuclear factor 1α, herein referred to as HNF1α. The gene for the MODYL locus has been identified as hepatocyte nuclear factor 4 α (HNF4α). The gene for the MODY4 locus has been identified as hepatocyte nuclear factor 1α (HNF1β).

In one embodiment of the present invention, the nucleic acid sequences disclosed herein find utility as hybridization probes or amplification primers. In certain embodiments, these probes and primers consist of oligonucleotide fragments. Such fragments should be of sufficient length to provide specific hybridization to an RNA or DNA sample extracted from tissue. The sequences typically will be 10–20 nucleotides, but may be longer. Longer sequences, e.g., 40, 50, 100, 500 and even up to full length, are preferred for certain embodiments.

Nucleic acid molecules having contiguous stretches of about 10, 15, 17, 20, 30, 40, 50, 60, 75 or 100 or 500 nucleotides from a sequence selected from the group comprising SEQ ID NO:1, SEQ ID NO:3, SEQ ID NO:5, SEQ ID NO:7, HNF1α and its mutants are contemplated. In other embodiments nucleotides from a sequence selected from the group comprising SEQ ID NO:78, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, HNF4α and its mutants are contemplated. In still other embodiments nucleotides from a sequence. These probes will be useful in a variety of hybridization embodiments, such as Southern and northern blotting. In some cases, it is contemplated that probes may be used that hybridize to multiple target sequences without compromising their ability to effectively diagnose diabetes (MODY1, MODY3, and MODY4). In certain embodiments, it is contemplated that multiple probes may be used for hybridization to a single sample.

Various probes and primers can be designed around the disclosed nucleotide sequences. Primers may be of any length but, typically, are 10–20 bases in length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The values of n in the algorithm above for the nucleic acid sequences is: SEQ ID NO:1, n=3238 for HNF1α, SEQ ID NO:78 n=1441 for HNF4α, SEQ ID NO: 128.

The use of a hybridization probe of between 17 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional analogs of these sequences.

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

In an alternative embodiment, the HNF1α, HNF1β or HNF4α nucleic acids employed may actually encode antisense constructs that hybridize, under intracellular conditions, to an HNF1α, HNF1β or HNF4α nucleic acid, respectively. The term "antisense construct" is intended to refer to nucleic acids, preferably oligonucleotides, that are complementary to the base sequences of a target DNA or RNA. Antisense oligonucleotides, when introduced into a target cell, specifically bind to their target nucleic acid and interfere with transcription, RNA processing, transport, translation and/or stability.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the HNF1α, HNF1β, HNF4α gene sequence may be employed in the context of antisense construction, short oligonucleotides are easier to make and increase in vivo accessibility. However, both binding affinity and sequence specificity of an antisense oligonucleotide to its complementary target increases with increasing length. It is contemplated that antisense oligonucleotides of 8, 9, 10, 11, 12, 13, 14, 15, 16, 17, 18, 19, 20, 25, 30, 35, 40, 45, 50, 60, 70, 80, 90, 100 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase 11. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, and HNF1α (see for example, FIG. 22), HNF1β or HNF4α promoter (see for example, FIG. 13). The partial sequence of the human HNF1β gene including promoter has also been identified by the present inventors and deposited in the GenBank database under accession numbers U90279-90287 and U96079 (SEQ ID NO: 128). Another preferred embodiment is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 1 and 2 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

PROMOTER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
α-Globin
β-Globin
c-fos
c-HA-ras
Insulin
Neural Cell Adhesion Molecule (NCAM)
$\alpha_1$-Anti-trypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 2

| Element | Inducer |
|---|---|
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| β-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

Use of the baculovirus system will involve high level expression from the powerful polyhedron promoter.

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In various embodiments of the invention, the expression construct may comprise a virus or engineered construct derived from a viral genome. The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressing proteins of interest or (ii) to transform cells in vitro or in vivo to provide therapeutic polypeptides in a gene therapy scenario.

In some embodiments, the vector is HSV. Because HSV is neurotropic, it has generated considerable interest in treating nervous system disorders. Since insulin-secreting pancreatic β-cells share many features with neurons, HSV may be useful for delivering genes to β-cells and for gene therapy of diabetes. Moreover, the ability of HSV to establish latent infections in non-dividing neuronal cells without integrating into the host cell chromosome or otherwise altering the host cell's metabolism, along with the existence of a promoter that is active during latency. And though much attention has focused on the neurotropic applications of HSV, this vector also can be exploited for other tissues.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings.

F. Encoded Proteins

Once the entire coding sequence of a marker-associated gene has been determined, the gene can be inserted into an appropriate expression system. The gene can be expressed in any number of different recombinant DNA expression systems to generate large amounts of the polypeptide product, which can then be purified and used to vaccinate animals to generate antisera with which further studies may be conducted.

Examples of expression systems known to the skilled practitioner in the art include bacteria such as *E. coli,* yeast such as *Saccharomyces cerevisia* and *Pichia pastoris,* baculovirus, and mammalian expression systems such as in COS or CHO cells. In one embodiment, polypeptides are expressed in *E. coli* and in baculovirus expression systems. A complete gene can be expressed or, alternatively, fragments of the gene encoding portions of polypeptide can be produced.

In one embodiment, the gene sequence encoding the polypeptide is analyzed to detect putative transmembrane sequences. Such sequences are typically very hydrophobic and are readily detected by the use of standard sequence analysis software, such as MacVector (IBI, New Haven, Conn. The presence of transmembrane sequences is often deleterious when a recombinant protein is synthesized in many expression systems, especially *E. coli,* as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Therefore, antibodies to these sequences will not prove useful for in vivo or in situ studies. Deletion of transmembrane-encoding sequences from the genes used for expression can be achieved by standard techniques. For example, fortuitously-placed restriction enzyme sites can be used to excise the desired gene fragment, or PCR-type amplification can be used to amplify only the desired part of the gene. The skilled practitioner will realize that such changes must be designed so as not to change the translational reading frame for downstream portions of the protein-encoding sequence.

In one embodiment, computer sequence analysis is used to determine the location of the predicted major antigenic determinant epitopes of the polypeptide. Software capable of carrying out this analysis is readily available commercially, for example MacVector (1131, New Haven, Conn. The software typically uses standard algorithms such as the Kyte/Doolittle or Hopp/Woods methods for locating hydrophilic sequences which are characteristically found on the surface of proteins and are, therefore, likely to act as antigenic determinants.

Once this analysis is made, polypeptides can be prepared that contain at least the essential features of the antigenic determinant and that can be employed in the generation of antisera against the polypeptide. Minigenes or gene fusions encoding these determinants can be constructed and inserted into expression vectors by standard methods, for example, using PCR methodology.

The gene or gene fragment encoding a polypeptide can be inserted into an expression vector by standard subcloning techniques. In one embodiment, an *E. coli* expression vector is used that produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass., the FLAG system (IBI, New Haven, Conn., and the 6xHis system (Qiagen, Chatsworth, Calif.

Some of these systems produce recombinant polypeptides bearing only a small number of additional amino acids, which are unlikely to affect the antigenic ability of the recombinant polypeptide. For example, both the FLAG system and the 6xHis system add only short sequences, both of that are known to be poorly antigenic and which do not adversely affect folding of the polypeptide to its native conformation. Other fusion systems produce polypeptide where it is desirable to excise the fusion partner from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md. or Factor Xa (New England Biolabs, Beverley, Mass. Recombinant bacterial cells, for example *E coli,* are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

In another embodiment, the expression system used is one driven by the baculovirus polyhedron promoter. The gene encoding the polypeptide can be manipulated by standard techniques in order to facilitate cloning into the baculovirus vector. One baculovirus vector is the pBlueBac vector (Invitrogen, Sorrento, Calif. The vector carrying the gene for the polypeptide is transfected into *Spodoptera frugiperda* (Sf9) cells by standard protocols, and the cells are cultured and processed to produce the recombinant antigen. See Summers et al., A MANUAL OF METHODS FOR BACULOVIRUS VECTORS AND INSECT CELL CULTURE PROCEDURES, Texas Agricultural Experimental Station.

As an alternative to recombinant polypeptides, synthetic peptides corresponding to the antigenic determinants can be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

In one embodiment, amino acid sequence variants of the polypeptide can be prepared. These may, for instance, be minor sequence variants of the polypeptide that arise due to natural variation within the population or they may be homologues found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below in the following section.

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and -charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR can be used to prepare a range of cDNAs encoding peptides lacking successively longer fragments of the C-terminus of the protein. The immunoprotective activity of each of these peptides then identifies those fragments or domains of the polypeptide that are essential for this activity. Further experiments in which only a small number of amino acids are removed at each iteration then allows the location of the antigenic determinants of the polypeptide.

Another embodiment for the preparation of the polypeptides according to the invention is the use of peptide mimetics. Mimetics are peptide-containing molecules that mimic elements of protein secondary structure. See, for example, Johnson et al.,"Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within an polypeptide can be predicted by computer-based algorithms as discussed above. Once the component amino acids of the turn are determined, peptide mimetics can be constructed to achieve a similar spatial orientation of the essential elements of the amino acid side chains.

Modification and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982).

TABLE 3

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Senne | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

G. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

H. Expression and Purification of Encoded Proteins

1. Expression of Proteins from Cloned cDNAs

The cDNA species specified in SEQ ID NO: 1, SEQ ID NO:3, SEQ ID NO:5, SEQ ID NO:7, and HNF1α can be expressed as encoded peptides or proteins. In other embodiments cDNA species specified in SEQ ID NO:78, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, and HNF4α can be expressed as encoded peptides or proteins. The DNA species specified in SEQ ID NO: 128 and HNF1β can be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as $E.$ $coli$ and $B.$ $subtilis$ transformed with recombinant phage DNA, plasmid DNA or cosmid DNA expression vectors.

Certain examples of prokaryotic hosts are $E.$ $coli$ strain RR1, $E.$ $coli$ LE392, $E.$ $coli$ B, $E.$ $coli$ $\chi$ 1776 (ATCC No. 31537) as well as $E.$ $coli$ W3110 (F-, lambda-,prototrophic, ATCC No. 273325); bacilli such as $Bacillus$ $subtilis;$ and other enterobacteriaceae such as $Salmonella$ $typhimurium,$ $Serratia$ $marcescens,$ and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, $E.$ $coli$ is often transformed using pBR322, a plasmid derived from an $E.$ $coli$ species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as $E.$ $coli$ LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid contains the trpl gene, which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, $Autograph$ $californica$ nuclear polyhidrosis virus (AcNPV) is used as a vector to express foreign genes. The virus grows in $Spodoptera$ $frugiperda$ cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect $Spodoptera$ $frugiperda$ cells in which the inserted gene is expressed (e.g., U.S. Pat. No. 4,215,051).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HinDIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk, hgprt or aprt cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colberre-Garapin et al., 1981); and hygro, which confers resistance to hygromycin.

It is contemplated that the isolated nucleic acids of the invention may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

2. Purification of Expressed Proteins

Further aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or β-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., *Biochem. Biophys. Res. Comm.*, 76:425, 1977). It will therefore be appreciated that under differing electrophoresis conditions, the apparent molecular weights of purified or partially purified expression products may vary.

I. Preparation of Antibodies Specific for Encoded Proteins

Antibody Generation

For some embodiments, it will be desired to produce antibodies that bind with high specificity to the protein product(s) of an isolated nucleic acid selected from the group comprising SEQ ID NO:1, SEQ ID NO:3, SEQ ID NO:5, SEQ ID NO:7 or any other mutant of HNF1α, SEQ ID NO:78, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, or any other mutant of HNF4α, SEQ ID NO:128 (HNF1β) or any mutant of HNF1β. Means for preparing and characterizing antibodies are well known in the art (See, e.g., Antibodies: A Laboratory Manual, Cold Spring Harbor Laboratory, 1988; incorporated herein by reference).

Methods for generating polyclonal antibodies are well known in the art. Briefly, a polyclonal antibody is prepared by immunizing an animal with an antigenic composition and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or in some cases the animal can be used to generate MAbs. For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol.

These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this low frequency does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and thus they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or by expression of full-length gene or of gene fragments in *E. coli*.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99m}$Tc, are other useful labels that can be conjugated to antibodies. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$ by ligand exchange process, for example, by reducing pertechnate with stannous solution, chelating the reduced technetium onto a Sephadex column and applying the antibody to this column or by direct labelling techniques, e.g., by incubating pertechnate, a reducing agent such as $SNCl_2$, a buffer solution such as sodium-potassium phthalate solution, and the antibody.

It will be appreciated by those of skill in the art that monoclonal or polyclonal antibodies specific for HNF1α, HNF1β or HNF4α (for proteins that are mutated in MODY3, MODY4, and MODY1) will have utilities in several types of applications. These can include the production of diagnostic kits for use in detecting or diagnosing MODY3, MODY4, and MODY1 type diabetes. The skilled practitioner will realize that such uses are within the scope of the present invention.

J. Immunodetection Assays

The immunodetection methods of the present invention have evident utility in the diagnosis of conditions such as MODY3, MODY4, and MODY1 related NIDDM. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with MODY3, MODY4 or MODY1, the detection of an antigen encoded by an HNF1α nucleic acid, HNF4α nucleic acid, HNF1 β nucleic acid, or a decrease in the levels of such an antigen, in comparison to the levels in a corresponding biological sample from a normal subject is indicative of a patient with MODY3, MODY4, or MODY1. The basis for such diagnostic methods lies, in part, with the finding that the nucleic acid HNF1α, HNF1β and HNF4α mutants identified in the present invention are responsible for MODY3, MODY4, and MODY1 related diabetes, respectively. Hence, it can be inferred that at least some of these mutations produce elevated levels of encoded proteins, that may also be used as markers for MODY3, MODY4 or MODY1.

Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

1. Immunodetection Methods

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a HNF1α or HNF4α mutant encoded protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a HNF1α, HNF1β or HNF4α antigen, such as a pancreatic β-cell, a homogenized tissue extract, an isolated cell, a cell membrane preparation, separated or purified forms of any of the above protein-containing compositions, or even any biological fluid that comes into contact with diabetic tissue, including blood.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, ie., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

2. Immunohistochemistry

The antibodies of the present invention may also be used in conjunction with both fresh-frozen and formalin-fixed, paraffin-embedded tissue blocks prepared for study by immunohistochemistry (IHC). For example, each tissue block consists of 50 mg of residual "pulverized" diabetic tissue. The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" diabetic tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

3. ELISA

As noted, it is contemplated that the encoded proteins or peptides of the invention will find utility as immunogens, e.g., in connection with vaccine development, in immunohistochemistry and in ELISA assays. One evident utility of the encoded antigens and corresponding antibodies is in immunoassays for the detection of HNF1α, HNF1β and HNF4α, mutant proteins, as needed in diagnosis and prognostic monitoring of MODY.

Immunoassays, in their most simple and direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the encoded proteins of the invention are immobilized onto a selected surface exhibiting protein affinity, such as a well in a polystyrene microtiter plate. Then, a test composition suspected of containing the HNF1α, HNF1β or HNF4α mutant, such as a clinical sample, is added to the wells. After binding and washing to remove non-specifically bound immune complexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the mutant HNF1α, HNF1β or HNF4α antigen are immobilized onto the well surface and then contacted with the antibodies of the invention. After binding and washing to remove non-specifically bound immune complexes, the bound antigen is detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the mutant HNF1α protein, mutant HNF1β protein or mutant HNF4α protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control MODY3, MODY4 or MODY1 and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween™. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween™, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this label will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween™).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

4. Use of Antibodies for Radioimaging

The antibodies of this invention will be used to quantify and localize the expression of the encoded marker proteins. The antibody, for example, will be labeled by any one of a variety of methods and used to visualize the localized concentration of the cells producing the encoded protein. Such an assay also will reveal the subcellular localization of the protein, which can have diagnostic and therapeutic applications.

In accordance with this invention, the monoclonal antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}$Gd, $^{55}$Mn, $^{162}$Dy, $^{52}$Cr, and $^{56}$Fe.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example, 30 minutes to 48 hours, the area of the subject under investigation is examined by routine imaging techniques such as MRI, SPECT, planar scintillation imaging or newly emerging imaging techniques. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue can be determined.

It will be apparent to those of skill in the art that a similar approach may be used to radio-image the production of the encoded HNF1α HNF1β or HNF4α mutant proteins in human patients. The present invention provides methods for the in vivo diagnosis of MODY3, MODY4 or MODY1 in a patient. Such methods generally comprise administering to a patient an effective amount of an HNF1α, HNF1β or HNF4α mutant specific antibody, to which antibody is conjugated a marker, such as a radioactive isotope or a spin-labeled molecule, that is detectable by non-invasive methods. The antibody-marker conjugate is allowed sufficient time to come into contact with reactive antigens that are present within the tissues of the patient, and the patient is then exposed to a detection device to identify the detectable marker.

5. Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

K. Detection and Quantitation of Nucleic Acid Species

One embodiment of the instant invention comprises a method for identification of HNF1α, HNF1β or HNF4α mutants in a biological sample by amplifying and detecting nucleic acids corresponding to HNF1α, HNF1β or HNF4α mutants. The biological sample can be any tissue or fluid in which these mutants might be present. Various embodiments include β and α-cells of pancreatic islets, bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to HNF1α, HNF1β or HNF4α mutants are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a statistically significant reference group of normal patients and MODY or indeed MODY dependent diabetics and non MODY dependent diabetics. In this way, it is possible to correlate the amount of HNF1α, HNF1β or HNF4α mutants detected with various clinical states.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

2. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labelling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989); Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific-sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA" ) molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M.A., In: PCR PROTOCOLS: A GUIDE TO METHODS AND APPLICATIONS, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., 1989), incorporated herein by reference in its entirety.

3. RNase Protection Assay

Methods for genetic screening by identifying mutations associated with most genetic diseases such as diabetes must be able to assess large regions of the genome. Once a relevant mutation has been identified in a given patient, other family members and affected individuals can be screened using methods which are targeted to that site. The ability to detect dispersed point mutations is critical for genetic counseling, diagnosis, and early clinical intervention as well as for research into the etiology of cancer and other genetic disorders. The ideal method for genetic screening would quickly, inexpensively, and accurately detect all types of widely dispersed mutations in genomic DNA, cDNA, and RNA samples, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others (Cotton, 1989). The more common procedures currently in use include direct sequencing of target regions amplified by PCR™ and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations. U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as +.

Currently available RNase mismatch cleavage assays, including those performed according to U.S. Pat. No. 4,946, 773, require the use of radiolabeled RNA probes. Myers and Maniatis in U.S. Pat. No. 4,946,773 describe the detection of base pair mismatches using RNase A Other invenstigators have described the use of *E.coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay as first described by Melton et al. (1984) was used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations by Myers and Maniatis (1985) and by Winter and Perucho (1985). In this type of RNase A mismatch cleavage assay, radiolabeled RNA probes transcribed in vitro from wild type sequences, are hybridized to complementary target regions derived from test samples. The test target generally comprises DNA (either genomic DNA or DNA amplified by cloning in plasmids or by PCR™), although RNA targets (endogenous mRNA) have occasionally been used (Gibbs and Caskey, 1987; Winter et al., 1985). If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches (Ellis et al., 1994; Lishanski et al., 1994).

By hybridizing each strand of the wild type probe in RNase cleavage mismatch assays separately to the complementary Sense and Antisense strands of the test target, two different complementary mismatches (for example, A-C and G-U or G-T) and therefore two chances for detecting each mutation by separate cleavage events, was provided. Myers et al. (1985) used the RNase A cleavage assay to screen 615 bp regions of the human β-globin gene contained in recombinant plasmid targets. By probing with both strands, they were able to detect most, but not all, of the β-globin mutations in their model system. The collection of mutants included examples of all the 12 possible types of mismatches between RNA and DNA: rA/dA, rC/dC, rU/dC, rC/dA, rC/dT, rU/dG, rH/dA, ro/dG, rU/dG, rA/dC, rG/dT, and rA/dG.

Myers et. al. (1985) showed that certain types of mismatch were more frequently and more completely cleaved by RNase A than others. For example, the rC/dA, rC/dC, and rC/dT mismatches were cleaved in all cases, while the rG/dA mismatch was only cleaved in 13% of the cases tested and the rG/dT mismatch was almost completely resistant to cleavage. In general, the complement of a difficult-to-detect mismatch was much easier to detect. For example, the refractory rG/dT mismatch generated by probing a G to A mutant target with a wild type sense-strand probe, is complemented by the easily cleaved rC/dA mismatch generated by probing the mutant target with the wild type antisense strand. By probing both target strands, Myers and Maniatis (1986) estimated that at least 50% of all single-base mutations would be detected by the RNase A cleavage assay. These authors stated that approximately one-third of all possible types of single-base substitutions would be detected by using a single probe for just one strand of the target DNA (Myers et al., 1985).

In the typical RNase cleavage assays, the separating gels are run under denaturing conditions for analysis of the cleavage products. This requires the RNase to be inactivated by treating the reaction with protease (usually Proteinase K, often in the presence of SDS) to degrade the RNase. This reaction is generally followed by an organic extraction with a phenol/chloroform solution to remove proteins and residual RNase activity. The organic extraction is then followed by concentration and recovery of the cleavage products by alcohol precipitation (Myers et al., 1985; Winter et al., 1985; Theophilus et al., 1989).

4. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

5. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

6. Kit Components

All the essential materials and reagents required for detecting MODY markers in a biological sample may be assembled together in a kit. This generally will comprise pre-selected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in SEQ ID NO:3, SEQ ID NO:7 or SEQ ID NO:5, along with the cDNAs for HNF1α (SEQ ID NO:1) HNF1β (SEQ ID NO:128) and HNF4α (SEQ ID NO:78). In other embodiments preferred pairs of primers for amplification are selected to amplify sequences specified in SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54.

In another embodiment, such kits will comprise hybridization probes specific for MODY3, chosen from a group including nucleic acids corresponding to the sequences specified in SEQ ID NO:1, SEQ ID NO:3, SEQ ID NO:5, and SEQ ID NO:7, along with the cDNAs for HNF1α (SEQ ID NO:1). In yet another embodiment such kits will comprise probes specific for MODY 1 chosen from a group including nucleic acids corresponding to the sequences specified in SEQ ID NO:78, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, along with the cDNAs for HNF4α (SEQ ID NO:78). In still another embodiment such kits will comprise probes specific for MODY4 chosen from a group including nucleic acids corresponding to the sequences specified in SEQ ID NO:128, HNF1β or any of the exons shown in FIG. 27A–FIG. 27I, or Genbank accession numbers U90279-90287 and U96079, incorporated herein by reference.

Such kits generally will comprise, in suitable means, distinct containers for each individual reagent and enzyme as well as for each marker hybridization probe.

L. Use of RNA Fingerprinting to Identify MODY3, MODY4, and MODY1 Markers

RNA fingerprinting is a means by which RNAs isolated from many different tissues, cell types or treatment groups can be sampled simultaneously to identify RNAs whose relative abundances vary. Two forms of this technology were developed simultaneously and reported in 1992 as RNA fingerprinting by differential display (Liang and Pardee, 1992; Welsh et al., 1992). (See also Liang and Pardee, U.S. Pat. No. 5,262,311, incorporated herein by reference in its entirety.) Some of the experiments described herein were performed similarly to Donahue et al., *J. Biol Chem.* 269: 8604–8609,1994.

All forms of RNA fingerprinting by PCR are theoretically similar but differ in their primer design and application. The most striking difference between differential display and other methods of RNA fingerprinting is that differential display utilizes anchoring primers that hybridize to the poly A tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo dT and any two of the four deoxynucleosides. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis and ethidium bromide staining or autoradiography. A side by side comparison of fingerprints obtained from for example tumor versus normal tissue samples using the same oligonucleotide primers identifies mRNAs that are differentially expressed.

RNA fingerprinting technology has been demonstrated as being effective in identifying genes that are differentially expressed in cancer (Liang et al., 1992; Wong et al., 1993; Sager et al., 1993; Mok et al., 1994; Watson et al., 1994; Chen et al., 1995; An et al., 1995). The present invention utilizes the RNA fingerprinting technique to identify genes that are differentially expressed in diabetes.

Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from MODY3, MODY4, and MODY1 patients. By determining that the concentration of a specific mRNA species varies, it is shown that the gene encoding the specific mRNA species is differentially expressed. This technique can be used to confirm that mRNA transcripts shown to be differentially regulated by RNA fingerprinting are differentially expressed in MODY related diabetes.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

M. Methods for Activation of Gene Expression

In one embodiment of the present invention, there are provided methods for the increased gene expression or activation in a cell. This is particularly useful where there is an aberration in the gene product or gene expression is not sufficient for normal function. This will allow for the alleviation of symptoms of MODY3 type diabetes experienced as a result of mutation in HNF1α, MODY4 type diabetes experienced as a result of mutation in HNF1β and MODY1 type diabetes experienced as a result of mutation in HNF4α.

The general approach to increasing gene expression as mediated by HNF1α, HNF1β or HNF4α according to the present invention, will be to provide a cell with an HNF1α, HNF1β or HNF4α polypeptide, thereby permitting the transcription promotional activity of HNF1α, HNF1β or HNF4α to take effect. While it is conceivable that the protein may be delivered directly, a preferred embodiment involves providing a nucleic acid encoding an HNF1α, HNF1β or HNF4α polypeptide, i.e., an HNF1α, HNF1β or HNF4α gene, to the cell. Following this provision, the HNF1α HNF1β or HNF4α polypeptide is synthesized by the host cell's transcriptional and translational machinery, as well as any that may be provided by the expression construct. Cis-acting regulatory elements necessary to support the expression of the HNF1α HNF1β or HNF4α gene will be provided, in the form of an expression construct. It also is possible that, expression of the virally-encoded HNF1α, HNF1β or HNF4α could be stimulated or enhanced, or the expressed polypeptide stabilized, thereby achieving the same or similar effect.

In order to effect expression of constructs encoding HNF1α, HNF1β or HNF4α genes, the expression construct must be delivered into a cell. One mechanism for delivery is via viral infection, where the expression construct is encapsulated in a viral particle which will deliver either a replicating or non-replicating nucleic acid. In certain embodiments an HSV vector is used, although virtually any vector would suffice.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et. al., 1990), and receptor-mediated transfection (Wu and Wu, 1987; Wu and Wu, 1988). Some of these techniques may be successfully adapted for in vivo or ex vivo use, as discussed below.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well. Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

Other expression constructs which can be employed to deliver a nucleic acid encoding an HNF1α, HNF1β or HNF4α transgene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994). Mannose can be used to target the mannose receptor on liver cells. Also, antibodies to CD5 (CLL), CD22 (lymphoma), CD25 (T-cell leukemia) and MAA (melanoma) can similarly be used as targeting moieties. In other embodiments, the delivery vehicle may comprise a ligand and a liposome.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use - the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

N. Methods for Blocking Mutant HNF1α, HNF1β and HNF4α Action

In another embodiment of the present invention, there is contemplated the method of blocking the function of mutated HNF1α in MODY3, HNF1β in MODY4, and HNF4α in MODY 1. In this way, it may be possible to curtail the effects of the mutation in diabetes. In addition, it may prove effective to use this sort of therapeutic intervention in combination with more traditional diabetes therapies, such as the administration of insulin.

The general form that this aspect of the invention will take is the provision, to a cell, of an agent that will inhibit mutated HNF1α, HNF1β or HNF4α function. Four such agents are contemplated. First, one may employ an antisense nucleic acid that will hybridize either to the mutated HNF1α, HNF1β or HNF4α gene or the mutated HNF1α, HNF1β or HNF4a gene transcript, thereby preventing transcription or translation, respectively. The considerations relevant to the design of antisense constructs have been presented above. Second, one may utilize a mutated HNF1α-, HNF1β- or HNF1α-binding protein or peptide, for example, a peptidomimetic or an antibody that binds immunologically to a mutated HNF1α, HNF1β or HNF4α respectively, the binding of either will block or reduce the activity of the mutated HNF1α, HNF1β and HNF4α respectively. The methods of making and selecting peptide binding partners and antibodies are well known to those of skill in the art. Third, one may provide to the cell an antagonist of mutated HNF1α, HNF1β or HNF4α for example, the trans-activation target sequence, alone or coupled to another agent. And fourth, one may provide an agent that binds to the mutated HNF1α, HNF1β or HNF4α target without the same functional result as would arise with mutated HNF1α, HNF1β or HNF4α binding.

Provision of an HNF1α, HNF1β or HNF4α gene, a mutated HNF1α, HNF1β or HNF4α protein, or a mutated HNF1α, HNF1β or HNF4α antagonist, would be according to any appropriate pharmaceutical route. The formulation of such compositions and their delivery to tissues is discussed below. The method by which the nucleic acid, protein or chemical is transferred, along with the preferred delivery route, will be selected based on the particular site to be treated. Those of skill in the art are capable of determining the most appropriate methods based on the relevant clinical considerations.

Many of the gene transfer techniques that generally are applied in vitro can be adapted for ex vivo or in vivo use. For example, selected organs including the liver, skin, and muscle tissue of rats and mice have been bombarded in vivo (Yang et al., 1990; Zelenin et al, 1991). Naked DNA also has been used in clinical settings to effect gene therapy. These approaches may require surgical exposure of the target tissue or direct target tissue injection. Nicolau et al. (1987) accomplished successful liposome-mediated gene transfer in rats after intravenous injection.

Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. Thus, it is envisioned that DNA encoding an antisense construct also may be transferred in a similar manner in vivo.

Where the embodiment involves the use of an antibody that recognizes a mutated HNF1α, HNF1β or HNF4α polypeptide, consideration must be given to the mechanism by which the antibody is introduced into the cell cytoplasm. This can be accomplished, for example, by providing an expression construct that encodes a single-chain antibody version of the antibody to be provided. Most of the discussion above relating to expression constructs for antisense versions of HNF1α, HNF1β or HNF4α genes will be relevant to this aspect of the invention. Alternatively, it is possible to present a bifunctional antibody, where one antigen binding arm of the antibody recognizes an HNF1α, HNF1β or HNF4α polypeptide and the other antigen binding arm recognizes a receptor on the surface of the cell to be targeted. Examples of suitable receptors would be an HSV glycoprotein such as gB, gC, gD, or gH. In addition, it may be possible to exploit the Fc-binding function associated with HSV gE, thereby obviating the need to sacrifice one arm of the antibody for purposes of cell targeting.

Advantageously, one may combine this approach with more conventional diabetes therapy options.

O. Pharmaceuticals and In vivo Methods for the Treatment of Disease

Aqueous pharmaceutical compositions of the present invention will have an effective amount of an HNF1α, HNF1β or HNF4α expression construct, an antisense HNF1α, HNF1β or HNF4α expression construct, an expression construct that encodes a therapeutic gene along with HNF1α, HNF1β or HNF4α, a protein or compound that inhibits mutated HNF1α, HNF1β or HNF4α function respectively, such as an anti-mutant HNF1α antibody, an anti-mutant HNF1β antibody or an anti-mutant HNF4α antibody, or a mutated HNF1α polypeptide, mutated HNF1β polypeptide or a mutated HNF4α polypeptide. Such compositions generally will be dissolved or dispersed in a pharmaceutically acceptable carrier or aqueous medium. An "effective amount," for the purposes of therapy, is defined at that amount that causes a clinically measurable difference in the condition of the subject. This amount will vary depending on the substance, the condition of the patient, the type of treatment, the location of the lesion, etc.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredients, its use in the therapeutic compositions is contemplated. Supplementary active ingredients, such as other anti-diabetic agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains mutated HNF1α, HNF1β or HNF4α inhibitory compounds alone or in combination with a conventional diabetes therapy agents as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

P. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Altered Insulin Secretory Responses To Glucose In Diabetic And Nondiabetic Subjects With Mutations In The Diabetes Mellitus Susceptibility Gene MODY3 On Chromosome 12

The present Example determines whether alterations in the dose-response relationships between plasma glucose concentration and insulin secretion rate (ISR) can be identified in subjects who have inherited an at-risk MODY3 allele but who have not yet developed overt diabetes.

1. Methods

Subjects from MODY3 Pedigrees

Figure 1:
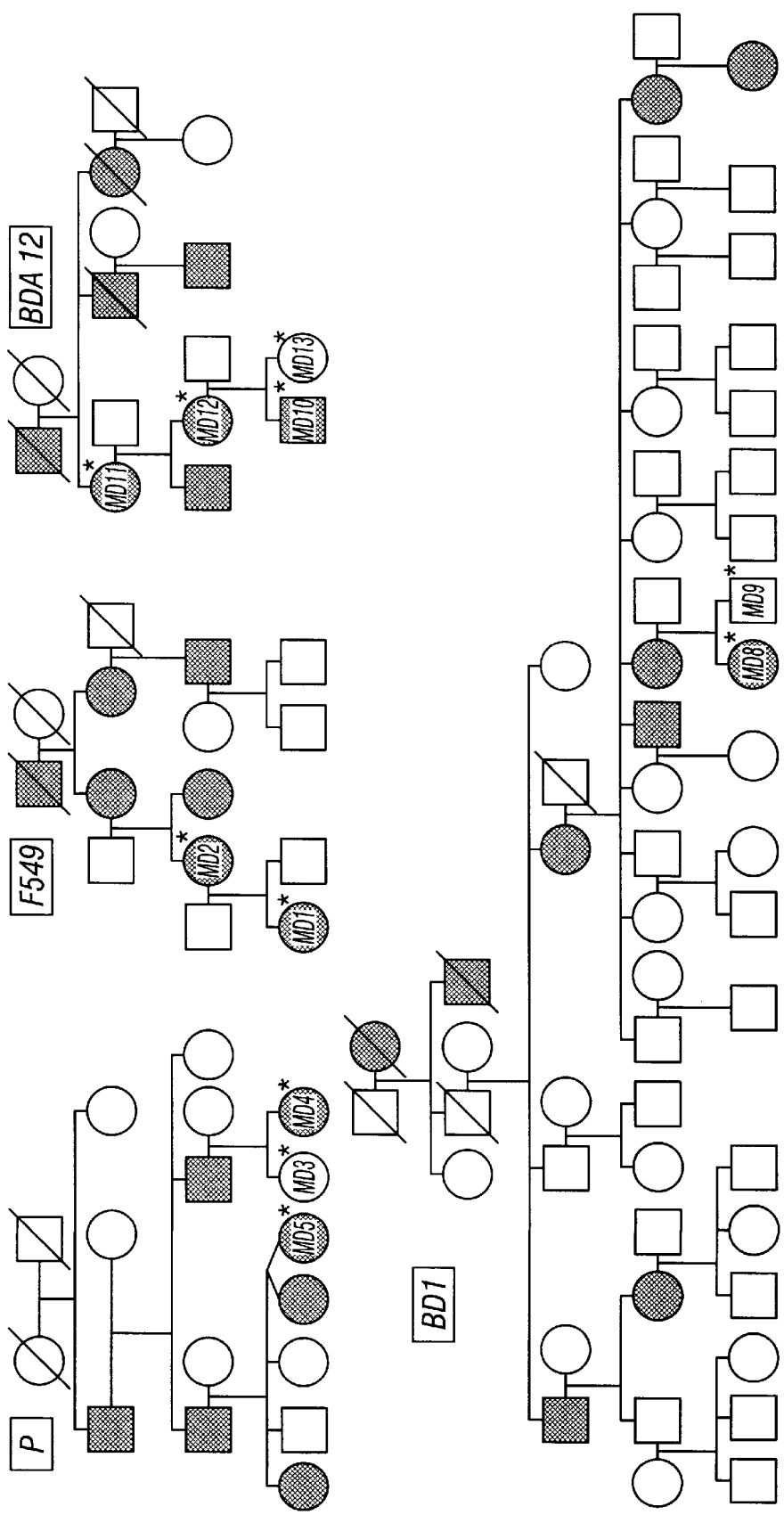
FIG. 1. Pedigrees of MODY3 families. The individuals studied in the Clinical Research Center at the University of Chicago are indicated by MD-1-5 and 8-13 and those with NIDDM, IGT and NGT are shown by black symbols, shaded symbols and open symbols, respectively. The asterisks indicate that these individuals have inherited the at-risk haplotype associated with MODY3 in that family. The genotypes and haplotypes for the P family have been described (Menzel et al., 1995) and the pairwise lod score between MODY and the D12S76/D12S321 haplotype in this family is 2.06 at a recombination fraction of 0.00. The pairwise lod score between MODY and D12S76 in pedigree F549 is 0.65 at a recombination fraction of 0.00 (Vaxillaire et al., 1995). The pedigrees BDA1 and BDA12 have not been previously described. MODY co-segregates with markers tightly linked to MODY3 in these families with pairwise lod scores between MODY and D12S86 of 1.94 and 0.60, respectively, at a recombination fraction of 0.00.

Thirteen Caucasian subjects who were positive for MODY3 markers on chromosome 12q were studied. Two subjects were members of a French pedigree F549 (Vaxillaire et al.,1995), three were from the P pedigree from Michigan (Menzel et al., 1995), two from a New York pedigree the H pedigree depicted in FIG. 1, two were from a Liverpool pedigree, the BDA1 pedigree and four from a Nottingham pedigree, the BDA12 pedigree (FIG. 1). Each subject was typed with a series of DNA markers in the region of MODY3 to determine whether or not they had inherited the at-risk haplotype segregating with MODY in that family. The diabetes status of each subject except for MD13, had been determined by oral glucose tolerance testing (OGTT) according to the World Health Organization (WHO) criteria (WHO Study Group on Diabetes Mellitus, 1985) and confirmed at the time of the studies by the measurement of glycosylated hemoglobin. Based on the results of the OGTT and glycosylated hemoglobin values within or above the normal range for the inventors'laboratory (<7.4%) subjects were divided into diabetic and nondiabetic groups.

Nondiabetic MODY3 subjects (n=6).

The clinical profiles of these subjects are described in Table 4. All had normal fasting glucose and glycosylated hemoglobin (<7.4%) levels at the time of this study. At the time of study 4 subjects had IGT (MD1, MD4, MD9, MD13) and 2 subjects had normal glucose tolerance (NGT) (MD3, MD5). Based on previous glucose tolerance testing MD1 had IGT, MD3 consistently demonstrated NGT on serial OGTTs, MD4 was diagnosed with IGT in 6/93 and has persistent IGT with a 2-h postprandial blood glucose level of 147 mg/dl, MD5 was initially diagnosed with IGT and subsequently had 2 normal OGTTs, with 2-h blood glucose values of 130 mg/dl and 105 mg/dl, respectively, MD9 had IGT, with a 2-h post-challenge blood glucose level was 167 mg/dl with no other blood glucose level above 200 mg/dl and MD13 had IGT with elevated postprandial blood glucose levels in the past up to 160 mg/dl. Age of diagnosis refers to the age at which abnormal glucose tolerance was diagnosed. None of these subjects were ever diagnosed with NIDDM.

Diabetic MODY3 subjects (n=7).

Clinical profiles are shown in Table 4. All subjects had been treated with oral hypoglycemic agents except for MD8 who was taking insulin which was discontinued two days prior to the study and MD12 who was treated with diet alone. All subjects had discontinued treatment with oral hypoglycemic agents at least three weeks prior to being studied. As shown in Table 4, fasting plasma glucose and total glycosylated hemoglobin levels were higher in the diabetic group and fasting insulin levels were lower. The diabetic group was also significantly older than the other two groups.

Nondiabetic controls.

The control subjects consisted of 5 males and one female (5 Caucasians and 1 African American) who did not have a personal or family history of NIDDM. They were all within 20% of ideal body weight, had no medical illnesses and were not receiving any medications. Data from four of the control subjects have previously been published (Byrne et al., 1994; Byrne et al., 1995a). BMI was not significantly different between the control and diabetic or nondiabetic MODY3 groups.

Female volunteers had regular menstrual cycles and were studied only in the early follicular phase. The study was approved by the Institutional Review Board of the University of Chicago Medical Center and all subjects and/or parents provided written informed consent.

Experimental Protocol

Studies began at 0800 h with subjects in the recumbent position after a 12-h overnight fast. An intravenous catheter was placed in each forearm, one for blood sampling and one for glucose administration. In all experiments, the arm containing the sampling catheter was maintained in a heating blanket or hot hand box to ensure arterialization of the venous sample.

Graded glucose infusion studies.

These studies were designed to characterize the dose-response relationships between glucose and insulin secretion rate (ISR). In order to eliminate potentially confounding effects of differences in the basal glucose concentration, each study began with the administration of a small bolus of insulin intravenously (0.007 U/kg) followed by a low dose continuous infusion of insulin to lower the fasting plasma glucose to similar levels in all groups (target plasma glucose=5 mM). After a period of 20 min during which time the exogenously administered insulin was allowed to decay, samples were drawn at 10 min intervals for 30 min to define baseline insulin, glucose and C-peptide levels. An intravenous infusion of 20% dextrose was then started at a rate of 1 mg/kg/min, followed by infusions of 2 mg/kg/min, 3 mg/kg/min, 4 mg/kg/min, 6 mg/kg/min and 8 mg/kg/min. Each infusion rate was administered for a period of 40 min. Insulin, C-peptide and glucose concentrations were measured at 10, 20, 30 and 40 min into each infusion period.

Effects of prolonged intravenous glucose administration on insulin secretory responses to graded glucose infusions.

At the completion of the graded glucose infusion study described above, glucose was infused intravenously for a 42-h period at a rate of 4–6 mg/kg/min in order to determine if the insulin secretory responses to glucose could be primed by exposure to mild hyperglycemia. Subjects also consumed three carbohydrate enriched meals during the second day of this glucose infusion. At the conclusion of the 42-h infusion period, the infusion rate was reduced over a 60 min period and then stopped. Thirty minutes later, the graded glucose infusion study was repeated. Plasma glucose levels were obtained every four hours during the 42-h glucose infusion.

Assays.

Plasma glucose was measured by the glucose oxidase technique (YSI analyzer, Yellow Springs, Ohio). The coefficient of variation of this method is <2%. Serum insulin was assayed by a double antibody technique (Morgan and Lazarow, 1963). The average intra-assay coefficient of variation was 6%. Plasma C-peptide was measured as previously described (Faber et al., 1978). The lower limit of sensitivity of the assay was 0.02 pmol/ml and the intra-assay coefficient of variation averaged 6%. All samples were measured in duplicate. Assays were performed at the University of Chicago.

Data Analysis

Estimation of ISRs. ISRs were derived by deconvolution of plasma C-peptide concentrations assuming a two-compartmental model of C-peptide clearance kinetics (Van Cauter et al., 1992; Eaton et al., 1980; Polonsky et al., 1986).

Relationship between glucose and ISRs.

The relationship between plasma glucose and ISR was explored in each individual by analyzing the data from the graded glucose infusion studies. Baseline glucose, insulin, C-peptide and ISRs were calculated as the mean of the values in the -30, -20, -10 and 0 min samples. During each glucose infusion period, average glucose and ISRs were calculated. Mean ISRs for each period were then plotted against the corresponding mean glucose level, thereby establishing a dose-response relationship between glucose and ISR. Mean ISRs were determined for 1 mM glucose concentration intervals by calculating the area under the curve for each interval using the trapezoidal rule. This area was divided by 1 mM to obtain the correct units (pmol/min).

Statistical Analyses

All results are expressed as mean±SEM. Data analysis was performed using the Statistical Analysis System (SAS Version 6 Edition for Personal Computers, SAS Institute, Inc., Cary, N.C.). The significance of differences between the groups was determined using paired or unpaired t-tests or analysis of variance where appropriate. Tukey's studentized range test was used for post hoc comparisons. Pearson's correlation coefficient was used to evaluate correlations between pairs of parameters.

2. Results

Glucose, Insulin and ISR During Graded Intravenous Glucose Infusion

Figure 2A:
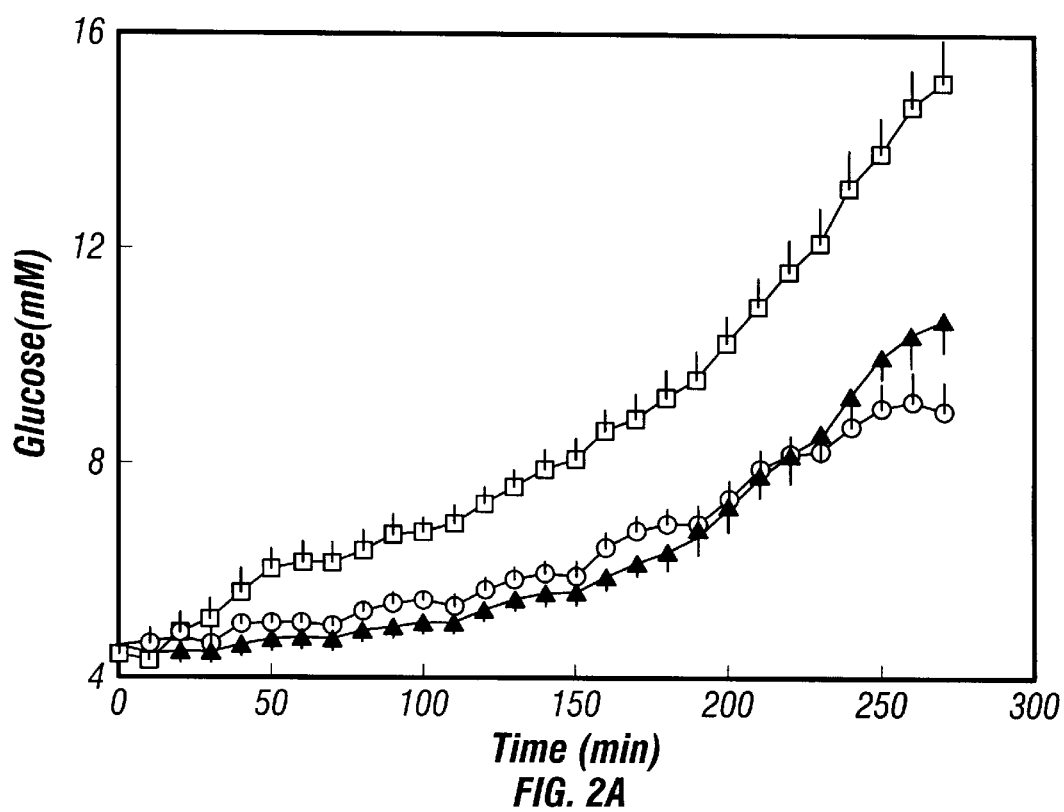
FIG. 2A and FIG. 2B. Average glucose (FIG. 2A), insulin (FIG. 2B) and insulin secretion rate (ISR) (FIG. 2C) profiles in 7 diabetic MODY3 subjects (□), 6 nondiabetic MODY3 subjects (▲) and 6 control subjects (○), during the stepped glucose infusion studies. After a 30 min period of baseline sampling, glucose was infused at rates of 1, 2, 3, 4, 6, and 8 mg $-kg^{-1}$ $-min^{-1}$. Each infusion rate was administered for a period of 40 min and glucose, insulin and C-peptide were measured at 10, 20, 30 and 40 min into each period.
Figure 2B:
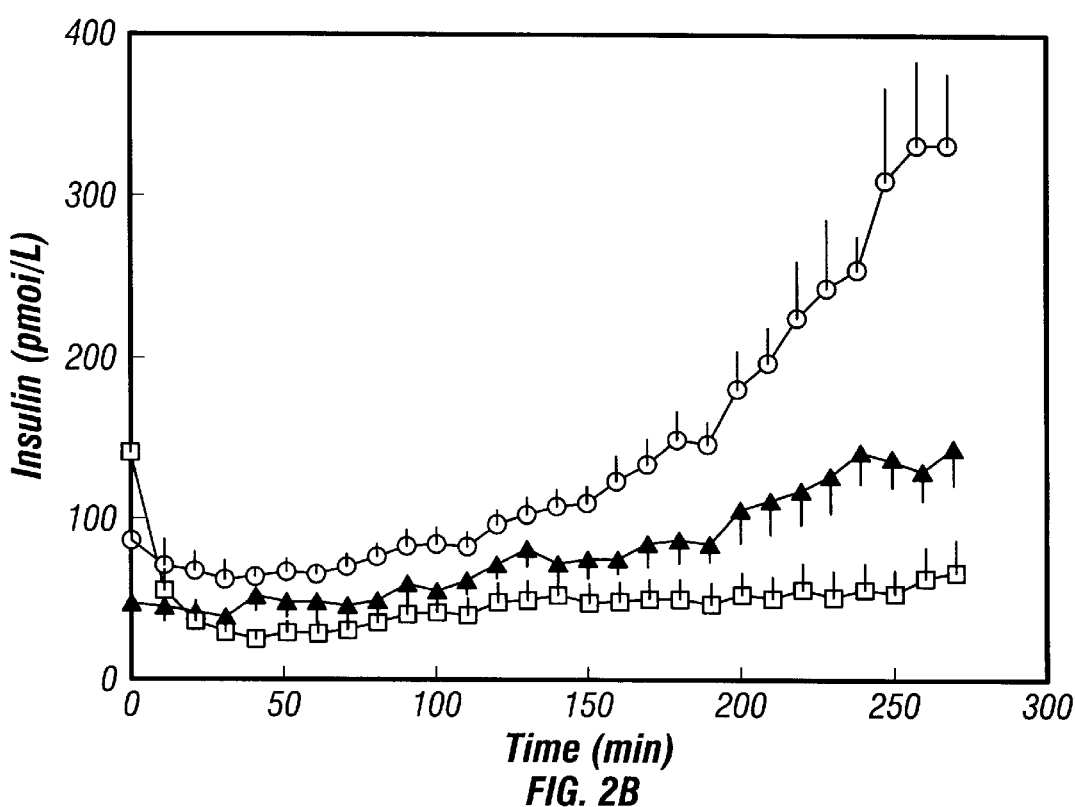

Fasting plasma glucose levels were higher in the MODY3 diabetic group compared to the nondiabetic group or controls (7.5±0.7 mM vs. 4.5±0.2 mM and 4.7±0.2, respectively; P>0.0008). The corresponding fasting plasma insulin levels were lower in the diabetic MODY3 group compared to nondiabetics and controls (Table 4). Glucose, insulin and ISR responses to the glucose infusions are shown in FIG. 2A, FIG. 2B and FIG. 2C, respectively. Average glucose concentrations over the duration of the study were higher in the diabetic MODY3 subjects compared to the nondiabetic MODY3 and control subjects (8.5±0.4 mM vs. 6.3±0.3 mM and 64±0.2; P<0.0002) (FIG. 2A). Average insulin levels were lower in the diabetic and nondiabetic MODY3 groups than in the controls (57.4±8.2 pmol/L and 79.8±11.0 vs. 139.3±14.7 pmol/L; P<0.0006) (FIG. 2B). Average ISR's were significantly lower in diabetic compared to the nondiabetic MODY3 subjects and the controls (116±18.8 pmol/min vs. 179.7±19.9 pmol/min and 1995±18.7; P<0.02) (FIG. 2C).

TABLE 5

| | Insulin Secreted between 5 and 9 mM glucose | | |
|---|---|---|---|
| ID | Baseline | Post-glucose | Priming effect % |
| Non-diabetic MODY3 | | | |
| MD1 | 188.1 | 221.6 | 17.9 |
| MD3 | 164.5 | 255 | 55 |
| MD4 | 136.6 | 208.3 | 52.5 |
| MD5 | 297.5 | 342.5 | 15.1 |
| MD9 | 249.1 | 292.1 | 34.5 |
| MD13 | 248.1 | 234.2 | −5.9 |
| MEAN | 214.3 ± 24.8 | 259 ± 20.6 | 35 ± 8 |
| Diabetic MODY3 | | | |
| MD2 | 67.4 | 68.9 | 2.2 |
| MD6 | 131.5 | 109.1 | −17 |
| MD7 | 144.6 | 85.2 | −41 |
| MD8 | 156.6 | 189.3 | 20.9 |
| M10 | 63.7 | 34.9 | −45 |
| M11 | 38.2 | 28.4 | −26 |
| M12 | 102.6 | 115.1 | 12.2 |
| MEAN | 100.8 ± 17.3* | 90.0 ± 20.8* | −13.4 ± 9.8* |
| Controls | | | |
| C05 | 318.1 | 356.8 | 12.2 |
| C07 | 209.5 | 272.1 | 29.2 |
| C09 | 166.9 | 223.1 | 33.7 |
| C12 | 235.6 | 381.6 | 62.0 |
| C13 | 215.6 | 306.5 | 42.2 |
| C18 | 120.1 | 180.5 | 50.3 |
| MEAN | 211 ± 27 | 287 ± 32 | 38 ± 7 |
| p value | p < 0.004 | P < 0.002 | p < 0.009 |

The amount of insulin secreted as glucose was raised from 5 to 9 mM in study subjects before and after a priming intravenous infusion of glucose. Asterisks refer to statistically significant differences between the diabetic subjects and those in the other two groups using Tukey's studentized range test for post-hoc comparisons.

TABLE 4

| | Kindred/Generation/Glucose | | | | | Age of | Fasting | Fasting | |
|---|---|---|---|---|---|---|---|---|---|
| ID | Subject | Tolerance | Sex | Age | BMI | Diagnosis | Glucose mM | Insulin pmol/l | Glycohemoglobin |
| Non-Diabetic MODY 3 | | | | | | | | | |
| MD1 | F549 IV-1 | IGT | F | 17.0 | 24.0 | 12 | 4.69 | 43.0 | 6.0 |
| MD3 | P IV-6 | NGT | F | 19.0 | 17.9 | | 3.86 | 23.1 | 5.1 |
| MD4 | P IV-7 | IGT | F | 14.0 | 17.1 | 12 | 4.47 | 33.8 | 5.1 |
| MD5 | P IV-5 | NGT | F | 15.0 | 18.8 | 13 | 4.22 | 63.6 | 5.1 |
| MD9 | BDA1 V-12 | IGT | M | 14.0 | 20.0 | 12 | 4.77 | 69.9 | 6.4 |
| MD13 | BDA12 IV-2 | IGT | F | 14.0 | 23.7 | 12 | 5.17 | 60.9 | 6.4 |
| Mean ± SEM | | | | 15.5 ± 0.9 | 20.4 ± 1.2 | | 4.5 ± 0.2 | 49.1 ± 7.6 | 5.7 ± 0.3 |
| Diabetic MODY3 | | | | | | | | | |
| MD2 | F549 III-2 | NIDDM | F | 41 | 23.2 | 30 | 8.89 | 35.0 | 7.5 |
| MD6 | H IV-1 | NIDDM | F | 17 | 23.6 | 16 | 7.39 | 24.7 | 10.6 |
| MD7 | H IV-2 | NIDDM | F | 15 | 19.4 | 14 | 7.11 | 48.8 | 8.9 |
| MD8 | BDA1 V-11 | NIDDM | F | 17 | 20.9 | 12 | 4.22 | | 7.6 |
| M10 | BDA 12-II-1 | NIDDM | F | 67 | 26.1 | 27 | 8.67 | 29.8 | 8.4 |
| M11 | BDA 12 IV-1 | NIDDM | M | 17 | 17.8 | 14 | 10.1 | 16.6 | 10.1 |
| M12 | BDA 12 III-2 | NIDDM | F | 46 | 21.4 | 14 | 6.19 | 43.0 | 7.6 |
| Mean ± SEM | | | | 31.4 ± 7.7 | 21.4 ± .9 | | 7.51 ± 0.7* | 33 ± 4.8* | 8.7 ± 0.5* |
| Controls | | | | | | | | | |
| Mean ± SEM | | | | 17.7 ± .2 | 21.1 ± 0.7 | | 4.7 ± 0.2 | 69.9 ± 8 | <6.2 |
| P value | | | | p > 0.08 | p > 0.8 | | P < 0.0008 | P < 0.007 | P < 0.0004 |

Demographic data on the study subjects. Age of diagnosis refers to the age at which diabetes or IGT was diagnosed. MD3 is the only MODY3 subject who had demonstrated consistently normal glucose tolerance. p values refer to the results of analysis of variance comparing the three groups. The asterisks denote statistically significant differences between the diabetic subjects and the other two groups using Tukey's studentized range test for post-hoc comparisons.

Changes in Insulin Sensitivity

Insulin resistance estimated by the Homeostasis Model Assessment Method (HOMA) (Matthews et al., 1985) failed to demonstrate significant differences between the groups (diabetic MODY3: 1.9±0.2; nondiabetic MODY3: 1.7±0.3; controls: 2.4±0.2; P=0.11).

Dose-response Relationship Between Glucose and ISR

Figure 3:
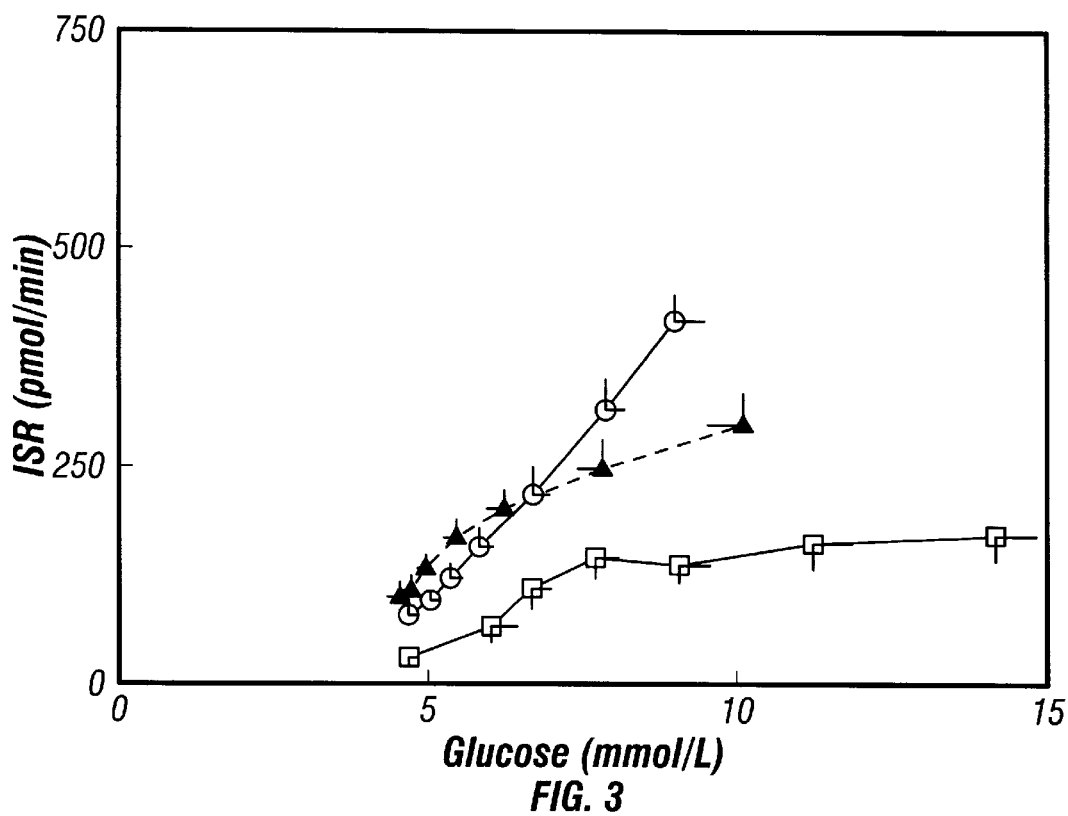
FIG. 3. Relationship between average plasma glucose concentrations and ISR's during the stepped glucose infusion studies in 7 diabetic MODY3 subjects (□), 6 nondiabetic MODY3 subjects (▲) and 6 control subjects (○). The lowest glucose levels and ISR's were measured under basal conditions, and subsequent levels were obtained during glucose infusion rates of 1, 2, 3, 4, 6 and 8 mg $kg^{-1}$ $-min^{-1}$, respectively.

The ISR in the three groups was compared at the same plasma glucose level by plotting the mean ISR at each glucose infusion rate against the corresponding mean glucose level. The resulting glucose-ISR dose-response relationships are shown in FIG. 3. Over the 5–9 mM glucose concentration interval the diabetic MODY3 group secreted significantly less insulin than subjects in the nondiabetic MODY3 and control groups (101±17 pmol/min vs. 214±25 pmol/min and 211±27 pmol/min, respectively; P<0.004). The mean insulin secretion rate did not differ between these latter two groups.

The dose response curves (FIG. 3) indicate that the insulin secretion rates were similar in nondiabetic MODY subjects and controls at lower glucose concentrations. The amount of insulin secreted as the glucose concentration was increased from 5–7 mM was similar in these two groups (180±19 vs. 160±17 pmol/min; P=0.45). Over the 7–8 mM glucose interval the nondiabetic MODY3 subjects secreted 243.5±31.5 pmol/min compared to 284.7±30.5 pmol/min in controls P=0.37. From 8–9 mM glucose they secreted 257.1±35.0 pmol/min compared to 354.0±43.4 pmol/min in controls P=012 (FIG. 3). As the glucose concentration was increased from 7–8 mM to 8–9 mM the increase in insulin secretion rate in the nondiabetic MODY3 subjects was significantly less than in the controls (37.3±13.5 vs. 75.7±9.5 pmol/min; P<0.05).

Effect of Low-dose Glucose Infusion on Relationships Between Glucose and ISR

Mean glucose levels achieved during the 42-h constant glucose infusion were significantly higher in the diabetic compared to the nondiabetic MODY3 group and controls (14.9±0.6 mM vs. 10.0±1.4 mM vs. 6.6±0.3 mM; P<0.0001). The glucose infusion was discontinued after 42-h and low dose insulin was administered resulting in a fall in the plasma glucose concentration to similar levels in the two groups. The graded intravenous glucose infusion study was then repeated in each subject.

Figure 4A:
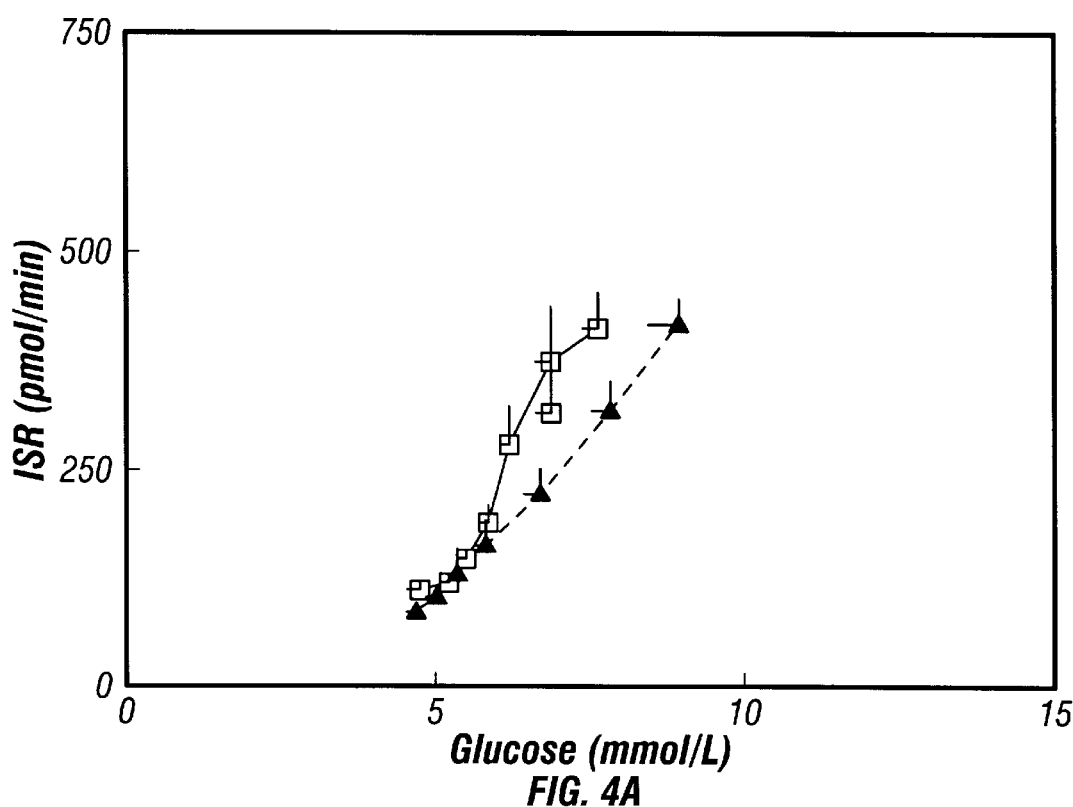
FIG. 4A, FIG. 4B, and FIG. 4C. Graded intravenous glucose infusions were administered to 6 controls (A), 6 nondiabetic MODY3 subjects (B) and 7 diabetic MODY3 subjects (C) after an overnight fast (baseline (▲)) and after a 42-h intravenous infusion of glucose (postglucose (□)) at a rate of 4–6 mg $kg^{-1}$ $-min^{-1}$.
Figure 4B:
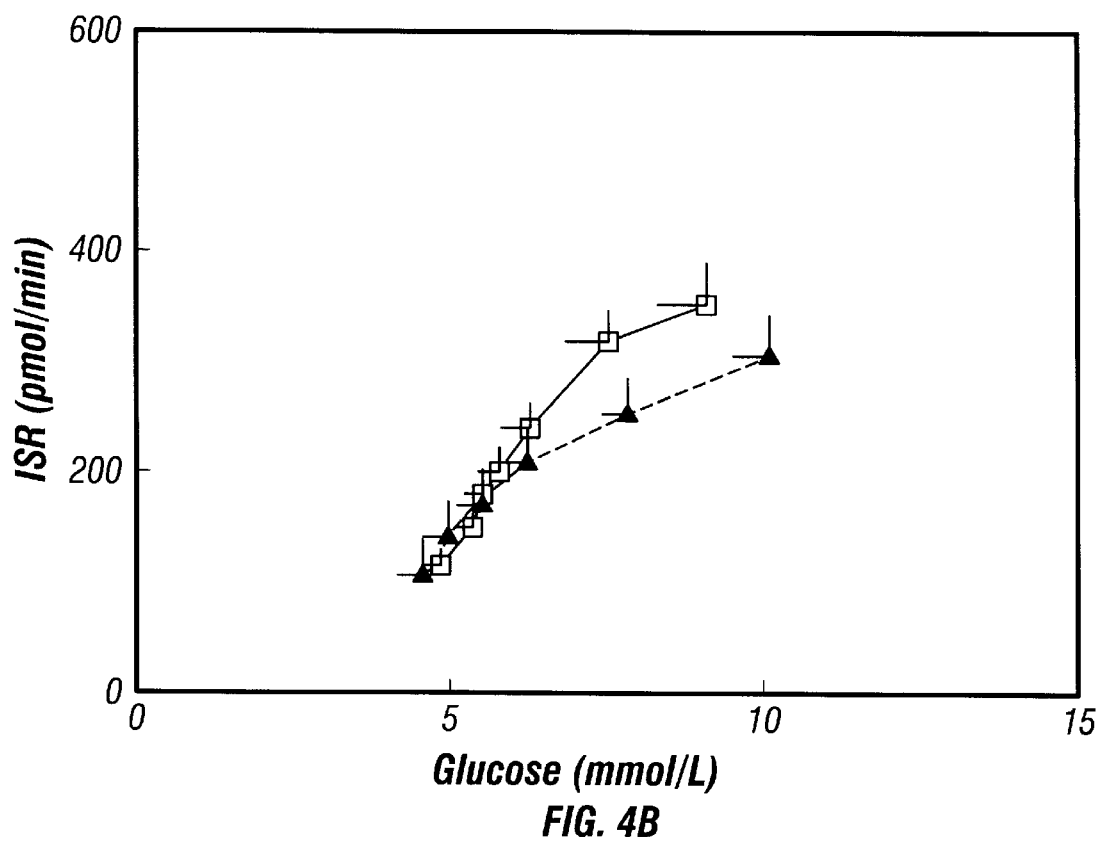
Figure 4C:
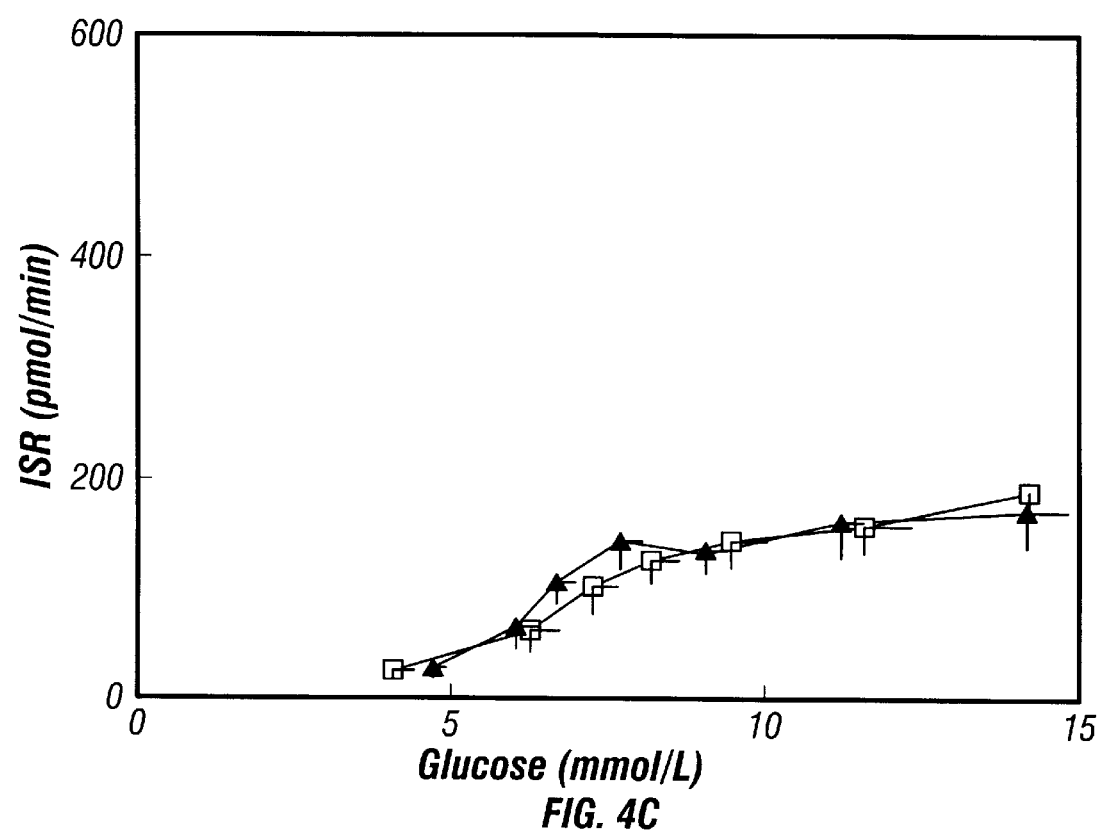

In order to quantify the priming effect of glucose on insulin secretion, the average ISR measured during each glucose infusion rate was plotted against the average plasma glucose concentration and compared with values obtained before glucose infusion. Over the glucose concentration range between 5 and 9 mM glucose, control subjects secreted 211±27 pmol/min before and 287±32 pmol/min (P<0.005) insulin after glucose infusion (FIG. 4A). There was a shift in the glucose-ISR does-response curves upwards and to the left, with ISR increasing by 38±7%. The nondiabetic MODY3 group increased their ISR from 214±25 pmol/min to 259±21 pmol/min (P<0.03) (FIG. 4B). The diabetic MODY3 group had a small and non significant 13±10% decrease in ISR after glucose administration (101±17 pmol/min to 90±21 pmol/min; P>0.9) (FIG. 4C). Individual values for ISR from 5–9 mM glucose before and after low-dose glucose infusion are given in Table 5.

Relationship Between Glycosylated Hemoglobin Levels and Parameters of the Insulin Secretory Response to Glucose There was a significant negative correlation between glycosylated hemoglobin and percent priming (r=−0.78; P<0.002) and between glycosylated hemoglobin and ISR from 5–9 mM glucose (r=−0.61; P<0.03). By contrast there was no significant decrease in ISR as glucose concentrations rose from 7–8 to 8–9 mM with increasing glycosylated hemoglobin levels (r=−0.07; P=0.82).

3. Discussion

Basal glucose levels were higher and insulin levels were lower in MODY3 subjects with diabetes compared to nondiabetic subjects or normal healthy controls. In response to the graded glucose infusion, insulin secretion rates were significantly lower in the diabetic subjects over a broad range of glucose concentrations. Insulin secretion rates in the nondiabetic MODY3 subjects were not significantly different from the controls at plasma levels <8 mM. As glucose rose above this level, however, the increase in insulin secretion is these subjects was significantly reduced. Administration of glucose by intravenous infusion for 42-h resulted in a significant increase in the amount of insulin secreted over the 5–9 mM glucose concentration range in the controls and nondiabetic MODY3 subjects (by 38% and 35%, respectively) but no significant change was observed in the diabetic MODY3 subjects. In conclusion, in nondiabetic MODY3 subjects insulin secretion demonstrates a diminished ability to respond when blood glucose exceeds 8 mM. The priming effect of glucose on insulin secretion is preserved. Thus, β-cell dysfunction is present prior to the onset of overt hyperglycemia in this form of MODY. The defect in insulin secretion in the nondiabetic MODY3 subjects differ from that reported previously in nondiabetic MODY1 or mildly diabetic MODY2 subjects.

EXAMPLE 2

Mutations in HNF1α Relating to MODY3 Type Diabetes

1. Materials and Methods

Isolation of partial sequence of the human HNF1α gene.

The PAC clone, 254A7, containing the human HNF1α, gene was isolated from a library (Genome Systems, St. Louis, Mo.) by screening PAC DNA pools with PCR and the primers HNF1P1 (5'-TACACCACTCTGGCAGCCACACT-3' SEQ ID NO:10) and HNF1P2 (5'-CGGTGGGTACATTGGTGACAGAAC-3' SEQ ID NO:11). The sequences of the exons and flanking introns were determined after subcloning fragments of the 254A7 into pGEM-4Z (Promega Biotec, Madison, Wis.) or pBluescript SK+ (Stratagene, La Jolla, Calif.) and sequencing using primers based on the sequence of the human HNF1α cDNA (Bach et al., 1990; and Bach and Yaniv, 1993) and selected using the conserved exon-intron organization of the mouse and rat genes (Bach et al., 1992) as a guide. Sequencing was carried out using a AmpliTaq FS Dye Terminator Cycle Sequencing Kit (ABI, Foster City, Calif.) on an ABI Prism® 377 DNA Sequencer (ABI). The sequences of the exon 2/intron 2, exon 3/intron 3, intron 6/exon 7, and intron 8/exon 9/intron 9 junctions were determined by directly sequencing PCR products generated by amplification of PAC 254A7 or human genomic DNA. FIG. 11 shows the cDNA sequence of HNF1α.

Screening of HNF1α gene for mutations

The ten exons and flanking introns of the HNF1α gene of an affected subject from families in which of which MODY cosegregated with markers spanning the MODY3 region of chromsome 12 in subjects with the MODY3-form of NIDDM were amplified using PCR and specific primers (Table 6). PCR conditions were denaturation at 94° C. for 5 min following by 35 cycles of denaturation at 94° C. for 30 sec, annealing at 62° C. for 30 sec (except for exon 9—annealing temperature was 60° C.) and extension at 72° C. for 45 sec, and final extension at 72° C. for 10 min. The PCR products were purified using a Centricon-100 membrane (Amicon, Beverly, Mass.) and sequenced from both ends using the primers shown in Table 6, a AmpliTaq FS Dye Terminator Cycle Sequencing Kit and ABI Prism® 377 DNA Sequencer. The presence of the specific mutation in other family members was assessed by amplifying and directly sequencing the appropriate exon. At least 40 normal unrelated healthy non-diabetic non-Hispanic white subjects (80 chromosomes) were also similarly screened. DNA polymorphisms identified during the course of screening patients for mutations were characterized by PCR and direct sequencing, or digestion with an appropriate restriction endonuclease and gel electrophoresis.

TABLE 7-continued

DNA polymorphisms identified in coding region of human HNF1α gene

| Exon | Codon | Nucleotide change | Frequency |
|---|---|---|---|
| Intron 7 | nt-7 | G→A | G, 0.57; A, 0.43 |
| Intron 9 | nt-44 | C→T | C, 0.96; T, 0.04 |
| Intron 9 | nt-24 | T→C | T, 0.59; C, 0.41 |

Table 8 shows a summary of mutations identified in human HNF1α in patients with MODY3. Sixteen exemplary mutations are identified in the HNF-1α gene in MODY3

TABLE 6

Sequences of primers used to amplify and directly sequence exons and flanking introns of the human HNF1α gene

| Exon | Forward primer (5'–3') | Reverse primer (5'–3') | Product size (bp) |
|---|---|---|---|
| 1 | GGCAGGCAAACGCAACCCACG (SEQ ID NO:12) | GAAGGGGGGCTCGTTAGGAGC (SEQ.ID NO:13) | 483 |
| 2 | CATGCACAGTCCCCACCCTCA (SEQ ID NO:14) | CTTCCAGCCCCCACCTATGAG (SEQ ID NO:15) | 384 |
| 3 | GGGCAAGGTCAGQGGAATGGA (SEQ ID NO:16) | CAGCCCAGACCAAACCAGCAC (SEQ ID NO:17) | 306 |
| 4 | CAGAACCCTCCCCTTCATGCC (SEQ ID NO:18) | GGTGACTGCTGTCAATGGGAC (SEQ ID NO:19) | 404 |
| 5 | GCCTCCCTAGGGACTGCTCCA (SEQ ID NO:20) | GGCAGACAGGCAGATGGCCTA (SEQ IDNO:21) | 347 |
| 6 | TGGAGCAGTCCCTAGGGAGGC (SEQ ID NO:22) | GTTGCCCCATGAGCCTCCCAC (SEQ ID NO:23) | 320 |
| 7 | GGTCTTGGGCAGGGGTGGGAT (SEQ ID NO:24) | CTGCAATGCCTGCCAGGCACC (SEQ ID NO:25) CCCCTGCATCCATTGACAGCC* (SEQ ID NO:26) | 345 |
| 8 | GAGGCCTGGGACTAGGGCTGT (SEQ ID NO:27) | CTCTGTCACAGGCCGAGQGAG (SEQID Nd:28) | 228 |
| 9 | CCTGTGACAGAGCCCCTCACC (SEQ ID NO:29) CAGAGCCCCTCACCCCCACAT* (SEQ ID NO:30) | CGGACAGCAACAGAAGGGGTG (SEQD NO:31) | 286 |
| 10 | GTACCCCTAGGGACAGGCAGG SEQ ID NO:32) | ACCCCCCAAGCAGGCAGTACA (SEQ ID NO:33) | 247 |

* = primer used only for sequencing

2, Results

Table 7 identifies the DNA polymorphisms identified in the coding region of HNF1α gene. Of course these are exemplary polymorphisms and those of skill in the art will easily be able to employ the methods and descriptions set forth in the present invention to identify other polymorphisms.

TABLE 7

DNA polymorphisms identified in coding region of human HNF1α gene

| Exon | Codon | Nucleotide change | Frequency |
|---|---|---|---|
| 1 | 17 | CTC(Leu)→CTG (Leu) | C, 0.57; G, 0.43 |
| 1 | 27 | ATC(Ile)→CTC (Leu) | A, 0.63; C, 0.37 |
| 1 | 98 | CCC(Ala)→GTC (Val) | C, 0.98; T,0.02 |
| 4 | 279 | GGG(Gly)→GGC (Gly) | G, 0.69; C, 0.31 |
| 7 | 459 | CTG(Leu)→TTG (Leu) | C, 0.63; T, 0.37 |
| 7 | 487 | AGC(Ser)→AAC (Asn) | G, 0.68; C, 0.32 |
| 8 | 515 | ACG(Thr)→ACA(Thr) | G, 0.79; A, 0.21 |
| Intron 1 | nt-91 | A→G | A, 0.88; G, 0.12 |
| Intron 1 | nt-42 | G→A | G, 0.66; A, 0.34 |
| Intron 2 | nt-51 | T→A | T, 0.85; A, 0.15 |
| Intron 2 | nt-23 | C→T | C, 0.88; T, 0.12 |
| Intron 5 | nt-47 | C→T | C, 0.99; T, 0.01 | patients but were not present in unaffected individuals. These mutations include frameshifts in exons 1, 4, 6, and 9, missense coding in exons 2, and 7 as well as abnormal splicing in introns 5 and 9. The results described herein demonstrate that mutations in this transcription factor can cause diabetes mellitus and focuses attention on the role of HNF-1α in determining normal pancreatic β-cell function.

TABLE 8

Summary Of Mutations In Human HNF1α In Patients With MODY3

| Location | Mutation/Location | Effect | Family |
|---|---|---|---|
| Exon 1 | R55G56fsdelGAGGG | Frameshift | F593 |
| | codon 122 | Y→C | R213 |
| | codon 131 | R→Q | H,GL |
| | codon 142 | S→F | F515 |
| | codon 159 | R→Q | F384 |
| | codon 171 | R→X | F Pierre |
| Exon 4 | P291fsinsC | Frameshift | EA,SW,G17, G18,M13 |
| | P291fsdelC | Frameshift | FS4 |
| | G292fsdelG | Frameshift | F159 |
| Intron 5 | IVS5nt − 2A→G | abnormal splice | P |

TABLE 8-continued

Summary Of Mutations In Human HNF1α In Patients With MODY3

| Location | Mutation/Location | Effect | Family |
|---|---|---|---|
| Exon 6 | P379fsdelCT | Frameshift | R,F632 |
|  | P379fsinsC | Frameshift | F549 |
|  | Q401fsdelC | Frameshift | G19 |
| Exon 7 | codon 447 | P→L | A,Danish-1 |
| Exon 9 | T547E548fsdelTG | Frameshift | ber |
| Intron 9 | IVS9nt + 1G→A | abnormal splice | GK |

3. Discussion

Linkage analysis localized MODY3 to a 10 cM interval of chromosome 12 between the markers D12S86 and D12S342 (Vaxillaire et al., 1995) and then to a 5 cM interval between the markers D12S86 and D12S807/D12S820 (Menzel, S. et al. 1995). A combined YAC, BAC and PAC contig spanning D12S86 and D12S807 (FIG. 9) was generated using information in public databases (Chumakov et al. 1995; Hudson et al. 1995) and screening appropriate libraries (YAC and BAC, Research Genetics, Huntsville, Ala.; and PAC, Genome Systems, St. Louis, Mo.) with STSs from the MODY3 region. The physical map allowed localization of new polymorphisms as they were reported as well as to generate new markers to further localize recombination events in key individuals. Such studies refined the localization of MODY3 to the 3 cM interval between D12S 1666 and the polymorphic STS UC-39. Fluorescence in situ chromosomal hybridization using the BAC 162B15 mapped the contig to chromosome band 12q24.2.

This combination of genetic and physical mapping information was used to begin a systematic search for MODY3. Using a combination of approaches including testing genes known to be on the long arm of chromosome 12 to see if they mapped into the contig, exon-trapping (Church, et al. 1994), and cDNA selection (Kaplan et al., 1992) using human pancreatic islet cDNA (clinical studies had shown that insulin secretion was abnormal in MODY3 patients, and thus islets were a likely site of expression of MODY3 mRNA and protein), the inventors identified 14 genes encoding known proteins (γ-subunit of AMP-activated protein kinase, citron, the GTP-binding protein H-ray, paxillin, acidic ribosomal phosphoprotein PO, pancreatic phospholipase A2, splicing factor SRp30, cyctochrome C oxidase subunit VIa, short chain acyl CoA dehydrogenase, HNF1-α, thyroid receptor interactor (TRIP14) protein, $Ca^{2+}$/calmodulin-dependent protein kinase, $P_{2\times4}$ purinoceptor and restin), 5 pseudogenes (metallopanstimulin-like, cell surface heparin binding protein-like, ribosomal protein L12-like, nucleoside diphosphate kinase-like and ADP ribosylation factor-like), 12 ESTs (yq81d09, yd50d03, IB383, hbc3028, yu36h05, yn75d09, yz51b06, yd88g07, ym03h09, ym30e05, WI-6178/c-01h06, WI-6239/c-04b12) and 9 unknown genes (FIG. 9).

These genes were being systematically sequenced in affected and unaffected subjects using nested PCR and illegitimate transcription of lymphoblastoid RNA (Kaplan et al., 1992), as well as PCR of individual exons of the gene. Comparison of the sequences of the pancreatic phospholipase A2, γ-subunit of AMP-activated protein kinase, H-ray, cytochrome C oxidase subunit VIA, acidic ribosomal phosphoprotein PO, paxillin, splicing factor SRp30, short chain acyl CoA dehydrogenase, and $P_{2\times4}$ purinoceptor genes from patients and controls revealed a number of polymorphisms but no MODY3-associated mutations.

Figure 5A:
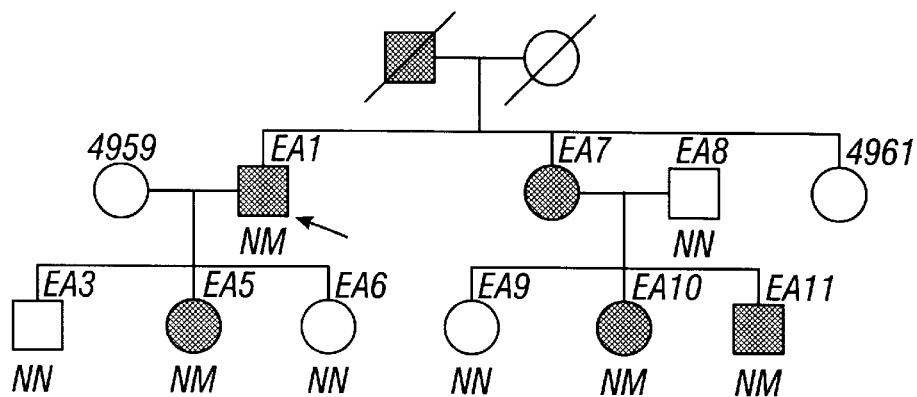
FIG. 5A, FIG. 5B, FIG. 5C, FIG. 5D, FIG. 5E, FIG. 5F and FIG. 5G. MODY3 pedigrees showing co-segregation of mutant HNF1α allele with diabetes mellitus. Males are noted by square symbols and females by circles. Individuals with NIDDM are noted by black symbols and those with gestational-onset diabetes or impaired glucose tolerance by shaded symbols. A diagonal line through the symbol indicates that the individual is deceased.
Figure 5B:
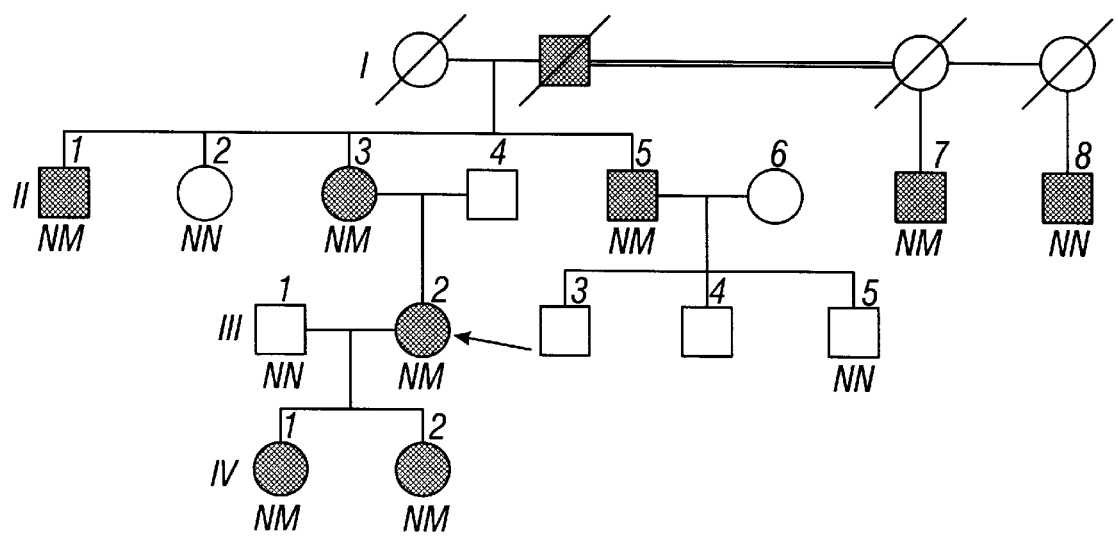
Figure 5C:
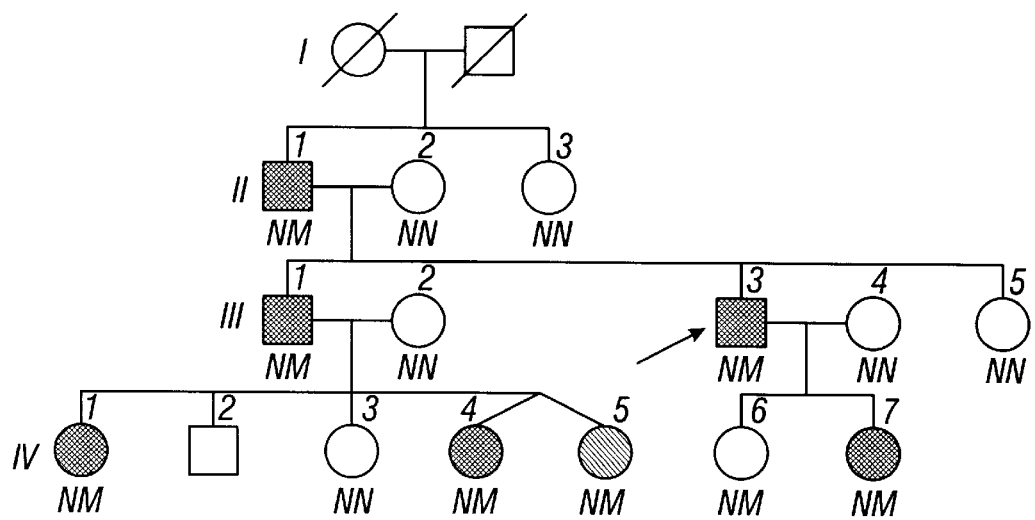
Figure 5D:
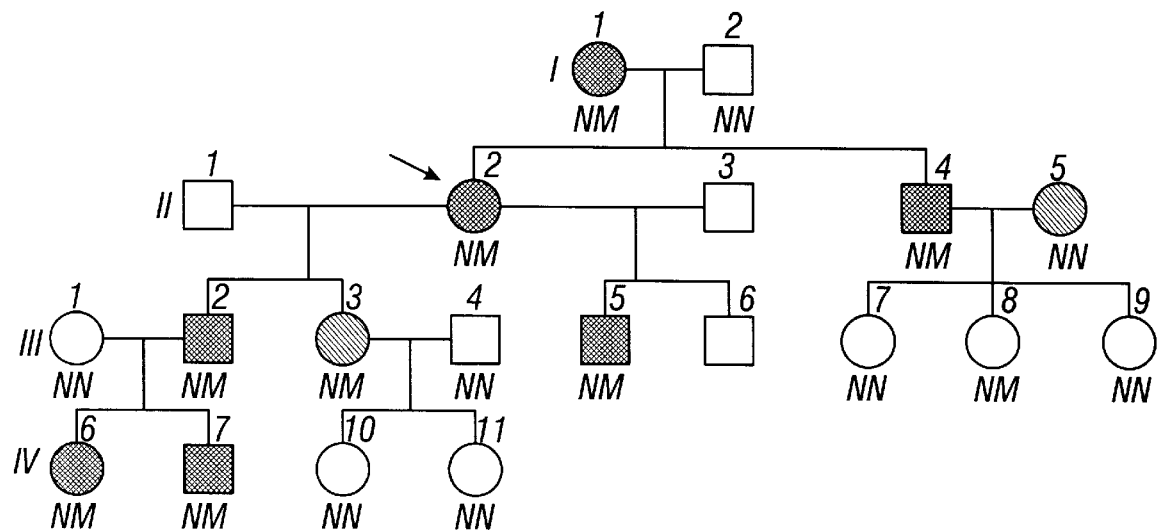
Figure 5E:
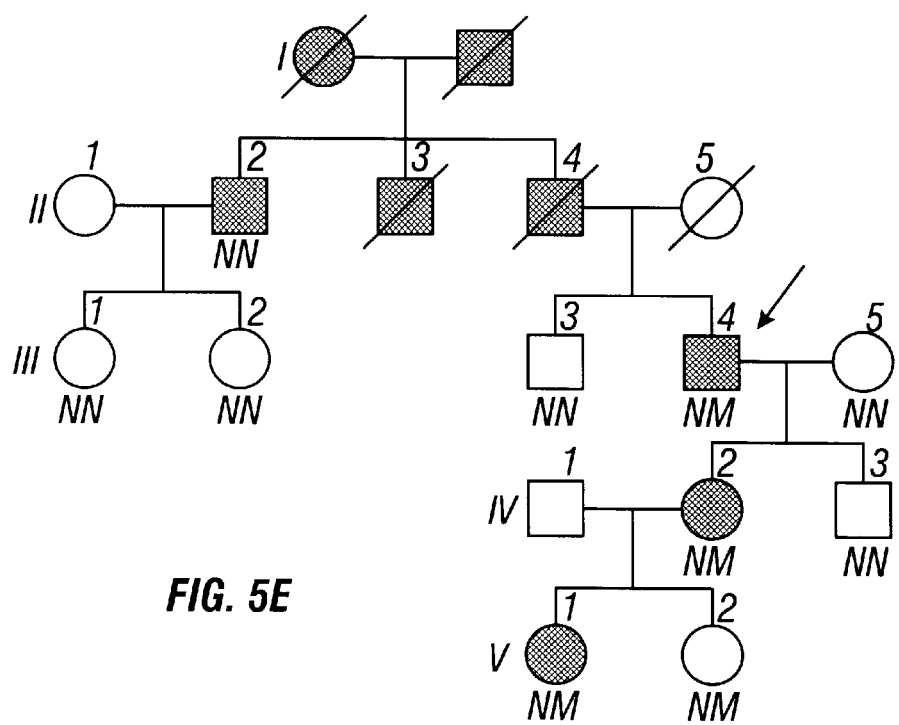
Figure 5F:
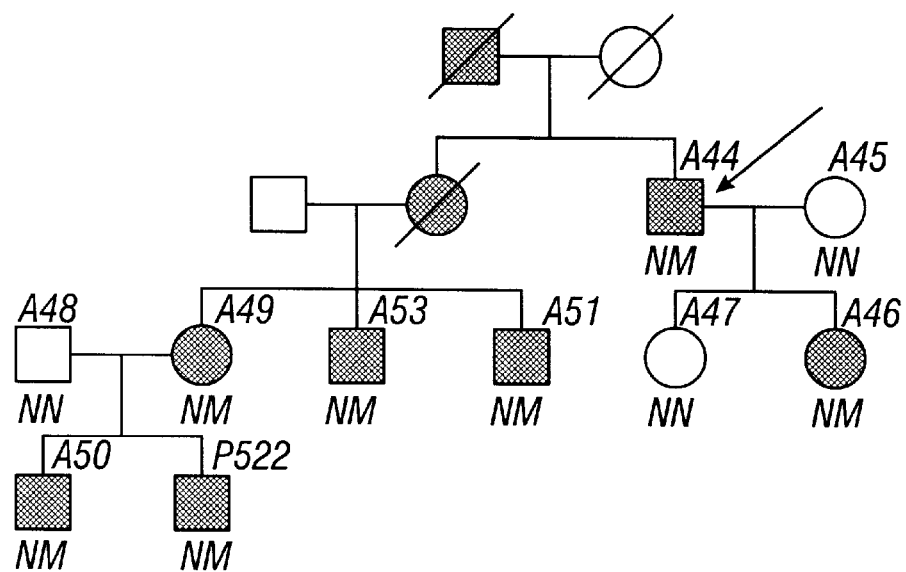
Figure 5G:
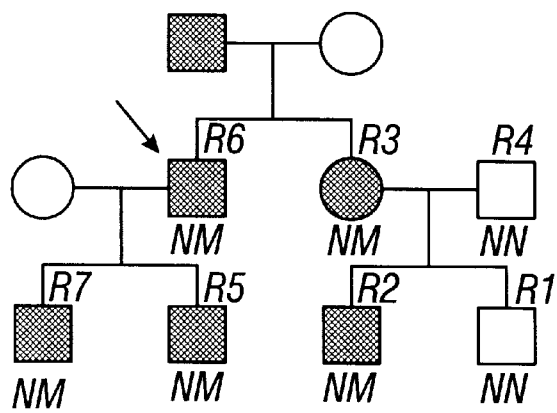

The HNF-1α gene was localized in the interval containing MODY3 using PCR and HNF-1α gene-specific primers (FIG. 9). HNF-1α cDNAs were also isolated at high frequency by cDNA selection from human pancreatic islet cDNA using PAC 254A7, a result consistent with the report of Emens et al. (1992) showing that HNF-1α was expressed in hamster insulinoma cells and functioned as a weak transactivator of the rat insulin I gene. The human HNF-1α gene was isolated and partially sequenced to provide the exon-intron organization and the sequences of introns from which primers could be selected for PCR. The human gene consists of 10 exons with introns 1–8 located in the same positions as in the rat and mouse genes (Bach et al., 1992). Intron 9 interrupts codon 590 (phase 1) and is not present in the rat and mouse genes but does occur in the chicken gene (Horlein et al., 1993) consistent with loss of this intron during the period when humans and rodents shared their last common ancestor. Amplification and direct sequencing of exon 4 of subject EAI (Edinburgh pedigree, FIG. 5A) showed an insertion of a C in codon 289 (Pro) resulting in a frameshift and premature termination (designated P289fsinsC) (FIG. 10). This mutation was present in all affected members and no unaffected members of this family. It was also not found on screening 55 healthy non-diabetic white subjects (110 chromosomes). Hence it was concluded that the HNF-1α gene is MODY3 and led the inventors to sequence the HNF-1α gene in other families in which NIDDM cosegregated with markers from the MODY3 region.

Fifteen additional mutations were found (Table 8), all of which co-segregated with NIDDM, and did not occur in any of at least 50 healthy non-diabetic white subjects. However, there were individuals in several pedigrees (GK pedigree, III-3; Ber pedigree, V-2; and P pedigree, IV-5 and IV-6) who had inherited the mutant chromosome (and at-risk chromosome 12 haplotype) but who were non-diabetic or showed only evidence of impaired glucose intolerance or diabetes during pregnancy. These individuals will likely develop NIDDM in the future. In addition, one subject with NIDDM did not have the mutant allele (Ber pedigree, II-2). He was diagnosed with NIDDM at 65 years of age at which time he was mildly obese with a body mass index of 27 $kg/m^2$ suggesting a diagnosis of late-onset NIDDM rather than MODY. Such heterogeneity within MODY families has been noted previously (Bell et al. 1991; Vionnet 1992) and is due to the high frequency of late-onset NIDDM which affects 10% or more of individuals over age 65 years (Kenny et al., 1995). In addition to the mutations listed in Table 8, three amino acid polymorphisms (I/L27, A/V98 and S/N487), four silent polymorphisms (in codons for L17, G288, L459 and T515) and seven polymorphisms in introns were found in the HNF-1α gene (Tables 7 and 8).

Sixteen different mutations in the HNF-1α gene were identified in patients with the MODY3-form of diabetes. The splicing and frameshift mutations would be predicted to result in the expression of a truncated protein having at least amino acids 1–290 of the native protein. The missense mutations, R131Q and P447L, are of residues that are conserved in human, rat, mouse, hamster, chicken, Xenopus and salmon HNF-1α and the structurally-related transcription factor human HNF-1β suggesting that these residues are functionally important.

HNF-1α is one of a group of transcription factors expressed in liver that act together to confer tissue-specific expression of genes in this tissue (Tronche et al., 1992; Bach et al., 1990). It is also found in kidney, intestine, stomach and pancreas, including islets of Langerhans, and at low levels in spleen and testis suggesting that it plays a role in transcriptional regulation in these tissues as well. HNF-1α is composed of three functional domains: an NH$_2$-terminal dimerization domain (amino acids 1–32), a DNA binding domain with POU-like and homeodomain-like motifs (amino acids 150–280) and a COOH-terminal transactivation domain (amino acids 281–631). The functional form of HNF-1α is a dimer and HNF-1α may form homodimers or heterodimers with the structurally-related protein HNF-1β (Mendel et al., 1991)

Pontoglio et al. (1996) have generated mice that lack HNF-1α. Homozygous HNF-1α-deficient animals failed to thrive and usually died around the time of weaning. They also suffered from phenylketonuria and renal tubular dysfunction. However, the homozygous HNF-1α-deficient mice did not appear to be diabetic as they had normal blood glucose levels and a normal response to an intravenous bolus injection of glucose. The massive glucosuria in these animals though may have masked the presence of diabetes mellitus. The insulin secretory responses of heterozygous HNF-1α-deficient mice, animals that may be most similar to human subjects with HNF-1α mutations and MODY, were not reported. In view of the present findings that mutations in the HNF-1α gene causes early-onset NIDDM, more detailed evaluation of β-cell and liver function in HNF-1α-deficient mice is indicated.

The mechanism by which mutations in the HNF-1α gene when present on a single allele can cause diabetes is unclear however, it is possible that a partial deficiency of HNF-1α could lead to β-cell dysfunction and diabetes. Alternatively, mutations in HNF-1α may cause diabetes by a dominant-negative mechanism (Herskowitz, 1987) by interfering with the function of wild-type HNF-1α and other proteins which act in concert with HNF-1α to regulate transcription in the β-cell and/or liver. All of the HNF-1α gene mutations identified to date would result in the synthesis of a mutant protein impaired in DNA binding or transactivation but not dimerization. These mutant proteins could form non-productive dimers with the product of the normal HNF-1α allele or other proteins such as HNF-1β and thereby impair the normal function of HNF- 1 α.

The inventors have previously shown that diabetes mellitus in the Zucker diabetic fatty rat, a rodent model of obesity and NIDDM, is associated with decreased expression of a large number of β-cell genes including genes such as insulin whose expression is restricted to the β-cell as well as others with a much broader tissue distribution (Tokuyama, et al. 1995). Thus, it is believed that NIDDM is likely to be a disorder of transcription with genetic or acquired defects affecting key proteins that regulate transcription leading to β-cell dysfunction and diabetes.

EXAMPLE 3

Mutations in HNF4α Relating to MODY1 Type Diabetes

The PAC clone, 114E13, 130B8, 207N8, containing the human HNF4α gene was isolated from a library (Genome Systems, St. Louis, Mo.) by screening PAC DNA pools with PCR and the primers HNF4P1 (5'-CACCTGGTGATCACGTGGTC-3' SEQ ID NO:81) and HNF4P2 (5'-GTAAGGCTCAAGTCATCTCC-3' SEQ ID NO:82). The sequences of the exons and flanking introns were determined by directly sequencing using primers based on the sequence of the human HNF4α cDNA (Chaitier et al., 1994; Drewes et al., 1996) and selected using the conserved exon-intron organization of the mouse (Taraviras et al, 1994) as a guide. Sequencing was carried out using a AmpliTaq FS Dye Terminator Cycle Sequening Kit (ABI, Foster City, Calif.) on an ABI Prism TM 377 DNA Sequencer (ABI).

Screening of HNF4α gene for mutations.

The eleven exons and flanking introns of the HNF4α gene of an affected subject from families in which of MODY cosegregated with markers spanning the MODY1 region of chromosome 20 subjects with the MODY1-form of NIDDM were amplified using PCR and specific primers (Table 9). PCR conditions were denaturation at 94° C. for 5 min following by 35 cycles of denaturation at 94° C. for 30 sec, annealing at 60° C. for 30 sec and extension at 72° C. for 30 sec, and final extension at 72° C. for 10 min. The PCR products were purified using a Centricon-100 membrane (Amicon, Beverly, Mass.) and sequenced from both ends using the primers shown in Table 9, a AmpliTaq FS Dye Terminator Cycle Sequencing Kit and ABI Prism™ 377 DNA Sequencer. The presence of the specific mutation in other family members was assessed by digestion with Bta3 restriction endonuclease that resulted from mutation and gel electrophoresis. At least 100 normal unrelated healthy non-diabetic non-Hispanic white subjects (200 normal chromosomes) were also similarly screened. DNA polymorphisms identified during the course of screening patients for mutations were characterized by PCR and direct sequencing, or digestion with an appropriate restriction endonuclease and gel electrophoresis.

TABLE 9

DNA Sequences of PCR Primers for MODY1

| Exon | Forward primer (5'–3') | Reverse primer (5'–3') | Product size (bp) |
| --- | --- | --- | --- |
| 1 | GGGCACTGGGAGGAGGCAGT (SEQ ID NO:56) | GCCTGTAGGACCAACCTACC (SEQ ID NO:57) | 340 |
| 1b | TCTGGTGTGCACGACTGCAC (SEQ ID NO:58) | CTGGAGCTGCAGCCTCATAC (SEQ ID NO:59) | 356 |
| 2 | ATGGCTCCCTTAGATGCCTG (SEQ ID NO:60) | CCACTCAGGGAGAAGACAGACCT (SEQ ID NO:61) | 321 |
| 3 | CCTAGTTCTGTCCTAAGAGG (SEQ ID NQ:62) | GTCATAAAGTGTGGCTACAG (SEQ ID NO:63) | 253 |
| 4 | CCACCCCCTACTCCATCCCTGT (SEQ ID NO:64) | CCCTCCCGTCAGCTGCTCCA (SEQ ID NO:65) | 272 |
| 5 | GTGCAGGGGACAGAGAATGC (SEQ ID NO:66) | AATCAAGCCAGTCCACGGCTAT (SEQ ID NO 67) | 322 |
| 6 | GCCCAGCGTCACTGAGTTGGCTA (SEQ ID NO: 68) | TTGCCTGGGTGAGTGCCATG (SEQ ID NO:69) | 234 |

TABLE 9-continued

DNA Sequences of PCR Primers for MODY1

| Exon | Forward primer (5'–3') | Reverse primer (5'–3') | Product size (bp) |
|---|---|---|---|
| 7 | GCACCAGCTATCTTGCCAAC (SEQ ID NO:70) | AGGAGAAGTCTGGCAGAGCG (SEQ ID NO:71) | 315 |
| 8 | CTCCTTGTGTGACACAAGTC (SEQ ID NO:72) | CTCACTGTGTGAGGCCTGTC (SEQ ID NO:73) | 407 |
| 9 | TGGTTGATTGGCCACGCCTG (SEQ ID NO:74) | ATCCTGGTTCTACCTTCTAG (SEQ ID NO:75) | 341 |
| 10 | CATTTACTCCCACAAAGGCT (SEQ ID NO:76) | GACCACGTGATCACCAGGTG (SEQ ID NO:77) | 277 |

Table 10 identifies the DNA polymorphisms and mutations identified in the coding region of the HNF4α gene. Of course, these are exemplary polymorphisms and those of skill in the art will easily be able to employ the methods and descriptions set forth in the present invention to identify other polymorphisms. FIG. 7 shows an alignment of the HNF4α protein sequence from humans with sequences from human mouse, X. Laves and Drosophila. The putative DNA binding sites are underlined and the putative ligand binding sites are in bold. The DNA sequences for exon 1, exon 1b, exon 2, exon 3, exon 4, exon 5 exon 6 exon 7 exon 8 exon 9 and exon 10 of HNF4α are shown in FIG. 8A, FIG. 8B, FIG. 8C, FIG. 8D FIG. 8E, FIG. 8F, FIG. 8G, FIG. 8H, FIG. 8I, FIG. 8J, and FIG. 8K, and SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, and SEQ ID NO:54, respectively. It is contemplated that mutations in any of these exons, or the related intron regions therebetween, of HNF4α will result in MODY1 type diabetes.

TABLE 10

Polymorphisms and Mutations in the Human HNF4α Gene

| Location | | Nucleotide change | Frequency |
|---|---|---|---|
| Exon | Codon | | |
| 4 | 130 | ACT (Thr)-ATT(Ile) | C:T = 105:5 C-0.05, T-0.05 |
| 7 | 273 | GAT(Asp)-GAC(Asp) | T:C = 169:1 T-0.994, C-0.006 |
| 7 | 268 | GAG(Gln)-TAG(stop) | 0/216 control chromosomes |

The R-W pedigree, which includes more than 360 members spanning 6 generations and 74 members with diabetes including those with MODY, has been studied prospectively since 1958 (Fajans, 1989). The members of this family are descendants of a man who was born in East Prussia in 1809 and emigrated to Detroit, Mich. in 1861 _ with his four sons, three of whom were diabetic, and five daughters, one of whom was diabetic (Fajans, 1989; Fajans et al.,1994). Linkage studies have shown that the gene responsible for MODY in this family, MODY1, is tightly linked to markers in chromosome band 20q12-q13.1 with a multipoint lod score >14 in those branches of the family in which MODY is segregating (Bell, et al. 1991; Bowden, et al.,1992; Irwin, et al., 1994). The analysis of key recombinants in the R-W pedigree localized MODY1 to a 13-cM interval (~7 Mb) between D20S 169 and D20S 176, an interval which also includes the gene encoding HNF-4 (Stoffel, M. et al., 1996). The demonstration in the previous examples that mutations in the HNF-1α gene are the cause of the MODY3-form of NIDDM prompted the inventors to screen the HNF-4α gene for mutations in the R-W pedigree.

The human HNF-4α gene consists of 11 exons with the introns being located in the same positions as in the mouse gene (Tavaviras, et al., 1994). Alternative splicing generates a family of HNF-4α mRNAs, HNF-4 1, 2 and 4, the latter two of which contain inserts of 30 and 90 nucleotides, respectively (Tavaviras et al.,1994; Laine et al., 1994; Drewes, 1996). Of these, HNF-4 2 mRNA appears to be the most abundant transcript in many tissues. In contrast to a previous report (Drewes et al., 1996), the inventors studies show that HNF-4α mRNA encodes a truncated and presumably nonfunctional form of HNF-4α. The sequence of exon 1B, the exon encoding the insertion in HNF-4α mRNA revealed an additional T between nucleotides 219 and 220 in both alleles of five unrelated individuals (10 chromosomes) not present in the cDNA sequence (Drewes et al., 1996) which causes a frameshift and the generation of a protein of 98 amino acids whose function, if any, is unknown. The 11 exons of the HNF-4α gene of two affected, V-20 and 22, and one unaffected, VI-9, subject from the R-W pedigree were amplified and the PCR products sequenced directly. The sequences were identical to one another and to the cDNA (Drewes et al., 1996; Laine et al., 1994)) except for a C→T substitutions in exon 4, codon 130 and exon 7, codon 268. The C→T substitution in codon 130 results in a Thr (ACT) →Ile (ATT) substitution and is a polymorphism (T/I130) with a frequency of the Ile allele in a group of 55 unrelated nondiabetic non-Hispanic white subjects of 5%. The C→T substitution in codon 268 results in a nonsense mutation CAG (Gln)→TAG (AM) (Q268X). The nonsense mutation was confirmed by cloning and sequencing PCR products derived from both alleles. The Q268X mutation created a site for the enzyme Bfa I with digestion of the normal allele generating fragments of 281 and 34 bp, and the mutant allele, 152, 129 and 34 bp and facilitating testing for this mutation in other members of the R-W pedigree. In the R-W pedigree, Ile130 and the amber mutation at codon 268 were present in the same allele.

The Q269X mutation cosegregated with the at-risk haplotype and NIDDM in the R-W pedigree and was not observed on screening 108 healthy nondiabetic non-Hispanic white subjects (216 normal chromosomes). Seven subjects in the R-W pedigree who have inherited the mutant allele (V-18, 37 and 48; and VI-6, 11, 15 and 20) have normal glucose tolerance. The ages of five of these subjects (V-48, and VI-6, 11, 15 and 20) are less than 25 years and thus, they are still within the age range when diabetes usually develops in at-risk individuals in this family. Of the others, subject V-18 is 44 years of age and has shown normal glucose on all oral glucose tolerance tests, and subject V-37 who is 36 years of age had one glucose tolerance test characteristic of impaired glucose tolerance and one of diabetes at ages 16–17 years but for the past 19 years each glucose tolerance test has been normal even though she has a low insulin response to orally administered glucose. She is very lean and active, and has increased sensitivity to insulin during the frequently sampled intravenous glucose tolerance test. During a prolonged low dose glucose infusion, she became markedly hyperglycemic (Herman, et al. 1994; Byrne, et al. 1995). Two subjects (V-1 and 4) who have the mutation were considered nondiabetic based on medical history and their affection status needs to be evaluated by oral glucose tolerance testing. The results indicate that the nonsense mutation in the HNF-4α gene in the R-W pedigree is highly but not completely penetrant although the age of diabetes onset is variable.

In addition to subjects who inherited the Q268X mutation but are presently nondiabetic, there are subjects in the R-W pedigree who have NIDDM but did not inherit the Q268X mutation or at-risk haplotype. Subject IV-9 was diagnosed with NIDDM at 48 years of age and was hyperinsulinemic, a diagnosis consistent with late-onset NIDDM rather than MODY. The inventors also tested her six children, one of whom had NIDDM and another impaired glucose tolerance, and all had two normal alleles. Similarly, 10 children of subject III-7, five of whom had NIDDM were also tested, and none had inherited the Q268X mutation, suggesting that the NIDDM in this branch of the R-W family is of a different etiology. Finally, the five nondiabetic children of III-11 were also tested and all were normal. The presence of both MODY and late-onset NIDDM in the R-W family has been noted previously (Bell, et al. 1991; Bowden, et al, 1992). The MODY phenotype results from a mutation in the HNF-4α gene. The cause(s) of the late-onset NIDDM is unknown.

HNF-4 is a member of the steroid/thyroid hormone receptor superfamily and is expressed at highest levels in liver, kidney and intestine (Xanthopoulos et al., 1991; Sladek et al., 1990). It is also expressed in pancreatic islets and insulinoma cells (Miquerol, et al 1994). In liver, HNF-4α is a key regulator of hepatic gene expression and is a major activator of HNF-1α which in turn activates expression of a large number of liver-specific genes including those involved in glucose, cholesterol and fatty acid metabolism (Sladek et al., 1990; Kuo et al., 1992). Its expression in kidney, intestine and pancreatic islets implies that it plays a central role in tissue-specific regulation of gene expression in these tissues as well, although its specific function in nonhepatic tissues has not been addressed. Homozygous loss of functional HNF-4α protein causes embryonic lethality characterized by defects in gastrulation underscoring the key role played by this transcription factor in development and differentiation (Chen et al., 1994). The phenotype of the heterozygous animals was not described and further studies are necessary to determine if they represent a mouse model of MODY.

HNF-4α defines a subclass of nuclear receptors which reside primarily in the nucleus and bind to their recognition site and regulate transcription as homodimers (Sladek et al., 1994; Kuo et al., 1992). The key role played by HNF-4α in the regulation of hepatic gene expression is well established (Sladek et al., 1994; Kuo et al., 1992). However, its role as well as that of HNF-1α, the MODY3 product and a downstream target of HNF-4α action, in regulating gene expression in the insulin-secreting pancreatic β-cell is largely unknown, although Emens et al.(1992) have shown that HNF-1α is a weak transactivator of the insulin gene. Thus, the mechanism by which mutations in HNF-4α result in an autosomal dominant form of NIDDM characterized by pancreatic—cell dysfunction is unclear. The nonsense mutation in HNF-4α found in the R-W family is predicted to result in the synthesis of a protein of 267 amino acids with an intact DNA binding domain. However, it is missing the regions involved in dimerization and transcriptional activation in other members of the steroid/thyroid hormone superfamily Zhang, et al., 1994; Bourguet, et al., 1995; Renaud, et al. 1995; Wagner, R. L. et al. 1995) and as a consequence is predicted to be unable to dimerize, bind to its recognition site and activate transcription. Thus, the dominant inheritance is due to a reduction in the amount of HNF-4α per se rather than a dominant negative mechanism. The decreased levels of functional HNF-4α appear to have a critical effect on β-cell function perhaps as a consequence of decreased HNF-1α gene expression, mutations in this gene also leading to MODY as described in the examples above. Prediabetic subjects with mutations in either the HNF-4α or HNF-1α genes exhibit similar abnormalities in glucose-stimulated insulin secretion with normal insulin secretion rates at lower glucose concentrations but lower than normal rates as the glucose concentration increases (Byrne et al., 1995), a result consistent with HNF-4α and HNF-1α affecting a common pathway in the pancreatic β-cell. The absence of overt hepatic, renal or gastrointestinal dysfunction in affected members of the R-W pedigree suggests that the levels of HNF-4α in these tissues, although possibly lower than normal, are sufficient to ensure normal function or that alternative pathways are sufficient for expression of key genes. However, detailed studies of hepatic glucose production and metabolism have not performed in subjects from the R-W pedigree and it is possible that subtle alterations in these processes may be present.

The demonstration that MODY can result from mutations in the HNF-1α and HNF-4α genes suggests that this form of NIDDM is primarily a disorder of abnormal gene expression. In this regard, genes encoding other proteins in the HNF-1α /HNF-4α regulatory cascade such as other members of the HNF-1 (Mendel et al., 1994) and HNF-4 families (Drewes et al., 1996) as well as HNF-3 (Lai et al., 1993), HNF-6 (Lemaigre, et al. 1996).), and perhaps dimerization cofactor of HNF-1 (Mendel et al., 1991) should be considered as candidates for other forms of MODY and/or late-onset NIDDM. The role of HNF-4α in the development of the more common late-onset NIDDM is unknown. There is no evidence for linkage of markers flanking the HNF-4α gene with late-onset NIDDM in Mexican Americans or Japanese implying that mutations in the HNF-4α gene are unlikely to be a significant genetic factor contributing to the development of late-onset NIDDM. However, acquired defects in HNF4α expression may contribute, at least in part, to the β-cell dysfunction which characterizes late-onset NIDDM (Polonsky et al., 1996) especially if it plays a central role in regulating gene expression in the pancreatic β-cell as suggested by its association with MODY. Furthermore, the similarity between HNF-4α and ligand dependent transcription factors raises the possibility that HNF-4α and the genes it regulates respond to an unidentified ligand. The identification of such a ligand by the methods of the present invention will lead to new approaches for treating diabetes.

EXAMPLE 4

Organization and Partial Sequence of the HNF 4α /MODY1 Gene and Identification of Missense Mutation, R127W, in a Japanese Family with MODY HNF-4α is a member of the nuclear receptor superfamily, a class of ligand-activated transcription factors. A nonsense mutation in the gene encoding this transcription factor has been recently found in a white family with one form of maturity-onset diabetes of the young, MODY1. In the present example, the inventors report the exon-intron organization and partial sequence of the human HNF-4α gene. In addition, the inventors have screened the twelve exons, flanking introns and minimal promoter region for mutations in a group of 57 unrelated Japanese subjects with early-onset NIDDM/MODY of unknown cause. Eight nucleotide substitutions were noted, of which one resulted in the mutation of a conserved arginine residue, Arg127 (CGG)→Trp (TGG) (designated R127W), located in the T-box, a region of the protein that may play a role in HNF-4α dimerization and DNA binding. This mutation was not found in 214 unrelated nondiabetic subjects (53 Japanese, 53 Chinese, 51 white and 57 African-American). The R127W mutation was only present in three of five diabetic members in this family indicating that it is not the only cause of diabetes in this family. The remaining seven nucleotide substitutions were located in the proximal promoter region and introns. They are not predicted to affect the transcription of the gene or mRNA processing and represent polymorphisms and rare variants. The results suggest that mutations in the HNF-4α gene may cause early-onset NIDDM/MODY in Japanese but they are less common than mutations in the HNF-1α/MODY3 gene. The information on the sequence of the HNF-4α gene and its promoter region will facilitate the search for mutations in other populations and studies of the role of this gene in determining normal pancreatic β-cell function.

1. Methods

Isolation and partial sequence of the human HNF-4α gene

Three P1-derived artificial chromosome (PAC) clones, 114E13, 130B8 and 207N8, containing the human HNF-4α gene were isolated by screening PAC DNA pools (Genome System, St. Louis, Mo.) by PCR™ with HNF-4α specific primers (Yamagata et al., 1996a). The partial sequence of the HNF-4α gene was determined using DNA from PAC's 114E13 and 207N8 and sequence-specific primers with an AmpliTaq FS Dye Terminator Cycle Sequencing Kit and ABI Prism™ 377 DNA sequencer (ABI, Foster City, Calif.). The promoter sequence was examined for transcription factor binding sites using MatInspector (Quandt et al., 1995) and TFSEARCH (Version 1.3 http//www.genome.ad.gp/kit/tfsearch.html). The sequences of alternatively-spliced mRNAs were confirmed by sequencing PCR™ products generated by amplification of human liver cDNA using specific primers.

Screening of the HNF-4α gene for mutations

The 12 exons, flanking introns and minimal promoter region were screened for mutations by amplifying and directly sequencing both strands of the PCR™ product using specific primers (the sequences of the primers are available at www.diabetes.org/diabetes). The sequence of the missense mutation (R127W) was confirmed by cloning the PCR™ product into pGEM-T (Promega, Madison, Wis.) and sequencing clones representing both alleles. The R127W mutation leads to loss of a Msp I site and subjects were tested for the presence of this mutation by digestion of the PCR™ product of exon 4 with Msp I, separation of the fragments by electrophoresis on a 3% NuSieve® 3:1 agarose gel (FMC BioProducts, Rockland, Me.) and visualization by ethidium bromide staining. The sequences of the DNA polymorphisms are based on sequencing both strands of the PCR™ product and were not confirmed directly by cloning and sequencing the PCR™ product.

Subjects

The study population consisted of 57 unrelated Japanese subjects attending the Diabetes Clinic, Tokyo Women's Medical College who were diagnosed with NIDDM before 25 years of age and/or who were members of families in which NIDDM was present in three or more generations: age at diagnosis, 20.1±7.5 years (mean±SE); male/female, 31/26; and treatment, insulin—36, oral hypoglycemic agents—10, and diet—11. Thirty-two of the subjects met strict criteria for a diagnosis of MODY (i.e., NIDDM in at least three generations with autosomal dominant transmission and diagnosis before 25 years of age in at least one affected subject). NIDDM was diagnosed using the criteria of the World Health Organization (Bennett et al., 1994). At the time of recruitment, informed consent was obtained from each subject and a blood sample was taken for DNA isolation. Fifty-three unrelated nondiabetic Japanese subjects were tested for each nucleotide substitution and mutation to determine if the sequence change was a polymorphism or disease-associated mutation. In addition, 53 Chinese (15), 51 white (16), and 57 African-American unrelated nondiabetic subjects (16) were tested for the R127W mutation 2. Results Organization and partial sequence of human HNF-4α gene. The human HNF-4α gene (gene symbol, TCF14) consists of 12 exons spanning approximately 30 kb, of which about 10 kb were sequenced including 1 kb of the promoter region (the gene sequence is available at www.diabetes.org/diabetes). Human HNF-4α mRNA is alternatively spliced (Hata et al., 1992; Chartier et al., 1994; Drewes et al., 1996; Kritis et al., 1996) which may generate as many as six different forms of HNF-4α (FIG. 12). HNF-4α2 is the predominant form present in many adult tissues including liver, kidney and intestine. The inventors have used RT-PCR™ to determine which HNF-4α transcripts are expressed in human pancreatic islets. This analysis showed that islets express mRNAs for HNF-4α1, 2 and 3. The inventors could not detect islet transcripts that included exons 1C and 1B although transcripts containing these two exons could be detected in human liver by RT-PCR™.

The sequence of 1 kb of the promoter region of the human HNF-4α gene was determined (FIG. 13). The comparison of the sequences of the human and mouse genes showed regions of sequence conservation that included the predicted start of transcription and the binding sites for several transcription factors including HNF-6, AP-1, HNF-3, HNF-1α and NF-1. The transcription start site for the human gene has not been determined directly but has been inferred from studies of the mouse gene which showed multiple start sites spread over a 10 bp interval (Zhong et al., 1994; Tavaviras et al., 1994) of which one was defined as nucleotide +1 (Zhong et al., 1994). The sequence homology in the promoter of the human and mouse genes suggests that transcription of the HNF-4α gene may be regulated in a similar manner. In this regard, Zhong et al. (Zhong et al., 1994) have shown that the major promoter activity in a hepatoma cell line was associated with a 126 bp fragment of the mouse promoter (nucleotides 289–414 in FIG. 13). There is 83% identity between the human and mouse sequences in this minimal promoter region.

Mutations and polymorphisms in the HNF-4α gene. The twelve exons, flanking introns and minimal promoter region were screened for mutations in 57 unrelated Japanese subjects with early-onset NIDDM/MODY. This analysis revealed one putative mutation (FIG. 14) and seven DNA polymorphisms/variants (Table 11). The putative mutation in exon 4 at codon 127, CGG (Arg)→TGG (Trp) (R127W) alters a conserved amino acid that is located in the T-box, a region implicated in receptor dimerization and DNA binding (Lee et al., 1993; Rastinejad et al., 1995; Gronemeyer and Moras, 1995; Jiang and Sladek et al., 1997). The C→T substitution in codon 127 results in the loss of a site for the enzyme Msp I and digestion of the normal allele generates fragments of 104, 91, and 76 bp, whereas the mutant allele generates fragments of 104 and 167 bp. PCR™-RFLP analysis showed that the R127W mutation was not present in any of 214 unrelated nondiabetic subjects of different ethnic groups (53 Japanese, 53 Chinese, 51 white and 57 African-American).

TABLE 11

DNA Polymorphisms/Variants in the Human HNF-4α Gene in Japanese Subjects

| Location | Nucleotide | Substitution | Allele frequency Early-onset NIDDM/ MODY | Nondiabetic |
|---|---|---|---|---|
| Promoter | nt 922 | G→A | G-0.99, A-0.01 | G-1.00, A-0.00 |
| Intron 1A | nt 1364 (+109) | T→C | T-0.99, A-0.01 | T-1.00, C-0.00 |
|  | nt 1486 (−21) | G→A | G-0.99, A-0.01 | G-0.99, A-0.01 |
| Intron 1C | nt 2218 (−105) | G→A | G-0.99, A-0.01 | G-1.00, A-0.00 |
| Intron 1B | nt 2420 (+8) | A→G | G-0.99, A-0.01 | G-0.99, A-0.01 |
|  | nt 3142 (−38) | T→C | T-0.28, C-0.72 | T-0.24, C-0.76 |
|  | nt 3175 (−5) | C→T | C-0.84, T-0.16 | C-0.86, T-0.14 |

The R127W mutation was present in three of five diabetic members of the J2-21 family, a MODY family characterized by severe microvascular complications (Iwasaki et al., 1988) (FIG. 15). In addition, subject II-2 must be a carrier since she has children with both normal homozygous and heterozygous genotypes. The age at diagnosis of diabetes in two of the four subjects with the R127W mutation was <25 years (subject II-2, 16 years; and subject III14, 17 years). One of the subjects with the R127W mutation was diagnosed with diabetes at 90 years of age indicating the variable penetrance of the mutant allele. Another subject, the 12 year-old son of subject III-4, has inherited the mutant allele but is nondiabetic. However, he is not yet beyond the age at risk and may develop diabetes in the future. There are two subjects with diabetes in the J2-21 family who did not inherit the at-risk allele (subjects III-3 and -6). Such etiological heterogeneity has been noted previously (Bell et al., 1991).

The seven DNA polymorphisms/variants were located in the promoter region and the introns (Table 11, FIG. 13). In subject J2-96 (FIG. 15), there was a G→A substitution at nucleotide 922 in the proximal promoter region which changes the human sequence so that it more closely resembles the sequence of the mouse gene (FIG. 13). This substitution was not found on screening 53 nondiabetic subjects. Since this substitution does not alter a conserved residue or disrupt the binding site for one of the factors predicted to regulate transcription of the HNF-4α gene, the inventors believe that it is a rare variant rather than a diabetes-associated mutation. However, further studies are necessary to distinguish between these two possibilities.

The six substitutions found in introns (Table 11) do not disrupt the conserved GT and AG dinucleotides of the splice donor and acceptor sites, respectively, and are thus unlikely to affect splicing. The substitutions at nucleotides 1486, 2420, 3142 and 3175 were found in both diabetic and nondiabetic Japanese subjects indicating that they are polymorphisms rather than diabetes-associated mutations. The substitutions at nucleotides 1364 and 2218 were found only in two different unrelated subjects with early-onset NIDDM/ MODY. The inventors believe that these are rare variants rather than diabetes-associated mutations as they are not near the splice donor and acceptor sites but are rather in the central portion of the intron.

EXAMPLE 5

Hepatic Function in a Family with a Nonsense Mutation (R154X) in HNF 4α/MODY1 Gene MODY is a genetically heterogeneous monogenic disorder characterized by autosomal dominant inheritance, onset usually before 25 years of age and abnormal pancreatic β-cell function. Mutations in the hepatocyte nuclear factor (HNF)4α/MODY 1, glucokinase/MODY2 and HNF-1α/MODY3 genes can cause this form of diabetes. In contrast to the glucokinase and HNF-1α genes, mutations in the HNF-4α gene are a relatively uncommon cause of MODY and the inventors' understanding of the MODY1 form of diabetes is based on studies of only a single family, the R-W pedigree. Here the inventors report the identification of another family with MODY1 and the first in which there has been a detailed characterization of hepatic function. The affected members of this family, Dresden-11 have inherited a nonsense mutation, R154X in the HNF-4α gene and are predicted to have reduced levels of this transcription factor in the tissues in which it is expressed including pancreatic islets, liver, kidney and intestine. Subjects with the R154K mutation exhibited a diminished insulin secretory response to oral glucose. HNF-4α plays a central role in tissue-specific regulation of gene expression in the liver including the control of synthesis of proteins involved in cholesterol and lipoprotein metabolism and the coagulation cascade. However, subjects with the R154X mutation showed no abnormalities in lipid metabolism or coagulation except for a paradoxical 3.3-fold increase in serum lipoprotein(a) levels. Nor was there any evidence of renal dysfunction in these subjects. The results suggest that MODYI is primarily a disorder of β-cell function.

1. Methods

Subjects.

The study population consisted of members of twelve unrelated families with early-onset NIDDM ascertained through the Department of Internal Medicine III, University Clinic Carl Gustav Carus of the Technical University, Dresden, Germany. Families were selected based on the presence of non-insulin-dependent (type 2) diabetes mellitus (NIDDM) in two or more generations with diagnosis before 35 years of age in at least one subject. Sufficient family data were available to suggest a diagnosis of MODY in nine of these families (i.e., NIDDM in three generations with autosomal dominant inheritance and onset before 25 years of age in at least one affected subject) (Fajans et al., 1994). The remaining three families were classified as having early-onset NIDDM. The average age at diagnosis of diabetes in affected members of these twelve families was 29.9±2.8 years (range, 14–60 years) (mean±SEM) and included 18 men and 13 women of whom 12, 12 and 7 were being treated with insulin, oral hypoglycemic agents and diet, respectively. At the time of recruitment, informed consent was obtained from each subject and blood and urine samples were obtained for DNA isolation and clinical testing.

Screening HNF-4α gene for mutations.

The minimal promoter region (nucleotides −21 to −459) (Zhong et al., 1994) and 10 exons encoding the HNF-4α form (Drewes et al., 1996) of HNF-4α were screened for mutations by polymerase chain reaction (PCR™) amplification and direct sequencing of both strands of the amplified PCR™ product as described previously (Yamagata et al., 1996). Sequence changes were confirmed by cloning the PCR™ product into pGEM-4Z (Promega, Madison, Wis.) and sequencing clones derived from both alleles. The sequences of the primers for the amplification and sequencing of the minimal promoter region are P 1,5'-CAAGGATCCAGAAGATTGGC-3' (SEQ ID NO:120), and P2, 5'-CGTCCTCTGGGAAGATCTGC-3' (SEQ ID NO:121); the size of the PCR™ product is 479 bp. The sequence of the promoter of the human HNF-4α gene has been deposited in the GenBank database with accession number U72959.

Linkage analysis.

Family members were typed with the markers D20S43, D20S89, D20S96, D20S119, D20S169 and D20S424, all of which are tightly linked to the HNF-4α gene (Stoffel et al., 1996). Tests for linkage were carried out using the haplotype formed from these markers and assuming a recombination frequency between adjacent markers of 0.001 with the computer program ILINK (Lathrop et al., 1984; Lathrop and Lalouel, 1984). The frequencies of the haplotypes were estimated from the data. The analysis assumed a disease allele frequency of 0.001 and two liability classes. Liability class 1 included individuals who were 25 years of age with penetrances of 0.00, 0.95 and 0.95 for the normal homozygote, heterozygote and susceptible homozygote, respectively. Liability class 2 included individuals who were <25 years of age with penetrances of 0.00, 0.60 and 0.95 for the normal homozygote, heterozygote and susceptible homozygote, respectively. The affection status of the one subject with impaired glucose tolerance was coded as affected. The maximum expected lod score (ELOD) was determined using the computer program SLINK (Ott, 1989; Weeks et al., 1990).

Clinical Studies.

A standard 75 g oral glucose tolerance test was given to subjects after a 12 h overnight fast. Treatment with insulin and oral hypoglycemic agents was discontinued 12 h and 24 h, respectively, before testing. Blood samples for glucose, insulin, C-peptide and proinsulin were drawn at 0, 30, 60, 90 and 120 min. Fasting blood samples were also drawn for the measurement of insulin, islet cell and glutamic acid decarboxylase (GAD) antibodies, glycosylated hemoglobin ($HbA_{1c}$), lipoprotein(a), apolipoproteins AI, AII, B, CII, CIII and E, cholesterol (total and in VLDL, LDL, HDL, HDL2 and HDL3), triglycerides (total and in VLDL and LDL+HDL), coagulation time (QUICK test) and partial thromboplastin time (PTT), fibrinogen, von Willebrand factor antigen (vWFr:Ag), plasminogen activator inhibitor-1 (PAI-1), tissue-type plasminogen activator (tPA), alanine aminotransferase, γ-glutamyl transferase, bilirubin, albumin, total protein, hemoglobin, creatinine, urea, amylase, lipase and uric acid. A urine sample (from a 24-hour collection of urine) was taken for measurements of creatinine and microalbumin.

Assays.

Blood glucose was measured with a hexokinase method (Boehringer-Mannheim, Mannheim, Germany), plasma insulin and C-peptide by radioimmunoassay (DPC Biermann GmbH, Bad Nauheim, Germany; and C peptide RIA Diagnostic Systems Laboratories, Sinsheim, Germany, respectively), plasma proinsulin by ELISA (DRG Instruments, Marburg, Germany), $HbA_{1c}$ by HPLC (DIAMAT Analyzer, Bio-Rad, Munich, Germany), fibrinogen by the Clauss method (Fibrinogen A Kit, Boehringer-Mannheim), PAI-1 by bioimmunoassay and ELISA (TC® Actibind PAI-1 and TCO PAI-1 ELISA, Technoclone/ Immuno GmbH Deutschland, Heidelberg, Germany), tPA by ELISA (TintElize® tPA, Biopool AB, Umeå, Sweden), vWFr:Ag enzymatically (ELISA Asserachrom® vWF, Boehringer-Mannheim), insulin- and GAD-Ab by ELISA and radioimmunoassay (Elias, Freiburg, Germany), islet cell-Ab by an immunofluorescence assay (using a positive sample from EUROIMMUN Immunologie GmbH, Groβ Grönau, Germany), coagulation and partial thromboplastin time by the AMAX Analyzer (Munich, Germany). Total cholesterol, cholesterol in VLDL, HDL, LDL+HDL, and HDL3 were measured by the CHOD-PAP, total triglycerides and triglycerides in VLDL and LDL+HDL by the GPO-PAP method using the Ciba Corning 550 Express Clinical Chemistry Analyzer (Boehringer-Mannheim). HDL2-cholesterol was calculated using the formula HDL2=HDL-HDL3. Samples for the measurement of cholesterol, triglycerides in VLDL, HDL, LDL+HDL were prepared by preparative ultracentrifugation using a Beckman Optima tabletop TLX ultracentrifuge with a TLA-120.2 rotor. Serum creatinine, urea, uric acid, total protein, alanine aminotransferase, γ-glutamyl transferase, bilirubin, amylase and urine creatinine were measured using the BM Hitachi 717 Chemistry Analyzer (Boehringer Mannheim). Lipase was measured using the Monarch System (Sigma Germany, Munich, Germany). Apolipoproteins AI, AII and B and urine microalbumin were measured using the Behring-Nephelometer BN II (Behringwerke, Marburg, Germany). Apolipoproteins CIII and E were measured using the Sebia System (Fulda, Germany), apolipoprotein CII using the RID System (WAK, Bad Homburg, Germany).

2. Results

Identification of a nonsense mutation in the HNF-4α gene.

Twelve families with early-onset NIDDM/MODY were ascertained for genetic studies of MODY in subjects of German ancestry. Mutations in the HNF-1α/MODY3 gene (Yamagata et al., 1996) were found in three of these families (Kaisaki et al., 1997). The HNF-4α gene was screened for mutations in one affected subject from the remaining nine families. There was a C→T substitution in codon 154 of exon 4 in the proband (II-4) of family Dresden-11 (FIG. 16) which generated a nonsense mutation CGA (Arg)→TGA (OP) (R154X, FIG. 17). The R154X mutation would result in the synthesis of a truncated protein of 153 amino acids with an intact DNA binding domain but lacking the ligand binding and transactivation domain (Sladek et al., 1990). In addition to this mutation, there was a silent C→T substitution in the codon for Ala58 (GCC/GCT) in one subject which did not cosegregate with MODY/early-onset NIDDM.

The presence of the R154X mutation in other members of the Dresden-11 family was determined by PCR™ amplification and direct sequencing of exon 4. The R154X mutation cosegregated with MODY in the Dresden-11 family (FIG. 16). All diabetic subjects had the R154X mutation as did a 14-year old male (III-2) with impaired glucose tolerance. The at-risk haplotype showed some evidence for linkage with MODY with a lod score of 1.20 at a recombination of 0.00 (the maximum expected lod score in this pedigree is 1.20).

Age at diagnosis.

Three subjects were diagnosed with NIDDM between 15–25 years of age and two others at 28 and 44 years (FIG. 16). The subject, I-1, diagnosed with diabetes at 44 years of age had proliferative retinopathy at the time of diagnosis suggesting that the onset of diabetes had been many years earlier.

Clinical severity of diabetes.

The diabetes in the Dresden-11 family was severe and all the diabetic subjects were treated with either insulin or oral hypoglycemic agents. Subjects with diabetes of long duration (e.g., I-1, II-4) had diabetic complications including proliferative retinopathy, macrovascular disease (coronary heart disease) and peripheral polyneuropathy. Surprisingly, none of the subjects with the R154X mutation had evidence of nephropathy. Thus, the diabetic phenotype of the Dresden-11 family is very similar to that seen in the R-W pedigree (Fajans et al., 1994). None of the subjects in the Dresden-11 family were positive for islet, insulin or GAD antibodies.

Insulin-secretory response.

Previous studies have shown that prediabetic subjects with a mutation in HNF-4α exhibit a characteristic defect in the normal pattern of glucose-stimulated insulin secretion as well as abnormalities in other measures of normal β-cell function (Herman et al., 1994; Byrne et al., 1995). The OGTT studies showed a profound reduction in insulin secretion accompanied by diminished C-peptide and proinsulin levels in subjects with the R154X mutation (FIG. 18).

Lipid levels.

None of the subjects with the R154X mutation showed evidence of secondary hypertriglyceridemia, even though several (I-1, II-4, III-1) had poor metabolic control with $HbA_{1c}$ levels of 10.6, 8.8 and 10.1, respectively (Table 12).

TABLE 12

Clinical Parameters of the Dresden-11 family

| Parameter | Genotype Normal/Mutant | Normal/Normal (female/male) | Reference values |
|---|---|---|---|
| Age at diagnosis (years) | 26.40 ± 3.47 | — | — |
| Current age (years) | 35.50 ± 7.58 | 62/41 | — |
| n (females/males) | 2/4 | 1/1 | — |
| BMI (kg/m$^2$) | 25.21 ± 1.15 | 41.08/22.86 | <25.00 |
| HbA$_{1c}$ (%) | 8.13 ± 0.78 | 5.60/5.30 | <6.50 |
| Basal insulin (nM) | 0.067 ± 0.005 | 0.080/0.040 | 0.059–0.253 |
| Basal C-peptide (nM) | 0.60 ± 0.08 | 0.68/0.45 | <1.06 |
| Cholesterol (mM), total | 4.72 ± 0.41 | 5.03/5.01 | <5.20 |
| in VLDL (mM) | 0.79 ± 0.31 | 0.21/0.70 | 0.10–1.40 |
| in LDL (mM) | 2.86 ± 0.25 | 3.62/3.34 | 1.80–5.10 |
| in HDL (mM) | 1.17 ± 0.18 | 1.32/1.26 | 0.80–2.50 |
| in HDL2 (mM) | 0.31 ± 0.06 | 0.44/0.27 | 0.10–0.60 |
| in HDL3 (mM) | 0.86 ± 0.12 | 0.88/0.99 | 0.80–1.90 |
| Triglycerides (mM), total | 0.70 ± 0.13 | 0.65/1.45 | 0.40–2.80 |
| in VLDL (mM) | 0.43 ± 0.13 | 0.34/1.06 | 0.10–2.10 |
| in LDL + HDL (mM) | 0.28 ± 0.02 | 0.33/0.47 | 0.20–0.80 |
| Lipoprotein (a) (mg/l) | 816.0 ± 90.4 | 3.0/6.0 | <250.0 |
| ApoB (g/l) | 1.38 ± 0.22 | 1.33/1.38 | 0.72–1.50 |
| ApoAI (g/l) | 1.66 ± 0.16 | 1.89/2.00 | 1.12–1.75 |
| ApoAII (g/l) | 0.32 ± 0.02 | 0.290.53 | 0.30–0.70 |
| ApoE (mg/l) | 61.2 ± 12.2 | 65.0/55.0 | 13.0–76.0 |
| ApoCII (mg/l) | 36.0 ± 5.3 | 36.0/61.0 | 7.0–63.0 |
| ApoCIII (mg/l) | 26.7 ± 3.7 | 23.0/36.0 | 16.0–45.0 |
| General liver and kidney function | | | |
| Hemoglobin (mM) | 9.7 ± 0.4 | 9.2/10.8 | 8.6–12.1 |
| Creatinine (μM) | 91.5 ± 5.6 | 73.0/80.0 | <124.0 |
| Urea (mM) | 5.6 ± 0.8 | 6.6/1.0 | 3.6–8.9 |

TABLE 12-continued

Clinical Parameters of the Dresden-11 family

| Parameter | Genotype Normal/Mutant | Normal/Normal (female/male) | Reference values |
|---|---|---|---|
| Total protein (g/l) | 72.7 ± 1.7 | 77.2/84.0 | 65.0–85.0 |
| Albumin (g/l) | 38.6 ± 1.0 | 38.5/43.5 | 37.0–53.0 |
| Alanine aminotranferase (μmol/(ls)) | 0.39 ± 0.06 | 0.39/0.91 | 0–.10–0.67 |
| γ-glutamyl transferase (μmol/(ls)) | 0.54 ± 0.12 | 0.55/1.11 | 0.18–0.83 |
| Bilirubin (μM), total | 16.7 ± 5.2 | 13.7/24.3 | 1.0–16.0 |
| Uric acid (μM) | 249 ± 28 | 317/359 | 208–416 |
| Exocrine pancreatic function | | | |
| Amylase (U/l) | 56.8 ± 6.7 | 30.0/58.0 | 17.0–115.0 |
| Lipase (μmole/(ls)) | 1.22 ± 0.40 | 0.20/3.00 | 0.38–3.40 |
| Coagulation parameters | | | |
| Coagulation time (%) | 117 ± 6 | 108/125 | 70–120 |
| Partial thromboplastin time (s) | 33 ± 1 | 29/35 | 30–40 |
| Fibrinogen (g/l) | 3.54 ± 0.23 | 2.89/3.69 | 1.50–4.00 |
| Von Willebrand Factor Antigen (%) | 103 ± 11 | 145/115 | 70–200 |
| PAI-1 (ng/ml), total | 36 ± 8 | 102/40 | 30–80 |
| tPA (ng/ml) | 10.6 ± 1.5 | 17.2/16.0 | 2.0–10.0 |
| Urine analysis | | | |
| Creatinine(mM) | 8.36 ± 0.88 | 7.96/2.86 | 4.66–18.00 |
| Microalbumin (mg/24 h) | <2.2 | 13.5/<2.2 | 2.2–18.0 |

Values are means±SEM (standard error of means). The two normal subjects are shown with the single values. Reference values are those from the Institute of Clinical Laboratory Diagnostics, University Clinic Carl Gustav Carus, Dresden.

Hepatic and renal function.

HNF-4α is expressed in the liver and kidney and as such mutations in HNF-4α might be expected to affect the normal function of these tissues (Sladek et al., 1990; Cereghini, 1996). In this regard, HNF-4α regulates the expression of a number of apolipoproteins including AI, AIV, B and CIII (Cereghini, 1996). The serum apolipoprotein levels and lipoprotein fractions were normal in the subjects with the R154X mutation except for lipoprotein(a) levels, which were elevated 3.3-fold (Table 12). Lipoprotein(a) levels have been reported to be elevated in subjects with NIDDM in some studies (Nakagawa et al., 1996; Hirata et al., 1995) but not others (Durlach et al., 1996; Chico et al., 1996). However, an elevation in lipoprotein(a) levels in subjects with HNF-4α deficiency appears paradoxical as expression of lipoprotein(a) is controlled by HNF-1α (Wade et al., 1994) which is in turn regulated by HNF-4α (Cereghini, 1996). Thus, lower lipoprotein(a) levels, not higher, would be expected in subjects with the R154X mutation. Further studies will be necessary to determine the relationship between lipoprotein(a) levels and mutations in HNF-4α.

HNF-4α also regulates the expression of albumin, fibrinogen and the coagulation factors VII, VIII, IX and X (Cereghini, 1996; Erdmann and Heim, 1995; Figueiredo and Brownlee, 1995; Naka and Brownlee, 1996; Hung and High, 1996). The serum levels of albumin and fibrinogen and measurements of coagulation time were normal in subjects with the R154X mutation (Table 12). HNF-4α is also expressed in the kidney although the identity of the target genes in this organ are unknown (Sladek et al., 1990;

Cereghini, 1996). The urinary creatinine and microalbumin levels were normal in subjects with the R154X mutation (Table 12) suggesting that renal function was not impaired in subjects with mutations in the HNF4α gene.

EXAMPLE 6

Diminished Insulin and Glucagon Secretory Responses to Arginine in Nondiabetic Subject with a Mutation in HNF4α/MODY1 Gene Nondiabetic subjects with the Q268X mutation in the hepatocyte nuclear factor (HNF)-4α/MODY1 gene have impaired glucose-induced insulin secretion. To ascertain the effects of the nonglucose secretagogue arginine on insulin and glucagon secretion in these subjects, we studied 18 members of the RW pedigree: 7 nondiabetic mutation negative (ND[−]), 7 nondiabetic mutation positive (ND[+]), and 4 diabetic mutation positive (D[+]). We gave arginine as a 5 g bolus followed by a 25 minute infusion at basal glucose concentrations and after glucose infusion to clamp plasma glucose at ~200 mg/dl. The acute insulin response (AIR), the 10–60 minute insulin area under the curve (AUC), and the insulin secretion rate (ISR) were compared as were acute glucagon response (AGR) and glucagon AUC. The ND[+] and D[+] groups had decreased insulin AUC and ISR and decreased glucose potentiation of AIR, insulin AUC, and ISR to arginine administration when compared to the ND[−] group. At basal glucose concentrations, glucagon AUC was greatest for ND[−], intermediate for ND[+], and lowest for D[+] group. During the hyperglycemic clamp there was decreased suppression of glucagon AUC for both ND[+] and D[+] groups compared to the ND[−] group. The decreased ISR to arginine in the ND[+] group compared to the ND[−] group, magnified by glucose potentiation, indicates that HNF-4α affects the signaling pathway for arginine-induced insulin secretion. The decrease in glucagon AUC and decreased suppression of glucagon AUC with hyperglycemia suggest that mutations in HNF-4α may lead to a-cell as well as β-cell secretory defects or to a reduction in pancreatic islet mass.

1. Methods

Subjects

Eighteen members of the RW pedigree from branches II-2 and II-5, generations III, IV, and V, were studied (Fajans, 1990; Fajans et al., 1994). The study was reviewed and approved by the Institutional Review Board of the University of Michigan Medical Center, and all subjects and/or parents provided written informed consent. The glycemic status of each subject was determined by oral glucose tolerance test (OGTT) as defined by the National Diabetes Data Group (NDDG) (1979). Each subject was originally typed with a series of DNA markers on chromosome 20q to determine whether he or she has inherited the extended at-risk haplotype (defined by alleles at the loci ADA, D20S17, D20S79, and D20S4) associated with MODY1 (Bell et al., 1991; Bowden et al., 1992; Cox et al., 1992; Rothschild et al., 1993). When the Q268X mutation in the HNF-4α gene was shown to be the cause of MODY1 in the RW pedigree (Yamagata et al., 1996a), subjects were tested directly for this mutation. All the subjects included in this study, except nondiabetic individual GM11626, have been tested for the presence of the Q268X mutation. However, his nondiabetic father, IV-16, was tested and he does not have the Q268X mutation. Based on the OGTT results and the presence or absence of the Q268X mutation or at-risk haplotype, the family members were subdivided into three groups:

Nondiabetic 0268X mutation-negative group (ND[−])

Seven nondiabetic mutation-negative subjects were studied. GM identification numbers (Human Genetic Mutant Cell Repository) as given by Bell et al. (1991), RW pedigree generation and person numbers as given by Fajans et al. (1994), and age at the time of study were: GM10085, IV-22, 45 years; GM11429, IV-41, 32 years; GM11626, offspring of IV-16, 17 years; GM10153, offspring of IV-17, 18 years; GM11579, offspring of IV-19, 16 years; GM11331, offspring of IV-21, 21 years: and GM11333, offspring of IV-21, 22 years. Four of these subjects were offspring of diabetic parents (GM10085, GM11429, GM10153, and GM11579).

Nondiabetic Q 268X mutation-positive group (ND[+])

This group included seven subjects. Two subjects never had diabetes or impaired glucose tolerance on OGTT: GM11090, offspring of IV-143, 16 years; and GM10668, offspring of IV-141, 16 years. Five subjects had previous abnormalities of glucose tolerance but none had ever had an abnormal fasting plasma glucose or glycosylated hemoglobin concentration. Two had single diabetic OGTTs 4 and 22 years, respectively, before the study but had numerous normal glucose tolerance tests subsequently: GM10018, IV-168, 25 years; and GM8072, IV-143, 39 years. Three subjects had fulfilled NDDG diagnostic criteria for diabetes by OGTT in the past. Prior to the study they had normal OGTTs on 2, 4 and 5 occasions, over 2, 4 and 4 years, respectively. They were: GM11600, offspring of IV-143, 14 years; GM8759, IV-166, 31 years; and GM8073, offspring of IV-143, 19 years.

Diabetic Q 268X mutation-positive group (D[+])

The four subjects in this group had consistently diabetic OGTTs for 6 or more years or had mild fasting hyperglycemia (<200 mg/dl) when untreated. They were GM8106, III-35, 59 years; GM7974, IV-141, 43 years; GM8107, IV-165, 26 years; and GM10724, offspring of IV-142, 17 years. Subject GM8106 was treated with tolbutamide between 1958 and 1968 and with chlorpropamide since May, 1995. When untreated, his highest fasting plasma glucose was 160 mg/dl and his highest total glycosylated hemoglobin 9.1% (normal <6.3%). On 100 mg of chlorpropamide per day, his fasting plasma glucose was 91 mg/dl and glycosylated hemoglobin was 5.3%. Chlorpropamide was discontinued for 26 days before the study and fasting plasma glucose was 99 mg/dl and total glycosylated hemoglobin concentration was 5.8% on the day of the study. Subject GM7974 was treated with diet alone. She had diabetic OGTTs intermittently since 1969; OGTTs were consistently diabetic since 1990. Her fasting plasma glucose was 84 mg/dl and her total glycosylated hemoglobin was 6.9% at the time of the study. Subject GM8107's highest fasting plasma glucose was 192 mg/dl and highest total glycosylated hemoglobin was 9.5% when untreated. When treated with glyburide 1.25 mg daily, she had normal fasting and postprandial plasma glucose concentrations and a total glycosylated hemoglobin of 6.7%. Glyburide was discontinued 11 days before the study. Her fasting plasma glucose concentration was 106 mg/dl and her total glycosylated hemoglobin was 6.9% on the day of the study. Subject GM10725 had been treated with glyburide 2.5 mg twice daily since 1989. Her highest total glycosylated hemoglobin concentration was 9.0%. She discontinued medication 5 days before the study and her fasting plasma glucose was 158 mg/dl and her total glycosylated hemoglobin was 7.7% at the time of the study.

Protocol

Subjects were studied in the University of Michigan General Clinical Research Center (CRC). Subjects were admitted to the CRC in the evening and studied in the recumbent position after a 10–12 hour overnight fast. An intravenous sampling catheter was inserted in a retrograde direction in a dorsal vein of the hand and the hand was kept in a wooden box thermostatically heated to 60° C. to achieve arterialization of venous blood. A second catheter for insulin, arginine and glucose administration was inserted into the contralateral antecubital vein. In subjects with fasting hyperglycemia, a small intravenous bolus of human regular insulin (0.007 U/kg or approximately 0.5 U) was given at −50 minutes to lower the plasma glucose to approximately 75 mg/dl.

Blood samples for measurement of basal glucose, insulin, C-peptide, and glucagon concentrations were obtained at −30, −20, −10, and 0 minutes. At 0 minutes, arginine was administered. The total arginine dose was calculated as 0.41 gm/kg body weight to a maximum of 30 grams. At time 0, 5 grams of arginine was administered as an IV bolus over 30 seconds and at time 5 minutes, the remaining arginine was infused with a pump at a constant rate over 25 minutes. Samples were drawn at 2, 3, 5, 7, 10, 20, and 30-minutes for measurement of glucose, insulin, C-peptide, and glucagon. Following the first arginine bolus and infusion, there was a 60 minute washout period. Blood samples for measurement of the same constituents were obtained at 40, 50, 60, 70, 80, and 90 minutes. At 90 minutes, glucose (150 mg/kg) was administered over 30 seconds and a variable rate infusion of 20% dextrose with 10 mEq KCl/l was begun to clamp the plasma glucose level at 200 mg/dl for the remainder of the study, as determined by frequent bedside blood glucose measurements. Blood samples for the above constituents were obtained at 92, 93, 95, 97, 100, 110, 120, 130, 140, and 150 minutes. At 150 minutes, arginine (0.41 gm/kg, maximum 30 grams) was again administered as a 5 gram bolus followed after 5 minutes by an infusion over 25 minutes, as previously, and samples were drawn at 152, 153, 155, 157, 160, 170, 180, 190, 200, 210, 220, 230, and 240 minutes for measurement of glucose, insulin, C-peptide, and glucagon.

Assay procedures

All blood samples were collected on ice and stored at −70° C. until assayed. Plasma glucose was measured on a Kodak Ektachem 700 Analyzer using a hexokinase method (intra-assay coefficient of variation [CV] 1.7% at 5.0 mmol and 1.2% at 16.1 mmol). Immunoreactive insulin was measured by double-antibody radioimmunoassay (RIA) (intra-assay CV 6.4%) (Hayashi et al., 1977). C-peptide was measured by a specific RIA (intra-assay CV 3.9%) (Faber et al., 1978). Glucagon was measured by double-antibody radioimmunoassay (intra-assay CV 3.2%) (Hayashi et al., 1977). All samples were measured in duplicate and their means were used. Samples from individual subjects were measured in a single assay. All assays were performed in the Michigan Diabetes Research and Training Center Chemistry Core laboratory.

Data analysis

Acute insulin responses (AIR), acute C-peptide responses (ACR), and acute glucagon responses (AGR) were calculated as the mean of the 2, 3, 4, and 5 minute hormone levels minus the mean of the −10, −5, and 0 minute hormone levels. Glucose, insulin, C-peptide, and glucagon areas under the curve were calculated with the trapezoidal rule for the time interval 10 to 60 minute when the arginine bolus was administered at time 0 and the arginine infusion began at time 5 minutes. Baseline values, calculated as the mean hormone levels measured at −10, −5, and 0 minutes immediately preceding the arginine bolus, were subtracted from the areas under the curve. Insulin secretion rates were calculated by deconvolution of C-peptide values (Polonsky et al., 1986). All of these indices of insulin secretion were assessed during arginine administration at baseline glucose levels, during glucose administration, and during arginine administration during the hyperglycemic clamp. Slope of potentiation was calculated as the difference between the AIR or ACR to arginine obtained during the hyperglycemic clamp and at baseline glucose levels divided by the difference between these two glucose levels (Halter et al., 1979). Results are expressed as means±standard error of the mean. Statistical significance of differences among groups was assessed with chi-square and unpaired t-tests. The primary comparisons of interest were between the ND[−] and ND[+] group. P<0.05 was defined as the limit of statistical significance.

2. Results

Eighteen members of the RW Pedigree were studied: Seven non-diabetic mutation negative (ND[−]), seven non-diabetic mutation positive (ND[+]), and four diabetic mutation positive (D[+]) (Table 13). There were no significant differences among groups with regard to gender or age, although D[+] subjects tended to be older. All subjects were non-obese. Fasting glucose and insulin levels did not differ significantly among groups although D[+] subjects tended to have higher glucose levels and lower insulin levels. Fasting C-peptide levels were lower in D[+] subjects compared to ND[−] subjects. Fasting glucagon levels did not differ among groups. Glycosylated hemoglobin concentration did not differ between the two nondiabetic groups, but was higher in the D[+] group.

TABLE 13

Characteristics of Subjects from RW Pedigree by Glucose Tolerance and Mutation Status

| Glucose Tolerance Genotype* | Nondiabetic [−] | Nondiabetic [+] | Diabetic [+] |
|---|---|---|---|
| Number and gender (M/F) | 5/2 | 3/4 | 1/3 |
| Age (years) | 24 ± 4 | 23 ± 4 | 36 ± 9 |
| Body Mass Index (kg/m$^2$) | 25.2 ± 1.5 | 23.1 ± 1.0 | 22.5 ± 0.4 |
| Fasting glucose (mg/dl) | 91 ± 2 | 87 ± 2 | 112 ± 16 |
| Fasting insulin (μU/ml) | 10 ± 1 | 11 ± 2 | 7 ± 1 |
| Fasting C-peptide (ng/ml) | 1.8 ± 0.1** | 1.6 ± 0.2 | 1.3 ± 0.2 |
| Fasting glucagon (pg/ml) | 73 ± 6 | 64 ± 9 | 77 ± 12 |
| Glycosylated hemoglobin | 5.5 ± 0.1** | 5.7 ± 0.2** | 7.8 ± 0.4 |

*[−] = Normal/Normal
[+] = Normal/Q268X Mutation
**p < 0.05 vs. diabetic [+]
All values are mean ± SEM FIG. 19 demonstrates the protocol and illustrates concentrations of glucose (FIG. 19A), insulin (FIG. 19B), C-peptide (FIG. 19C), and glucagon (FIG. 19D) during the three phases of the study. These were: A) administration of arginine (bolus and infusion) at basal glucose concentrations, B) administration of glucose (bolus and variable rate infusion) to clamp the glucose level at 200 mg/dl, and C) administration of arginine (bolus and infusion) during the hyperglycemic clamp.

Table 14 summarizes average glucose levels; acute insulin responses (AIR) and C-peptide responses (ACR) to arginine; and hormone areas under the curve (AUC) and insulin secretion rate (ISR) measured 10 to 60 minutes following commencement of the three study phases. These are A) administration of arginine at basal glucose concentrations, B) administration of glucose, and C) administration of arginine during the hyperglycemic clamp.

TABLE 14

Plasma Concentrations of Glucose, Acute Insulin and C-peptide Responses (AIR and ACR), Areas Under the Curve (AUC 10–60 minutes) for Insulin and C-peptide and Insulin Secretion Rate (ISR) during administration of A) Arginine at basal glucose concentrations (Bolus and Infusion), B) Glucose (Bolus and Infusion) and C) Arginine (Bolus and Infusion) during hyperglycemic clamp.

| Period Group Number | Nondiabetic (−) n = 7 | Nondiabetic (+) n = 7 | Diabetic (+) n = 4 |
|---|---|---|---|
| A. Arginine administration at basal glucose concentration | | | |
| Glucose (mg/dl)* | 107 ± 3 | 102 ± 2 | 115 ± 15 |
| AIR ($\mu$U/ml) | 48 ± 10 | 70 ± 19 | 27 ± 7 |
| ACR (ng/ml) | 3.05 ± 0.61 | 3.25 ± 0.44 | 2.19 ± 0.55 |
| $AUC_I$ (ng/ml) | 78.5 ± 7.7 | 25.6 ± 5.5$^\dagger$ | 3.5 ± 0.8$^{\ddagger\S}$ |
| $AUC_C$ (ng/ml) | 205 ± 12 | 71 ± 9$^\dagger$ | 38 ± 6$^{\ddagger\S}$ |
| ISR ($\mu$g) | 76 ± 6 | 31 ± 3$^{II}$ | 16 ± 3$^{\P\S}$ |
| B. Glucose administration | | | |
| Glucose (mg/dl)* | 207 ± 2 | 207 ± 5 | 203 ± 7 |
| AIR ($\mu$U/ml) | 72 ± 10 | 63 ± 15 | 16 ± 6$^\P$ |
| ACR (ng/ml) | 4.03 ± 0.61 | 2.83 ± 0.54 | 1.25 ± 0.58$^\#$ |
| $AUC_I$ (ng/ml) | 43.9 ± 6.3 | 47.1 ± 11.4 | 16.1 ± 4.1$^\P$ |
| $AUC_C$ (ng/ml) | 131 ± 12 | 103 ± 16 | 61 ± 22$^\#$ |
| ISR ($\mu$g) | 63 ± 4 | 51 ± 6 | 33 ± 2$^\P$ |
| C. Arginine administration during hyperglycemic clamp | | | |
| Glucose (mg/dl)* | 198 ± 2 | 209 ± 7 | 201 ± 6 |
| AIR ($\mu$U/ml) | 271 ± 33 | 162 ± 36** | 50 ± 10$^{\ddagger\S}$ |
| ACR (ng/ml) | 10.33 ± 1.31 | 5.87 ± 0.72$^{II}$ | 3.21 ± 0.91$^{\P\S}$ |
| $AUC_I$ (ng/ml) | 628 ± 69 | 149 ± 40$^\dagger$ | 25 ± 7$^{\ddagger\S}$ |
| $AUC_C$ (ng/ml) | 739 ± 52 | 209 ± 40$^\dagger$ | 109 ± 42$^\ddagger$ |
| ISR ($\mu$g) | 276 ± 18 | 101 ± 19$^\dagger$ | 54 ± 16$^\ddagger$ |

*mean for period 10–60 minutes
All values are mean ± SEM
**$p \leq 0.05$
$^{II}p \leq 0.01$
$^\dagger p \leq 0.001$, ND[+] vs ND[−]
$^\# p < 0.05$
$^\P p < 0.01$
$^\ddagger p < 0.001$, D[+] vs ND[−]
$^\S p < 0.05$ D[+] vs ND[+]

Effects of Arginine and Glucose on Insulin Secretion

Administration of Arginine at Basal Glucose Concentrations

At baseline, glucose levels did not differ among the groups (Table 13). After the 5 g arginine bolus, AIR and ACR did not differ among groups but tended to be lower for the D[+] group (Table 14). During and after the subsequent arginine infusion, glucose levels were slightly higher at 10, 20, and 30 minute intervals in the ND[−] as compared to the ND[+] group (FIG. 19) but the average glucose levels during the 10–60 minute time interval (Table 14) and the glucose area under the curve (1171±99 vs. 1012±141 mg/dl, respectively, p=0.37) did not differ. Insulin and C-peptide levels rose to a peak at 30 minutes in the ND[−] group but were markedly decreased in both the ND[+] and D[+] groups (FIG. 19). The insulin area under the curve ($AUC_I$) and C-peptide area under the curve ($AUC_C$) were significantly reduced in ND[+] group compare to ND[−] group (Table 14). They were further reduced in D[+] group compared to the ND[+] group (Table 14). ISR was significantly reduced in ND[+] compared to ND[−] subjects and further reduced in D[+] compared to ND[+] subjects (Table 14).

Administration of Glucose

Glucose levels did not differ among the groups during the bolus and the variable rate glucose infusion (Table 14). AIR and ACR to glucose did not differ between the ND[+] and ND[−] groups but were significantly reduced in the D[+] group compared to the ND[−] group (FIG. 19, Table 14).

$AUC_I$, $AUC_C$, and ISR during the glucose infusion did not differ between the ND[−] and ND[+] groups (Table 14). They were reduced in the D[+] group compared to the ND[−] group (Table 14).

Administration of Arginine during the Hyperglycemic Clamp

Glucose levels did not differ among the groups during the variable rate glucose infusion and second arginine bolus and infusion (Table 14). At hyperglycemic plasma glucose levels, as compared to euglycemic levels, AIR and ACR to arginine, and $AUC_I$, $AUC_C$ and ISR were enhanced and differences among groups were greatly magnified (FIG. 19, Table 14). All indices of insulin secretion were significantly reduced in the ND[+] group compared to the ND[−] group and there was a further reduction in the D[+] group (Table 14).

FIG. 20A and FIG. 20B demonstrates the slopes of potentiation for insulin and C-peptide, respectively. Glucose potentiation of arginine-stimulated insulin secretion was reduced in both the ND[+] (0.80±0.18) and D[+] (0.24±0.04) groups compared to the ND[−] group (2.12±0.25, p<0.001). The insulin slope of potentiation was also reduced in D[+] group compared to ND[+] group (p<0.05). Glucose potentiation of arginine-stimulated C-peptide secretion was also reduced in the ND[+] (0.02±0.00) and D[+] (0.01±0.00) groups compared to the ND[−] group (0.07±0.01, p<0.01).

Effects of Arginine on Plasma Glucagon Concentrations

At baseline, glucagon levels did not differ among groups (Table 13). Acute glucagon responses to the 5 g bolus of arginine administered at basal glucose concentrations did not differ significantly among ND[−], ND[+], and D[+] groups (104±19, 92±16, and 82±23 pg/ml, respectively). On the other hand, the glucagon area under the curve (10–60 minutes) during and following the arginine infusion at basal glucose concentrations was reduced in D[+] compared to ND[−] subjects (4,778±1,087 vs. 7,549±639 pg/ml, p<0.05). ND[+] subjects showed intermediated volumes (5,772±734 pg/ml; p=0.09 vs. ND[−] group). During the hyperglycemic clamp there were no significant differences among glucagon areas under the curve for any of the groups (4,237±406, 3.963±508, and 2,941±568 pg/ml, for ND[−], ND[+] and D[+], respectively). To assess the impact of glucose infusion on the glucagon response to arginine in the three study groups, the inventors assessed the differences in glucagon area under the curve between the euglycemic and hyperglycemic periods. Decreases in glucagon areas induced by the hyperglycemic clamp between the first and the second arginine infusion were 3312±404, 1809±387, and 1836±535 pg/ml for the ND[−], ND[+] and D[+] groups, respectively (p<0.02 ND[−] vs. ND[+]).

EXAMPLE 7

MODY Due to Mutations in the HNF-4α Binding Site in the HNF-1α Gene Promoter

Recent studies have shown that mutations in the transcription factor hepatocyte nuclear factor (HNF)-1α are the cause of one form of maturity-onset diabetes of the young, MODY3. These studies have identified mutations in the mRNA and protein coding regions of this gene that result in the synthesis of an abnormal mRNA or protein. Here, the inventors report an Italian family in which an A→C substitution at nucleotide−58 of the promoter region of the HNF-1α gene cosegregates with MODY. This mutation is located in a highly conserved region of the promoter and disrupts the binding site for the transcription factor HNF-4α, mutations in the gene encoding HNF-4α being another cause of MODY (MODY1). This result demonstrates that decreased levels of HNF-1α per se can cause MODY. Moreover, it indicates that both the promoter and coding regions of the HNF-1α gene should be screened for mutations in subjects thought to have MODY because of mutations in this gene.

1. Method

Subjects

The MODY family Italy-1 was ascertained through the diabetes clinic of Santo Spirito's Hospital. Affection status was determined using criteria of the National Diabetes Data Group. The affection status of unaffected family members was defined as normal or impaired based on the results of a standard 75 g OGTT. This study had institutional approval and all subjects gave informed consent.

Linkage analysis

Family members were genotyped with the markers D12S321, D12S76 and UC-39 all of which are tightly linked to the HNF-1α gene (MODY3) (Yamagata et al., 1996). The forward and reverse primers for the polymorphic sequence tagged site (STS) UC-39 are 5'-GCAACAGAGCAAGACTCCATCTCA-3' (SEQ ID NO: 122) and 5'-GAGTTTAATGGAAGAACTAACC-3' (SEQ ID NO:123) respectively, and the PCR included initial denaturation at 94° C. for 5 min and 35 cycles of denaturation at 94° C. for 1 min, annealing at 63° C. for 1 min and extension at 72° C. for 1 min with a final extension at 72° C. for 10 min. The forward primer was labeled with $^{32}$P and the MgCl$_2$ concentration in the reaction was 1.0 mM. The PCR was carried out in a GeneAmp 9600 PCR System (Perkin Elmer, Norwalk, Conn.). The PCR products were separated by electrophoresis on a 5% polyacrylamide sequencing gel and visualized by autoradiography. Tests for linkage were carried out using the haplotype formed from D12S321, D12S76 and UC-39 and assuming a recombination frequency between adjacent markers of 0.001 with the computer program MLINK from the LINKAGE package (version 5.1) (Lathrop et al., 1985). The frequencies of the haplotypes were estimated from the data. The analysis assumed a disease allele frequency of 0.001 and two liability classes. Liability class 1 included individuals whose age was ≧25 years of age with penetrances of 0.00, 0.95 and 0.95 for the normal homozygote, heterozygote and susceptible homozygote, respectively. Liability class 2 included individuals <25 years of age with penetrances of 0.00, 0.50 and 0.95 for the normal homozygote, heterozygote and susceptible homozygote, respectively. The affection status of the one subject with impaired glucose tolerance was coded as unknown.

Identification of mutations

Each exon and minimal promoter region of the HNF-1α gene of subjects II-5 and III-1 were screened for mutations as described previously (Yamagata et al., 1996; Kaisaki et al., 1997). The mutation was confirmed by cloning the PCR product into pGEM-4Z and sequencing clones derived from both alleles. The presence of the mutation in other family members and unrelated nondiabetic subjects was tested by PCR amplification of the proximal promoter region and direct sequencing.

2. Results

Linkage studies

The NIDDM in the pedigree Italy-1 has the clinical features of MODY including autosomal dominant inheritance and age at diagnosis <25 years in multiple family members (FIG. 21). The six affected members are treated with either insulin (individuals II-1, II-5 and III-9) or oral hypoglycemic agents (II-7, II-1 and III-2). The three subjects on insulin therapy showed evidence of diabetic complications including retinopathy (II-1 and II-5) and nephropathy (III-9). One member of this pedigree, III-6, has impaired glucose tolerance.

The polymorphic markers D12S321, D12S76 and UC-39 which are closely linked to the HNF-1α gene (order: cen—D12S321—D12S76—HNF-1α—UC—39—qter) were typed in this family. The haplotype 3-3-7 co-segregated with MODY with no obligate recombinants (FIG. 21). One subject with IGT (age, 18 years) also inherited this haplotype as did two unaffected young women, individuals III-5 and III-13, of 21 and 14 years of age, respectively. These three subjects may be at risk of developing diabetes in the future. The LOD score in this family was 1.28 at a recombination fraction of 0.00. Although this LOD score does not meet formal criteria for establishing linkage (ie. the LOD score is <3.0), the p-value associated with the evidence for linkage is 0.008 which is sufficient to justify a search for mutations in the HNF-1α gene.

Mutation screening.

Two diabetic subjects, II-5 and III-1, were screened for mutations in the HNF-1α gene. No mutations were found on screening the mRNA/protein coding regions, exons 1–10, although the subjects were heterozygous for several previously described polymorphisms (Yamagata et al., 1996). Since no mutations were found in the coding region of the HNF-1α gene, the proximal promoter region was screened. This analysis revealed that both affected subjects were heterozygous for an A→C substitution at nucleotide −58 which is located in a highly conserved region of the promoter of the HNF-1α gene that includes the binding site for HNF-4α (FIG. 22) (Tian and Schibler et al., 1991; Kuo et al., 1992). Since this mutation does not lead to gain or loss of a site for a restriction endonuclease, it was tested for by PCR amplification and direct sequencing. The A→C substitution at nucleotide −58 co-segregated with the at-risk haplotype in the Italy-1 pedigree (FIG. 21) and was not present in a sample of 50 unrelated white subjects implying that it is the mutation responsible for MODY in this family.

EXAMPLE 8

Mutation in HNF-1β associated with MODY

HNF-1α and HNF-4α are members of a complex transcriptional regulatory network which includes other homeodomain proteins and nuclear receptors as well as members of the forkhead/winged helix and leucine zipper CCAAT/enhancer binding protein families (Cereghini, 1996). The inventors have screened two other members of this network, HNF-1β(Mendel et al., 1991a; De Simone et al., 1991; Rey-Campos et al., 1991; Bach and Yaniv, 1993) and the bifunctional protein dimerization cofactor of HNF-1 (DCoH)/pterin-4-carbinolamine dehydratase (PCBD) (Mendel et al., 1991b; Citron et al., 1992) for mutations in Japanese subjects with MODY. No diabetes-associated mutations were found in DCoH. However, the inventors found one subject with a nonsense mutation, R177X, in HNF-1β which co-segregated with early-onset diabetes. The identification of mutations in three members of the HNF-family of transcription factors indicates the importance of this regulatory network in the maintenance of glucose homeostasis.

1. Methods

Study population.

The study population consisted of 57 unrelated Japanese subjects attending the Diabetes Clinic of Tokyo Women's Medical College who were diagnosed with NIDDM before 25 years of age and/or who were members of families in which NIDDM was present in three or more generations: age at diagnosis, 20.1±7.5 years (mean±SE); male/female, 31/26; and treatment, insulin—36, oral hypoglycemic agents—10, and diet—11. These subjects had been screened for mutations in the HNF-1/MODY3 gene and all were negative for mutations in this gene (Lazzaro et al., 1992). Thirty-two of the subjects met strict criteria for a diagnosis of MODY (i.e., NIDDM in at least three generations with autosomal dominant transmission and diagnosis before 25 years of age in at least one affected subject). NIDDM was diagnosed using the criteria of the World Health Organization (Bennett, 1994). At the time of recruitment, informed consent was obtained from each subject and a blood sample was taken for DNA isolation. Fifty-three unrelated nondiabetic Japanese subjects were tested for each nucleotide substitution and mutation to determine if the sequence change was a polymorphism or disease-associated mutation.

Pedigree J2-20.

The proband (subject III-2, FIG. 25) presented with glucosuria at 10 years of age and was hospitalized. She was diagnosed with diabetes and treated with insulin for two days and then with diet only for two years. At 12 years of age, she resumed insulin therapy (28 U/day). She came to clinical attention again at 21 years because of a pyelonephritis and poorly controlled diabetes. At 23 years of age, she was admitted to the hospital of Tokyo Women's Medical College because of blurred vision. Her urine C-peptide levels at this time were 3.2 g/day (normal, 50±25 g/day) indicating low insulin secretory capacity. Despite persistent high blood glucose levels, she had no history of ketosis. The subject was diagnosed with NIDDM based on her clinical course. Subject III-3 presented with general fatigue at 15 years of age. He had gained 15 kg during the previous three months and his weight at the time of presentation was 75 kg. He was diagnosed with diabetes and was treated first with insulin and then diet and exercise. He was well controlled when he maintained his weight at 60 kg. At 18 years of age, he had gained weight again and insulin treatment was initiated, His urinary C-peptide at this time was 57.5 g/day with fasting C-peptide and glucose levels of 2.4 ng/ml and 106 mg/dl, respectively. There was no history of ketosis and he was diagnosed with NIDDM. He presently shows diminished pancreatic-cell function with no increase in C-peptide levels following administration of glucagon. All individuals shown in FIG. 25 were invited to participate in this study but many declined to do so.

Isolation and partial sequence of human HNF-1β gene.

The PAC clone 319P12 containing the human HNF-1β gene was isolated from a library (Genome Systems, St. Louis, Mo.) by screening PAC DNA pools using polymerase chain reaction (PCR™) and the primers vHNFP1 (5'-CCTCATGGAGAAACATCCTAAGT-3') (SEQ ID NO:124) and vHNFP2 (5'-AGGGAGTGCACGGCTGAGCTCCTG-3') (SEQ ID NO: 125). The sequences of the exons, flanking introns and promoter region were determined by sequencing PCR™ products and appropriate restriction fragments cloned into pGEM®-4Z (Promega, Madison, Wis.) with an AmpliTaq FS Dye Terminator cycle sequencing kit (Perkin-Elmer, Norwalk, Conn.) and ABI Prism™ 377 DNA sequencer. Primers for PCRr and sequencing were selected using the exon-intron organization of the human HNF-1α gene (Yamagata et al., 1996a) as a guide since related genes often have similar exon-intron organizations. The partial sequence of the human HNF-1β gene including promoter has been deposited in the GenBank database under accession numbers U90279–90287 and U96079.

Mutation screening.

The nine exons, flanking introns and minimal promoter region of the HNF-1β gene were amplified using PCR™ and specific primers (Table 17) and the PCR™ products were sequenced from both ends as described above. PCR™ for exon 1 was carried out using ELONGASE Enzyme™ Mix (Life Technologies, Grand Island, N.Y.) with denaturation at 94° C. for 1 min followed by 35 cycles of denaturation at 94° C. for 30 s, annealing at 55° C. for 30 s and extension at 68° C. for 1 min, and final extension at 68° C. for 10 min. PCR™ for exons 2–9 was carried out using Taq DNA polymerase and 1.5 mM $MgCl_2$ with denaturation at 94° C. for 5 min followed by 35 cycles of denaturation at 94° C. for 30 s, annealing at 60° C. for 30 s and extension at 72° C. for 30 s, and extension at 72° C. for 10 min. The sequence of each mutation was confirmed by cloning the PCR™ product into pGEM® -T Easy (Promega, Madison, Wis.) and sequencing clones representing both alleles. Exons 2–4 of the DCoH gene were amplified using Taq DNA polymerase/1.5 mM $MgCl_2$ and specific primers (Table 16) and sequenced as described above. Exon 1 of the DCoH gene encoding the 5'-untranslated region and the initiating Met was refractory to PCR™ amplification and therefore was not screened for mutations. The presence of a specific mutation or polymorphism in other individuals was determined by PCR-RFLP analysis if it resulted in the gain/loss of a site for a restriction endonuclease, or PCR™ and direct sequencing if there was no change in a site.

Linkage studies.

The human HNF-1β (STS WI-7310) and DCoH genes were mapped and confirmed to YACs 969C9 (chromosome 17) (Schuler et al., 1996) and 849H3 (chromosome 10), respectively. The adjacent polymorphic STSs D17S1788 and D10S1688 were tested for linkage with NIDDM in Japanese affected sib pairs (258 and 268 possible pairs, respectively). In the genome-wide screen of Mexican American affected sib pairs 23, the HNF-1βand DCoH genes are in the intervals D17S1293-D17S1299 and D10S589-D10S535, respectively (Schuler et al., 1996).

Transactivation studies of normal and mutant human HNF-1β.

The construct pcDNA3.1-HNF-1β was prepared by cloning the type A human HNF-1β cDNA (nucleotides 195-2783 inclusive, GenBank Accession No. X58840; SEQ ID NO:128) into pcDNA3.1+(Invitrogen, Carlsbad, Calif.). The R177X mutation was introduced by site-directed mutagenesis (QuikChange™ mutagenesis kit; Stratagene, La Jolla, Calif.) to generate pcDNA3.1-HNF-1β-R177X. The reporter gene construct pGL3-RA was prepared by cloning the promoter of the rat albumin gene, nucleotides −170 to +5 (Ringeisen et al., 1993), into the firefly luciferase reporter vector pGL3-Basic (Promega, Madison, Wis.). The sequences of all constructs were confirmed. HeLa cells were transfected for 5 hr using lipofectAMINE™ (GIBCO BRL, Gaithersburg, Md.) with 500 ng of pGL3-RA, 250 ng of pcDNA3.1-HNF-1β or pcDNA3.1-HNF-1β-R177X, and 25 ng of pRL-SV40 to control for efficiency of transfection. pcDNA3.1+DNA was added to each transfection so that the final amount of DNA added was 2 g. After 24 h, the transactivation activity of the normal and mutant HNF-1β proteins was measured using the Dual-Luciferase™ Reporter Assay System (Promega, Madison, Wis.).

2. Results

The nine exons, flanking introns and minimal promoter region of the human HNF-1β gene (TCF2) which encode all forms of HNF-1β were screened for mutations in 57 unrelated Japanese subjects with MODY. This analysis revealed four nucleotide substitutions, a C T substitution in codon 177 (exon 2) in the proband from family J2-20 which generated a nonsense mutation CGA (Arg) TGA (OP) (R177X) (FIG. 24), an uncommon silent mutation in codon 463 (exon 7) for which one subject was homozygous, and two polymorphisms in intron 8 (Table 15), neither of which is predicted to affect RNA splicing. The nonsense mutation R177X was not found on screening 53 unrelated non-diabetic Japanese subjects. One nondiabetic subject was heterozygous for the silent mutation in codon 463 (Table 15).

TABLE 15

Mutations and DNA polymorphisms in human HNF-1β and DCoH genes

| | Location | | Frequency | |
|---|---|---|---|---|
| Site | Codon | Nucleotide Change | Patients (n = 57) | Controls |
| A. HNF-1β | | | | |
| Exon 2 | 177 | CGA(Arg)→TGA (OP) | C-0.99; T-0.01 | C-1.00; T-0.00 |
| Exon 7 | 463 | GCC(Ala)→GCT (Ala) | C-0.98; T-0.02 | C-0.99; T-0.01 |
| Intron 8 | nt 48 | Insertion C | C-0.12 | C-0.17 |
| Intron 8 | nt −22 | C→T | C-0.71; T0.29 | C-0.68; T-0.32 |
| B. DCoH | | | | |
| Exon 4 | nt 9306 | A→G | A-0.82 | A-0.80; G-0.20 |

DNA polymorphisms found in introns are noted relative to the splice donor or acceptor site. (nt=nucleotide). In the HNF1β gene the C→T substitution in codon 463 and the C-insertion polymorphism in intron 8 nt 48, result in the gain of a Dde I site and loss of a Nae I, respectively. In the human DCoH gene (Genbank accession no. L41560, incorporated herein by reference), the nt 9306 is in the region encoding the 3'-untranslated region of DcoH mRNA and is 36 nucleotides after the translation termination codon.

Family J2-20 shows bilineal inheritance of diabetes (FIG. 25). The R177X mutation, which was maternally inherited, is associated with early-onset NIDDM, progression to insulin treatment and severe complications. The earlier age at diagnosis in the proband and her brother may be due to the inheritance of diabetes-susceptibility genes from both parents. The paternal diabetes gene which may potentiate the effect of the HNF-1β mutation is unknown but is not another known MODY gene as mutations were not found in the HNF-1α and HNF-4α and glucokinase genes of the proband (Iwasaki, et al., 1997; Furuta et al., 1997; Iwasaki et al., 1995). The proband's older brother had been healthy until developing a common cold and died one week later of diabetic ketoacidosis. The proband's maternal grandparents, both of whom are deceased, were not known to have diabetes. However, she has a maternal uncle with mild diet-controlled NIDDM diagnosed at 60 years of age. The difference in phenotype between the proband's mother and maternal uncle and the absence of diabetes in the maternal grandparents suggest that the R177X mutation may represent a new mutation in the proband's mother. The father and two paternal uncles have late-onset NIDDM treated with oral hypoglycemic agents. The proband's paternal grandmother was reported to have had diabetes. The presence of MODY and late-onset NIDDM within the same family is not unusual and has been reported previously (Bell et al., 1991). With respect to the presence of nephropathy in the subjects with the R177X mutation in HNF-1β, it is interesting to note that HNF-1β is expressed at highest levels in kidney (Mendel et al., 1991a; De Simone et al., 1991; Rey-Campos et al., 1991; Bach and Yaniv, 1993; Lazzaro et al., 1992) and perhaps decreased levels of this transcription factor contribute to renal dysfunction.

HNF-1β contains a bipartite DNA binding region consisting of a POU-like element and a homeodomain (Mendel et al., 1991a; De Simone et al., 1991; Rey-Campos et al., 1991; Bach and Yaniv, 1993). The R177X mutation is located at the end of the POU-like domain and generates a protein of 176 amino acids having the $NH_2$-dimerization and POU domains (Cereghini, 1996; Mendel et al., 1991a; De Simone et al., 1991; Rey-Campos et al., 1991; Bach and Yaniv, 1993). This truncated protein cannot stimulate transcription of a rat albumin promoter-linked reporter gene and does not inhibit the activity of wild-type HNF-1β (Table 16). This suggests that the R177X mutation represents a loss of function mutation which results in decreased HNF-1β levels and a corresponding reduction in expression of HNF-1β target genes.

TABLE 16

Transactivation activity of human HNF-1β and R177X mutation.

| Construct | Normalized Activity (Firefly Luciferase/ Renilla luciferase) |
|---|---|
| pcDNA 3.1 | 3.5 ± 0.5 |
| pc DNA 3.1-HNF-1β | 25.1 ± 3.2 |
| pcDNA 3.1-R177X | 3.8 ± 1.0 |
| pcDNA 3.1-HNF1β+ pcDNA 3.1-R177X | 32.2 ± 2.8 |

The activity of each construct was measured in triplicate and the mean ±SD is shown. These results are representative of at least two independent experiments.

TABLE 17

Seqences of PCR primers used for amplification and sequencing of human HNF-1 (TCF2) and DCoH (PCBD) genes

| Region | Forward primer (5'–3') | Reverse primer (5'–3') | Product size (bp) |
|---|---|---|---|
| A. HNF-1 (TCF2) | | | |
| Promoter | CATGAACCCCGAAGAGTGGTG (SEQ ID NO:90) | GCCTCCAGACACCTGTTACT SEQ ID NO:91 | 423 |
| Exon 1-1 | GGCGATCATGGCAAGTTAGAAG SEQ ID NO:92 | TTGGTGAGAGTATGGAAGACC SEQ ID NO:93 | 392 |
| Exon 1-2 | GGGGTTTGCTTGTQAAACTCC SEQ ID NO:94 | TTGGTGGGAAACGGGCTTGG SEQ ID NO:95 | 536 |

TABLE 17-continued

Seqences of PCR primers used for amplification and sequencing
of human HNF-1 (TCF2) and DCoH (PCBD) genes

| Region | Forward primer (5'–3') | Reverse primer (5'–3') | Product size (bp) |
|---|---|---|---|
| Exon 2 | CTCCCACTAGTACCTCTAACC SEQ ID NO:96 | GAGAGGGCAAAGGTCACTTCAG SEQ ID NO:97 | *291 |
| Exon 3 | AGTGAAGGCTACAGACCCTATC SEQ ID NO:98 | TTCCTGGGTCTGTGTACTTGC SEQ ID NQ:99 | 365 |
| Exon 4-1 | TGTGTTTTGGGCCAAGCACCA SEQ ID NO:100 | AACCAGATAAGATCCGTGGC SEQ ID NO:101 | 381 |
| Exon 4-2 | AACCAGACTCACAGCCTGAACC SEQ ID NO: 102 | TCACAGGGCAATGGCTGAAC SEQ ID NO:103 | 293 |
| Exon 5 | IGCCGAGTCATTGTTCCAGG SEQ ID NO:104 | CCTCTTATCTTATCAGCTCCAG SEQ ID NO:105 | 276 |
| Exon 6 | CTGCTCTTTGTGGTCCAAGTCC SEQ ID NO:106 | GAGTTTGAAGGAGACCTACAG SEQ ID NO:107 | 288 |
| Exon 7 | ATCCACCTCTCCTTATCCCAG SEQ ID NO:108 | ACTTCCGAGAAAGTTCAGACC SEQ ID NO:109 | 340 |
| Exon 8 | TTTGCCTGTGTATGCACCTTG SEQ ID NO:110 | GCCGAGTCCATGCTTGCCAC SEQ ID NO:111 | 257 |
| Exon 9 | CTTTGCTGGTTGAGTTGGGC SEQ ID NO:112 | TTCCATGACAGCTGCCCAGAG SEQ ID NO:113 | 208 |
| B. DCoH (PCBD) Exon 2 | TAAAGGTTGGAGCCCCTCTG SEQ ID NO:114 | TTGTAAG6TGACCCCATCAG SEQ ID NO:115 | 264 |
| Exon 3 | TTGGTGATGTCCAGAAGTCC SEQ ID NO:116 | CAGAATGTGTCAGAGTTCGC SEQ ID NO:117 | 213 |
| Exon 4 | CTCCCTCCTCCTGTTCTTAAGTG SEQ ID NO:118 | CTGGACTCCCAGTTCAGTCA SEQ ID NO:119 | 205 |

Human DCoH is a protein of 104 amino acids (including the initiating methionine) (Thony et al., 1995). Exons 2–4 which encode amino acids 2–104 were screened for mutations in the 57 unrelated Japanese subjects with MODY described above. The sequences were identical to one another except for an A G polymorphism located in the 3'-untranslated region (Table 15), the frequency of which was not different between MODY and nondiabetic subjects. Thus, mutations in DCoH do not appear to contribute to the development of MODY in Japanese.

The frequency of HNF-1β mutations in the inventors' study population of Japanese subjects with MODY is 2% (1/57) which is the same as for mutations in HNF4α (Furuta et al., 1997) whereas the frequency of HNF-1α mutations is about 8% (Iwasaki, et al., 1997) (the frequency of glucokinase mutations in this sample is unknown). However, genetic variation in HNF-1β or DCoH is unlikely to be a major factor contributing to the more common late-onset NIDDM as there is no evidence for linkage of markers adjacent to these genes with diabetes in Japanese or Mexican American affected sib pairs (Hanis et al., 1996).

The association of a mutation in HNF-1β with diabetes indicates the importance of the HNF-regulatory network in determining pancreatic-cell function. Moreover, HNF-1β is not able to compensate for the reduction in HNF-1β activity implying that the primary target genes for these transcription factors in pancreatic β-cells are different. The identification of these target genes will provide a better understanding of the molecular mechanisms that determine normal-cell function and may lead to new approaches for treating diabetes.

EXAMPLE 9

Elucidation of the Genes Responsible for Additional MODY Disease States

The inventors have identified that various MODY-type diabetes disease states are caused by mutations in various HNF proteins in the diseased individuals. However, the inventors are also aware of families that exhibit classic "MODY" disease states that are not caused by mutations in HNF1α, HNF1β, or HNF4α. Therefore, one aspect of this invention is to continue to screen the genetic complement of these families to determine the genes that cause these additional MODY disease states. Such screening can be done in the manner successfully used by the inventors to screen for the causes of MODY1, MODY2, and MODY 3. One of ordinary skill will be able and motivated in view of the teachings of this application, to work towards elucidating genes that, when mutated, cause additional MODY disease states. Once such genes are elucidated, all aspects diagnostic, treatment, and other aspects of the invention will be realizable by those of skill in the art for those additional MODY causations. In order to achieve these aspects of the invention, one will simply have to modify procedures and protocols taught in this specification to be appropriate to the specific gene determined to cause a MODY disease state.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Breast Cancer Res. Treat.,* 16: 182 (#151), 1990.
Allred et al, *Breast Cancer Res. Treat.,* 16: 182(#149), 1990.
An et al., Proc. *Amer. Assn. Canc. Res.,* 36: 82, 1995.
Antibodies: A Laboratory Manual, Cold Spring Harbor Laboratory, Cold Spring Harbor Press, Cold Spring Harbor, New York, 1988.
Bach, and Yaniv, *EMBO J.,* 12:4229–4242, 1993.
Baichwal and Sugden, In: Kucherlapati R, ed. Gene transfer. New York: Plenum Press, pp. 117–148, 1986.
Barnett et al., *Diabetologia* 20:87–93 (1981).
Baumheuter et al., *Genes and Development,* 4:372–379 1990
Bell, et al., *Proc. Natl. Acad. Sci. USA,* 88:1484–1488, 1991.
Bellus, *J. Macromol. Sci. Pure Appl. Chem,* A31(1): 1355–1376, 1994.
Bennett, et al., "In: *Joslin's Diabetes Mellitus,* 13$^{th}$ ed., Kahn CR, Weir GC Eds., Philadelphia, Lea & Febiger, p. 193–200, 1994.
Benvenisty and Neshif, *Proc. Nat'l Acad. Sci. USA,* 83:9551–9555, 1986.
Bittner et al, *Methods in Enzymol,* 153:516–544, 1987.
Bourguet, et al., *Nature,* 375:377–382 (1995).
Bowden, et al., *Am. J. Hum. Genet.* 50:607–618 (1992).
Bowden, et al., *Diabetes,* 41:88–92 (1992).
Brown et al., *Breast Cancer Res. Treat.,* 16: 192(#191), 1990.
Byrne, et al., *Am. J. Physiol.,* 268:E21–27, 1995a.
Byrne, et al., *Diabetes,* 44(6):699–704, 1995b.
Byrne, et al., *J. Clin. Invest.,* 93:1120–1130, 1994.
Cammidge, P. J., *Br. Med. J.,* 2:738–741 (1928).
Capaldi et al., *Biochem. Biophys. Res. Comm.,* 76:425, 1977
Cereghini, et al., *FASEB J.,* 10:267–282, 1996.
Chartier, et al., *Gene,* 147:269–272, 1994.
Chen and Okayama, *Mol. Cell Biol.,* 7:2745–2752, 1987.
Chen et al., *Proc. Am. Urol. Assn.,* 153: 267A, 1995.
Chen, et al. *Genes & Dev.,* 8:2466–2477 (1994).
Chico, et al., *Diabetes Res. Clin. Pr.,* 33: 105–110, 1996.
Citron, et al., *Proc. Natl. Acad. Sci. USA,* 89:11891–11894, 1992.
Colberre-Garapin et al., *J. Mol. Biol.,* 150: 1, 1981.
Cotton, R. G. H., *Biochem J.,* 263:1–10 (1989).
Courtois et al., *Proc. Nat'l. Acad. Sci. USA,* 85:7937–7941 (1988).
Courtois et al; *Science* 238:688–692 (1987).
Cox, et al., *Diabetes,* 41:401–407, 1992.
Davey et al., EPO No. 329 822.
De Simone, et al., *EMBO J.,* 10: 1435–1443 1991.
Donahue et al., *J. Biol. Chem.,* 269: 8604–8609, 1994
Drewes, et al., G. U. Molec. *Cell Biol,* 16:925–931 (1996).
Dubensky et al., *Proc. Nat'l Acad. Sci. USA,* 81:7529–7533, 1984.
Durlach, et al., *Diabetes & Metabolism,* 22:319–323, 1996.
Eaton, et al.,*J. Clin. Endocrinol. Metab.,* 51:520–528, 1980.
Ellis, L. A. et al., *Nucleic Acids Res.,* 22:2710–2711 (1994).
Emens, et al., *Proc. Natl. Acad. Sci. U.S.A.,* 89:7300–7304 (1992).
Erdmann and Heim, *J. Biol. Chem.,* 270:22988–22996, 1995.
European Patent Application No. 139,417A
European Patent Application No. 320 308
Faber, et al., *Diabetes,* 27(Suppl.1): 170–177, 1978.
Fajans, et al., *Life Sci.,* 55:413–422, 1994.
Fajans, *Diabetes Care,* 13:49–64, 1990 (Erratum 13:910, 1990).
Fajans, S. S., *Diab./Metab. Rev.* 5, 579–606 (1989).
Fechheimer et al., *Proc. Nat'l Acad. Sci. USA,* 84:8463–8467, 1987.
Ferkol et al., *FASEB J.,* 7:1081–1091, 1993.
Figueiredo and Brownlee, *J. Biol. Chem.,* 270:11828–11838, 1995.
Frain et al. *Cell,* 59:145–157 (1989).
Fraley et al., *Proc. Natl. Acad. Sci. USA,* 76:3348–3352, 1979.
Freifelder, Physical Biochemistry Applications to Biochemistry and Molecular Biology, 2$^{nd}$ ed. Wm. Freeman and Co., New York, N.Y., 1982.
Freshner, Second Edition, Oxford/New York, IRL Press, Oxford University Press, 1992.
Froguel, et al., *N. Engl. J. Med.,* 328:697–702, 1993.
Froguel, et al., *Nature* (Lond.), 356:162–164, 1992 (Erratum 357:607, 1992).
Frohman, *PCR PROTOCOLS: A GUIDE TO METHODS AND APPLICATIONS,* Academic Press, N.Y., 1990.
Furuta, et al., "Diabetes, 46:IN PRESS, 1997.
Gefter et al., *Somatic Cell Genet.,* 3: 231–236, 1977.
German et al., 1990 *JBC* 265, 22063–22066
Ghosh and Bachhawat, In: Wu G. and C. Wu ed. Liver diseases, targeted diagnosis and therapy using specific receptors and ligands. New York: Marcel Dekker, pp. 87–104, 1991.
Gibbs, and Caskey, *Science* 236: 303–305 (1987).
Gingeras et al., PCT Application WO 88/10315.
Goding, 1986, In Monoclonal Antibodies: Principles and Practice, 2d ed., Orlando, Fla., Academic Press, 1986, pp. 60–61, and 71–74.
Gopal, *Mol. Cell Biol.,* 5:1188–1190, 1985.
Graham and van der Eb, *Virology,* 52:456–467, 1973.
Great Britain Patent Application No. 2 202 328
Gronemeyer and Moras, *Nature,* 375:190–191, 1995.
Halter, et al.,*J. Clin. Endocrinol. Metab.,* 48:946–954, 1979.
Hanis, et al., *Nature Genet.,* 13:161–166 (1996).
Hansen et al., *Current Opinion in Genetics and Development,* 3:246–253, 1993.
Harland and Weintraub,*J. Cell Biol.,* 101:1094–1099, 1985.
Hayashi, et al., *J. Clin. Endocrinol. Metab.,* 44:681–94, 1977.
Herman, et al *Diabetes* 43, 40–46 (1994) [Errata, *Diabetes* 43:1171 (1994)].
Hess et al., *J. Adv. Enzyme Reg.,* 7:149, 1968.
Hirata, et al., *Diabetologia,* 38:1434–1442, 1995.
Hitzeman et al., *J. Biol. Chem.,* 255:2073, 1980.
Holland et al., *Biochemistry,* 17:4900, 1978.
Hung and High, *J. Biol. Chem.,* 271:2323–2331, 1996.
Innis et al., *PCR Protocols,* Academic Press, Inc., San Diego Calif., 1990.
Inouye et al., *Nucleic Acids Res.,* 13: 3101–3109, 1985.
Irwin, et al., *Proc. Natl. Acad. Sci.* U.S.A., 91:11684–11688 (1994).
Iwasaki, et al., *Diab. Res. & Clin. Pract.,* 4:237–240, 1988.
Iwasaki, et al., *Diabetes,* 46:IN PRESS, 1997.
Iwasaki, et al. *J. Japan Diab.* Soc., 39:409–416 (1996).
Iwaski, et al., *Acta Diabetol* 32:17–22, 1995.
Jiang and Sladek, *J. Biol. Chem.,* 272:1218–1225, 1997.
Jiang, et al., *Molec. Cell. Biol.* 15:5131–5143 (1995).
Johnson et al., In BIOTECHNOLOGY AND PHARMACY, Pezzuto et al., Eds., Chapman and Hall, New York (1993)
Jones, *Genetics,* 85: 12, 1977.
Kaisaki, et al., *Diabetes,* 46:528–535, 1997.
Kaneda et al., *Science,* 243:375–378, 1989.
Kato et al., *J. Biol. Chem.,* 266:3361–3364, 1991.
Kingsman et al., *Gene,* 7: 141, 1979.
Klein et al., *Nature,* 327:70–73, 1987.
Kohler and Milstein, *Eur. J. Immunol.,* 6:511–519, 1976.
Kohler and Milstein, *Nature,* 256:495–497, 1975.

Kritis, et al., *Gene*, 173:275–280, 1996.
Kuo et al., *Nature* 355:457–461, 1992.
Kuo, et al., *Nature,* 355:457–461, 1990.
Kwoh et al., *Proc. Nat. Acad. Sci.* USA, 86: 1173, 1989.
Kyte and Doolittle, *J. Mol. Biol.,* 157(1):105–132, 1982.
Lai, et al., *Proc. Natl. Acad. Sci.* U.S.A., 90:10421–10423 (1993).
Laine, et al., *Gene* 147:269–272 (1994).
Lathrop and Lalouel, *Am. J. Hum. Genet.,* 36:460–465, 1984.
Lathrop, et al., *Am J Hum Genet* 37:482498, 1985
Lathrop, et al., *Proc. Natl. Acad. Sci.* USA, 81:3443–3446, 1984.
Lazzaro, et al., *Development,* 114:469–479, 1992.
Leahy, et al., *Diabetologia,* 36:1238–1244, 1993.
Lederman et al., *Lancet* 345, 648, 1995.
Lee, et al., *Science,* 260:1117–1121, 1993.
Lemaigre, et al. *Proc. Natl. Acad. Sci. U.S.A.* 93, 9460–9464 (1996).
Liang and Pardee, *Science,* 257: 967–971, 1992.
Lishanski et al., *Proc. Nat'l. Acad. Sci USA.,* 91:2674–2678 (1994).
Lowry etal., *Cell,* 22: 817, 1980.
Mangelsdorf, et al. *Cell,* 83:835–839 (1995).
Matthews, et al., *Diabetologia,* 28:412–419, 1985.
Melton, et al, *Nucleic Acids Res.,* 12:7035–7056, (1984).
Mendel and Crabtree, 1991, *JBC* 266:677–680
Mendel, et al *Science* 254, 1762–1767 (1991b).
Mendel, et al, *Genes & Dev.* 5, 1042–1056 (1991a).
Menzel, et al., *Diabetes,* 44:1408–1413, 1995.
Miller et al., PCT Application WO 89/06700
Miquerol, L. et al. *J. Biol. Chem.,* 269:8944–8951 (1994).
Mok et al., *Gynecol. Oncol.,* 52: 247–252, 1994.
Morgan and Lazarow, *Diabetes,* 12:115–126, 1963.
Mulligan et al., *Proc. Nat'l Acad. Sci. USA,* 78: 2072, 1981.
Myers and Maniatis in U.S. Pat. No. 4,946,733
Myers and Maniatis, *Cold Spring Harbor Symposium on Quantitative Biology,* Vo. LI, pp. 18275–18284 (1986)
Myers and Maniatis, *Science,* 230:1242–1246 (1985).
Naka and Brownlee, *Brit. J. Haematol.,* 92:231–240, 1996.
Nakagawa, et al., *Jap. J. Nephrol.,* 38:513–518, 1996.
Nakamura et al., In: *Handbook of Experimental Immunology* (4[th] Ed.), Weir, E., Herzenberg, L. A., Blackwell, C., Herzenberg, L. (eds). Vol. 1, Chapter 27, Blackwell Scientific Publ., Oxford, 1987.
Nicolas & Rubenstein, "Retroviral vectors," In: *Vectors: A survey of molecular cloning vectors and their uses,* Rodriguez & Denhardt (eds.), Stoneham: Butterworth, pp. 493–513, 1988.
Nicolau and Sene, "Liposome-mediated DNA transfer in eukaryotic cells," *Biochem. Biophys. Acta,* 721:185–190, 1982.
O'Hare et al., *Proc. Nat'l Acad. Sci. USA,* 78: 1527, 1981.
Ohara et al, *Proc. Nat'l Acad. Sci. USA,* 86: 5673–5677, 1989.
Ott, *Proc. Natl. Acad. Sci. USA,* 86:4175–4178, 1989.
PCT Application No. PCT/US87/00880
PCT Application No. PCT/US89/01025
PCT Application No. WO 88/10315
Perales et al., *Proc. Natl. Acad. Sci. USA,* 91:4086–4090, 1994.
Polonsky, et al., *J. Clin. Invest.,* 77:98–105, 1986.
Polonsky, et al., *N. Engl. J. Med.* 334, 777–783 (1996).
Potter et al, *Proc. Nat'l Acad. Sci. USA,* 81:7161–7165, 1984.
Quandt, et al., *Nucl. Acids Res.,* 23:4878–4884, 1995.
Rastinejad, etal., *Nature,* 375:203–211, 1995.
Remington's Pharmaceutical Sciences 15[th] Edition, pages 1035–1038 and 1570–1580
Renaud, et al *Nature* 378, 681–689 (1995).
Rey-Campos, et al., *EMBO J.,* 10:1445–1457, 1991.
Ridgeway, In: Rodriguez R. L., Denhardt D. T., ed. Vectors: A survey of molecular cloning vectors and their uses. Stoneham: Butterworth, pp. 467–492, 1988.
Ringeisen, etal., *J. Biol. Chem.,* 268:25706–25711, 1993.
Rippe et al, *Mol. Cell Biol.,* 10:689–695, 1990.
Rothschild, et al., *Am. J. Hum. Genet.,* 52:110–23, 1993.
Sager et al., *FASEB J.,* 7: 964–970, 1993.
Sambrook et al., *Molecular Cloning: A Laboratory Manual,* 2d Ed., Cold Spring Harbor Laboratory Press, Cold Spring Harbor, N.Y., 1989.
Santerre et al. 1984
Schuler, et al., *Science,* 274:540–546, 1996.
Sladek, et al., *Genes & Dev.* 4, 2353–2365 (1990).
Stinchcomb et al., *Nature,* 282: 39, 1979.
Stoffel, M. et al. *Proc. Natl. Acad. Sci. U.S.A.,* 93:3937–3941 (1996).
Summers et al. A MANUAL OF METHODS FOR BACULOVIRUS VECTORS AND INSECT CELL CULTURE PROCEDURES, Texas Agriculture Experimental Station.
Szybalska et al., *Proc. Nat'l Acad. Sci. USA,* 48: 2026, 1962.
Tavaviras, et al, *Mech. Dev.,* 48:67–79, 1994.
Temin, In: *Gene Transfer,* Kucherlapati (ed.), New York: Plenum Press, pp. 149–188, 1986.
Theophilus, et al., *Nucleic Acids Research,* 17:(19): 7707–7722. 1989
Thöny, et al., *Biochem. Biophys. Res. Commun.,* 210:966–973, 1995
Tian and Schibler, *Genes Dev* 5:2225–2234, 1991.
Tschemper et al., *Gene,* 10: 157, 1980.
Tur-Kaspa et al., *Mol. Cell Biol.,* 6:716–718, 1986.
U.S. Pat. No. 3,817,837
U.S. Pat. No. 3,850,752
U.S. Pat. No. 3,939,350
U.S. Pat. No. 3,996,345
U.S. Pat. No. 4,215,051
U.S. Pat. No. 4,275,149
U.S. Pat. No. 4,277,437
U.S. Pat. No. 4,366,241
U.S. Pat. No. 4,554,101
U.S. Pat. No. 4,683,195
U.S. Pat. No. 4,683,202
U.S. Pat. No. 4,800,159
U.S. Pat. No. 4,883,750
U.S. Pat. No. 5,262,311
U.S. Pat. No. 5,279,721
Van Cauter, et al., *Diabetes,* 41:368–377, 1992.
Vaxillaire, et al., *Nature Genetics,* 9:418–423, 1995
Wade, etal., *J. Biol. Chem.,* 269:19757–19765, 1994.
Wagner et al., *Science,* 260:1510–1513, 1993.
Wagner et al., *Science,* 260:1510–1513, 1990.
Wagner, et al. *Nature* 378, 690–697 (1995)
Walker et al., *Proc. Nat'l Acad. Sci. USA* 89:392–396 1992.
Wanke et al., J B C 1991, 6068–6072
Ward, et al., *Diabetes,* 37:723–729, 1988.
Watson et al., *Cancer Res.,* 54: 4598–4602, 1994.
Weeks, et al, *Am. J. Hum. Genet.,* 47:A204, 1990.
Welsh et al., *Nucleic Acids Res.,* 20: 4965–4970, 1992.
WHO Study Group on Diabetes Mellitus, *Technical Report Series* 727, World Health Organization, Geneva, 1985.
Wigler et al., *Cell,* 11: 223, 1977.
Wigler et al., *Proc. Nat'l Acad. Sci. USA,* 77: 3567, 1980.
Winter and Perucho, *Proc. Nat'l Acad. Sci USA,* 82:7575–7579 (1985).

WO 90/07641 filed Dec. 21, 1990
Wong et al., *Gene,* 10:87–94, 1980.
Wong et al., *Int. J. Oncol.,* 3: 13–17, 1993.
Wu and Wu, *Adv. Drug Delivery Rev.,* 12:159–167, 1993.
Wu and Wu, *Adv. Drug Delivery Rev.,* 12:159–167, 1993.
Wu and Wu, *Biochemistry,* 27:887–892, 1988.
Wu and Wu, *J. Biol. Chem.,* 262:4429–4432, 1987.
Wu et al, *Genomics,* 4: 560, 1989.

Xanthopoulos, et al., *Proc. Natl. Acad. Sci. U.S.A.* 88, 3807–3811 (1991).
Yamagata, et al., *Nature,* 384:458–460, 1996a.
Yamagata, et al., *Nature,* 384:455–458, 1996b.
Yang et al., *Proc. Nat'l Acad. Sci. USA,* 87:9568–9572, 1990.
Zhang, et al., *Molec. Cell. Biol.* 14,4311–4323 (1994).
Zhong, et al., *Mol. Cell. Biol.,* 14:7276–7284, 1994.

```

What is claimed is:

1. A method for detecting whether a human has or has a propensity for a MODY diabetic disease state indicated by the presence or absence of a mutation in an HNF1α gene, an HNF4α gene, or an HNF1β gene of the human, said method comprising:

a) obtaining sample nucleic acid from a human; and b) analyzing the sample nucleic acid to detect a mutation in an HNF-encoding nucleic acid segment, wherein the mutation in an HNF-encoding nucleic acid segment is (I) a mutation which results in a change in the amino acid sequence of an HNF encoded polypeptide different from wildtype, or (ii) a mutation selected from the group consisting of a truncation, a substitution, a frameshift, a mutation which results in differential splicing of the HNF gene, and a mutation in the promoter region of the HNF gene, such that the expression or activity of the HNF encoded polypeptide is reduced or eliminated, and wherein the HNF-encoding nucleic acid segment is further defined as an HNF1α-encoding nucleic acid segment, an HNF4α-encoding nucleic acid segment, or an HNF1β-encoding nucleic acid segment;

wherein the mutation in the HNF-encoding nucleic acid segment is indicative of the human having a MODY diabetic disease state or having a propensity for a MODY diabetic disease state indicated by a mutation in an HNF1α gene, an HNF4α gene, or an HNF1β gene of the human.

2. The method of claim 1, wherein the HNF-encoding nucleic acid is an HNF1α-encoding nucleic acid.

3. The method of claim 1, wherein the HNF-encoding nucleic acid is an HNF4α-encoding nucleic acid.

4. The method of claim 1, wherein the HNF-encoding nucleic acid is an HNF1β-encoding nucleic acid.

5. The method of claim 1, wherein the nucleic acid is DNA.

6. The method of claim 1, wherein the step of analyzing the HNF-encoding nucleic acid comprises sequencing the HNF-encoding nucleic acid to obtain a sequence.

7. The method of claim 6, wherein the obtained sequence of the HNF encoding nucleic acid is compared to a native nucleic acid sequence of an HNF gene.

8. The method of claim 7, wherein the sequence of the HNF encoding nucleic acid is compared to a native nucleic acid sequence of HNF1α.

9. The method of claim 8, wherein the native nucleic acid sequence of HNF1α has a sequence set forth in SEQ ID NO:1.

10. The method of claim 7, wherein the sequence of the HNF-encoding nucleic acid is compared to a native nucleic acid sequence of HNF4α.

11. The method of claim 10, wherein the native nucleic acid sequence of HNF4α has a sequence set forth in SEQ ID NO:78.

12. The method of claim 7; wherein the sequence of the HNF-encoding nucleic acid is compared to a native nucleic acid sequence of HNF1β.

13. The method of claim 12, wherein the native nucleic acid sequence of HNF1β has a sequence set forth in SEQ ID NO:128.

14. The method of claim 1, wherein the HNF-encoding nucleic acid comprises at least one point mutation.

15. The method of claim 1, wherein the step of analyzing the HNF-encoding nucleic acid comprises PCR, an RNase protection assay, or an RFLP procedure.

16. The method of claim 1, further comprising detecting the presence of a mutation in an HNF encoding nucleic acid segment.

* * * * *

UNITED STATES PATENT AND TRADEMARK OFFICE
CERTIFICATE OF CORRECTION

PATENT NO. : 6,187,533 B1 Page 1 of 1
DATED : February 13, 2001
INVENTOR(S) : Graeme I. Bell, Kazuya Yamagata, Naohisa Oda, Pamela J. Kaisaki, Hiroto Furuta, Yukio Horikawa and Stephan Menzel It is certified that error appears in the above-identified patent and that said Letters Patent is hereby corrected as shown below:

<u>Title page,</u>
Item [75], please replace the inventor's name "Naohisha" with -- Naohisa --.

<u>Column 3,</u>
Line 23, please delete "1" after "SEQ ID NO:" and insert -- 2 -- therefore.

Signed and Sealed this

Thirtieth Day of July, 2002

*Attest:*

*Attesting Officer*

JAMES E. ROGAN
*Director of the United States Patent and Trademark Office*

                           SEQUENCE LISTING (1) GENERAL INFORMATION:

(iii) NUMBER OF SEQUENCES: 147

(2) INFORMATION FOR SEQ ID NO:1:

(i) SEQUENCE CHARACTERISTICS:
        (A) LENGTH: 3238 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 988
        (D) OTHER INFORMATION: /mod_base= OTHER
            /note= "N = A, C, G, or T"

(ix) FEATURE:
        (A) NAME/KEY: CDS
        (B) LOCATION: join(24..986, 990..1916)

(xi) SEQUENCE DESCRIPTION: SEQ ID NO:1:

CGTGGCCCTG TGGCAGCCGA GCC ATG GTT TCT AAA CTG AGC CAG CTG CAG        50
                         Met Val Ser Lys Leu Ser Gln Leu Gln
                          1               5

ACG GAG CTC CTG GCG GCC CTG CTC GAG TCA GGG CTG AGC AAA GAG GCA      98
Thr Glu Leu Leu Ala Ala Leu Leu Glu Ser Gly Leu Ser Lys Glu Ala
 10              15                  20                  25

CTG ATC CAG GCA CTG GGT GAG CCG GGG CCC TAC CTC CTG GCT GGA GAA     146
Leu Ile Gln Ala Leu Gly Glu Pro Gly Pro Tyr Leu Leu Ala Gly Glu
                 30                  35                  40

GGC CCC CTG GAC AAG GGG GAG TCC TGC GGC GGC GGT CGA GGG GAG CTG     194
Gly Pro Leu Asp Lys Gly Glu Ser Cys Gly Gly Gly Arg Gly Glu Leu
                 45                  50                  55

GCT GAG CTG CCC AAT GGG CTG GGG GAG ACT CGG GGC TCC GAG GAC GAG     242
Ala Glu Leu Pro Asn Gly Leu Gly Glu Thr Arg Gly Ser Glu Asp Glu
                 60                  65                  70

ACG GAC GAC GAT GGG GAA GAC TTC ACG CCA CCC ATC CTC AAA GAG CTG     290
Thr Asp Asp Asp Gly Glu Asp Phe Thr Pro Pro Ile Leu Lys Glu Leu
 75                  80                  85

GAG AAC CTC AGC CCT GAG GAG GCG GCC CAC CAG AAA GCC GTG GTG GAG     338
Glu Asn Leu Ser Pro Glu Glu Ala Ala His Gln Lys Ala Val Val Glu
 90                  95                 100                 105

ACC CTT CTG CAG GAG GAC CCG TGG CGT GTG GCG AAG ATG GTC AAG TCC     386
Thr Leu Leu Gln Glu Asp Pro Trp Arg Val Ala Lys Met Val Lys Ser
                 110                 115                 120

TAC CTG CAG CAG CAC AAC ATC CCA CAG CGG GAG GTG GTC GAT ACC ACT     434
Tyr Leu Gln Gln His Asn Ile Pro Gln Arg Glu Val Val Asp Thr Thr
                 125                 130                 135

GGC CTC AAC CAG TCC CAC CTG TCC CAA CAC CTC AAC AAG GGC ACT CCC     482
Gly Leu Asn Gln Ser His Leu Ser Gln His Leu Asn Lys Gly Thr Pro
                 140                 145                 150
```

```
ATG AAG ACG CAG AAG CGG GCC GCC CTG TAC ACC TGG TAC GTC CGC AAG        530
Met Lys Thr Gln Lys Arg Ala Ala Leu Tyr Thr Trp Tyr Val Arg Lys
    155                 160                 165

CAG CGA GAG GTG GCG CAG CAG TTC ACC CAT GCA GGG CAG GGA GGG CTG        578
Gln Arg Glu Val Ala Gln Gln Phe Thr His Ala Gly Gln Gly Gly Leu
170                 175                 180                 185

ATT GAA GAG CCC ACA GGT GAT GAG CTA CCA ACC AAG AAG GGG CGG AGG        626
Ile Glu Glu Pro Thr Gly Asp Glu Leu Pro Thr Lys Lys Gly Arg Arg
                    190                 195                 200

AAC CGT TTC AAG TGG GGC CCA GCA TCC CAG CAG ATC CTG TTC CAG GCC        674
Asn Arg Phe Lys Trp Gly Pro Ala Ser Gln Gln Ile Leu Phe Gln Ala
                205                 210                 215

TAT GAG AGG CAG AAG AAC CCT AGC AAG GAG GAG CGA GAG ACG CTA GTG        722
Tyr Glu Arg Gln Lys Asn Pro Ser Lys Glu Glu Arg Glu Thr Leu Val
            220                 225                 230

GAG GAG TGC AAT AGG GCG GAA TGC ATC CAG AGA GGG GTG TCC CCA TCA        770
Glu Glu Cys Asn Arg Ala Glu Cys Ile Gln Arg Gly Val Ser Pro Ser
        235                 240                 245

CAG GCA CAG GGG CTG GGC TCC AAC CTC GTC ACG GAG GTG CGT GTC TAC        818
Gln Ala Gln Gly Leu Gly Ser Asn Leu Val Thr Glu Val Arg Val Tyr
250                 255                 260                 265

AAC TGG TTT GCC AAC CGG CGC AAA GAA GAA GCC TTC CGG CAC AAG CTG        866
Asn Trp Phe Ala Asn Arg Arg Lys Glu Glu Ala Phe Arg His Lys Leu
                    270                 275                 280

GCC ATG GAC ACG TAC AGC GGG CCC CCA GGG CCA GGC CCG GGA CCT            914
Ala Met Asp Thr Tyr Ser Gly Pro Pro Pro Gly Pro Gly Pro Gly Pro
                285                 290                 295

GCG CTG CCC GCT CAC AGC TCC CCT GGC CTG CCT CCA CCT GCC CTC TCC        962
Ala Leu Pro Ala His Ser Ser Pro Gly Leu Pro Pro Pro Ala Leu Ser
            300                 305                 310

CCC AGT AAG GTC CAC GGT GTG CGC TNT GGA CAG CCT GCG ACC AGT GAG       1010
Pro Ser Lys Val His Gly Val Arg     Gly Gln Pro Ala Thr Ser Glu
        315                 320                 325

ACT GCA GAA GTA CCC TCA AGC AGC GGC GGT CCC TTA GTG ACA GTG TCT       1058
Thr Ala Glu Val Pro Ser Ser Ser Gly Gly Pro Leu Val Thr Val Ser
330                 335                 340

ACA CCC CTC CAC CAA GTG TCC CCC ACG GGC CTG GAG CCC AGC CAC AGC       1106
Thr Pro Leu His Gln Val Ser Pro Thr Gly Leu Glu Pro Ser His Ser
345                 350                 355                 360

CTG CTG AGT ACA GAA GCC AAG CTG GTC TCA GCA GCT GGG GGC CCC CTC       1154
Leu Leu Ser Thr Glu Ala Lys Leu Val Ser Ala Ala Gly Gly Pro Leu
                365                 370                 375

CCC CCT GTC AGC ACC CTG ACA GCA CTG CAC AGC TTG GAG CAG ACA TCC       1202
Pro Pro Val Ser Thr Leu Thr Ala Leu His Ser Leu Glu Gln Thr Ser
            380                 385                 390

CCA GGC CTC AAC CAG CAG CCC CAG AAC CTC ATC ATG GCC TCA CTT CCT       1250
Pro Gly Leu Asn Gln Gln Pro Gln Asn Leu Ile Met Ala Ser Leu Pro
        395                 400                 405

GGG GTC ATG ACC ATC GGG CCT GGT GAG CCT GCC TCC CTG GGT CCT ACG       1298
Gly Val Met Thr Ile Gly Pro Gly Glu Pro Ala Ser Leu Gly Pro Thr
    410                 415                 420

TTC ACC AAC ACA GGT GCC TCC ACC CTG GTC ATC GGC CTG GCC TCC ACG       1346
Phe Thr Asn Thr Gly Ala Ser Thr Leu Val Ile Gly Leu Ala Ser Thr
425                 430                 435                 440

CAG GCA CAG AGT GTG CCG GTC ATC AAC AGC ATG GGC AGC AGC CTG ACC       1394
Gln Ala Gln Ser Val Pro Val Ile Asn Ser Met Gly Ser Ser Leu Thr
                445                 450                 455

ACC CTG CAG CCC GTC CAG TTC TCC CAG CCG CTG CAC CCC TCC TAC CAG       1442
Thr Leu Gln Pro Val Gln Phe Ser Gln Pro Leu His Pro Ser Tyr Gln
            460                 465                 470
```

```
CAG CCG CTC ATG CCA CCT GTG CAG AGC CAT GTG ACC CAG AGC CCC TTC      1490
Gln Pro Leu Met Pro Pro Val Gln Ser His Val Thr Gln Ser Pro Phe
            475                 480                 485

ATG GCC ACC ATG GCT CAG CTG CAG AGC CCC CAC GCC CTC TAC AGC CAC      1538
Met Ala Thr Met Ala Gln Leu Gln Ser Pro His Ala Leu Tyr Ser His
            490                 495                 500

AAG CCC GAG GTG GCC CAG TAC ACC CAC ACG GGC CTG CTC CCG CAG ACT      1586
Lys Pro Glu Val Ala Gln Tyr Thr His Thr Gly Leu Leu Pro Gln Thr
505                 510                 515                 520

ATG CTC ATC ACC GAC ACC ACC AAC CTG AGC GCC CTG GCC AGC CTC ACG      1634
Met Leu Ile Thr Asp Thr Thr Asn Leu Ser Ala Leu Ala Ser Leu Thr
                525                 530                 535

CCC ACC AAG CAG GTC TTC ACC TCA GAC ACT GAG GCC TCC AGT GAG TCC      1682
Pro Thr Lys Gln Val Phe Thr Ser Asp Thr Glu Ala Ser Ser Glu Ser
            540                 545                 550

GGG CTT CAC ACG CCG GCA TCT CAG GCC ACC ACC CTC CAC GTC CCC AGC      1730
Gly Leu His Thr Pro Ala Ser Gln Ala Thr Thr Leu His Val Pro Ser
            555                 560                 565

CAG GAC CCT GCC GGC ATC CAG CAC CTG CAG CCG GCC CAC CGG CTC AGC      1778
Gln Asp Pro Ala Gly Ile Gln His Leu Gln Pro Ala His Arg Leu Ser
            570                 575                 580

GCC AGC CCC ACA GTG TCC TCC AGC AGC CTG GTG CTG TAC CAG AGC TCA      1826
Ala Ser Pro Thr Val Ser Ser Ser Ser Leu Val Leu Tyr Gln Ser Ser
585                 590                 595                 600

GAC TCC AGC AAT GGC CAG AGC CAC CTG CTG CCA TCC AAC CAC AGC GTC      1874
Asp Ser Ser Asn Gly Gln Ser His Leu Leu Pro Ser Asn His Ser Val
                605                 610                 615

ATC GAG ACC TTC ATC TCC ACC CAG ATG GCC TCT TCC TCC CAG              1916
Ile Glu Thr Phe Ile Ser Thr Gln Met Ala Ser Ser Ser Gln
            620                 625                 630

TAACCACGGC ACCTGGGCCC TGGGGCCTGT ACTGCCTGCT TGGGGGGTGA TGAGGGCAGC    1976

AGCCAGCCCT GCCTGGAGGA CCTGAGCCTG CCGAGCAACC GTGGCCCTTC CTGGACAGCT    2036

GTGCCTCGCT CCCCACTCTG CTCTGATGCA TCAGAAAGGG AGGGCTCTGA GGCGCCCCAA    2096

CCCGTGGAGG CTGCTCGGGG TGCACAGGAG GGGGTCGTGG AGAGCTAGGA GCAAAGCCTG    2156

TTCATGGCAG ATGTAGGAGG GACTGTCGCT GCTTCGTGGG ATACAGTCTT CTTACTTGGA    2216

ACTGAAGGGG GCGGCCTATG ACTTGGGCAC CCCCAGCCTG GCCTATGGA GAGCCCTGGG     2276

ACCGCTACAC CACTCTGGCA GCCACACTTC TCAGGACACA GGCCTGTGTA GCTGTGACCT    2336

GCTGAGCTCT GAGAGGCCCT GGATCAGCGT GGCCTTGTTC TGTCACCAAT GTACCCACCG    2396

GGCCACTCCT TCCTGCCCCA ACTCCTTCCA GCTAGTGACC CACATGCCAT TTGTACTGAC    2456

CCCATCACCT ACTCACACAG GCATTTCCTG GGTGGCTACT CTGTGCCAGA GCCTGGGGCT    2516

CTAACTGCCT GAGCCCAGGG AGGCCGAAGC TAACAGGGAA GGCAGGCAGG GCTCTCCTGG    2576

TCTTCCCATC CCCAGCGATT CCCTCTCCCA GGCCCCATGA CCTCCAGCTT TCCTGTATTT    2636

CTTCCCAAGA GCATGATGCC TCTGAGGCCA GCCTGGCCTC CTGCCTCTAC TGGGAAGGCT    2696

ACTTCGGGGC TGGGAAGTCG TCCTTACTCC TGTGGGAGCC TCGCAACCCG TGCCAAGTCC    2756

AGGTCCTGGT GGGGCAGCTC CTCTGTCTCG AGCGCCCTGC AGACCCTGCC CTTGTTTGGG    2816

GCAGGAGTAG CTGAGCTCAC AAGGCAGCAA GGCCCGAGCA GCTGAGCAGG GCCGGGGAAC    2876

TGGCCAAGCT GAGGTGCCCA GGAGAAGAAA GAGGTGACCC CAGGGCACAG GAGCTACCTG    2936

TGTGGACAGG ACTAACACTC AGAAGCCTGG GTGCCTGGCT GGCTGAGGGC AGTTCGCAGC    2996

CACCCTGAGG AGTCTGAGGT CCTGAGCACT GCCAGGAGGG ACAAAGGAGC CTGTGAACCC    3056

AGGACAAGCA TGGTCCCACA TCCCTGGGCC TGCTGCTGAG AACCTGGCCT TCAGTGTACC    3116
```

```
GCGTCTACCC TGGGATTCAG GAAAAGGCCT GGGGTGACCC GGCACCCCCT GCAGCTTGTA      3176

GCCAGCCGGG GCGAGTGGCA CGTTTATTTA ACTTTTAGTA AAGTCAAGGA GAAATGCGGT      3236

GG                                                                    3238
```

(2) INFORMATION FOR SEQ ID NO:2:

(i) SEQUENCE CHARACTERISTICS:
        (A) LENGTH: 630 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Ser Lys Leu Ser Gln Leu Gln Thr Glu Leu Leu Ala Ala Leu
 1               5                  10                  15

Leu Glu Ser Gly Leu Ser Lys Glu Ala Leu Ile Gln Ala Leu Gly Glu
                20                  25                  30

Pro Gly Pro Tyr Leu Leu Ala Gly Glu Gly Pro Leu Asp Lys Gly Glu
            35                  40                  45

Ser Cys Gly Gly Gly Arg Gly Glu Leu Ala Glu Leu Pro Asn Gly Leu
        50                  55                  60

Gly Glu Thr Arg Gly Ser Glu Asp Glu Thr Asp Asp Gly Glu Asp
 65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Pro Ala Leu Ser Pro Ser Lys Val His Gly Val
305                 310                 315                 320
```

```
Arg Gly Gln Pro Ala Thr Ser Glu Thr Ala Glu Val Pro Ser Ser Ser
                325                 330                 335

Gly Gly Pro Leu Val Thr Val Ser Thr Pro Leu His Gln Val Ser Pro
            340                 345                 350

Thr Gly Leu Glu Pro Ser His Ser Leu Leu Ser Thr Glu Ala Lys Leu
        355                 360                 365

Val Ser Ala Ala Gly Gly Pro Leu Pro Pro Val Ser Thr Leu Thr Ala
370                 375                 380

Leu His Ser Leu Glu Gln Thr Ser Pro Gly Leu Asn Gln Gln Pro Gln
385                 390                 395                 400

Asn Leu Ile Met Ala Ser Leu Pro Gly Val Met Thr Ile Gly Pro Gly
                405                 410                 415

Glu Pro Ala Ser Leu Gly Pro Thr Phe Thr Asn Thr Gly Ala Ser Thr
            420                 425                 430

Leu Val Ile Gly Leu Ala Ser Thr Gln Ala Gln Ser Val Pro Val Ile
        435                 440                 445

Asn Ser Met Gly Ser Ser Leu Thr Thr Leu Gln Pro Val Gln Phe Ser
450                 455                 460

Gln Pro Leu His Pro Ser Tyr Gln Gln Pro Leu Met Pro Pro Val Gln
465                 470                 475                 480

Ser His Val Thr Gln Ser Pro Phe Met Ala Thr Met Ala Gln Leu Gln
                485                 490                 495

Ser Pro His Ala Leu Tyr Ser His Lys Pro Glu Val Ala Gln Tyr Thr
            500                 505                 510

His Thr Gly Leu Leu Pro Gln Thr Met Leu Ile Thr Asp Thr Thr Asn
        515                 520                 525

Leu Ser Ala Leu Ala Ser Leu Thr Pro Thr Lys Gln Val Phe Thr Ser
530                 535                 540

Asp Thr Glu Ala Ser Ser Glu Ser Gly Leu His Thr Pro Ala Ser Gln
545                 550                 555                 560

Ala Thr Thr Leu His Val Pro Ser Gln Asp Pro Ala Gly Ile Gln His
                565                 570                 575

Leu Gln Pro Ala His Arg Leu Ser Ala Ser Pro Thr Val Ser Ser Ser
            580                 585                 590

Ser Leu Val Leu Tyr Gln Ser Ser Asp Ser Ser Asn Gly Gln Ser His
        595                 600                 605

Leu Leu Pro Ser Asn His Ser Val Ile Glu Thr Phe Ile Ser Thr Gln
610                 615                 620

Met Ala Ser Ser Ser Gln
625                 630

(2) INFORMATION FOR SEQ ID NO:3:

(i) SEQUENCE CHARACTERISTICS:
        (A) LENGTH: 3238 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 988
        (D) OTHER INFORMATION: /mod_base= OTHER
            /note= "N = A, C, G, or T"

(ix) FEATURE:
        (A) NAME/KEY: CDS
        (B) LOCATION: join(24..986, 990..1916)
```

(xi) SEQUENCE DESCRIPTION: SEQ ID NO:3:

```
CGTGGCCCTG TGGCAGCCGA GCC ATG GTT TCT AAA CTG AGC CAG CTG CAG         50
                         Met Val Ser Lys Leu Ser Gln Leu Gln
                          1               5

ACG GAG CTC CTG GCG GCC CTG CTC GAG TCA GGG CTG AGC AAA GAG GCA        98
Thr Glu Leu Leu Ala Ala Leu Leu Glu Ser Gly Leu Ser Lys Glu Ala
 10              15                  20                  25

CTG ATC CAG GCA CTG GGT GAG CCG GGG CCC TAC CTC CTG GCT GGA GAA       146
Leu Ile Gln Ala Leu Gly Glu Pro Gly Pro Tyr Leu Leu Ala Gly Glu
                 30                  35                  40

GGC CCC CTG GAC AAG GGG GAG TCC TGC GGC GGC GGT CGA GGG GAG CTG       194
Gly Pro Leu Asp Lys Gly Glu Ser Cys Gly Gly Gly Arg Gly Glu Leu
                 45                  50                  55

GCT GAG CTG CCC AAT GGG CTG GGG GAG ACT CGG GGC TCC GAG GAC GAG       242
Ala Glu Leu Pro Asn Gly Leu Gly Glu Thr Arg Gly Ser Glu Asp Glu
             60                  65                  70

ACG GAC GAC GAT GGG GAA GAC TTC ACG CCA CCC ATC CTC AAA GAG CTG       290
Thr Asp Asp Asp Gly Glu Asp Phe Thr Pro Pro Ile Leu Lys Glu Leu
 75                  80                  85

GAG AAC CTC AGC CCT GAG GAG GCG GCC CAC CAG AAA GCC GTG GTG GAG       338
Glu Asn Leu Ser Pro Glu Glu Ala Ala His Gln Lys Ala Val Val Glu
 90              95                 100                 105

ACC CTT CTG CAG GAG GAC CCG TGG CGT GTG GCG AAG ATG GTC AAG TCC       386
Thr Leu Leu Gln Glu Asp Pro Trp Arg Val Ala Lys Met Val Lys Ser
                110                 115                 120

TAC CTG CAG CAG CAC AAC ATC CCA CAG CAG GAG GTG GTC GAT ACC ACT       434
Tyr Leu Gln Gln His Asn Ile Pro Gln Gln Glu Val Val Asp Thr Thr
                125                 130                 135

GGC CTC AAC CAG TCC CAC CTG TCC CAA CAC CTC AAC AAG GGC ACT CCC       482
Gly Leu Asn Gln Ser His Leu Ser Gln His Leu Asn Lys Gly Thr Pro
            140                 145                 150

ATG AAG ACG CAG AAG CGG GCC GCC CTG TAC ACC TGG TAC GTC CGC AAG       530
Met Lys Thr Gln Lys Arg Ala Ala Leu Tyr Thr Trp Tyr Val Arg Lys
            155                 160                 165

CAG CGA GAG GTG GCG CAG CAG TTC ACC CAT GCA GGG CAG GGA GGG CTG       578
Gln Arg Glu Val Ala Gln Gln Phe Thr His Ala Gly Gln Gly Gly Leu
170                 175                 180                 185

ATT GAA GAG CCC ACA GGT GAT GAG CTA CCA ACC AAG AAG GGG CGG AGG       626
Ile Glu Glu Pro Thr Gly Asp Glu Leu Pro Thr Lys Lys Gly Arg Arg
                190                 195                 200

AAC CGT TTC AAG TGG GGC CCA GCA TCC CAG CAG ATC CTG TTC CAG GCC       674
Asn Arg Phe Lys Trp Gly Pro Ala Ser Gln Gln Ile Leu Phe Gln Ala
                205                 210                 215

TAT GAG AGG CAG AAG AAC CCT AGC AAG GAG GAG CGA GAG ACG CTA GTG       722
Tyr Glu Arg Gln Lys Asn Pro Ser Lys Glu Glu Arg Glu Thr Leu Val
                220                 225                 230

GAG GAG TGC AAT AGG GCG GAA TGC ATC CAG AGA GGG GTG TCC CCA TCA       770
Glu Glu Cys Asn Arg Ala Glu Cys Ile Gln Arg Gly Val Ser Pro Ser
            235                 240                 245

CAG GCA CAG GGG CTG GGC TCC AAC CTC GTC ACG GAG GTG CGT GTC TAC       818
Gln Ala Gln Gly Leu Gly Ser Asn Leu Val Thr Glu Val Arg Val Tyr
250                 255                 260                 265

AAC TGG TTT GCC AAC CGG CGC AAA GAA GAA GCC TTC CGG CAC AAG CTG       866
Asn Trp Phe Ala Asn Arg Arg Lys Glu Glu Ala Phe Arg His Lys Leu
                270                 275                 280

GCC ATG GAC ACG TAC AGC GGG CCC CCC CCA GGG CCA GGC CCG GGA CCT       914
Ala Met Asp Thr Tyr Ser Gly Pro Pro Pro Gly Pro Gly Pro Gly Pro
            285                 290                 295
```

```
GCG CTG CCC GCT CAC AGC TCC CCT GGC CTG CCT CCA CCT GCC CTC TCC        962
Ala Leu Pro Ala His Ser Ser Pro Gly Leu Pro Pro Pro Ala Leu Ser
        300                 305                 310

CCC AGT AAG GTC CAC GGT GTG CGC TNT GGA CAG CCT GCG ACC AGT GAG       1010
Pro Ser Lys Val His Gly Val Arg     Gly Gln Pro Ala Thr Ser Glu
        315                 320                 325

ACT GCA GAA GTA CCC TCA AGC AGC GGC GGT CCC TTA GTG ACA GTG TCT       1058
Thr Ala Glu Val Pro Ser Ser Ser Gly Gly Pro Leu Val Thr Val Ser
        330                 335                 340

ACA CCC CTC CAC CAA GTG TCC CCC ACG GGC CTG GAG CCC AGC CAC AGC       1106
Thr Pro Leu His Gln Val Ser Pro Thr Gly Leu Glu Pro Ser His Ser
345                 350                 355                 360

CTG CTG AGT ACA GAA GCC AAG CTG GTC TCA GCA GCT GGG GGC CCC CTC       1154
Leu Leu Ser Thr Glu Ala Lys Leu Val Ser Ala Ala Gly Gly Pro Leu
            365                 370                 375

CCC CCT GTC AGC ACC CTG ACA GCA CTG CAC AGC TTG GAG CAG ACA TCC       1202
Pro Pro Val Ser Thr Leu Thr Ala Leu His Ser Leu Glu Gln Thr Ser
                380                 385                 390

CCA GGC CTC AAC CAG CAG CCC CAG AAC CTC ATC ATG GCC TCA CTT CCT       1250
Pro Gly Leu Asn Gln Gln Pro Gln Asn Leu Ile Met Ala Ser Leu Pro
                395                 400                 405

GGG GTC ATG ACC ATC GGG CCT GGT GAG CCT GCC TCC CTG GGT CCT ACG       1298
Gly Val Met Thr Ile Gly Pro Gly Glu Pro Ala Ser Leu Gly Pro Thr
        410                 415                 420

TTC ACC AAC ACA GGT GCC TCC ACC CTG GTC ATC GGC CTG GCC TCC ACG       1346
Phe Thr Asn Thr Gly Ala Ser Thr Leu Val Ile Gly Leu Ala Ser Thr
425                 430                 435                 440

CAG GCA CAG AGT GTG CCG GTC ATC AAC AGC ATG GGC AGC AGC CTG ACC       1394
Gln Ala Gln Ser Val Pro Val Ile Asn Ser Met Gly Ser Ser Leu Thr
            445                 450                 455

ACC CTG CAG CCC GTC CAG TTC TCC CAG CCG CTG CAC CCC TCC TAC CAG       1442
Thr Leu Gln Pro Val Gln Phe Ser Gln Pro Leu His Pro Ser Tyr Gln
                460                 465                 470

CAG CCG CTC ATG CCA CCT GTG CAG AGC CAT GTG ACC CAG AGC CCC TTC       1490
Gln Pro Leu Met Pro Pro Val Gln Ser His Val Thr Gln Ser Pro Phe
                475                 480                 485

ATG GCC ACC ATG GCT CAG CTG CAG AGC CCC CAC GCC CTC TAC AGC CAC       1538
Met Ala Thr Met Ala Gln Leu Gln Ser Pro His Ala Leu Tyr Ser His
        490                 495                 500

AAG CCC GAG GTG GCC CAG TAC ACC CAC ACG GGC CTG CTC CCG CAG ACT       1586
Lys Pro Glu Val Ala Gln Tyr Thr His Thr Gly Leu Leu Pro Gln Thr
505                 510                 515                 520

ATG CTC ATC ACC GAC ACC ACC AAC CTG AGC GCC CTG GCC AGC CTC ACG       1634
Met Leu Ile Thr Asp Thr Thr Asn Leu Ser Ala Leu Ala Ser Leu Thr
            525                 530                 535

CCC ACC AAG CAG GTC TTC ACC TCA GAC ACT GAG GCC TCC AGT GAG TCC       1682
Pro Thr Lys Gln Val Phe Thr Ser Asp Thr Glu Ala Ser Ser Glu Ser
                540                 545                 550

GGG CTT CAC ACG CCG GCA TCT CAG GCC ACC ACC CTC CAC GTC CCC AGC       1730
Gly Leu His Thr Pro Ala Ser Gln Ala Thr Thr Leu His Val Pro Ser
            555                 560                 565

CAG GAC CCT GCC GGC ATC CAG CAC CTG CAG CCG GCC CAC CGG CTC AGC       1778
Gln Asp Pro Ala Gly Ile Gln His Leu Gln Pro Ala His Arg Leu Ser
        570                 575                 580

GCC AGC CCC ACA GTG TCC TCC AGC AGC CTG GTG CTG TAC CAG AGC TCA       1826
Ala Ser Pro Thr Val Ser Ser Ser Ser Leu Val Leu Tyr Gln Ser Ser
585                 590                 595                 600

GAC TCC AGC AAT GGC CAG AGC CAC CTG CTG CCA TCC AAC CAC AGC GTC       1874
Asp Ser Ser Asn Gly Gln Ser His Leu Leu Pro Ser Asn His Ser Val
            605                 610                 615
```

```
ATC GAG ACC TTC ATC TCC ACC CAG ATG GCC TCT TCC TCC CAG         1916
Ile Glu Thr Phe Ile Ser Thr Gln Met Ala Ser Ser Ser Gln
            620                 625                 630

TAACCACGGC ACCTGGGCCC TGGGGCCTGT ACTGCCTGCT TGGGGGGTGA TGAGGGCAGC  1976

AGCCAGCCCT GCCTGGAGGA CCTGAGCCTG CCGAGCAACC GTGGCCCTTC CTGGACAGCT  2036

GTGCCTCGCT CCCCACTCTG CTCTGATGCA TCAGAAAGGG AGGGCTCTGA GGCGCCCAA   2096

CCCGTGGAGG CTGCTCGGGG TGCACAGGAG GGGGTCGTGG AGAGCTAGGA GCAAAGCCTG  2156

TTCATGGCAG ATGTAGGAGG GACTGTCGCT GCTTCGTGGG ATACAGTCTT CTTACTTGGA  2216

ACTGAAGGGG GCGGCCTATG ACTTGGGCAC CCCCAGCCTG GCCTATGGA GAGCCCTGGG   2276

ACCGCTACAC CACTCTGGCA GCCACACTTC TCAGGACACA GGCCTGTGTA GCTGTGACCT  2336

GCTGAGCTCT GAGAGGCCCT GGATCAGCGT GGCCTTGTTC TGTCACCAAT GTACCCACCG  2396

GGCCACTCCT TCCTGCCCCA ACTCCTTCCA GCTAGTGACC CACATGCCAT TTGTACTGAC  2456

CCCATCACCT ACTCACACAG GCATTTCCTG GGTGGCTACT CTGTGCCAGA GCCTGGGGCT  2516

CTAACTGCCT GAGCCCAGGG AGGCCGAAGC TAACAGGGAA GGCAGGCAGG GCTCTCCTGG  2576

TCTTCCCATC CCCAGCGATT CCCTCTCCCA GGCCCCATGA CCTCCAGCTT TCCTGTATTT  2636

CTTCCCAAGA GCATGATGCC TCTGAGGCCA GCCTGGCCTC CTGCCTCTAC TGGGAAGGCT  2696

ACTTCGGGGC TGGGAAGTCG TCCTTACTCC TGTGGGAGCC TCGCAACCCG TGCCAAGTCC  2756

AGGTCCTGGT GGGGCAGCTC CTCTGTCTCG AGCGCCCTGC AGACCCTGCC CTTGTTTGGG  2816

GCAGGAGTAG CTGAGCTCAC AAGGCAGCAA GGCCCGAGCA GCTGAGCAGG GCCGGGGAAC  2876

TGGCCAAGCT GAGGTGCCCA GGAGAAGAAA GAGGTGACCC CAGGGCACAG GAGCTACCTG  2936

TGTGGACAGG ACTAACACTC AGAAGCCTGG GTGCCTGGCT GGCTGAGGGC AGTTCGCAGC  2996

CACCCTGAGG AGTCTGAGGT CCTGAGCACT GCCAGGAGGG ACAAAGGAGC CTGTGAACCC  3056

AGGACAAGCA TGGTCCCACA TCCCTGGGCC TGCTGCTGAG AACCTGGCCT TCAGTGTACC  3116

GCGTCTACCC TGGGATTCAG GAAAAGGCCT GGGGTGACCC GGCACCCCCT GCAGCTTGTA  3176

GCCAGCCGGG GCGAGTGGCA CGTTTATTTA ACTTTTAGTA AAGTCAAGGA GAAATGCGGT  3236

GG                                                               3238

(2) INFORMATION FOR SEQ ID NO:4:

(i) SEQUENCE CHARACTERISTICS:
        (A) LENGTH: 630 amino acids
        (B) TYPE: amino acid
        (D) TOPOLOGY: linear (ii) MOLECULE TYPE: protein (xi) SEQUENCE DESCRIPTION: SEQ ID NO:4:

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95
```

```
Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Gln Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Leu Ile Glu Pro Thr Gly Asp
            180                 185                 190

Glu Leu Pro Thr Lys Lys Gly Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Ala Leu Ser Pro Ser Lys Val His Gly Val
305                 310                 315                 320

Arg Gly Gln Pro Ala Thr Ser Glu Thr Ala Glu Val Pro Ser Ser Ser
                325                 330                 335

Gly Gly Pro Leu Val Thr Val Ser Thr Pro Leu His Gln Val Ser Pro
            340                 345                 350

Thr Gly Leu Glu Pro Ser His Ser Leu Leu Ser Thr Glu Ala Lys Leu
        355                 360                 365

Val Ser Ala Ala Gly Gly Pro Leu Pro Pro Val Ser Thr Leu Thr Ala
    370                 375                 380

Leu His Ser Leu Glu Gln Thr Ser Pro Gly Leu Asn Gln Gln Pro Gln
385                 390                 395                 400

Asn Leu Ile Met Ala Ser Leu Pro Gly Val Met Thr Ile Gly Pro Gly
                405                 410                 415

Glu Pro Ala Ser Leu Gly Pro Thr Phe Thr Asn Thr Gly Ala Ser Thr
            420                 425                 430

Leu Val Ile Gly Leu Ala Ser Thr Gln Ala Gln Ser Val Pro Val Ile
        435                 440                 445

Asn Ser Met Gly Ser Ser Leu Thr Thr Leu Gln Pro Val Gln Phe Ser
    450                 455                 460

Gln Pro Leu His Pro Ser Tyr Gln Gln Pro Leu Met Pro Pro Val Gln
465                 470                 475                 480

Ser His Val Thr Gln Ser Pro Phe Met Ala Thr Met Ala Gln Leu Gln
                485                 490                 495

Ser Pro His Ala Leu Tyr Ser His Lys Pro Glu Val Ala Gln Tyr Thr
            500                 505                 510
```

-continued

```
His Thr Gly Leu Leu Pro Gln Thr Met Leu Ile Thr Asp Thr Thr Asn
        515                 520                 525

Leu Ser Ala Leu Ala Ser Leu Thr Pro Thr Lys Gln Val Phe Thr Ser
        530                 535                 540

Asp Thr Glu Ala Ser Ser Glu Ser Gly Leu His Thr Pro Ala Ser Gln
545                 550                 555                 560

Ala Thr Thr Leu His Val Pro Ser Gln Asp Pro Ala Gly Ile Gln His
                565                 570                 575

Leu Gln Pro Ala His Arg Leu Ser Ala Ser Pro Thr Val Ser Ser Ser
        580                 585                 590

Ser Leu Val Leu Tyr Gln Ser Ser Asp Ser Ser Asn Gly Gln Ser His
        595                 600                 605

Leu Leu Pro Ser Asn His Ser Val Ile Glu Thr Phe Ile Ser Thr Gln
        610                 615                 620

Met Ala Ser Ser Ser Gln
625                 630
```

(2) INFORMATION FOR SEQ ID NO:5:

(i) SEQUENCE CHARACTERISTICS:
(A) LENGTH: 3239 base pairs
(B) TYPE: nucleic acid
(C) STRANDEDNESS: single
(D) TOPOLOGY: linear (ix) FEATURE:
(A) NAME/KEY: modified_base
(B) LOCATION: 989
(D) OTHER INFORMATION: /mod_base= OTHER
   /note= "N = A, C, G, or T"

(ix) FEATURE:
(A) NAME/KEY: CDS
(B) LOCATION: 24..965

(xi) SEQUENCE DESCRIPTION: SEQ ID NO:5:

```
CGTGGCCCTG TGGCAGCCGA GCC ATG GTT TCT AAA CTG AGC CAG CTG CAG            50
                       Met Val Ser Lys Leu Ser Gln Leu Gln
                        1               5

ACG GAG CTC CTG GCG GCC CTG CTC GAG TCA GGG CTG AGC AAA GAG GCA          98
Thr Glu Leu Leu Ala Ala Leu Leu Glu Ser Gly Leu Ser Lys Glu Ala
 10              15                  20                  25

CTG ATC CAG GCA CTG GGT GAG CCG GGG CCC TAC CTC CTG GCT GGA GAA         146
Leu Ile Gln Ala Leu Gly Glu Pro Gly Pro Tyr Leu Leu Ala Gly Glu
             30                  35                  40

GGC CCC CTG GAC AAG GGG GAG TCC TGC GGC GGC GGT CGA GGG GAG CTG         194
Gly Pro Leu Asp Lys Gly Glu Ser Cys Gly Gly Gly Arg Gly Glu Leu
             45                  50                  55

GCT GAG CTG CCC AAT GGG CTG GGG GAG ACT CGG GGC TCC GAG GAC GAG         242
Ala Glu Leu Pro Asn Gly Leu Gly Glu Thr Arg Gly Ser Glu Asp Glu
             60                  65                  70

ACG GAC GAC GAT GGG GAA GAC TTC ACG CCA CCC ATC CTC AAA GAG CTG         290
Thr Asp Asp Asp Gly Glu Asp Phe Thr Pro Pro Ile Leu Lys Glu Leu
 75                  80                  85

GAG AAC CTC AGC CCT GAG GAG GCG GCC CAC CAG AAA GCC GTG GTG GAG         338
Glu Asn Leu Ser Pro Glu Glu Ala Ala His Gln Lys Ala Val Val Glu
 90                  95                 100                 105

ACC CTT CTG CAG GAG GAC CCG TGG CGT GTG GCG AAG ATG GTC AAG TCC         386
Thr Leu Leu Gln Glu Asp Pro Trp Arg Val Ala Lys Met Val Lys Ser
                110                 115                 120
```

```
TAC CTG CAG CAG CAC AAC ATC CCA CAG CGG GAG GTG GTC GAT ACC ACT      434
Tyr Leu Gln Gln His Asn Ile Pro Gln Arg Glu Val Val Asp Thr Thr
            125                 130                 135

GGC CTC AAC CAG TCC CAC CTG TCC CAA CAC CTC AAC AAG GGC ACT CCC      482
Gly Leu Asn Gln Ser His Leu Ser Gln His Leu Asn Lys Gly Thr Pro
                140                 145                 150

ATG AAG ACG CAG AAG CGG GCC GCC CTG TAC ACC TGG TAC GTC CGC AAG      530
Met Lys Thr Gln Lys Arg Ala Ala Leu Tyr Thr Trp Tyr Val Arg Lys
        155                 160                 165

CAG CGA GAG GTG GCG CAG CAG TTC ACC CAT GCA GGG CAG GGA GGG CTG      578
Gln Arg Glu Val Ala Gln Gln Phe Thr His Ala Gly Gln Gly Gly Leu
170                 175                 180                 185

ATT GAA GAG CCC ACA GGT GAT GAG CTA CCA ACC AAG AAG GGG CGG AGG      626
Ile Glu Glu Pro Thr Gly Asp Glu Leu Pro Thr Lys Lys Gly Arg Arg
                190                 195                 200

AAC CGT TTC AAG TGG GGC CCA GCA TCC CAG CAG ATC CTG TTC CAG GCC      674
Asn Arg Phe Lys Trp Gly Pro Ala Ser Gln Gln Ile Leu Phe Gln Ala
        205                 210                 215

TAT GAG AGG CAG AAG AAC CCT AGC AAG GAG GAG CGA GAG ACG CTA GTG      722
Tyr Glu Arg Gln Lys Asn Pro Ser Lys Glu Glu Arg Glu Thr Leu Val
                220                 225                 230

GAG GAG TGC AAT AGG GCG GAA TGC ATC CAG AGA GGG GTG TCC CCA TCA      770
Glu Glu Cys Asn Arg Ala Glu Cys Ile Gln Arg Gly Val Ser Pro Ser
    235                 240                 245

CAG GCA CAG GGG CTG GGC TCC AAC CTC GTC ACG GAG GTG CGT GTC TAC      818
Gln Ala Gln Gly Leu Gly Ser Asn Leu Val Thr Glu Val Arg Val Tyr
250                 255                 260                 265

AAC TGG TTT GCC AAC CGG CGC AAA GAA GAA GCC TTC CGG CAC AAG CTG      866
Asn Trp Phe Ala Asn Arg Arg Lys Glu Glu Ala Phe Arg His Lys Leu
                270                 275                 280

GCC ATG GAC ACG TAC AGC GGG CCC CCC CCC AGG GCC AGG CCC GGG ACC      914
Ala Met Asp Thr Tyr Ser Gly Pro Pro Pro Arg Ala Arg Pro Gly Thr
        285                 290                 295

TGC GCT GCC CGC TCA CAG CTC CCC TGG CCT GCC TCC ACC TGC CCT CTC      962
Cys Ala Ala Arg Ser Gln Leu Pro Trp Pro Ala Ser Thr Cys Pro Leu
                300                 305                 310

CCC CAGTAAGGTC CACGGTGTGC GCTNTGGACA GCCTGCGACC AGTGAGACTG          1015
Pro

CAGAAGTACC CTCAAGCAGC GGCGGTCCCT TAGTGACAGT GTCTACACCC CTCCACCAAG    1075

TGTCCCCCAC GGGCCTGGAG CCCAGCCACA GCCTGCTGAG TACAGAAGCC AAGCTGGTCT    1135

CAGCAGCTGG GGGCCCCCTC CCCCCTGTCA GCACCCTGAC AGCACTGCAC AGCTTGGAGC    1195

AGACATCCCC AGGCCTCAAC CAGCAGCCCC AGAACCTCAT CATGGCCTCA CTTCCTGGGG    1255

TCATGACCAT CGGGCCTGGT GAGCCTGCCT CCCTGGGTCC TACGTTCACC AACACAGGTG    1315

CCTCCACCCT GGTCATCGGC CTGGCCTCCA CGCAGGCACA GAGTGTGCCG GTCATCAACA    1375

GCATGGGCAG CAGCCTGACC ACCCTGCAGC CGTCCAGTT CTCCCAGCCG CTGCACCCCT     1435

CCTACCAGCA GCCGCTCATG CCACCTGTGC AGAGCCATGT GACCCAGAGC CCCTTCATGG    1495

CCACCATGGC TCAGCTGCAG AGCCCCCACG CCCTCTACAG CCACAAGCCC GAGGTGGCCC    1555

AGTACACCCA CACGGGCCTG CTCCCGCAGA CTATGCTCAT CACCGACACC ACCAACCTGA    1615

GCGCCCTGGC CAGCCTCACG CCCACCAAGC AGGTCTTCAC CTCAGACACT GAGGCCTCCA    1675

GTGAGTCCGG GCTTCACACG CCGGCATCTC AGGCCACCAC CCTCCACGTC CCCAGCCAGG    1735

ACCCTGCCGG CATCCAGCAC CTGCAGCCGG CCCACCGGCT CAGCGCCAGC CCACAGTGT     1795

CCTCCAGCAG CCTGGTGCTG TACCAGAGCT CAGACTCCAG CAATGGCCAG AGCCACCTGC    1855
```

```
TGCCATCCAA CCACAGCGTC ATCGAGACCT TCATCTCCAC CCAGATGGCC TCTTCCTCCC    1915

AGTAACCACG GCACCTGGGC CCTGGGGCCT GTACTGCCTG CTTGGGGGGT GATGAGGGCA    1975

GCAGCCAGCC CTGCCTGGAG GACCTGAGCC TGCCGAGCAA CCGTGGCCCT TCCTGGACAG    2035

CTGTGCCTCG CTCCCCACTC TGCTCTGATG CATCAGAAAG GGAGGGCTCT GAGGCGCCCC    2095

AACCCGTGGA GGCTGCTCGG GGTGCACAGG AGGGGGTCGT GGAGAGCTAG GAGCAAAGCC    2155

TGTTCATGGC AGATGTAGGA GGGACTGTCG CTGCTTCGTG GGATACAGTC TTCTTACTTG    2215

GAACTGAAGG GGGCGGCCTA TGACTTGGGC ACCCCCAGCC TGGGCCTATG GAGAGCCCTG    2275

GGACCGCTAC ACCACTCTGG CAGCCACACT TCTCAGGACA CAGGCCTGTG TAGCTGTGAC    2335

CTGCTGAGCT CTGAGAGGCC CTGGATCAGC GTGGCCTTGT TCTGTCACCA ATGTACCCAC    2395

CGGGCCACTC CTTCCTGCCC CAACTCCTTC CAGCTAGTGA CCCACATGCC ATTTGTACTG    2455

ACCCCATCAC CTACTCACAC AGGCATTTCC TGGGTGGCTA CTCTGTGCCA GAGCCTGGGG    2515

CTCTAACTGC CTGAGCCCAG GGAGGCCGAA GCTAACAGGG AAGGCAGGCA GGGCTCTCCT    2575

GGTCTTCCCA TCCCCAGCGA TTCCCTCTCC CAGGCCCCAT GACCTCCAGC TTTCCTGTAT    2635

TTCTTCCCAA GAGCATGATG CCTCTGAGGC CAGCCTGGCC TCCTGCCTCT ACTGGGAAGG    2695

CTACTTCGGG GCTGGGAAGT CGTCCTTACT CCTGTGGGAG CCTCGCAACC CGTGCCAAGT    2755

CCAGGTCCTG GTGGGGCAGC TCCTCTGTCT CGAGCGCCCT GCAGACCCTG CCCTTGTTTG    2815

GGGCAGGAGT AGCTGAGCTC ACAAGGCAGC AAGGCCCGAG CAGCTGAGCA GGGCCGGGGA    2875

ACTGGCCAAG CTGAGGTGCC CAGGAGAAGA AAGAGGTGAC CCCAGGGCAC AGGAGCTACC    2935

TGTGTGGACA GGACTAACAC TCAGAAGCCT GGGTGCCTGG CTGGCTGAGG GCAGTTCGCA    2995

GCCACCCTGA GGAGTCTGAG GTCCTGAGCA CTGCCAGGAG GGACAAAGGA GCCTGTGAAC    3055

CCAGGACAAG CATGGTCCCA CATCCCTGGG CCTGCTGCTG AGAACCTGGC CTTCAGTGTA    3115

CCGCGTCTAC CCTGGGATTC AGGAAAAGGC CTGGGGTGAC CCGGCACCCC CTGCAGCTTG    3175

TAGCCAGCCG GGGCGAGTGG CACGTTTATT TAACTTTTAG TAAAGTCAAG GAGAAATGCG    3235

GTGA                                                                3239

(2) INFORMATION FOR SEQ ID NO:6:

(i) SEQUENCE CHARACTERISTICS:
        (A) LENGTH: 314 amino acids
        (B) TYPE: amino acid
        (D) TOPOLOGY: linear (ii) MOLECULE TYPE: protein (xi) SEQUENCE DESCRIPTION: SEQ ID NO:6:

Met Val Ser Lys Leu Ser Gln Leu Gln Thr Glu Leu Leu Ala Ala Leu
 1               5                  10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95
```

```
Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
            115                 120                 125

Pro Gln Arg Glu Val Val Asp Thr Thr Gly Leu Asn Gln Ser His Leu
            130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Leu Ile Glu Glu Pro Thr Gly Asp
                180                 185                 190

Glu Leu Pro Thr Lys Lys Gly Arg Arg Asn Arg Phe Lys Trp Gly Pro
            195                 200                 205

Ala Ser Gln Gln Ile Leu Phe Gln Ala Tyr Glu Arg Gln Lys Asn Pro
            210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
            275                 280                 285

Pro Pro Pro Arg Ala Arg Pro Gly Thr Cys Ala Ala Arg Ser Gln Leu
            290                 295                 300

Pro Trp Pro Ala Ser Thr Cys Pro Leu Pro
305                 310

(2) INFORMATION FOR SEQ ID NO:7:

(i) SEQUENCE CHARACTERISTICS:
        (A) LENGTH: 3236 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 988
        (D) OTHER INFORMATION: /mod_base= OTHER
            /note= "N = A, C, G, or T"

(ix) FEATURE:
        (A) NAME/KEY: CDS
        (B) LOCATION: join(24..986, 990..1271)

(xi) SEQUENCE DESCRIPTION: SEQ ID NO:7:

CGTGGCCCTG TGGCAGCCGA GCC ATG GTT TCT AAA CTG AGC CAG CTG CAG         50
                        Met Val Ser Lys Leu Ser Gln Leu Gln
                         1               5

ACG GAG CTC CTG GCG GCC CTG CTC GAG TCA GGG CTG AGC AAA GAG GCA       98
Thr Glu Leu Leu Ala Ala Leu Leu Glu Ser Gly Leu Ser Lys Glu Ala
 10                  15                  20                  25

CTG ATC CAG GCA CTG GGT GAG CCG GGG CCC TAC CTC CTG GCT GGA GAA      146
Leu Ile Gln Ala Leu Gly Glu Pro Gly Pro Tyr Leu Leu Ala Gly Glu
                 30                  35                  40

GGC CCC CTG GAC AAG GGG GAG TCC TGC GGC GGT CGA GGG GAG CTG           194
Gly Pro Leu Asp Lys Gly Glu Ser Cys Gly Gly Arg Gly Glu Leu
             45                  50                  55
```

```
GCT GAG CTG CCC AAT GGG CTG GGG GAG ACT CGG GGC TCC GAG GAC GAG        242
Ala Glu Leu Pro Asn Gly Leu Gly Glu Thr Arg Gly Ser Glu Asp Glu
         60                  65                  70

ACG GAC GAC GAT GGG GAA GAC TTC ACG CCA CCC ATC CTC AAA GAG CTG        290
Thr Asp Asp Asp Gly Glu Asp Phe Thr Pro Pro Ile Leu Lys Glu Leu
     75                  80                  85

GAG AAC CTC AGC CCT GAG GAG GCG GCC CAC CAG AAA GCC GTG GTG GAG        338
Glu Asn Leu Ser Pro Glu Glu Ala Ala His Gln Lys Ala Val Val Glu
 90                  95                 100                 105

ACC CTT CTG CAG GAG GAC CCG TGG CGT GTG GCG AAG ATG GTC AAG TCC        386
Thr Leu Leu Gln Glu Asp Pro Trp Arg Val Ala Lys Met Val Lys Ser
                 110                 115                 120

TAC CTG CAG CAG CAC AAC ATC CCA CAG CGG GAG GTG GTC GAT ACC ACT        434
Tyr Leu Gln Gln His Asn Ile Pro Gln Arg Glu Val Val Asp Thr Thr
             125                 130                 135

GGC CTC AAC CAG TCC CAC CTG TCC CAA CAC CTC AAC AAG GGC ACT CCC        482
Gly Leu Asn Gln Ser His Leu Ser Gln His Leu Asn Lys Gly Thr Pro
         140                 145                 150

ATG AAG ACG CAG AAG CGG GCC GCC CTG TAC ACC TGG TAC GTC CGC AAG        530
Met Lys Thr Gln Lys Arg Ala Ala Leu Tyr Thr Trp Tyr Val Arg Lys
     155                 160                 165

CAG CGA GAG GTG GCG CAG CAG TTC ACC CAT GCA GGG CAG GGA GGG CTG        578
Gln Arg Glu Val Ala Gln Gln Phe Thr His Ala Gly Gln Gly Gly Leu
170                 175                 180                 185

ATT GAA GAG CCC ACA GGT GAT GAG CTA CCA ACC AAG AAG GGG CGG AGG        626
Ile Glu Glu Pro Thr Gly Asp Glu Leu Pro Thr Lys Lys Gly Arg Arg
                 190                 195                 200

AAC CGT TTC AAG TGG GGC CCA GCA TCC CAG CAG ATC CTG TTC CAG GCC        674
Asn Arg Phe Lys Trp Gly Pro Ala Ser Gln Gln Ile Leu Phe Gln Ala
             205                 210                 215

TAT GAG AGG CAG AAG AAC CCT AGC AAG GAG GAG CGA GAG ACG CTA GTG        722
Tyr Glu Arg Gln Lys Asn Pro Ser Lys Glu Glu Arg Glu Thr Leu Val
         220                 225                 230

GAG GAG TGC AAT AGG GCG GAA TGC ATC CAG AGA GGG GTG TCC CCA TCA        770
Glu Glu Cys Asn Arg Ala Glu Cys Ile Gln Arg Gly Val Ser Pro Ser
     235                 240                 245

CAG GCA CAG GGG CTG GGC TCC AAC CTC GTC ACG GAG GTG CGT GTC TAC        818
Gln Ala Gln Gly Leu Gly Ser Asn Leu Val Thr Glu Val Arg Val Tyr
250                 255                 260                 265

AAC TGG TTT GCC AAC CGG CGC AAA GAA GAA GCC TTC CGG CAC AAG CTG        866
Asn Trp Phe Ala Asn Arg Arg Lys Glu Glu Ala Phe Arg His Lys Leu
                 270                 275                 280

GCC ATG GAC ACG TAC AGC GGG CCC CCC CCA GGG CCA GGC CCG GGA CCT        914
Ala Met Asp Thr Tyr Ser Gly Pro Pro Pro Gly Pro Gly Pro Gly Pro
             285                 290                 295

GCG CTG CCC GCT CAC AGC TCC CCT GGC CTG CCT CCA CCT GCC CTC TCC        962
Ala Leu Pro Ala His Ser Ser Pro Gly Leu Pro Pro Pro Ala Leu Ser
         300                 305                 310

CCC AGT AAG GTC CAC GGT GTG CGC TNT GGA CAG CCT GCG ACC AGT GAG       1010
Pro Ser Lys Val His Gly Val Arg     Gly Gln Pro Ala Thr Ser Glu
     315                 320                 325

ACT GCA GAA GTA CCC TCA AGC AGC GGC GGT CCC TTA GTG ACA GTG TCT       1058
Thr Ala Glu Val Pro Ser Ser Ser Gly Gly Pro Leu Val Thr Val Ser
330                 335                 340

ACA CCC CTC CAC CAA GTG TCC CCC ACG GGC CTG GAG CCC AGC CAC AGC       1106
Thr Pro Leu His Gln Val Ser Pro Thr Gly Leu Glu Pro Ser His Ser
345                 350                 355                 360

CTG CTG AGT ACA GAA GCC AAG CTG GTC TCA GCA GCT GGG GGC CCC CTC       1154
Leu Leu Ser Thr Glu Ala Lys Leu Val Ser Ala Ala Gly Gly Pro Leu
                 365                 370                 375
```

```
CCC CGT CAG CAC CCT GAC AGC ACT GCA CAG CTT GGA GCA GAC ATC CCC      1202
Pro Arg Gln His Pro Asp Ser Thr Ala Gln Leu Gly Ala Asp Ile Pro
        380                 385                 390

AGG CCT CAA CCA GCA GCC CCA GAA CCT CAT CAT GGC CTC ACT TCC TGG      1250
Arg Pro Gln Pro Ala Ala Pro Glu Pro His His Gly Leu Thr Ser Trp
        395                 400                 405

GGT CAT GAC CAT CGG GCC TGG TGAGCCTGCC TCCCTGGGTC CTACGTTCAC         1301
Gly His Asp His Arg Ala Trp
        410                 415
```

| | |
|---|---|
| CAACACAGGT GCCTCCACCC TGGTCATCGG CCTGGCCTCC ACGCAGGCAC AGAGTGTGCC | 1361 |
| GGTCATCAAC AGCATGGGCA GCAGCCTGAC CACCCTGCAG CCCGTCCAGT TCTCCCAGCC | 1421 |
| GCTGCACCCC TCCTACCAGC AGCCGCTCAT GCCACCTGTG CAGAGCCATG TGACCCAGAG | 1481 |
| CCCCTTCATG GCCACCATGG CTCAGCTGCA GAGCCCCCAC GCCCTCTACA GCCACAAGCC | 1541 |
| CGAGGTGGCC CAGTACACCC ACACGGGCCT GCTCCCGCAG ACTATGCTCA TCACCGACAC | 1601 |
| CACCAACCTG AGCGCCCTGG CCAGCCTCAC GCCCACCAAG CAGGTCTTCA CCTCAGACAC | 1661 |
| TGAGGCCTCC AGTGAGTCCG GCTTCACAC GCCGGCATCT CAGGCCACCA CCCTCCACGT | 1721 |
| CCCCAGCCAG GACCCTGCCG GCATCCAGCA CCTGCAGCCG GCCCACCGGC TCAGCGCCAG | 1781 |
| CCCCACAGTG TCCTCCAGCA GCCTGGTGCT GTACCAGAGC TCAGACTCCA GCAATGGCCA | 1841 |
| GAGCCACCTG CTGCCATCCA ACCACAGCGT CATCGAGACC TTCATCTCCA CCCAGATGGC | 1901 |
| CTCTTCCTCC CAGTAACCAC GGCACCTGGG CCCTGGGGCC TGTACTGCCT GCTTGGGGGG | 1961 |
| TGATGAGGGC AGCAGCCAGC CCTGCCTGGA GGACCTGAGC CTGCCGAGCA CCGTGGCCC | 2021 |
| TTCCTGGACA GCTGTGCCTC GCTCCCCACT CTGCTCTGAT GCATCAGAAA GGGAGGGCTC | 2081 |
| TGAGGCGCCC CAACCCGTGG AGGCTGCTCG GGGTGCACAG GAGGGGGTCG TGGAGAGCTA | 2141 |
| GGAGCAAAGC CTGTTCATGG CAGATGTAGG AGGGACTGTC GCTGCTTCGT GGGATACAGT | 2201 |
| CTTCTTACTT GGAACTGAAG GGGGCGGCCT ATGACTTGGG CACCCCAGC CTGGGCCTAT | 2261 |
| GGAGAGCCCT GGGACCGCTA CACCACTCTG GCAGCCACAC TTCTCAGGAC ACAGGCCTGT | 2321 |
| GTAGCTGTGA CCTGCTGAGC TCTGAGAGGC CCTGGATCAG CGTGGCCTTG TTCTGTCACC | 2381 |
| AATGTACCCA CCGGGCCACT CCTTCCTGCC CCAACTCCTT CCAGCTAGTG ACCCACATGC | 2441 |
| CATTTGTACT GACCCCATCA CCTACTCACA CAGGCATTTC CTGGGTGGCT ACTCTGTGCC | 2501 |
| AGAGCCTGGG GCTCTAACTG CCTGAGCCCA GGGAGGCCGA AGCTAACAGG GAAGGCAGGC | 2561 |
| AGGGCTCTCC TGGTCTTCCC ATCCCCAGCG ATTCCCTCTC CCAGGCCCCA TGACCTCCAG | 2621 |
| CTTTCCTGTA TTTCTTCCCA AGAGCATGAT GCCTCTGAGG CCAGCCTGGC CTCCTGCCTC | 2681 |
| TACTGGGAAG CTACTTCGG GGCTGGGAAG TCGTCCTTAC TCCTGTGGGA GCCTCGCAAC | 2741 |
| CCGTGCCAAG TCCAGGTCCT GGTGGGGCAG CTCCTCTGTC TCGAGCGCCC TGCAGACCCT | 2801 |
| GCCCTTGTTT GGGGCAGGAG TAGCTGAGCT CACAAGGCAG CAAGGCCCGA GCAGCTGAGC | 2861 |
| AGGGCCGGGG AACTGGCCAA GCTGAGGTGC CCAGGAGAAG AAAGAGGTGA CCCCAGGGCA | 2921 |
| CAGGAGCTAC CTGTGTGGAC AGGACTAACA CTCAGAAGCC TGGGTGCCTG GCTGGCTGAG | 2981 |
| GCAGTTCGC AGCCACCCTG AGGAGTCTGA GGTCCTGAGC ACTGCCAGGA GGGACAAAGG | 3041 |
| AGCCTGTGAA CCCAGGACAA GCATGGTCCC ACATCCCTGG GCCTGCTGCT GAGAACCTGG | 3101 |
| CCTTCAGTGT ACCGCGTCTA CCCTGGGATT CAGGAAAAGG CCTGGGGTGA CCCGGCACCC | 3161 |
| CCTGCAGCTT GTAGCCAGCC GGGGCGAGTG GCACGTTTAT TTAACTTTTA GTAAAGTCAA | 3221 |
| GGAGAAATGC GGTGG | 3236 |

(2) INFORMATION FOR SEQ ID NO:8:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Ser Lys Leu Ser Gln Leu Gln Thr Glu Leu Leu Ala Ala Leu
  1               5                  10                  15

Leu Glu Ser Gly Leu Ser Lys Glu Ala Leu Ile Gln Ala Leu Gly Glu
             20                  25                  30

Pro Gly Pro Tyr Leu Leu Ala Gly Glu Gly Pro Leu Asp Lys Gly Glu
         35                  40                  45

Ser Cys Gly Gly Gly Arg Gly Glu Leu Ala Glu Leu Pro Asn Gly Leu
     50                  55                  60

Gly Glu Thr Arg Gly Ser Glu Asp Glu Thr Asp Asp Gly Glu Asp
 65                  70                  75                  80

Phe Thr Pro Pro Ile Leu Lys Glu Leu Glu Asn Leu Ser Pro Glu Glu
                 85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
290                 295                 300

Pro Gly Leu Pro Pro Ala Leu Ser Pro Ser Lys Val His Gly Val
305                 310                 315                 320

Arg Gly Gln Pro Ala Thr Ser Glu Thr Ala Glu Val Pro Ser Ser Ser
                325                 330                 335

Gly Gly Pro Leu Val Thr Val Ser Thr Pro Leu His Gln Val Ser Pro
            340                 345                 350

Thr Gly Leu Glu Pro Ser His Ser Leu Leu Ser Thr Glu Ala Lys Leu
        355                 360                 365
```

```
Val Ser Ala Ala Gly Gly Pro Leu Pro Arg Gln His Pro Asp Ser Thr
    370                 375                 380

Ala Gln Leu Gly Ala Asp Ile Pro Arg Pro Gln Pro Ala Ala Pro Glu
385                 390                 395                 400

Pro His His Gly Leu Thr Ser Trp Gly His Asp His Arg Ala Trp
                405                 410                 415
```

(2) INFORMATION FOR SEQ ID NO:9:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 7
        (D) OTHER INFORMATION: /mod_base= OTHER
            /note= "N = A, C, G, or T"

(xi) SEQUENCE DESCRIPTION: SEQ ID NO:9:

GTTAATNATT ACC                                                        13

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:10:

TACACCACTC TGGCAGCCAC ACT                                    23

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

CGGTGGGTAC ATTGGTGACA GAAC                                 24

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:12:

GGCAGGCAAA CGCAACCCAC G                                         21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

GAAGGGGGGC TCGTTAGGAG C                                         21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

CATGCACAGT CCCCACCCTC A          21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

CTTCCAGCCC CCACCTATGA G          21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:16:

GGGCAAGGTC AGGGGAATGG A          21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:17:

CAGCCCAGAC CAAACCAGCA C          21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

CAGAACCCTC CCCTTCATGC C          21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

GGTGACTGCT GTCAATGGGA C          21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

GGCAGACAGG CAGATGGCCT A                                               21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:21:

GCCTCCCTAG GGACTGCTCC A                                               21

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:22:

TGGAGCAGTC CCTAGGGAGG C                                               21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

GTTGCCCCAT GAGCCTCCCA C                                               21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:24:

GGTCTTGGGC AGGGGTGGGA T                                               21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:25:

CTGCAATGCC TGCCAGGCAC C                                               21

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:26:

CCCCTGCATC CATTGACAGC C                                        21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:27:

GAGGCCTGGG ACTAGGGCTG T                                        21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:28:

CTCTGTCACA GGCCGAGGGA G                                        21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:29:

CCTGTGACAG AGCCCCTCAC C                                        21

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:30:

CGGACAGCAA CAGAAGGGGT G                                        21

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:31:

CAGAGCCCCT CACCCCCACA T                                        21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:32:

GTACCCCTAG GGACAGGCAG G                                              21

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:33:

ACCCCCCAAG CAGGCAGTAC A                                              21

(2) INFORMATION FOR SEQ ID NO:34:

(i) SEQUENCE CHARACTERISTICS:
        (A) LENGTH: 671 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 104..217

(xi) SEQUENCE DESCRIPTION: SEQ ID NO:34:

GCAGAGAGGG CACTGGGAGG AGGCAGTGGG AGGGCGGAGG GCGGGGGCCT TCGGGGTGGG      60

CGCCCAGGGT AGGGCAGGTG GCCGCGGCGT GGAGGCAGGG AGA ATG CGA CTC TCC     115
                                                 Met Arg Leu Ser
                                                   1

AAA ACC CTC GTC GAC ATG GAC ATG GCC GAC TAC AGT GCT GCA CTG GAC     163
Lys Thr Leu Val Asp Met Asp Met Ala Asp Tyr Ser Ala Ala Leu Asp
  5                  10                  15                  20

CCA GCC TAC ACC ACC CTG GAA TTT GAG AAT GTG CAG GTG TTG ACG ATG     211
Pro Ala Tyr Thr Thr Leu Glu Phe Glu Asn Val Gln Val Leu Thr Met
                 25                  30                  35

GGC AAT GGTAGGTGGG GGCAGATGTG CCCAGGTGTG CCAGTGGGGG CAGGTGTGCC      267
Gly Asn

TGGGTCCAGG AGCAGATCTT TGGCACTCAA CTTTGGGGTG GGAGGAGAAT GATACAAAAT    327

GGTAGGTTGG TCCTACAGGC CAGCACAGGT GTTGCCAAGT GAAGCCCATG TGCCCAGGCA    387

CAGTGATCAC AGGCATTCTG GGTGAAGGGA GGCCTGCAAG GGCCAATTTC AGCAAAAGT     447

CGATCCCGGC TATTCCTCCC AGGCCCTTCC AGTCCTCACT GCCTCACAGT GGCTCTGCTT    507

GGCGCTTGGC ACAGTGACAT GATGGTGAGC TCCCCCTTGG TGCCCAGCTC CAGCGATTCA    567

GCCCAGCACG GCCCCTTCGT GAACCCCTTG GGCCTAGGTT CAGAGAGACG GCAAGGGATG    627

TTGTATCCCT GGAGATGGTG GTTGGAGACA TAACCGCATT TCTC                    671

(2) INFORMATION FOR SEQ ID NO:35:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:35:

```
Met Arg Leu Ser Lys Thr Leu Val Asp Met Asp Met Ala Asp Tyr Ser
 1               5                  10                  15
Ala Ala Leu Asp Pro Ala Tyr Thr Thr Leu Glu Phe Glu Asn Val Gln
                20                  25                  30
Val Leu Thr Met Gly Asn
            35
```

(2) INFORMATION FOR SEQ ID NO:36:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(286..312, 316..375)

(xi) SEQUENCE DESCRIPTION: SEQ ID NO:36:

```
TGGATGTTTG TACATGTGTG CTGTGTGTGC GGGTCATAGA GCACATGTGT TTGTGCATGC     60

GGACCTGTTG GAGTGCCCTG TTCTTCCTGC ATCTTTATCC TGTATGGGCG TTTTGTCGTG    120

TGCCCATATT TGTACCTGCT GTGTATATAT GCAGTTCCCT GTGCTGCGGG CGGGGGTCAG    180

CGGTCTCTGG TGTGCACGAC TGCACAGACC CAAATGCAGG ACTCTGTTGT TGCCACTCAC    240

CAAGTGAGAT TCATATCAGC AACATGTCCG TTTGTCTCTG AGCAG ATT TGT TGC        294
                                                 Ile Cys Cys
                                                   1

CGC TGC GTC TCG CCA GAT TGA GGC ATC CCC TCC GAC ATC ACT GGA GCA      342
Arg Cys Val Ser Pro Asp     Gly Ile Pro Ser Asp Ile Thr Gly Ala
      5                  10                  15

TAT CTG GAG GGG TGG ACA GTT CTC CAC AGG GAG GTAGGGGAAA AGAGGAGGCC    395
Tyr Leu Glu Gly Trp Thr Val Leu His Arg Glu
     20                  25

CGGAAACCCC TCCTGGAGGG AAGAGCCCCA TCGGTCCCAG GCCAGCCTCA GAGGAGAGGG    455

GGCAGGCAGC TGGCTGAGGT CAGCCTGCCA CCCTGCTTCC TTCTGTGTCT TGGAGCCACT    515

CAGCCAGTAT GAGGCTGCAG CTCCAGCTGA GGTCTGGAAT CTTGTGGTCA GCTCAGCTAG    575

GGTGAGGAGG CAGCTGCTGG GCACTGCTTG TTGTCAGCTC AGCAGGTGCT CACCTGCCCC    635

TGCCGTCCAG TCACGTGTGA CCTTGGGCAT GTCACCTCCC CTATCCTGGC TTCTGTATCT    695

TCTACAAAAC AGGCTTCATT CCCCCAGGCC TGCTGGCTGG ACGGCTTTTA GGCCTGTCTG    755

AGGACCACGC CAGGAGCGCA AGGCAAAAAC ACACCAGAGA T                        796
```

(2) INFORMATION FOR SEQ ID NO:37:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:37:

```
Ile Cys Cys Arg Cys Val Ser Pro Asp Gly Ile Pro Ser Asp Ile Thr
 1               5                  10                  15
Gly Ala Tyr Leu Glu Gly Trp Thr Val Leu His Arg Glu
                20                  25
```

(2) INFORMATION FOR SEQ ID NO:38:

(i) SEQUENCE CHARACTERISTICS:
        (A) LENGTH: 634 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 326..499

(xi) SEQUENCE DESCRIPTION: SEQ ID NO:38:

```
CCCCTTGCGA GTTAGGAGGC CGGCTCCCAC CCCAGAAGGT GGCCAGGTTT TCATGCCTTC      60

CTAGAGAAAG CTGGGGCTGG TGGCCTCCAC CACAGGGAGA CGCAGACCCT CAGAAACAAG     120

TCTGTGAAGT CACAACCAGC CCCAGTTTAC AGATGTGAAA CTGAAGCTCC AAAAAGTCAG     180

GAGGTCACTG AGTGGGGAGG TGATGGAGTG GAACAGCCCC CAGATCTGGC TGAGGCCGAA     240

GCCCTGGAGA GATCCCCGCA AGGCTCCCTT AGATGCCTGA CATTCTGTTC TTCCTGAAGC     300

CTCACTCCCT TCTCTCCTGG CGCAG ACA CGT CCC CAT CAG AAG GCA CCA ACC       352
                             Thr Arg Pro His Gln Lys Ala Pro Thr
                              1               5

TCA ACG CGC CCA ACA GCC TGG GTG TCA GCG CCC TGT GTG CCA TCT GCG       400
Ser Thr Arg Pro Thr Ala Trp Val Ser Ala Pro Cys Val Pro Ser Ala
 10              15                  20                  25

GGG ACC GGG CCA CGG GCA AAC ACT ACG GTG CCT CGA GCT GTG ACG GCT       448
Gly Thr Gly Pro Arg Ala Asn Thr Thr Val Pro Arg Ala Val Thr Ala
             30                  35                  40

GCA AGG GCT TCT TCC GGA GGA GCG TGC GGA AGA ACC ACA TGT ACT CCT       496
Ala Arg Ala Ser Ser Gly Gly Ala Cys Gly Arg Thr Thr Cys Thr Pro
                 45                  50                  55

GCA GGTGAGGAGC CTCAATTTCT TCAGCTGGGA AATGGGCACA CTTGGGCTCA            549
Ala

TGGCCCCAAG GTCTGTCTTC TCCCTGAGTG GGTAGGTCCC AGAGACAGCT GCCCTTCAGG     609

GCCTTCAAGG CTCTTCTGGT TTTGT                                           634
```

(2) INFORMATION FOR SEQ ID NO:39:

(i) SEQUENCE CHARACTERISTICS:
        (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO:39:

```
Thr Arg Pro His Gln Lys Ala Pro Thr Ser Thr Arg Pro Thr Ala Trp
 1               5                  10                  15

Val Ser Ala Pro Cys Val Pro Ser Ala Gly Thr Gly Pro Arg Ala Asn
                 20                  25                  30

Thr Thr Val Pro Arg Ala Val Thr Ala Ala Arg Ala Ser Ser Gly Gly
             35                  40                  45

Ala Cys Gly Arg Thr Thr Cys Thr Pro Ala
 50                  55
```

(2) INFORMATION FOR SEQ ID NO:40:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ix) FEATURE:
    (A) NAME/KEY: CDS
    (B) LOCATION: join(171..173, 177..265)

(xi) SEQUENCE DESCRIPTION: SEQ ID NO:40:

```
AGAGAGTTCA TAGCACCTTT CCAGCTCCTG GTGGGTTCAA GAGAGAACTC CCGGGATGAA      60

GAGATGAGAG CACTGAGGTT GGGGGGTCAA CTGGATAGCC AGGGCCCTAG TTCTGTCCTA     120

AGAGGAGGAA GTTGTGTCTT CTCCATCCAA CCATCCAAAG CCCTCCCCAG ATT           173
                                                       Ile
                                                        1

TAG CCG GCA GTG CGT GGT GGA CAA AGA CAA GAG GAA CCA GTG CCG CTA      221
    Pro Ala Val Arg Gly Gly Gln Arg Gln Glu Glu Pro Val Pro Leu
         5                  10                  15

CTG CAG GCT CAA GAA ATG CTT CCG GGC TGG CAT GAA GAA GGA              263
Leu Gln Ala Gln Glu Met Leu Pro Gly Trp His Glu Glu Gly
            20                  25                  30

AGGTGAGCCT CGGCCCTCCC CGCCCCACCA CCACTGCCCC ACCTGCACCC ACAGCTCCCC    323

GACAGTCATT TACAACTGTA GCCACACTTT ATGACTCAGT GGCAGGCCCC AGGGTGACTG    383

GCTAATGGCT GAGAAGAGGG AGGGCCTGGA AATCTGACCA TAGGGAGCGG CTGGGCTTGG    443

TCTTGAGAAA GATTC                                                    458
```

(2) INFORMATION FOR SEQ ID NO:41:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:41:

```
Ile Pro Ala Val Arg Gly Gly Gln Arg Gln Glu Glu Pro Val Pro Leu
 1               5                  10                  15

Leu Gln Ala Gln Glu Met Leu Pro Gly Trp His Glu Glu Gly
            20                  25                  30
```

(2) INFORMATION FOR SEQ ID NO:42:

(i) SEQUENCE CHARACTERISTICS:
        (A) LENGTH: 662 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 84..188

(xi) SEQUENCE DESCRIPTION: SEQ ID NO:42:

```
TCCCACTCCT CATCAGTCAC AGACACCCCC ACCCCCTACT CCATCCCTGT TCTCCCTCCT     60

CACCTCTCTG TGCCTCCTCA CAG CCG TCC AGA ATG AGC GGG ACC GGA TCA       110
                         Pro Ser Arg Met Ser Gly Thr Gly Ser
                                      1               5

GCA CTC GAA GGT CAA GCT ATG AGG ACA GCA GCC TGC CCT CCA TCA ATG      158
Ala Leu Glu Gly Gln Ala Met Arg Thr Ala Ala Cys Pro Pro Ser Met
 10                  15                  20                  25

CGC TCC TGC AGG CGG AGG TCC TGT CCC GAC AGGTACCGGG GTGATCCTGC        208
Arg Ser Cys Arg Arg Arg Ser Cys Pro Asp
                30                  35
```

```
CACCCACCCA GGGGATCCCC CACACTACAG AGGAGCTCAC CTCCTCCACC TCCATTCTCC      268

CCAGCCAGGC CCTGGAGCAG CTGACGGGAG GGGCCTCAGA TATTACAGAA GGGACACTGA      328

GTGCGGTTTC ACATGGCCCA GTTTGCAGCA AGGGCAGGAA TCGAACCTGG CGCCCTGGGG      388

CACTTTCTAA TTCATCCTAC TGCCTGCATC CCACAGGCCA AGCAGAGTCT TCACCTTCAC      448

TGAGGGCCTG CGATCAGCTC AGCTCCGAGA GAACAGAGCA GTGGCTCAGT GGAGAGAGGT      508

GGCAAAGTGG GGCCCAGCCC TTCCCTTGCT GAGTGACCTT GGGCAAGTCA CAGCACCTCT      568

CTGAGCCATG GTTGCCTCAT TGTCAGAAAA GGATGATGAT TTTTTGCCCT GCTTCTCCTC      628

TAAGGCTGAC AGACTCCTTG GGGCTCTAAA GCTG                                 662
```

(2) INFORMATION FOR SEQ ID NO:43:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:43:

```
Pro Ser Arg Met Ser Gly Thr Gly Ser Ala Leu Glu Gly Gln Ala Met
 1               5                  10                  15

Arg Thr Ala Ala Cys Pro Pro Ser Met Arg Ser Cys Arg Arg Arg Ser
            20                  25                  30

Cys Pro Asp
        35
```

(2) INFORMATION FOR SEQ ID NO:44:

(i) SEQUENCE CHARACTERISTICS:
        (A) LENGTH: 647 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 185..340

(xi) SEQUENCE DESCRIPTION: SEQ ID NO:44:

```
TTCTCCCTCA TCCCTGCCTC CTCCCTCCCT CCGTTTTTAC CCTGAGCTTC CTTCAGAGCT       60

GGAGGGCACC CACTATCCAG CCCCCTCCCC ACATCTGATT CCAGGGAGGG GGCTCTGTGC      120

AGGGGACAGA GAATGCGGGA GGGCCCGGAC ATCTCCAGCA TTTTCTTCCC TGTATCTCTC      180

GAAG ATC ACC TCC CCC GTC TCC GGG ATC AAC GGC GAC ATT CGG GCG AAG      229
     Ile Thr Ser Pro Val Ser Gly Ile Asn Gly Asp Ile Arg Ala Lys
       1               5                  10                  15

AAG ATT GCC AGC ATC GCA GAT GTG TGT GAG TCC ATG AAG GAG CAG CTG      277
Lys Ile Ala Ser Ile Ala Asp Val Cys Glu Ser Met Lys Glu Gln Leu
                20                  25                  30

CTG GTT CTC GTT GAG TGG GCC AAG TAC ATC CCA GCT TTC TGC GAG CTC      325
Leu Val Leu Val Glu Trp Ala Lys Tyr Ile Pro Ala Phe Cys Glu Leu
            35                  40                  45

CCC CTG GAC GAC CAG GTGAGGATGG GCGTGGATGG TGGGCAGTAG TGGGCAGTGG       380
Pro Leu Asp Asp Gln
        50

GCGGGGCAGC CAGGGGGCTG CTGGCCCACC TGGGATATAG CCGTGGACTG GCTTGATTTT      440

ATTTTATTTA ACAAAATATG TAGTGCACAC ACGTGTCTGA AACTTTAAAT CACCTTACAA      500

ATATTAACTC AGTTAGCTCC TCCAACAACT CTATGAGGTA GGTACTAAGG TACTATTATT      560
```

```
ACTGCCATCT CATAGGTGAG AGATTGGGGC ACAGAGAGGT TAAGTAACCT GCTCAAGGTC      620

ACATAGCTAC TATCCAGCAT AGCTGGG                                          647

(2) INFORMATION FOR SEQ ID NO:45:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:45:

Ile Thr Ser Pro Val Ser Gly Ile Asn Gly Asp Ile Arg Ala Lys Lys
  1               5                  10                  15

Ile Ala Ser Ile Ala Asp Val Cys Glu Ser Met Lys Glu Gln Leu Leu
             20                  25                  30

Val Leu Val Glu Trp Ala Lys Tyr Ile Pro Ala Phe Cys Glu Leu Pro
         35                  40                  45

Leu Asp Asp Gln
         50

(2) INFORMATION FOR SEQ ID NO:46:

(i) SEQUENCE CHARACTERISTICS:
        (A) LENGTH: 844 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 429..515

(xi) SEQUENCE DESCRIPTION: SEQ ID NO:46:

ATTTTTACAA AGCACCCTTC ATAATTCTCC ATAGCTGGTC CATGGGTGGG AATTTGGGAC       60

CCACAGTTTT GGAACTTTTT GGGATCATAG ACCTTTTTGA GAATCTCAAA AAAGAAAAAA      120

AAGCACACAG AATGTTGCTT ACAGTTTCAT CAGGCACACA GAAGAGGCCC AGCACGAAGC      180

AGTTTCTTGC CCAAGGACAC AGCAGTTCAA GGACAGAGTC AGCGCGAGGT CTCTCAGCTC      240

TGAGCACATG TTCTTTCCCC TTCCAGGTTT CTAGTTTTAT GGGTAGTAGT TTTATGATGC      300

CCATTTCACA GTTCAGGCAG GTAGAGGCAG AGGGGAGCAT TAAGCTGACT TGCCCAGCGT      360

CACTGAGTTG GCTACGGGCA GCCTTCCCAA GGGTACAGAT GGCAAACACT GTTCCTTATC      420

TCTTTCAG GTG GCC CTG CTC AGA GCC CAT GCT GGC GAG CAC CTG CTG CTC      470
         Val Ala Leu Leu Arg Ala His Ala Gly Glu His Leu Leu Leu
           1               5                  10

GGA GCC ACC AAG AGA TCC ATG GTG TTC AAG GAC GTG CTG CTC CTA           515
Gly Ala Thr Lys Arg Ser Met Val Phe Lys Asp Val Leu Leu Leu
 15                  20                  25

GGTGAGGCGG CTGCCTGCCC TGGCCAGGGC TCCAGGAGG GTATGCCTAG CATGGCACTC      575

ACCCAGGCAA GGAGATTCAC ATGGTGGCAT GCAAGGGTGA GGGAGACTAG TCAGGAGTGG      635

CCCTGTCCTC AGGCTTGCAT TGGAGGGCTC CAGGACTCAG TTTTCAACTG GTACCCCAC      695

TCAGATGCAA GGAAATGTGG ATGCAAGTCA CCAAATTCCC AGCATTGAAG TCAGAGCACG      755

ATCAGGGTTA TCCCTGGAAT TACCTGTGCA TCCTTTTTTC TTTTGACAGA GTCTTGCTCT      815

GTCACTCAGG CTGGAGTGCA ATGATGTGA                                       844
```

(2) INFORMATION FOR SEQ ID NO:47:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:47:

```
Val Ala Leu Leu Arg Ala His Ala Gly Glu His Leu Leu Gly Ala
 1               5                  10                  15

Thr Lys Arg Ser Met Val Phe Lys Asp Val Leu Leu Leu
                20                  25
```

(2) INFORMATION FOR SEQ ID NO:48:

(i) SEQUENCE CHARACTERISTICS:
        (A) LENGTH: 937 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(485..529, 533..640)

(xi) SEQUENCE DESCRIPTION: SEQ ID NO:48:

```
GCAACACTAG TATTTTAATA TAACAATGCT ATGAGGGAGC TCGATTATTT ATCCTCATCT      60

TATAGATAAG AAAACTGAGG CACAGAGAGG TTAAGTAACT TATCCAACTA TAACCAGCTA     120

TCAGGGGCAG AGCCATTTAA GCAGGGCAGT GCAGTTCCAG AATCTGGTCC TTTAACCTTG     180

ATGCTTTGGT GCCTATCAGG TGACCTTTGA ATGTCATCGA TCTTGTGAGT CATGTTGGTA     240

AATGGAGCTT GGGTCATGTG AAAGAGGTCC TAGAAAGCCA AGTTCCAAGC TCAGCCGGAT     300

GACTCAAGGC AGCTTATCTT CTGAATCTGG GCCTCAGCTT CCTTACCTGT GAAATGGGAG     360

TCACCATCCC TGCAGGTCCT CCTCCCACAG GCACCAGCTA TCTTGCCAAC TTAAAAGCCA     420

AAACTAGAGG AGAGGGGTCA ACCCAAAGTG ACTTCCCATC CTCCCTCCCT CCCAACCCTT     480

CCAG GCA ATG ACT ACA TTG TCC CTC GGC ACT GCC CGG AGC TGG CGG AGA     529
     Ala Met Thr Thr Leu Ser Leu Gly Thr Ala Arg Ser Trp Arg Arg
      1               5                  10                  15

TGA GCC GGG TGT CCA TAC GCA TCC TTG ACG AGC TGG TGC TGC CCT TCC     577
    Ala Gly Cys Pro Tyr Ala Ser Leu Thr Ser Trp Cys Cys Pro Ser
                        20                  25                  30

AGG AGC TGC AGA TCG ATG ACA ATG AGT ATG CCT ACC TCA AAG CCA TCA     625
Arg Ser Cys Arg Ser Met Thr Met Ser Met Pro Thr Ser Lys Pro Ser
                35                  40                  45

TCT TCT TTG ACC CAG GTACAGTGCA CACCTCCTAA GCCATCCCTG ACTCTCTCTC      680
Ser Ser Leu Thr Gln
            50

CAGAACGCTC TGCCAGACTT CTCCTATTGG GTTCTGTACA CTGAGTTCAC AGCCTCATCT     740

CATGTTAACG ACAGCCAGGA GAGGCCGTTT TCATTTAACA GATGAGGCAA GTCAAGATTT     800

GAAGAGACAA TATGGCCGGG CGCAGTGGCT CACACCTGTA ATCCCATCAC TTTGGGAGGC     860

TGAGGCGGGC GGATCACCTG AGGTCAGGGG TCAAGATGAG CCTGGCTAAC ATGGAGAAAC     920

CCCATCTCTA CTTAAAA                                                    937
```

(2) INFORMATION FOR SEQ ID NO:49:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:49:

```
Ala Met Thr Thr Leu Ser Leu Gly Thr Ala Arg Ser Trp Arg Arg Ala
 1               5                  10                  15

Gly Cys Pro Tyr Ala Ser Leu Thr Ser Trp Cys Cys Pro Ser Arg Ser
            20                  25                  30

Cys Arg Ser Met Thr Met Ser Met Pro Thr Ser Lys Pro Ser Ser Ser
        35                  40                  45

Leu Thr Gln
    50
```

(2) INFORMATION FOR SEQ ID NO:50:

(i) SEQUENCE CHARACTERISTICS:
        (A) LENGTH: 978 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(376..387, 391..432, 436..534, 538..610)

(xi) SEQUENCE DESCRIPTION: SEQ ID NO:50:

```
GTGGCTCTGC CAACAACTGG CTGTGCGACC CAGGACAAGT CCTATCTTTG CACTGTGTCT    60

GGGTTTCCCC GTGTGTAAGA TGAGGCGGTT GCTAGGTGCT TATTGGATGC ATTCCTCAAG   120

TCCCGCCCTC CATCTCCTAT TCCCCTCTCT TCTGGTTTAG TGCTTAGGA AATGTGGCAG    180

AAATCTTTTT CTGCCTGTGT CTAGGAAATC ATAATTCATG CTGGCGTACC CTGGTTGTTG   240

AGGTCCCTGA ATCCTTGTGC CCACACTGCT GAAGACTCCT TGTGTGACAC AAGTCAGGGG   300

ACATCTGGGT CTTGACTCCC CAGATGCTCC AGGTGGACCC TGCTGCCCTC CCTTGCCCAC   360

CCTCTTCCAT TGTAG ATG CCA AGG GGC TGA GCG ATC CAG GGA AGA TCA AGC   411
          Met Pro Arg Gly     Ala Ile Gln Gly Arg Ser Ser
           1               5                  10

GGC TGC GTT CCC AGG TGC AGG TGA GCT TGG AGG ACT ACA TCA ACG ACC   459
Gly Cys Val Pro Arg Cys Arg     Ala Trp Arg Thr Thr Ser Thr Thr
            15                  20                  25

GCC AGT ATG ACT CGC GTG GCC GCT TTG GAG AGC TGC TGC TGC TGC TGC   507
Ala Ser Met Thr Arg Val Ala Ala Leu Glu Ser Cys Cys Cys Cys Cys
        30                  35                  40

CCA CCT TGC AGA GCA TCA CGT GGC AGA TGA TCG AGC AGA TCC AGT TCA   555
Pro Pro Cys Arg Ala Ser Arg Gly Arg     Ser Ser Arg Ser Ser Ser
            45                  50                  55

TCA AGC TCT TCG GCA TGG CCA AGA TTG ACA ACC TGT TGG AGG AGA TGC   603
Ser Ser Ser Ser Ala Trp Pro Arg Leu Thr Thr Cys Trp Arg Arg Cys
        60                  65                  70

TGC TGG GAGGTCCGTG CCAAGCCCAG GAGGGCGGG GTTGGATTGG GGACTCCCCA     659
Cys Trp
    75

GGAGACAGGC CTCACACAGT GAGCTCACCC CTCAGCTCCT TGGCTTCCCC ACTGTGCCGC   719

TTTGGGCAAG TTGCTTAACC TGTCTGTGCC TCAGTTTCCT CACCAGAAAA ATGGGAACAA   779

GGCAATGGTC TATTTGTTCA GGCACCGAGA ACCTAGCACG TGCCAGTCAC TGTTCTAAGT   839
```

```
GCTGGCAATT CAGCAAAGAA CAAGATCTTT GCCCTCGGGG AGGCTGTGTG TGTGTGATAT    899

GTATGGATGC GTGGATATCT GTGTATATGC CCGTATGTGC GTGCATGTGT ATATAAAGCC    959

TCACATTTTA TGATTTTGA                                                 978
```

(2) INFORMATION FOR SEQ ID NO:51:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO:51:

```
Met Pro Arg Gly Ala Ile Gln Gly Arg Ser Ser Gly Cys Val Pro Arg
 1               5                  10                  15

Cys Arg Ala Trp Arg Thr Thr Ser Thr Thr Ala Ser Met Thr Arg Val
            20                  25                  30

Ala Ala Leu Glu Ser Cys Cys Cys Cys Pro Pro Cys Arg Ala Ser
        35                  40                  45

Arg Gly Arg Ser Ser Arg Ser Ser Ser Ser Ser Ser Ser Ala Trp Pro
 50                  55                  60

Arg Leu Thr Thr Cys Trp Arg Arg Cys Cys Trp
 65                  70                  75
```

(2) INFORMATION FOR SEQ ID NO:52:

(i) SEQUENCE CHARACTERISTICS:
        (A) LENGTH: 984 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(443..490, 494..595)

(xi) SEQUENCE DESCRIPTION: SEQ ID NO:52:

```
GGGACACATA GATGCTATAA GTAGGTCAGT TGGCTGCAGC AGAGATGTGG GGGATGAGGC     60

TGAAAGGTGA GGCGGGACCA AATGGTTGAA GGACTTGCAC TCCAAGGAGC TTTGAGAGCC    120

ATTGATTACA TCCATTATGT TACTATGTGA CCAATACATT ACTCATTAGA ACATTTACGT    180

GATCTCAGAG CTTCCTTATA TGCACCTTGT TCCTTTCAAC TCACTTTTGT TCTCTTGGTT    240

TTTTGGGGTC CTCTTAACAC CCTCATGAAG TCTATAGATG GAATGGTAC ACCCTAGTTT     300

ACTAACCCAG GAATAGGTAC CCAACAGGCA CTGCCAATAT TGGATGGGCT GGTTGATTGG    360

CCACGCCTGA GGAAGATGGC GTCCCAAGGC CTGAGGTCTG CATCCCAGAC TCTCCATCCT    420

GATCGACCTT CTCTACCTGC AG GGT CCC CCA GCG ATG CAC CCC ATG CCC ACC    472
                         Gly Pro Pro Ala Met His Pro Met Pro Thr
                          1               5                  10

ACC CCC TGC ACC CTC ACC TGA TGC AGG AAC ATA TGG GAA CCA ACG TCA    520
Thr Pro Cys Thr Leu Thr     Cys Arg Asn Ile Trp Glu Pro Thr Ser
                15                      20                  25

TCG TTG CCA ACA CAA TGC CCA CTC ACC TCA GCA ACG GAC AGA TGT GTG    568
Ser Leu Pro Thr Gln Cys Pro Leu Thr Ser Ala Thr Asp Arg Cys Val
                30                  35                  40

AGT GGC CCC GAC CCA GGG GAC AGG CAG GTGGGCAAAC TCTGGGATTT           615
Ser Gly Pro Asp Pro Gly Asp Arg Gln
                45                  50
```

```
TACCTTGCAA AGGGTGAGGA TGGGGCTTAA GACAGGAGGC AGGAGAAAGT GGAGTCTAGA        675

AGGTAGAACC AGGATGCAAC AGTTTTCTGG GTTCCAGGGT AGGGAATAAA GGGCAAGATT        735

GTCCATTTGT TGAGGCTGTT TATTCAGTAA GGTGACTGAC AGCCTTTACT GAATGAAGCC        795

ATTGTTGGGA TGAGGCAATC CACTGGATGA GGTAACCCAT TGGGTGAAGA TGTCTTGGGT        855

GAGAATTCCA TTAGTTGACA TTGTCCATTA AGTAAAAGTG GTCATTGAAG TAAGGCTGCA        915

CAGTTGGGTA AGGCTATCCA TTAGACATTA GATGAGACTA CCCATTGGGT CAGGATGTCT        975

GCTGGGCTA                                                                984
```

(2) INFORMATION FOR SEQ ID NO:53:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:53:

```
Gly Pro Pro Ala Met His Pro Met Pro Thr Thr Pro Cys Thr Leu Thr
 1               5                  10                  15

Cys Arg Asn Ile Trp Glu Pro Thr Ser Ser Leu Pro Thr Gln Cys Pro
            20                  25                  30

Leu Thr Ser Ala Thr Asp Arg Cys Val Ser Gly Pro Asp Pro Gly Asp
        35                  40                  45

Arg Gln
    50
```

(2) INFORMATION FOR SEQ ID NO:54:

(i) SEQUENCE CHARACTERISTICS:
        (A) LENGTH: 1103 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(289..429, 433..477, 481..492, 496..603,
            607..630, 634..750, 754..810, 814..843, 847..1023,
            1027..1071, 1075..1103)

(xi) SEQUENCE DESCRIPTION: SEQ ID NO:54:

```
TTTGGGAGAA GCAGTCCAAG TCTGCATATC AAATAAATGA TGGAGGAGAT GGGTGGTAGG         60

ACCTTCCAGA CCTCATAAAA CTTAGGCTTT ATGATCTGGG ACTCACAGAA GGTTGAGCAA        120

TAAAAGACCT TAGGGATTAT CTGGCTTAAT TAATTCTCTC ATTTTATAGA GGAAGAAATT        180

AAGTCAAGGT GGGGCAGGGT GGGAGGGGAG AACTTTCCCG GGGCTCTTCA TTTACTCCCA        240

CAAAGGCTGG AATTTTGAGC AGCCCCTGTC TGTCTGTTTG TCCTTCCA GCC ACC CCT         297
                                                    Ala Thr Pro
                                                     1

GAG ACC CCA CAG CCC TCA CCG CCA GGT GGC TCA GGG TCT GAG CCC TAT         345
Glu Thr Pro Gln Pro Ser Pro Pro Gly Gly Ser Gly Ser Glu Pro Tyr
      5                  10                  15

AAG CTC CTG CCG GGA GCC GTC GCC ACA ATC GTC AAG CCC CTC TCT GCC         393
Lys Leu Leu Pro Gly Ala Val Ala Thr Ile Val Lys Pro Leu Ser Ala
 20                  25                  30                  35

ATC CCC CAG CCG ACC ATC ACC AAG CAG GAA GTT ATC TAG CAA GCC GCT         441
Ile Pro Gln Pro Thr Ile Thr Lys Gln Glu Val Ile     Gln Ala Ala
            40                  45                      50
```

```
GGG GCT TGG GGG CTC CAC TGG CTC CCC CCA GCC CCC TAA GAG AGC ACC         489
Gly Ala Trp Gly Leu His Trp Leu Pro Pro Ala Pro     Glu Ser Thr
                55                      60                      65

TGG TGA TCA CGT GGT CAC GGC AAA GGA AGA CGT GAT GCC AGG ACC AGT         537
Trp     Ser Arg Gly His Gly Lys Gly Arg Arg Asp Ala Arg Thr Ser
                    70                      75                  80

CCC AGA GCA GGA ATG GGA AGG ATG AAG GGC CCG AGA ACA TGG CCT AAG         585
Pro Arg Ala Gly Met Gly Arg Met Lys Gly Pro Arg Thr Trp Pro Lys
                        85                      90                  95

GCA CAT CCC ACT GCA CCC TGA CGC CCT GCT CTG ATA ACA AGA CTT             630
Ala His Pro Thr Ala Pro     Arg Pro Ala Leu Ile Thr Arg Leu
                    100                 105                 110

TGA CTT GGG GAG ACC CTC TAC TGC CTT GGA CAA CTT TCT CAT GTT GAA         678
    Leu Gly Glu Thr Leu Tyr Cys Leu Gly Gln Leu Ser His Val Glu
                            115                     120             125

GCC ACT GCC TTC ACC TTC ACC TTC ATC CAT GTC CAA CCC CCG ACT TCA         726
Ala Thr Ala Phe Thr Phe Thr Phe Ile His Val Gln Pro Pro Thr Ser
                            130                     135             140

TCC CAA AGG ACA GCC GCC TGG AGA TGA CTT GAG CCT TAC TTA AAC CCA         774
Ser Gln Arg Thr Ala Ala Trp Arg     Leu Glu Pro Tyr Leu Asn Pro
                        145                     150             155

GCT CCC TTC TTC CCT AGC CTG GTG CTT CTC CTC TCC TAG CCC CGG TCA         822
Ala Pro Phe Phe Pro Ser Leu Val Leu Leu Leu Ser     Pro Arg Ser
                    160                     165                 170

TGG TGT CCA GAC AGA GCC CTG TGA GGC TGG GTC CAA TTG TGG CAC TTG         870
Trp Cys Pro Asp Arg Ala Leu     Gly Trp Val Gln Leu Trp His Leu
                175                     180                     185

GGG CAC CTT GCT CCT CCT TCT GCT GCT GCC CCC ACC TCT GCT GCC TCC         918
Gly His Leu Ala Pro Pro Ser Ala Ala Ala Pro Thr Ser Ala Ala Ser
                    190                     195                 200

CTC TGC TGT CAC CTT GCT CAG CCA TCC CGT CTT CTC CAA CAC CAC CTC         966
Leu Cys Cys His Leu Ala Gln Pro Ser Arg Leu Leu Gln His His Leu
            205                     210                 215

TAC AGA GGC CAA GGA GGC CTT GGA AAC GAT TCC CCC AGT CAT TCT GGG         1014
Tyr Arg Gly Gln Gly Gly Leu Gly Asn Asp Ser Pro Ser His Ser Gly
    220                     225                     230

AAC ATG TTG TAA GCA CTG ACT GGG ACC AGG CAC CAG GCA GGG TCT AGA         1062
Asn Met Leu     Ala Leu Thr Gly Thr Arg His Gln Ala Gly Ser Arg
235                     240                     245

AGG CTG TGG TGA GGG AAG ACG CCT TTC TCC TCC AAC CCA AC                  1103
Arg Leu Trp     Gly Lys Thr Pro Phe Ser Ser Asn Pro
250                 255                     260

(2) INFORMATION FOR SEQ ID NO:55:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:55:

Ala Thr Pro Glu Thr Pro Gln Pro Ser Pro Gly Gly Ser Gly Ser
 1               5                  10                  15

Glu Pro Tyr Lys Leu Leu Pro Gly Ala Val Ala Thr Ile Val Lys Pro
                20                  25                  30

Leu Ser Ala Ile Pro Gln Pro Thr Ile Thr Lys Gln Glu Val Ile Gln
            35                  40                  45

Ala Ala Gly Ala Trp Gly Leu His Trp Leu Pro Pro Ala Pro Glu Ser
        50                  55                  60
```

-continued

```
Thr Trp Ser Arg Gly His Gly Lys Gly Arg Arg Asp Ala Arg Thr Ser
 65                 70                  75                  80

Pro Arg Ala Gly Met Gly Arg Met Lys Gly Pro Arg Thr Trp Pro Lys
             85                   90                  95

Ala His Pro Thr Ala Pro Arg Pro Ala Leu Ile Thr Arg Leu Leu Gly
            100                 105                 110

Glu Thr Leu Tyr Cys Leu Gly Gln Leu Ser His Val Glu Ala Thr Ala
        115                 120                 125

Phe Thr Phe Thr Phe Ile His Val Gln Pro Pro Thr Ser Ser Gln Arg
    130                 135                 140

Thr Ala Ala Trp Arg Leu Glu Pro Tyr Leu Asn Pro Ala Pro Phe Phe
145                 150                 155                 160

Pro Ser Leu Val Leu Leu Ser Pro Arg Ser Trp Cys Pro Asp Arg
                165                 170                 175

Ala Leu Gly Trp Val Gln Leu Trp His Leu Gly His Leu Ala Pro Pro
            180                 185                 190

Ser Ala Ala Pro Thr Ser Ala Ala Ser Leu Cys Cys His Leu Ala
            195                 200                 205

Gln Pro Ser Arg Leu Leu Gln His His Leu Tyr Arg Gly Gln Gly Gly
    210                 215                 220

Leu Gly Asn Asp Ser Pro Ser His Ser Gly Asn Met Leu Ala Leu Thr
225                 230                 235                 240

Gly Thr Arg His Gln Ala Gly Ser Arg Arg Leu Trp Gly Lys Thr Pro
                245                 250                 255

Phe Ser Ser Asn Pro
            260
```

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:56:

GGGCACTGGG AGGAGGCAGT      20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:57:

GCCTGTAGGA CCAACCTACC      20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:58:

TCTGGTGTGC ACGACTGCAC      20

```
(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:59:

CTGGAGCTGC AGCCTCATAC                                              20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:60:

AAGGCTCCCT TAGATGCCTG                                              20

(2) INFORMATION FOR SEQ ID NO:61:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:61:

CCACTCAGGG AGAAGACAGA CCT                                          23

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:62:

CCTAGTTCTG TCCTAAGAGG                                              20

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:63:

GTCATAAAGT GTGGCTACAG                                              20

(2) INFORMATION FOR SEQ ID NO:64:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:64:

CCACCCCCTA CTCCATCCCT GT                                           22
```

```
(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:65:

CCCTCCCGTC AGCTGCTCCA                                           20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:66:

GTGCAGGGGA CAGAGAATGC                                           20

(2) INFORMATION FOR SEQ ID NO:67:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:67:

AATCAAGCCA GTCCACGGCT AT                                        22

(2) INFORMATION FOR SEQ ID NO:68:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:68:

GCCCAGCGTC ACTGAGTTGG CTA                                       23

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:69:

TTGCCTGGGT GAGTGCCATG                                           20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:70:

GCACCAGCTA TCTTGCCAAC                                           20
```

-continued (2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:71:

AGGAGAAGTC TGGCAGAGCG                                                20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:72:

CTCCTTGTGT GACACAAGTC                                                20

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:73:

CTCACTGTGT GAGGCCTGTC                                                20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:74:

TGGTTGATTG GCCACGCCTG                                                20

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:75:

ATCCTGGTTC TACCTTCTAG                                                20

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:76:

CATTTACTCC CACAAAGGCT                                                20

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:77:

GACCACGTGA TCACCAGGTG                                                      20

(2) INFORMATION FOR SEQ ID NO:78:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 20..1414

(xi) SEQUENCE DESCRIPTION: SEQ ID NO:78:

```
CTCCAAAACC CTCGTCGAC ATG GAC ATG GCC GAC TAC AGT GCT GCA CTG GAC        52
                    Met Asp Met Ala Asp Tyr Ser Ala Ala Leu Asp
                     1               5                  10

CCA GCC TAC ACC ACC CTG GAA TTT GAG AAT GTG CAG GTG TTG ACG ATG        100
Pro Ala Tyr Thr Thr Leu Glu Phe Glu Asn Val Gln Val Leu Thr Met
             15                  20                  25

GGC AAT GAC ACG TCC CCA TCA GAA GGC ACC AAC CTC AAC GCG CCC AAC        148
Gly Asn Asp Thr Ser Pro Ser Glu Gly Thr Asn Leu Asn Ala Pro Asn
         30                  35                  40

AGC CTG GGT GTC AGC GCC CTG TGT GCC ATC TGC GGG GAC CGG GCC ACG        196
Ser Leu Gly Val Ser Ala Leu Cys Ala Ile Cys Gly Asp Arg Ala Thr
     45                  50                  55

GGC AAA CAC TAC GGT GCC TCG AGC TGT GAC GGC TGC AAG GGC TTC TTC        244
Gly Lys His Tyr Gly Ala Ser Ser Cys Asp Gly Cys Lys Gly Phe Phe
 60                  65                  70                  75

CGG AGG AGC GTG CGG AAG AAC CAC ATG TAC TCC TGC AGA TTT AGC CGG        292
Arg Arg Ser Val Arg Lys Asn His Met Tyr Ser Cys Arg Phe Ser Arg
                 80                  85                  90

CAG TGC GTG GTG GAC AAA GAC AAG AGG AAC CAG TGC CGC TAC TGC AGG        340
Gln Cys Val Val Asp Lys Asp Lys Arg Asn Gln Cys Arg Tyr Cys Arg
             95                 100                 105

CTC AAG AAA TGC TTC CGG GCT GGC ATG AAG AAG GAA GCC GTC CAG AAT        388
Leu Lys Lys Cys Phe Arg Ala Gly Met Lys Lys Glu Ala Val Gln Asn
        110                 115                 120

GAG CGG GAC CGG ATC AGC ACT CGA AGG TCA AGC TAT GAG GAC AGC AGC        436
Glu Arg Asp Arg Ile Ser Thr Arg Arg Ser Ser Tyr Glu Asp Ser Ser
    125                 130                 135

CTG CCC TCC ATC AAT GCG CTC CTG CAG GCG GAG GTC CTG TCC CGA CAG        484
Leu Pro Ser Ile Asn Ala Leu Leu Gln Ala Glu Val Leu Ser Arg Gln
140                 145                 150                 155

ATC ACC TCC CCC GTC TCC GGG ATC AAC GGC GAC ATT CGG GCG AAG AAG        532
Ile Thr Ser Pro Val Ser Gly Ile Asn Gly Asp Ile Arg Ala Lys Lys
                160                 165                 170

ATT GCC AGC ATC GCA GAT GTG TGT GAG TCC ATG AAG GAG CAG CTG CTG        580
Ile Ala Ser Ile Ala Asp Val Cys Glu Ser Met Lys Glu Gln Leu Leu
            175                 180                 185

GTT CTC GTT GAG TGG GCC AAG TAC ATC CCA GCT TTC TGC GAG CTC CCC        628
Val Leu Val Glu Trp Ala Lys Tyr Ile Pro Ala Phe Cys Glu Leu Pro
        190                 195                 200
```

```
CTG GAC GAC CAG GTG GCC CTG CTC AGA GCC CAT GCT GGC GAG CAC CTG        676
Leu Asp Asp Gln Val Ala Leu Leu Arg Ala His Ala Gly Glu His Leu
205                 210                 215

CTG CTC GGA GCC ACC AAG AGA TCC ATG GTG TTC AAG GAC GTG CTG CTC        724
Leu Leu Gly Ala Thr Lys Arg Ser Met Val Phe Lys Asp Val Leu Leu
220                 225                 230                 235

CTA GGC AAT GAC TAC ATT GTC CCT CGG CAC TGC CCG GAG CTG GCG GAG        772
Leu Gly Asn Asp Tyr Ile Val Pro Arg His Cys Pro Glu Leu Ala Glu
                240                 245                 250

ATG AGC CGG GTG TCC ATA CGC ATC CTT GAC GAG CTG GTG CTG CCC TTC        820
Met Ser Arg Val Ser Ile Arg Ile Leu Asp Glu Leu Val Leu Pro Phe
        255                 260                 265

CAG GAG CTG CAG ATC GAT GAC AAT GAG TAT GCC TAC CTC AAA GCC ATC        868
Gln Glu Leu Gln Ile Asp Asp Asn Glu Tyr Ala Tyr Leu Lys Ala Ile
            270                 275                 280

ATC TTC TTT GAC CCA GAT GCC AAG GGG CTG AGC GAT CCA GGG AAG ATC        916
Ile Phe Phe Asp Pro Asp Ala Lys Gly Leu Ser Asp Pro Gly Lys Ile
285                 290                 295

AAG CGG CTG CGT TCC CAG GTG CAG GTG AGC TTG GAG GAC TAC ATC AAC        964
Lys Arg Leu Arg Ser Gln Val Gln Val Ser Leu Glu Asp Tyr Ile Asn
300                 305                 310                 315

GAC CGC CAG TAT GAC TCG CGT GGC CGC TTT GGA GAG CTG CTG CTG CTG       1012
Asp Arg Gln Tyr Asp Ser Arg Gly Arg Phe Gly Glu Leu Leu Leu Leu
                320                 325                 330

CTG CCC ACC TTG CAG AGC ATC ACC TGG CAG ATG ATC GAG CAG ATC CAG       1060
Leu Pro Thr Leu Gln Ser Ile Thr Trp Gln Met Ile Glu Gln Ile Gln
        335                 340                 345

TTC ATC AAG CTC TTC GGC ATG GCC AAG ATT GAC AAC CTG TTG CAG GAG       1108
Phe Ile Lys Leu Phe Gly Met Ala Lys Ile Asp Asn Leu Leu Gln Glu
            350                 355                 360

ATG CTG CTG GGA GGG TCC CCC AGC GAT GCA CCC CAT GCC CAC CAC CCC       1156
Met Leu Leu Gly Gly Ser Pro Ser Asp Ala Pro His Ala His His Pro
365                 370                 375

CTG CAC CCT CAC CTG ATG CAG GAA CAT ATG GGA ACC AAC GTC ATC GTT       1204
Leu His Pro His Leu Met Gln Glu His Met Gly Thr Asn Val Ile Val
380                 385                 390                 395

GCC AAC ACA ATG CCC ACT CAC CTC AGC AAC GGA CAG ATG TGT GAG TGG       1252
Ala Asn Thr Met Pro Thr His Leu Ser Asn Gly Gln Met Cys Glu Trp
                400                 405                 410

CCC CGA CCC AGG GGA CAG GCA GCC ACC CCT GAG ACC CCA CAG CCC TCA       1300
Pro Arg Pro Arg Gly Gln Ala Ala Thr Pro Glu Thr Pro Gln Pro Ser
        415                 420                 425

CCG CCA GGT GCG TCA GGG TCT GAG CCC TAT AAG CTC CTG CCG GGA GCC       1348
Pro Pro Gly Ala Ser Gly Ser Glu Pro Tyr Lys Leu Leu Pro Gly Ala
            430                 435                 440

GTC GCC ACA ATC GTC AAG CCC CTC TCT GCC ATC CCC CAG CCG ACC ATC       1396
Val Ala Thr Ile Val Lys Pro Leu Ser Ala Ile Pro Gln Pro Thr Ile
445                 450                 455

ACC AAG CAG GAA GTT ATC TAGCAAGCCG CTGGGGCTTG GGGGCTC                 1441
Thr Lys Gln Glu Val Ile
460                 465

(2) INFORMATION FOR SEQ ID NO:79:

(i) SEQUENCE CHARACTERISTICS:
        (A) LENGTH: 465 amino acids
        (B) TYPE: amino acid
        (D) TOPOLOGY: linear (ii) MOLECULE TYPE: protein
```

(xi) SEQUENCE DESCRIPTION: SEQ ID NO:79:

```
Met Asp Met Ala Asp Tyr Ser Ala Ala Leu Asp Pro Ala Tyr Thr Thr
 1               5                  10                  15

Leu Glu Phe Glu Asn Val Gln Val Leu Thr Met Gly Asn Asp Thr Ser
            20                  25                  30

Pro Ser Glu Gly Thr Asn Leu Asn Ala Pro Asn Ser Leu Gly Val Ser
        35                  40                  45

Ala Leu Cys Ala Ile Cys Gly Asp Arg Ala Thr Gly Lys His Tyr Gly
50                  55                  60

Ala Ser Ser Cys Asp Gly Cys Lys Gly Phe Phe Arg Arg Ser Val Arg
65                  70                  75                  80

Lys Asn His Met Tyr Ser Cys Arg Phe Ser Arg Gln Cys Val Val Asp
                85                  90                  95

Lys Asp Lys Arg Asn Gln Cys Arg Tyr Cys Arg Leu Lys Lys Cys Phe
            100                 105                 110

Arg Ala Gly Met Lys Lys Glu Ala Val Gln Asn Glu Arg Asp Arg Ile
        115                 120                 125

Ser Thr Arg Arg Ser Ser Tyr Glu Asp Ser Ser Leu Pro Ser Ile Asn
    130                 135                 140

Ala Leu Leu Gln Ala Glu Val Leu Ser Arg Gln Ile Thr Ser Pro Val
145                 150                 155                 160

Ser Gly Ile Asn Gly Asp Ile Arg Ala Lys Lys Ile Ala Ser Ile Ala
                165                 170                 175

Asp Val Cys Glu Ser Met Lys Glu Gln Leu Leu Val Leu Val Glu Trp
            180                 185                 190

Ala Lys Tyr Ile Pro Ala Phe Cys Glu Leu Pro Leu Asp Asp Gln Val
        195                 200                 205

Ala Leu Leu Arg Ala His Ala Gly Glu His Leu Leu Leu Gly Ala Thr
    210                 215                 220

Lys Arg Ser Met Val Phe Lys Asp Val Leu Leu Leu Gly Asn Asp Tyr
225                 230                 235                 240

Ile Val Pro Arg His Cys Pro Glu Leu Ala Glu Met Ser Arg Val Ser
                245                 250                 255

Ile Arg Ile Leu Asp Glu Leu Val Leu Pro Phe Gln Glu Leu Gln Ile
            260                 265                 270

Asp Asp Asn Glu Tyr Ala Tyr Leu Lys Ala Ile Ile Phe Phe Asp Pro
        275                 280                 285

Asp Ala Lys Gly Leu Ser Asp Pro Gly Lys Ile Lys Arg Leu Arg Ser
    290                 295                 300

Gln Val Gln Val Ser Leu Glu Asp Tyr Ile Asn Asp Arg Gln Tyr Asp
305                 310                 315                 320

Ser Arg Gly Arg Phe Gly Glu Leu Leu Leu Leu Pro Thr Leu Gln
                325                 330                 335

Ser Ile Thr Trp Gln Met Ile Glu Gln Ile Gln Phe Ile Lys Leu Phe
            340                 345                 350

Gly Met Ala Lys Ile Asp Asn Leu Leu Gln Glu Met Leu Leu Gly Gly
        355                 360                 365

Ser Pro Ser Asp Ala Pro His Ala His His Pro Leu His Pro His Leu
    370                 375                 380

Met Gln Glu His Met Gly Thr Asn Val Ile Val Ala Asn Thr Met Pro
385                 390                 395                 400

Thr His Leu Ser Asn Gly Gln Met Cys Glu Trp Pro Arg Pro Arg Gly
                405                 410                 415
```

```
Gln Ala Ala Thr Pro Glu Thr Pro Gln Pro Ser Pro Pro Gly Ala Ser
            420                 425                 430

Gly Ser Glu Pro Tyr Lys Leu Leu Pro Gly Ala Val Ala Thr Ile Val
        435                 440                 445

Lys Pro Leu Ser Ala Ile Pro Gln Pro Thr Ile Thr Lys Gln Glu Val
    450                 455                 460

Ile
465

(2) INFORMATION FOR SEQ ID NO:80:

(i) SEQUENCE CHARACTERISTICS:
        (A) LENGTH: 2329 base pairs
        (B) TYPE: nucleic acid
        (C) STRANDEDNESS: single
        (D) TOPOLOGY: linear (xi) SEQUENCE DESCRIPTION: SEQ ID NO:80:

GGGGCCCTGA TTCACGGGCC GCTGGGGCAG GGTTGGGGGT TGGGGGTGCC CACAGGGTTG      60

GCTAGTGGGG TTTTGGGGGG GCAGTGGGTG CAAGGAGTTT GGTTTGTGTC TGCCGGCCGG     120

CAGGCAAACG CAACCACGCG GTGGGGGAGG CGGCTAGCGT GGTGGACGGC CCGCGTGGCC     180

CTGTGGCAGC CGAGCCATGG TTTCTAAACT GAGCCAGCTG CAGACGGAGC TCCTGGCGGC     240

CCTGCTCGAG TCAGGGCTGA GCAAAGAGGC ACTGATCCAG GCACTGGGTG AGCCGGGGCC     300

CTACCTCCTG GCTGGAGAAG GCCCCCTGGA CAAGGGGGAG TCCTGCGGCG GCGGTCGAGG     360

GGAGCTGGCT GAGCTGCCCA ATGGGCTGGG GGAGACTCGG GGCTCCGAGG ACGAGACGGA     420

CGACGATGGG GAAGACTTCA CGCCACCCAT CCTCAAAGAG CTGGAGAACC TCAGCCCTGA     480

GGAGGCGGCC CACCAGAAAG CCGTGGTGGA CCCCTTCTG CAGGAGGACC CGTGGCGTGT     540

GGCGAAGATG GTCAAGTCCT ACCTGCAGCA GCACAACATC CCACAGCGGG AGGTGGTCGA     600

TACCACTGGC CTCAACCAGT CCCACCTGTC CAACACCTC AACAAGGGCA CTCCCATGAA     660

GACGCAGAAG CGGGCCGCCC TGTACACCTG GTACGTCCGC AAGCAGCGAG AGGTGGCGCA     720

GCAGTTCACC CATGCAGGGC AGGGAGGGCT GATTGAAGAG CCCACAGGTG ATGAGCTACC     780

AACCAAGAAG GGGCGGAGGA ACCGTTTCAA GTGGGGCCCA GCATCCCAGC AGATCCTGTT     840

CCAGGCCTAT GAGAGGCAGA AGAACCCTAG CAAGGAGGAG CGAGAGACGC TAGTGGAGGA     900

GTGCAATAGG GCGGAATGCA TCCAGAGAGG GGTGTCCCCA TCACAGGCAC AGGGGCTGGG     960

CTCCAACCTC GTCACGGAGG TGCGTGTCTA CAACTGGTTT GCCAACCGGC GCAAAGAAGA    1020

AGCCTTCCGG CACAAGCTGG CCATGGACAC GTACAGCGGG CCCCCCCCAG GGCCAGGCCC    1080

GGGACCTGCG CTGCCCGCTC ACAGCTCCCC TGGCCTGCCT CCACCTGCCC TCTCCCCCAG    1140

TAAGGTCCAC GGTGTGCGCT ATGGACAGCC TGCGACCAGT GAGACTGCAG AAGTACCCTC    1200

AAGCAGCGGC GGTCCCTTAG TGACAGTGTC TACACCCCTC CACCAAGTGT CCCCCACGGG    1260

CCTGGAGCCC AGCCACAGCC TGCTGAGTAC AGAAGCCAAG CTGGTCTCAG CAGCTGGGGG    1320

CCCCCTCCCC CCTGTCAGCA CCCTGACAGC ACTGCACAGC TTGGAGCAGA CATCCCCAGG    1380

CCTCAACCAG CAGCCCCAGA ACCTCATCAT GGCCTCACTT CCTGGGGTCA TGACCATCGG    1440

GCCTGGTGAG CCTGCCTCCC TGGGTCCTAC GTTCACCAAC ACAGGTGCCT CCACCCTGGT    1500

CATCGGCCTG GCCTCCACGC AGGCACAGAG TGTGCCGGTC ATCAACAGCA TGGGCAGCAG    1560

CCTGACCACC CTGCAGCCCG TCCAGTTCTC CCAGCCGCTG CACCCCTCCT ACCAGCAGCC    1620

GCTCATGCCA CCTGTGCAGA GCCATGTGAC CCAGAGCCCC TTCATGGCCA CCATGGCTCA    1680
```

-continued

```
GCTGCAGAGC CCCCACGGTG AGCACCCTGT GCCCCACACA GCAGGAGATG ATGATAGAGG   1740

TTGGCTGTCA ATGGATGCAG GGGAAAGGGG TGCCTGGCAG GCATTGCAGT CTGCATGTGT   1800

CTCTGGGACA AGTGTTTTTC CGTGATTGAG GGTGTCTGCA GGCCAGTGTG TTCCCATGTG   1860

AATGCACGTA TCTGTGTGTG TGCACGACTG CTTGTGTGAG CAGATCCCTA GTCGTGTCTG   1920

GGTGTGTATC GGTTGTGCAT GCATTTGTGT GCATCCTGTG TTTCTCTGAA ACTCTTAGGG   1980

CCATATGAAT TTCTAAAATC TATTCAGATT TTAGAAAGGT AATCTGGGGC CAGGCGTGGT   2040

GGCTCATGCC TGTAATCCCA GCACTTTGGA AGGCCGAGGT GGGCAGATCA CTTGAGGTCA   2100

GGAGTTCAAG ACCAGCCTGG CCAACACGGT GAAACCCCGT CTCTACTAAA AGTACAAAAA   2160

TTAGCCAGGC GTGGAGCACG TGCCTGTAGT CCCAGCTACT TGGGAGGCTG AGGCAGAATC   2220

GCTTGAACCT GGGAGGCGGA GGTTGCAGTG AGCTGAGATT TGGCCACTGC ACTGCACTCC   2280

AGCCTGGGCA ACAGAGTGAG TACTCTGCCA AAAAAAAAAA AAAAAAAA                2329
```

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:81:

```
CACCTGGTGA TCACGTGGTC                                                 20
```

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:82:

```
GTAAGGCTCA AGTCATCTCC                                                 20
```

(2) INFORMATION FOR SEQ ID NO:83:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:83:

Glu Gly Cys Lys Gly
1           5

(2) INFORMATION FOR SEQ ID NO:84:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:84:

Glu Gly Cys Lys Ala
1           5

(2) INFORMATION FOR SEQ ID NO:85:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:85:

```
Asp Gly Cys Lys Gly
1               5
```

(2) INFORMATION FOR SEQ ID NO:86:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..36

(xi) SEQUENCE DESCRIPTION: SEQ ID NO:86:

```
GAC ACG TAC AGC GGC CCC CCC CCA GGG CCA GGC CCG        36
Asp Thr Tyr Ser Gly Pro Pro Pro Gly Pro Gly Pro
1               5                   10
```

(2) INFORMATION FOR SEQ ID NO:87:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:87:

```
Asp Thr Tyr Ser Gly Pro Pro Pro Gly Pro Gly Pro
1               5                   10
```

(2) INFORMATION FOR SEQ ID NO:88:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..36

(xi) SEQUENCE DESCRIPTION: SEQ ID NO:88:

```
GAC ACG TAC AGC GGC CCC CCC CCC AGG GCC AGG CCC        36
Asp Thr Tyr Ser Gly Pro Pro Pro Arg Ala Arg Pro
1               5                   10
```

(2) INFORMATION FOR SEQ ID NO:89:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:89:

Asp Thr Tyr Ser Gly Pro Pro Pro Arg Ala Arg Pro
 1               5                  10

(2) INFORMATION FOR SEQ ID NO:90:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:90:

CATGAACCCC GAAGAGTGGT G                                              21

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:91:

GCCTCCAGAC ACCTGTTACT                                                20

(2) INFORMATION FOR SEQ ID NO:92:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:92:

GGCGATCATG GCAAGTTAGA AG                                             22

(2) INFORMATION FOR SEQ ID NO:93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:93:

TTGGTGAGAG TATGGAAGAC C                                              21

(2) INFORMATION FOR SEQ ID NO:94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:94:

GGGGTTTGCT TGTGAAACTC C                                              21

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:95:

TTGGTGGGAA ACGGGCTTGG                    20

(2) INFORMATION FOR SEQ ID NO:96:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:96:

CTCCCACTAG TACCCTAACC                    20

(2) INFORMATION FOR SEQ ID NO:97:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:97:

GAGAGGGCAA AGGTCACTTC AG                 22

(2) INFORMATION FOR SEQ ID NO:98:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:98:

AGTGAAGGCT ACAGACCCTA TC                 22

(2) INFORMATION FOR SEQ ID NO:99:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:99:

TTCCTGGGTC TGTGTACTTG C                  21

(2) INFORMATION FOR SEQ ID NO:100:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:100:

TGTGTTTTGG GCCAAGCACC A                  21

(2) INFORMATION FOR SEQ ID NO:101:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:101:

AACCAGATAA GATCCGTGGC                                         20

(2) INFORMATION FOR SEQ ID NO:102:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:102:

AACCAGACTC ACAGCCTGAA CC                                      22

(2) INFORMATION FOR SEQ ID NO:103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:103:

TCACAGGGCA ATGGCTGAAC                                         20

(2) INFORMATION FOR SEQ ID NO:104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:104:

TGCCGAGTCA TTGTTCCAGG                                         20

(2) INFORMATION FOR SEQ ID NO:105:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:105:

CCTCTTATCT TATCAGCTCC AG                                      22

(2) INFORMATION FOR SEQ ID NO:106:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:106:

CTGCTCTTTG TGGTCCAAGT CC                                      22

(2) INFORMATION FOR SEQ ID NO:107:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:107:

GAGTTTGAAG GAGACCTACA G                                              21

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:108:

ATCCACCTCT CCTTATCCCA G                                              21

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:109:

ACTTCCGAGA AAGTTCAGAC C                                              21

(2) INFORMATION FOR SEQ ID NO:110:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:110:

TTTGCCTGTG TATGCACCTT G                                              21

(2) INFORMATION FOR SEQ ID NO:111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:111:

GCCGAGTCCA TGCTTGCCAC                                                20

(2) INFORMATION FOR SEQ ID NO:112:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:112:

CTTTGCTGGT TGAGTTGGGC                                                20

(2) INFORMATION FOR SEQ ID NO:113:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:113:

TTCCATGACA GCTGCCCAGA G                                                    21

(2) INFORMATION FOR SEQ ID NO:114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:114:

TAAAGGTTGG AGCCCCTCTG                                                      20

(2) INFORMATION FOR SEQ ID NO:115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:115:

TTGTAAGGTG ACCCCATCAG                                                      20

(2) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:116:

TTGGTGATGT CCAGAAGTCC                                                      20

(2) INFORMATION FOR SEQ ID NO:117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:117:

CAGAATGTGT CAGAGTTCGC                                                      20

(2) INFORMATION FOR SEQ ID NO:118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:118:

CTCCCTCCTG TTCTTAAGTG                                                      20

(2) INFORMATION FOR SEQ ID NO:119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:119:

CTGGACTCCC AGTTCAGTCA                   20

(2) INFORMATION FOR SEQ ID NO:120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:120:

CAAGGATCCA GAAGATTGGC                   20

(2) INFORMATION FOR SEQ ID NO:121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:121:

CGTCCTCTGG GAAGATCTGC                   20

(2) INFORMATION FOR SEQ ID NO:122:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:122:

GCAACAGAGC AAGACTCCAT CTCA              24

(2) INFORMATION FOR SEQ ID NO:123:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:123:

GAGTTTAATG GAAGAACTAA CC                22

(2) INFORMATION FOR SEQ ID NO:124:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:124:

CCTCATGGAG AAACATCCTA AGT               23

(2) INFORMATION FOR SEQ ID NO:125:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:125:

```
AGGGAGTGCA CGGCTGAGCT CCTG                                              24
```

(2) INFORMATION FOR SEQ ID NO:126:

(i) SEQUENCE CHARACTERISTICS:
        (A) LENGTH: 6254 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1287..4273
        (D) OTHER INFORMATION: /note= "N = A or G or C or T"

(xi) SEQUENCE DESCRIPTION: SEQ ID NO:126:

```
AGCCAGCACT GTTCTTGGCA CATGGTAATC TTAACATATT TTTTCCTACA GGGAGGCCTG        60

GTGTCAGGCC GGGAGTGGGG TGGAAGGGTC CCAAAATGGA TGGAAGGGCC CCAAAATGGC       120

CGTGAGCATC CTCTGCCCTT GAGAAGAGCT AGCCCAGCTG TCTAGAGCTC CCTGCTGCTG       180

CCGCTCTCGT AAGCAGCAAG CATTTTTGGC TCTCCTGTCT CAGCATGATG CCCCTACAAG       240

GTTCTTTCGG GGGTGGGACC CAACGCTGCT CTCCTGATGG CCTCCCTGGC TCCCAGCACC       300

TTCCATCCCA GCTGCTCAGG GCCCCTCACC TGCGCCTCCC CCACCCTCCC CTCTGCCCAC       360

TCCCATCGCA GGCCATAGCT CCCTGTCCCT CTCCGCTGCC ATGAGGCCTG CACTTTGCAG       420

GGCTGAAGTC CAAAGTTCAG TCCCTTCGCT AAGCACACGG ATAAATATGA ACCTTGGAGA       480

ATTTCCCCAG CTCCAATGTA AACAGAACAG GCAGGGGCCC TGATTCACGG GCCGCTGGGG       540

CCAGGGTTGG GGGTTGGGGG TGCCCACAGG GCTTGGCTAG TGGGGTTTTG GGGGGGCAGT       600

GGGTGCAAGG AGTTTGGTTT GTGTCTGCCG GCCGGCAGGC AAACGCAACC CACGCGGTGG       660

GGGAGGCGGC TAGCGTGGTG GACCCGGGCC GCGTGGCCCT GTGGCAGCCG AGCCATGGTT       720

TCTAAACTGA GCCAGCTGCA GACGGAGCTC CTGGCGGCCC TGCTCGAGTC AGGGCTGAGC       780

AAAGAGGCAC TGATCCAGGC ACTGGGTGAG CCGGGGCCCT ACCTCCTGGC TGGAGAAGGC       840

CCCCTGGACA AGGGGAGTC CTGCGGCGGC GGTCGAGGGG AGCTGGCTGA GCTGCCCAAT       900

GGGCTGGGGG AGACTCGGGG CTCCGAGGAC GAGACGGACG ACGATGGGGA AGACTTCACG       960

CCACCCATCC TCAAAGAGCT GGAGAACCTC AGCCCTGAGG AGGCGGCCCA CCAGAAAGCC      1020

GTGGTGGAGA CCCTTCTGCA GTAAGGAGCC CTGCCCCGTC CCCGCTCCCA GGAGAGCCTA      1080

GAGGGGCCCC CCTCAGCTCC TAACGAGCCC CCCTTCTGAG TTGAGTCCCC ATGACCTTCA      1140

GCCTTTAGCC TAGTTGCTGG GAAGGGGGAC AGGGCCCATG AGAGCCCAGG GGTCCTTGCT      1200

TGGAGGTTTG AGCCTCCAGC CCCTGAACTG CTCCTCTGCA GAGTCCCAAA TCCCATGAGC      1260

CCAGGCCTTT AGCCCAGTCC TTGGGCNAGG GGGACATTTC CCAGGGGGTC CAAGATGGGA      1320

GAAAAAGCAG TGAATTCACA ACTCAAATGC CCACCCACCC ATCCATCCAT CCGTCCATCC      1380

ACCCATTCAT CCATTCATCC ATTCACCCAT CCATCCATCC ACATATCTTC ATCTGTGTTG      1440

TGTGTCTGTG TATCCATGTT TCTAAACCTT TATCTGTTCC AGTGTCTGTA TCCATAGGCC      1500

TGTGTCCACG TTTGTCATGT GTGTGCGTCN ACAAGTCTCT GTCCTCATGA CCATGTGTCT      1560

GTGTCCCTGT GTCCTGGCAT AAATGACCAT ACCTCACCGT CCCTGAGTCT ATGTGTAGGC      1620

CCCTGGGCTC CATAACTGCT TTCATGCACA GTCCCCACCC TCAGAGTTGA CAAGGTTCCA      1680

GCACCCAGGA CCGCAGCCCC ACCTATGGGG AGAGACAGCC CTTGCTGAGC AGATCCCGTC      1740

CTTGCCCTCT CCCAGGGAGG ACCCGTGGCG TGTGGCGAAG ATGGTCAAGT CCTACCTGCA      1800
```

```
GCAGCACAAC ATCCCACAGC GGGAGGTGGT CGATACCACT GGCCTCAACC AGTCCCACCT    1860

GTCCCAACAC CTCAACAAGG GCACTCCCAT GAAGACGCAG AAGCGGGCCG CCCTGTACAC    1920

CTGGTACGTC CGCAAGCAGC GAGAGGTGGC GCAGCGTAAG TAATGACCCT ACCCCGCATC    1980

TTCCCTGGGA GGGCCCAGGA CTCTCCCCTA ACTCATAGGT GGGGGCTGGA AGCTTCACCA    2040

TCCCCATTAC ACAGACAGGT AGATGGAAAG GAAGTCAGTG GGATTCAACC TGCATTTATT    2100

ACCTATTCTG CGCCAGGCAC TCTGTGGGAC GGGAGTANAC TTGGTCCTGA ACATCCAAAG    2160

ATGAATGAAA TGGGTCCCTG CTTTCTTTTT CTTTTTTTAG ATACGTGACT CTGGAAAAAT    2220

ATGTAAGCTC TCTGAGCCTC AGCTTCTTCA TCTGTACAAT GGGGATAGTA AATGTGCCAA    2280

ATCAGAACAA ATGCTAATGC TTACCTGCAG TCTTGTACTG AGAAGGATGG TGAGATCATA    2340

TCTTGGGTTG GTAGGAAAGC ATTCAGGGAT TGATTAGTGA TGTTTGCCTT GAACACAGGT    2400

TAAGAAAGTG ATGGCATGTG TGCTGTGTGT TTGTCATCAG TAGATTAGAT GATTTCTAAG    2460

TTCTAGCTGT AAGCTCCTCT GGTTCAGCGC CATGGCAATG AGAAAGAATC AAGGGCAAGG    2520

TCAGGGGAAT GGACGAGGGA AGGTGAGAGT GGCCAGTACC CCACTCACGG CTTTCTGTGC    2580

CTGCAGAGTT CACCCATGCA GGGCAGGGAG GGCTGATTGA AGAGCCCACA GGTGATGAGC    2640

TACCAACCAA GAAGGGGCGG AGGAACCGTT TCAAGTGGGG CCCAGCATCC CAGCAGATCC    2700

TGTTCCAGGC CTATGAGAGG CAGAAGAACC CTAGCAAGGA GGAGCGAGAG GTACAACGGC    2760

GGGCGGGAAA CAGTGCTGGT TTGGTCTGGG CTGCGGCAAG GCCAGGGGAA GGGGAAGGTG    2820

ACTCTAGGTC CTGTAAAAGG CTGTCCAGTT GCCGAGAACT CCTGATATTG GCTTAGCCTG    2880

GCCCAGAAAA TTGAGAATAC TTGAACCTAA GCCCATTCCT CGCAGCCCCC CTGCACCNTG    2940

GACACCAAGC AACCCCTTCC ATGGATGCTC ACCCAATTCG ATTCTCTCTA CAATCCTATG    3000

GCTCTTTTGC TCACTTTATG AATGGAGAGA CTGAGGTCAG ACAGACTGTC AATTGCCCAA    3060

GGTCACACAG CAGACCTGGC ATTGGAACCC AGATCTGCCA GCCTCAAACC CTCCGGCAGA    3120

GNTCAGCTTC TCAGAACCCT CCCCTTCATG CCCAGGACAG GGTTCCTCTG AGCCTGGCCT    3180

GGAGGCTCAT GGGTGGCTAT TTCTGCAGGG CGGAATGCAT CCAGAGAGGG GTGTCCCCAT    3240

CACAGGCACA GGGGCTGGGC TCCAACCTCG TCACGGAGGT GCGTGTCTAC AACTGGTTTG    3300

CCAACCGGCG CAAAGAAGAA GCCTTCCGGC ACAAGCTGGC CATGGACACG TACAGCGGGC    3360

CCCCCCCAGG GCCAGGCCCG GGACCTGCGC TGCCCGCTCA CAGCTCCCCT GGCCTGCCTC    3420

CACCTGCCCT CTCCCCCAGT AAGGTCCACG GTAAGTGGTA TGTGGGGACA AGGGACACGT    3480

GGGAAGGTGG GAGGGTTGGG GAGGACTGTC CCATTGACAG CAGTCACCTA AACCTCTTTG    3540

CACGTCAGTT TGGTTCCATT CGCAGCTGAC CCAGGGATTG GCAAAAGGTA GAAACAAAGG    3600

CAGATTTGCT GGCTGCATAA AGGCAGACAG GCAGATGGCC TAAGCAAACC AATGGAGTTT    3660

GAAGTGCTGA GGGCTGTGGA GGCAGGGGAG GGCAGGGAAG TGGGGTGCTG AGGCAGGACA    3720

CTGCTTCCCT CTCCAGGTGT GCGCTATGGA CAGCCTGCGA CCAGTGAGAC TGCAGAAGTA    3780

CCCTCAAGCA GCGGCGGTCC CTTAGTGACA GTGTCTACAC CCCTCCACCA AGTGTCCCCC    3840

ACGGGCCTGG AGCCCAGCCA CAGCCTGCTG AGTACAGAAG CCAAGCTGGT GAGTGTCCTT    3900

GCTTGTAAGG AAAACCCAAC CTCATCTTTC CTTGGCAGGG AGATTCTGGA GCAGTCCCTA    3960

GGGAGGCCCT GTGGGACCC CGGCCCCCCG GACACAGCTT GGCTTCCCCT CGTAGGTCTC    4020

AGCAGCTGGG GGCCCCTCC CCCTGTCAG CACCCTGACA GCACTGCACA GCTTGGAGCA    4080

GACATCCCCA GGCCTCAACC AGCAGCCCCA GAACCTCATC ATGGCCTCAC TTCCTGGGGT    4140

CATGACCATC GGGCCTGGTG AGCCTGCCTC CCTGGGTCCT ACGTTCACCA ACACAGGTGC    4200
```

-continued

```
CTCCACCCTG GTCATCGGTA AGCTGGTGGG GATGGGTGGG CACCTGGGTG GGAGGCTCAT    4260

GGGGCAACCG CANAATCCAG GAGCTGGAAA AGCCACTGGG ACTCATTCAT TCATTCATTC    4320

ATTCATACAA CATGTTAGGA GAGGGAGCA GAGAACTGAC CCCATGGCCT TTGCACTGCT     4380

GTGGTACCCC AGGGCTCCAG GGAACCGCAG TTTGACAACT TTTGAACAAG TCACCGCTTG    4440

CTTTTCCCAT TAGCTTAGAC AAAGAGCTAA AGGCTCAGAG AGGGGGAATG ACTTGCCAGA    4500

GCCACTTAAA TTAGTGGCAG GTCCCAGTGG AGGGCTGTTT CCTGACCACC TTGCCCCTTC    4560

TTCCAAACCA CGGGCTCTGG GAAGGAGAGG TGGTGCCCTT GGGAGGTCTT GGGCAGGGGT    4620

GGGATATAAC TGGGGGGCCC AGCTGATTCC CTCCCCTTCC ACTCCAGGCC TGGCCTCCAC    4680

GCAGGCACAG AGTGTGCCGG TCATCAACAG CATGGGCAGC AGCCTGACCA CCCTGCAGCC    4740

CGTCCAGTTC TCCCAGCCGC TGCACCCCTC CTACCAGCAG CCGCTCATGC CACCTGTGCA    4800

GAGCCATGTG ACCCAGAACC CCTTCATGGC CACCATGGCT CAGCTGCAGA GCCCCACGG    4860

TGAGCACCCT GTGCCCCACA CAGCAGGAGA TGATGATAGA GGTTGGCTGT CAATGGATGC    4920

AGGGGAAAGG GGTGCCTGGC AGGCATTGCA GTCTGCATGT GTCTCTGGGA CAAGTGTGTT    4980

TCCGTGATTG AGGGTGTCTG CAGGCCAGTG TGTTCCCATG TGAATGCACG TATCTGTGTG    5040

TGTGCACGAC TGCTTGTGTG AGCAGATCCC TAGTGCGTGT CTGGGTGTGT ATCGGTTGTG    5100

CATGCATTTG TGTGCATGCC TGTGTTTCTC TGAAACTCTT AGGGCCATAT GAATTTCTAA    5160

AATCTATTCA GACCAGTTTT GAAAATCAGC CTTGGATCTC CAACTGCTGC CCAGTCTGGC    5220

TGTTCAGCAG GCCCCATGCC CCCCTTTCCC CAGTCTTGAG GCCTGGGACT AGGGCTGTCA    5280

GGCACGTTTG CCACGTCTGC CCCTCTCTCC CCTGCGGCCA GCCCTCTACA GCCACAAGCC    5340

CGAGGTGGCC CAGTACACCC ACACGGGCCT GCTCCCGCAG ACTATGCTCA TCACCGACAC    5400

CACCAACCTG AGCGCCCTGG CCAGCCTCAC GCCCACCAAG CAGGTAAGGT CCAGGCCTGC    5460

TGGCCCTCCC TCGGCCTGTG ACAGAGCCCC TCACCCCCAC ATCCCCCGGG CTCAGGAGGC    5520

TGCTCTGCTC CCCCAGGTCT TCACCTCAGA CACTGAGGCC TCCAGTGAGT CCGGGCTTCA    5580

CACGCCGGCA TCTCAGGCCA CCACCCTCCA CGTCCCCAGC CAGGACCCTG CCGGCATCCA    5640

GCACCTGCAG CCGGCCCACC GGCTCAGCGC CAGCCCCACA GGTGAGAGGC CCTGGCTCCA    5700

CCCCCTCCCT TACTGTCCCT GCCCCCTTCC ATGTTGGTCC CACCCCTTCT GTTGCTGTCC    5760

GTCACTGTGG GGCTGTGCAT GCAGCAGGCC TAGGGCTGCT GTGAGGAAGC ACTGGCAGGC    5820

GTGGAAGGGT GGGGTGGCTT CCATGAATCC AGTGTTCACA GTAAGATGTA CTCAGGCCAG    5880

TCCATGGGCG GCCGTGGACC CTGGCTGGGA GGCTCCCTTT GTTAAGAACC GAGGGTAGAG    5940

GTGTGACTTT GGGGTTCCTG TTATGTGCTG TGATCCAGGA GGTGTGGCCC TGCCTCCCCA    6000

TCCTGAGTAC CCCTAGGGAC AGGCAGGTGG GGTGGGTGTG GGTGCCTGGT GGGTGGCTAG    6060

CAGCCTTGTT TGCCTCTGCA GTGTCCTCCA GCAGCCTGGT GCTGTACCAG AGCTCAGACT    6120

CCAGCAATGG CCAGAGCCAC CTGCTGCCAT CCAACCACAG CGTCATCGAG ACCTTCATCT    6180

CCACCCAGAT GGCCTCTTCC TCCCAGTAAC CACGGCACCT GGGCCCTGGG GCCTGTACTG    6240

CCTGCTTGGG GGGT                                                     6254
```

(2) INFORMATION FOR SEQ ID NO:127:

(i) SEQUENCE CHARACTERISTICS:
        (A) LENGTH: 631 amino acids
        (B) TYPE: amino acid
        (C) STRANDEDNESS:
        (D) TOPOLOGY: linear (xi) SEQUENCE DESCRIPTION: SEQ ID NO:127:

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
                20                  25                  30

Pro Gly Pro Tyr Leu Leu Ala Gly Glu Gly Pro Leu Asp Lys Gly Glu
            35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
                100                 105                 110

Trp Arg Val Ala Lys Met Val Lys Ser Tyr Leu Gln Gln His Asn Ile
            115                 120                 125

Pro Gln Arg Glu Val Val Asp Thr Thr Gly Leu Asn Gln Ser His Leu
        130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
                180                 185                 190

Glu Leu Pro Thr Lys Lys Gly Arg Arg Asn Arg Phe Lys Trp Gly Pro
            195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
                260                 265                 270

Lys Glu Glu Ala Phe Arg His Lys Leu Ala Met Asp Thr Tyr Ser Gly
            275                 280                 285

Pro Pro Pro Gly Pro Gly Pro Gly Pro Ala Leu Pro Ala His Ser Ser
    290                 295                 300

Pro Gly Leu Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Val Ser Thr Leu Thr
370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
            405                 410                 415
```

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Asn Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Phe Thr
    530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
        595                 600                 605

His Leu Leu Pro Ser Asn His Ser Val Ile Glu Thr Phe Ile Ser Thr
    610                 615                 620

Gln Met Ala Ser Ser Ser Gln
625                 630

(2) INFORMATION FOR SEQ ID NO:128:

(i) SEQUENCE CHARACTERISTICS:
        (A) LENGTH: 6433 base pairs
        (B) TYPE: nucleic acid
        (C) STRANDEDNESS: single
        (D) TOPOLOGY: linear (xi) SEQUENCE DESCRIPTION: SEQ ID NO:128:

CATGAACCCC GAAGAGTAGT GTCTTCTCTC TGGACTAAAG CGGAACTGAG AACCGGTGGA      60

AAAGCCCCGC GCCTAGGCTG CAAGGCACTG GCTTAACAAG TCCAAAGGTT AGGTGAAGTT     120

TGGCTGATAA GCAGAACCAG TAAAAGAAGG TCTCTAGCCC CCCAGCGTGA GTACAATGGA     180

CCCTGGCAAA GCCCGCTCC CGGCCCAGGT CTTCTGCTCT CCAGGTCTGC CCCTCCGGCT      240

CTCCCTCTCT CCGGGTTTCC CCCTCCCCAC CATCATTTGC ATCCAGCCGA AAGCTGGGCC     300

CTTCCCACTA ATTTGCATAT CTTATATGGC CTAATGGTGG CGATCATGGC AAGTTAGAAG     360

TTTTCTGACT CCTTTCGGAG GAGCCTCCGG GACCCCGGGG AGTAACAGGT GTCTGGAGGC     420

TGAAGGGTGG AGGGGTTCCT GGATTTGGGG TTTGCTTGTG AAACTCCCCT CCACCCTCCT     480

CTCTCGCACC CACCCACCCC CTCACCCCCT TCTTTTTCCG TCCTTGGAAA ATGGTGTCCA     540

AGCTCACGTC GCTCCAGCAA GAACTCCTGA GCGCCCTGCT GAGCTCCGGG GTCACCAAGG     600

AGGTGCTGGT TCAGGCCTTG GAGGAGTTGC TGCCATCCCC GAACTTCGGG GTGAAGCTGG     660

AGACGCTGCC CCTGTCCCCT GGCAGCGGGG CCGAGCCCGA CACCAAGCCG GTCTTCCATA     720

CTCTCACCAA CGGCCACGCC AAGGGCCGCT TGTCCGGCGA CGAGGGCTCC GAGGACGGCG     780

-continued

```
ACGACTATGA CACACCTCCC ATCCTCAAGG AGCTGCAGGC GCTCAACACC GAGGAGGCGG      840

CGGAGCAGCG GGCGGAGGTG GACCGGATGC TCAGGTAGGC GCAGAGCCAG GTGGAGGGGA      900

CCCACCCGAA CCCCTGGAGC CCCGGCCCCG GGCCTGAGTG ACACTGCGCC CGACCACACT      960

CGCCAAGCCC GTTTCCCACC AAAAAATTCC CCCGGGGGGC GCTCTGCTTC TCTCCCAACA     1020

CCCGGACCCT TCCCAATCCC TTAGCGGGAC AACCCTGCGG CCCACCGGGC TTCTTCTCCC     1080

CAGGCCCAGG CCATCGTCCT CAGAAGAAAG GGATGAGGTG TACCGTACAG GGGCAGTCAC     1140

CTTCTCCTCT GTTTAGCTTC CATTTTGGCC TCATGTCTAC CCCAAAGTTG TAGCTTAGAT     1200

GGGGGGAAAA TTCAGAATTT TGCATAGACC ATAGGTAGCA CCCCCTAGAA AAAGAATGTT     1260

TCTCCCCAGA TGTCTCCCAC TAGTACCCTA ACCATCTGCT TGTCTGTCTA GTGAGGACCC     1320

TTGGAGGGCT GCTAAAATGA TCAAGGGTTA CATGCAGCAA CACAACATCC CCCAGAGGGA     1380

GGTGGTCGAT GTCACCGGCC TGAACCAGTC GCACCTCTCC CAGCATCTCA ACAAGGGCAC     1440

CCCTATGAAG ACCCAGAAGC GTGCCGCTCT GTACACCTGG TACGTCAGAA AGCAACGAGA     1500

GATCCTCCGA CGTAAGTGTT TTCATCCTGC CTCTGCCTCA ACCTGAAGTG ACCTTTGCCC     1560

TCTCACCCCA TTGGCTGCCT CAGTTTCCCT TTCATCGACA AGGCCTTGTG AGCACTTGGC     1620

AGATATGAGG AAGGTGGCAA GTAGATTTGG CCTTGGTGGT TGCTGTACAA TGGATTGGCT     1680

TCTGTCATGT TCTTCAGTCA CAGCCCCCTT GCTACCCAGC CAGTTGCTCT GAGGAGCCTG     1740

TCAGTGTGAT TGAGCTCACC CACTTGACAT CAAATACAGG AGTTCAGGAT GCAGAGTGTT     1800

GCTTCATCTC TGAAGGCCAG TGAGCCAAAG GGGAAAAAAT AATAATTTTC TTAAAACTAT     1860

AGCTGGCTAT GTTTGAGCTC CTTCAAAGAA AGGAAAAGGG TGGCTTTGCT GGAGCAACTG     1920

AGGTGGGCAG TAAGGGCCTG TGCTGAGGGC TCCCCATCTC CAGCTCCACA TGCAGTGAGA     1980

GAAGGTTGCA AAGCTTAGTT AGACGAGGGG AATAAACCTG TCTTCGTCCG TTGTCTGTCT     2040

GTCTGTCTGT CTGTCTGCTG AGTGAAGGCT ACAGACCCTA TCAAATCTAC TCCTTTCTCT     2100

TTTCAGAATT CAACCAGACA GTCCAGAGTT CTGGAAATAT GACAGACAAA AGCAGTCAGG     2160

ATCAGCTGCT GTTTCTCTTT CCAGAGTTCA GTCAACAGAG CCATGGGCCT GGGCAGTCCG     2220

ATGATGCCTG CTCTGAGCCC ACCAACAAGA AGATGCGCCG CAACCGGTTC AAATGGGGGC     2280

CCGCGTCCCA GCAAATCTTG TACCAGGCCT ACGATCGGCA AAAGAACCCC AGCAAGGAAG     2340

AGAGAGAGGC CTTAGTGGAG GAATGCAACA GGTAACACCA CCAGAAGCTC AGGTGGGCAG     2400

GTGGGCAAGT ACACAGACCC AGGAACCCTC CCCTCGGTCC TGGGATATTG AGACACTAGT     2460

TATACAGATA AGTGTGGCTA AATCAGAGCT TCTCAAAGTA TGTTCCACAG TGATTGTGTG     2520

TTTTGGGCCA AGCACCAACA AGTCCCCCCG CCCCCCTTCA CTCACCATCT CCCTCCATC     2580

CATTCCCAGG GCAGAATGTT TGCAGCGAGG GGTGTCCCCC TCCAAAGCCC ACGGCCTGGG     2640

CTCCAACTTG GTCACTGAGG TCCGTGTCTA CAACTGGTTT GCAAACCGCA GGAAGGAGGA     2700

GGCATTCCGG CAAAAGCTGG CCATGGACGC CTATAGCTCC AACCAGACTC ACAGCCTGAA     2760

CCCTCTGCTC TCCCACGGCT CCCCCCACCA CCAGCCCAGC TCCTCTCCTC CAAACAAGCT     2820

GTCAGGTAAG CAAAGGTTGG GCCTCACTGC CTCGGCAACC CAACCATCCT GGTTCTTGCC     2880

ACGGATCTTA TCTGGTTTAA GGGTTTTCAG AGGAGCAAAC GCTTTTGAGA TGATCCTAGG     2940

GCCGCTCTCT CATTGCCAGA ATATACTCCC CTGGAAATAA TGTGTGGCTC TGATCAGTTC     3000

CAAGGCACTG GGGATACATC AGTGAACAAA ACAAACGAGA TAAAAATTTC CTGCCCTCGT     3060

GGCGCTTACA TTCTAGAATT AAATAGAGAA CATGCCATAT TTACCCTGGA GAAAAGCAGC     3120

CGATATTTCT TGTGGGTGGA CAGGGGAGGA GAAAGCAACT TTATTTTCTT ATTACCCACC     3180
```

```
CTTGAAAACA AGAGGTGCCG AGTCATTGTT CCAGGACCCT GGTGGCACTA ATGTTCCCTA    3240

CTGGGTTTGT GTTGTTTTGC AGGAGTGCGC TACAGCCAGC AGGGAAACAA TGAGATCACT    3300

TCCTCCTCAA CAATCAGTCA CCATGGCAAC AGCGCCATGG TGACCAGCCA GTCGGTTTTA    3360

CAGCAAGTCT CCCCAGCCAG CCTGGACCCA GGCCACAATC TCCTCTCACC TGATGGTAAA    3420

ATGGTGAGTA CACCTGGGCC ATTGTCGCTC TGGAGCTGAT AAGATAAGAG GCAAAACAAA    3480

CACAACTTCT CACAAGGCCT GCCTCAAACA ATGAACCATT GTAGCCCCAT AGGGGAAAAT    3540

GAGGGCTGTC CAGAGTCGGA AAGGAGAGGT AGTGCTGGTG ACCCACCCTT TGGCGGGTAG    3600

AAAACCCAAA GTGATGGGAT TACAGGGGTG AAGCACCATG CCCAGCCAAT AATTGTTATT    3660

GAGTGAATGA AGGAATGAAT TTGAGAACTA GTCATGCCAA GGAATCGCTA AGTCACATCG    3720

TGTTGGAAAC TGCTCTTTGT GGTCCAAGTC CACCCATGTT TCTCTTGTTT TTTTCTCTCC    3780

ATCAGATCTC AGTCTCAGGA GGAGGTTTGC CCCCAGTCAG CACCTTGACG AATATCCACA    3840

GCCTCTCCCA CCATAATCCC CAGCAATCTC AAAACCTCAT CATGACACCC CTCTCTGGAG    3900

TCATGGCAAT TGCACAAAGT AAGTTCTATT CTTGGTTGGA AAACCTGGGG GCAGGGAGAA    3960

GAAGAATGGG AAGCAAATTA ATGTGGTGAA AAATAACTGT AGGTCTCCTT CAAACTCACC    4020

CACAACTAGT AAATTTGGTT TAACTTCTTT AGTTTCTCAT CTGTCTCCTT AAATCCAATA    4080

TTTGGATTGT TTAGCCTAAA ACAAGAAAAA ATTGTGGAAT GGATTTGGAT CCTGGTCACA    4140

GTTTAGCAGC TGTGCATCCT GGGTCAAATC ATTGAACCTA TGACTCTGGG AGACTCTCAG    4200

GCTTTAATCA GATCTGTTTA ATGCCCATCT CCAACCCACA ACTCATTGTG GAACTTGAGC    4260

AAGTAAATTA ATATCTCCAA GTCTCCGTTT CTTTACACTT GCCTCCCATG GAATCTCCTA    4320

TGTAACAGGC TCAGCCCGGT GACTGGGACA TTGAGCGGGG GCTCAAATGA TGGCATCCAT    4380

CCACCTCTCC TTATCCCAGG AGCTGTCTGT GTCTTTTCCT CTTGCTCCCA CAGGCCTCAA    4440

CACCTCCCAA GCACAGAGTG TCCCTGTCAT CAACAGTGTG GCCGGCAGCC TGGCAGCCCT    4500

GCAGCCCGTC CAGTTCTCCC AGCAGCTGCA CAGCCCTCAC CAGCAGCCCC TCATGCAGCA    4560

GAGCCCAGGC AGCCACATGG CCCAGCAGCC CTTCATGGCA GCTGTGACTC AGCTGCAGAA    4620

CTCACACAGT AAGGACACGG GCATGTGGAG GGAGGGAGCA CTCAGGACCC TCAGTGGCCA    4680

ACCACTTTCC CTCTCTGGGT CTGAACTTTC TCGGAAGTTT ATTGGCTTGG TCACTTTTCC    4740

CTGCCTATGA TCAACCGACT AAGACAATTT CTCAAGCATA ACTCTTGAGT GTTGCTGTAC    4800

CTTTTCTAGT CCTCTTCTCT ACCCCTGAGA TTCCCAGGGA AGGGTTTGAA TGACCTTTGC    4860

TCCCGTTCCG TACCGGAGGC CTCCCTGGTA GGAAATGTGT TCTGAGAGCA GGTGGTTTCT    4920

CCCTCACAGC CAAGCATCCA CATGCTTTCG GGAGTTGGTT ATGTGACTTG GAATTTACAT    4980

GAATCTTATG GATAACTAAT ATGAGAAATC CCCACTATAA CCACCAGCCC TTTTATCTAC    5040

CTGAGGAGAT GGGAGCTATG GTGTGGGATG GGGGCTCTGT ACCTGTGTCT TTGCCTGTGT    5100

ATGCACCTTG ATTCTGTCTT CACTCTGTCT CTCCAGTGTA CGCACACAAG CAGGAACCCC    5160

CCCAGTATTC CCACACCTCC CGGTTTCCAT CTGCAATGGT GGTCACAGAT ACCAGCAGCA    5220

TCAGTACACT CACCAACATG TCTTCAAGTA AACAGGTAAT GCCAGCAGGA TATGCGGGGG    5280

TTGGGGTGTG GGCAGGGTGT GATAAGGCCA TGGATGTGCA AAGGTTGTGG CAAGCATGGA    5340

CTCGGCCAGA AATTATATCC TCTTTGCTGG TTGAGTTGGG CATCATCTCC CTTAGAGAAG    5400

CCAAACTAAT GGCCCATGAC CCTGCCAAAT GACACAGCTG AGCACCCTCT CTCCTCTCTC    5460

TCTGCAGTGT CCTCTACAAG CCTGGTGATG CCCACACACC ACTTACTTCG TGCGCAACAA    5520

CAAGGACCCT GTTTTCCACA CCATCACCCT CTGGGCAGCT GTCATGGAAA AGCCCAGTGA    5580
```

```
CCTGACCAGC ACCTGCGAGA GGTCCCTGCT ACCTGACGGA CGTCCTGCTG GCACCTCAGA      5640

CAATCCACTC TCAGGAGGCG CAGCCCGAAG CCCAGTTTCC CTTCTATGCA GTATTGCCAC      5700

AATGCCTCTC CCACGATGTC AAGGACTCCT GTCTGTCCTG GAGGTGGGAG ACAAGGAACC      5760

ACCGAAGAGG AAGCAAGAAA GCCGTACTGT CTATGTTGTG ATCCTTCATC GAACAAACTG      5820

ATGCGAAAAC TTGAATCTGT TACTGAAATG AGGAGAGAAG GACATGTGCT ATTGAACTGA      5880

GCCAAACACA CTGTAAATAT CCACAGACTC CCTCCCCTGC CCCCATCCCA CATGATCTTG      5940

AGATTTCTTT TAAAGAAGTA AATTTGTCCA ATGGCTGTAA ACTATAAACT ACTGTAATTA      6000

AGTGCAATTT CCCCTCTGTG TCCTCTCCCC TCTGCCCTGT ATATAATACT AAAGTGTCTA      6060

TTAGTTTTCT TTGTAAAGGT CAGAGTCAAA ATTTCAAAAG TGATCTGTCC CCTCTCCCCT      6120

CATGGAGAAA CATCCTAAGT GGGAAGTGAA GCCCCTTGTC CTCTCCCGCG GGCCTGGACA      6180

CTTATGGGGA CAGCATACCT TGGACTGACT ACCAGCTAAC TCCAGTCTCC TGACATTAAG      6240

ACACACCTCT GGATCCCTGG AGGGGCTGAA TGTAGTGTGT CAGAGTAACA TGCCAGCTTC      6300

CTGTGGGCCA GGAGCTCAGC CTGCACTCCC TAAGAAACCC CAGGGCAGGG AAACTGGCTG      6360

TTTGATAGCA GAAGAAAAAG TTGCAGTCTC AAAAGCCTTC CATTAAAACA ATTTATTTTA      6420

TCACTAAAAA AAA                                                        6433
```

(2) INFORMATION FOR SEQ ID NO:129:

(i) SEQUENCE CHARACTERISTICS:
        (A) LENGTH: 609 amino acids
        (B) TYPE: amino acid
        (C) STRANDEDNESS:
        (D) TOPOLOGY: linear (xi) SEQUENCE DESCRIPTION: SEQ ID NO:129:

```
Met Val Ser Lys Leu Thr Ser Leu Gln Gln Glu Leu Leu Ser Ala Leu
1               5                   10                  15

Leu Ser Ser Gly Val Thr Lys Glu Val Leu Val Gln Ala Leu Glu Glu
                20                  25                  30

Leu Leu Pro Ser Pro Asn Phe Gly Val Lys Leu Glu Thr Leu Pro Leu
            35                  40                  45

Ser Pro Gly Ser Gly Ala Glu Pro Asp Thr Lys Pro Val Phe His Thr
        50                  55                  60

Leu Thr Asn Gly His Ala Lys Gly Arg Leu Ser Gly Asp Glu Gly Ser
65                  70                  75                  80

Glu Asp Gly Asp Asp Tyr Asp Thr Pro Pro Ile Leu Lys Glu Leu Gln
                85                  90                  95

Ala Leu Asn Thr Glu Glu Ala Ala Glu Gln Arg Ala Glu Val Asp Arg
            100                 105                 110

Met Leu Ser Glu Asp Pro Trp Arg Ala Ala Lys Met Ile Lys Gly Tyr
        115                 120                 125

Met Gln Gln His Asn Ile Pro Gln Arg Glu Val Val Asp Val Thr Gly
    130                 135                 140

Leu Asn Gln Ser His Leu Ser Gln His Leu Asn Lys Gly Thr Pro Met
145                 150                 155                 160

Lys Thr Gln Lys Arg Ala Ala Leu Tyr Thr Trp Tyr Val Arg Lys Gln
                165                 170                 175

Arg Glu Ile Leu Arg Gln Phe Asn Gln Thr Val Gln Ser Ser Gly Asn
            180                 185                 190

Met Thr Asp Lys Ser Ser Gln Asp Gln Leu Leu Phe Leu Phe Pro Glu
        195                 200                 205
```

```
Phe Ser Gln Gln Ser His Gly Pro Gly Gln Ser Asp Asp Ala Cys Ser
    210                 215                 220

Glu Pro Thr Asn Lys Lys Met Arg Arg Asn Arg Phe Lys Trp Gly Pro
225                 230                 235                 240

Ala Ser Gln Gln Ile Leu Tyr Gln Ala Tyr Asp Arg Gln Lys Asn Pro
                245                 250                 255

Ser Lys Glu Glu Arg Glu Ala Leu Val Glu Glu Cys Asn Arg Ala Glu
            260                 265                 270

Cys Leu Gln Arg Gly Val Ser Pro Ser Lys Ala His Gly Leu Gly Ser
        275                 280                 285

Asn Leu Val Thr Glu Val Arg Val Tyr Asn Trp Phe Ala Asn Arg Arg
    290                 295                 300

Lys Glu Glu Ala Phe Arg Gln Lys Leu Ala Met Asp Ala Tyr Ser Ser
305                 310                 315                 320

Asn Gln Thr His Ser Leu Asn Pro Leu Leu Ser His Gly Ser Pro His
                325                 330                 335

His Gln Pro Ser Ser Ser Pro Asn Lys Leu Ser Gly Gly Lys Gln
            340                 345                 350

Arg Leu Gly Leu Thr Ala Ser Ala Thr Gln Pro Ser Trp Phe Leu Pro
        355                 360                 365

Arg Ile Leu Ser Gly Leu Arg Val Phe Arg Gly Ala Asn Ala Phe Glu
    370                 375                 380

Met Ile Leu Gly Pro Leu Ser His Cys Gln Asn Ile Leu Pro Trp Lys
385                 390                 395                 400

Gly Val Arg Tyr Ser Gln Gln Gly Asn Asn Glu Ile Thr Ser Ser Ser
                405                 410                 415

Thr Ile Ser His His Gly Asn Ser Ala Met Val Thr Ser Gln Ser Val
            420                 425                 430

Leu Gln Gln Val Ser Pro Ala Ser Leu Asp Pro Gly His Asn Leu Leu
        435                 440                 445

Ser Pro Asp Gly Lys Met Ile Ser Val Ser Gly Gly Leu Pro Pro
450                 455                 460

Val Ser Thr Leu Thr Asn Ile His Ser Leu Ser His His Asn Pro Gln
465                 470                 475                 480

Gln Ser Gln Asn Leu Ile Met Thr Pro Leu Ser Gly Val Met Ala Ile
                485                 490                 495

Ala Gln Ser Leu Asn Thr Ser Gln Ala Gln Ser Val Pro Val Ile Asn
            500                 505                 510

Ser Val Ala Gly Ser Leu Ala Ala Leu Gln Pro Val Gln Phe Ser Gln
        515                 520                 525

Gln Leu His Ser Pro His Gln Gln Pro Leu Met Gln Gln Ser Pro Gly
    530                 535                 540

Ser His Met Ala Gln Gln Pro Phe Met Ala Ala Val Thr Gln Leu Gln
545                 550                 555                 560

Asn Ser His Met Tyr Ala His Lys Gln Glu Pro Pro Gln Tyr Ser His
                565                 570                 575

Thr Ser Arg Phe Pro Ser Ala Met Val Val Thr Asp Thr Ser Ser Ile
            580                 585                 590

Ser Thr Leu Thr Asn Met Ser Ser Ser Lys Gln Cys Pro Leu Gln Ala
        595                 600                 605

Trp
```

(2) INFORMATION FOR SEQ ID NO:130:

(i) SEQUENCE CHARACTERISTICS:
        (A) LENGTH: 10014 base pairs
        (B) TYPE: nucleic acid
        (C) STRANDEDNESS: single
        (D) TOPOLOGY: linear (xi) SEQUENCE DESCRIPTION: SEQ ID NO:130:

```
TGGGTTGCCT GTGACTGCAC TGGCGATACC CCCACAAAGC CCACTCTGAA GGTAGGAGAC      60

GGGTGGAGAG AAACAGGGGG ATGGCAAGGG GGATACGAAA CAGGGAGAGG GAGGAGGGGG     120

AAGAGGATGG ACGTCTACCA GGCCCCACTT GGTGCTTGAT TTATGCCATC TCATTTCCTT     180

CTCAAACCAC CCTTTGAAGT TGATTGTACA TTTTACAGAA AAGGAAACTG AGGCTCGGAG     240

AGGAGAATCA TTTACCCAAG GTCCCAGTTA GTAGACGGTA GGTGCCTGAA TGTAAATCCA     300

GGTCTCTGCC TGCTCCGGGA GGGGGTGGGG GTGAGGGAAA CAGGAGAATG TGATGGGAAA     360

ATCCGAGATG GAGCCAGCCT GGGCCAGAAA CACTGGGAGC TGTGGGAGAC GGAGAGGGGC     420

AGGGTGGGAT CACAGGGAGC AGGAGCGGGG AATTGGAGGT GAATCTGGCC CTCCCAAACT     480

TCCAGTCCAT TCTGCTCCCA GGGGAACCGG GAAACTGCGG GGGAACTGGA AGGGAGCTCC     540

CAGAACAAGG ATCCAGAAGA TTGGCATCTG GGGCCTGGGA TTTAGGTTTC TAAATCGTGG     600

GCCATGGGGC AGCCTTATCT CTGCAAAAGC ATTGAGGGTA GAAGTCAATG ATTTGGGAAG     660

TTATTGAATT AGGGGATCTC GGAGGTAGGC TGTCAGTGCC TGATAGTATC AGTTAGAATG     720

CCTGACTTGG GGTGACAATG GCTTGGAGGG GTGGGTGAGT CAAGGGTCAA ATGAGTGCCC     780

GTGAGTCATG ATGCCTGCCT TGTACAATTG ATAACTGAAC ATCGGTGAGT TAGGGCCCCA     840

GCAGTTGTAA TTAGCACCCC GGGTGTCAGC CAGAAACCAA CAAACAGCCA AATCCCTGCA     900

GCCCCGCCCA GCCTATCCAC CGGCGGGGGA CCGATTAACC ATTAACCCCC ACCCCTCCCC     960

GGCAGAGCCT CCACCCCTTC ACAGAGGCTA GGCCAAGACT CCCAGCAGAT CTTCCCAGAG    1020

GACGGTTTGA AAGGAAGGCA GAGAGGGCAC TGGGAGGAGG CAGTGGGAGG GCGGAGGGCG    1080

GGGGCCTTCG GGGTGGGCGC CCAGGGTAGG GCAGGTGGCC GCGGCGTGGA GGCAGGGAGA    1140

ATGCGACTCT CCAAAACCCT CGTCGACATG GACATGGCCG ACTACAGTGC TGCACTGGAC    1200

CCAGCCTACA CCACCCTGGA ATTTGAGAAT GTGCAGGTGT TGACGATGGG CAATGGTAGG    1260

TGGGGGCAGA TGTGCCCAGG TGTGCCAGTG GGGGCAGGTG TGCCTGGGTC CAGGAGCAGA    1320

TCTTTGGCAC TCAACTTTGG GGTGGGAGGA GAATGATACA AAATGGTAGG TTGGTCCTAC    1380

AGGCCAGCAC AGGTGTTGCC AAGTGAAGCC CATGTGCCCA GGCACAGTGA TCACAGGCAT    1440

TCTGGGTGAA GGGAGGCCTG CAAGGGCCAA TTTCCAGCAA AAGTCGATCC CGGCTATTCC    1500

TCCCAGGCCC TTCCAGTCCT CACTGCCTCA CAGTGGCTCT GCTTGGCGCT TGGCACAGTG    1560

ACATGATGGT GAGCTCCCCC TTGGTGCCCA GCTCCAGCGA TTCAGCCCAG CACGGCCCCT    1620

TCGTGAACCC CTTGGGCCTA GGTTCAGAGA GACGGCAAGG GATGTTGTAT CCCTGGAGAT    1680

GGTGGTTGGA GACATAACCG CATTTCTCGG TGTCTTTGGG ACTTTCCTAG GGAAATGAAA    1740

TTGGCACTTA GGGAAAATGG AGCTCTCAGG GAAGTTTTGC TAACTACGAA GCCAACTCAG    1800

CACTGTGTGT GTTGTGTGTG CGTTCGTGTG TGATAGTGAG TTTCCATGTA GGTTGTATGG    1860

GTGGGGTGAT GCCTTCAGGA ACCCATTTGC ATATGTGTGT TCATTTGTCT CTGTGTGTGA    1920

GTTCTGGGTC TATTTTCCTT TGTATTCATT GAGTGGGTCT GTGTTGTGT CTTAGGAGTT    1980

GCCCGTGTTG ATCTTGCTTA TGTATGTAAG TGTGTATGTG TGTGTACTTG TGTCTGTGGA    2040

TGTTTGTACA TGTGTGCTGT GTGTGCGGGT CATAGAGCAC ATGCGTTTGT GCATGCGGAC    2100
```

-continued

```
CTGTTGGAGT GCCCTGTTCT TCCTGCATCT TTATCCTGTA TGGGCGTTTT GTCGTGTGCC    2160
CATATTTGTA CCTGCTGTGT ATATATGCAG TTCCCTGTGC TGCGGGCGGG GGTCAGCGGT    2220
CTCTGGTGTG CACGACTGCA CAGACCCAAA TGCAGGACTC TGTTGTTGCC ACTCACCAAG    2280
TGAGATTCAT ATCAGCAACA TGTCCGTTTG TCTCTGAGCA GATTTTGTTG CCGCTGCGTC    2340
TCGCCAGATT GAGGCATCCC CTCCGACATC ACTGGAGCAT ATCTGGAGGG GTGGACAGTT    2400
CTCCACAGGG AGGTAGGGGA AAAGAGGAGG CCCGGAAACC CCTCCTGGAG GGAAGAGCCC    2460
CATCGGTCCC AGGCCAGCCT CAGAGGAGAG GGGGCAGGCA GCTGGCTGAG GTCAGCCTGC    2520
CACCCTGCTT CCTTCTGTGT CTTGGAGCCA CTCAGCCAGT ATGAGGCTGC AGCTCCAGCT    2580
GAGGTCTGGA ATCTTGTGGT CAGCTCAGCT AGGGTGAGGA GGCAGCTGCT GGGCACTGCT    2640
TGTTGTCAGC TCAGCAGGTG CTCACCTGCC CCTGCCGTCC AGTCACGTGT GACCTTGGGC    2700
ATGTCACCTC CCCTATCCTG GCTTCTGTAT CTTCTACAAA ACAGGCTTCA TTCCCCCAGG    2760
CCTGCTGGCT GGACGGCTTT TAGGCCTGTC TGAGGACCAC GCCAGGAGCG CAAGGCAAAA    2820
ACACACCAGA GATCCCCTTG CGAGTTAGGA GGCCGGCTCC CACCCCAGAA GGTGGCCAGG    2880
TTTTCATGCC TTCCTAGAGA AAGCTGGGGC TGGTGGCCTC CACCACAGGG AGACGCAGAC    2940
CCTCAGAAAC AAGTCTGTGA AGTCACAACC AGCCCCAGTT TACAGATGTG AAACTGAAGC    3000
TCCAAAAAGT CAGGAGGTCA CTGAGTGGGG AGGTGATGGA GTGGGAACAG CCCCCAGATC    3060
TGGCTGAGGC CGAAGCCCTG GAGAGATCCC CGCAAGGCTC CCTTAGATGC CTGACATTCT    3120
GCTCTTCCTG AAGCCTCACT CCCTTCTCTC CTGGCGCAGA CACGTCCCCA TCAGAAGGCA    3180
CCAACCTCAA CGCGCCCAAC AGCCTGGGTG TCAGCGCCCT GTGTGCCATC TGCGGGGACC    3240
GGGCCACGGG CAAACACTAC GGTGCCTCGA GCTGTGACGG CTGCAAGGGC TTCTTCCGGA    3300
GGAGCGTGCG GAAGAACCAC ATGTACTCCT GCAGGTGAGG AGCCTCAATT TCTTCAGCTG    3360
GGAAATGGGC ACACTTGGGC TCATGGCCCC AAGGTCTGTC TTCTCCCTGA GTGGGTAGGT    3420
CCCAGAGACA GCTGCCCTTC AGGGCCTTCA AGGCTCTTCT GGTTTTGTAA AAGACTTTGT    3480
GAATCCAAGA AGAGCATCTA TTCTAGGAAC CACATTTACT GATCATCAAG CTACTGGCTG    3540
CCGTTTATTG AGCTCTTATC ATATGCCAGG CACAATACTA AGTCTTTGTG TGTATTTACG    3600
TACTCCAGAG GTCAAGGTTC CCAACTCAGC TCTAACACCA ACCAGCAGAG CGACCCAGGA    3660
CCACATGTTG CCTCTCTGAG CCTCAGTTTT CCCATGTTTA GCAGGACAGG ACTGGGCTCT    3720
TAGAGAGTTC ATAGCACCTT TCCAGCTCCT GGTGGGTTCA AGAGAGAACT CCCGGGATGA    3780
AGAGATGAGA GCACTGAGGT TGGGGGGTCA ACTGGATAGC CAGGGCCCTA GTTCTGTCCT    3840
AAGAGGAGGA AGTTGTGTCT TCTCCATCCA ACCATCCAAA GCCCTCCCCA GATTTAGCCG    3900
GCAGTGCGTG GTGGACAAAG ACAAGAGGAA CCAGTGCCGC TACTGCAGGC TCAAGAAATG    3960
CTTCCGGGCT GGCATGAAGA AGGAAGGTGA GCCTCGGCCC TCCCCGCCCC ACCACCACTG    4020
CCCCACCTGC ACCCACAGCT CCCCGACAGT CATTTACAAC TGTAGCCACA CTTTATGACT    4080
CAGTGGCAGG CCCCAGGGTG ACTGGCTAAT GGCTGAGAAG AGGGAGGGCC TGGAAATCTG    4140
ACCATAGGGA GCGGCTGGGC TTGGTCTTGA GAAAGATTCT CCCACTCCTC ATCAGTCACA    4200
GACACCCCCA CCCCCTACTC CATCCCTGTT CTCCCTCCTC ACCTCTCTGT GCCTCCTCAC    4260
CCGTCCAGAA TGAGCGGGAC CGGATCAGCA CTCGAAGGTC AAGCTATGAG GACAGCAGCC    4320
TGCCCTCCAT CAATGCGCTC CTGCAGGCGG AGGTCCTGTC CCGACAGGTA CCGGGGTGAT    4380
CCTGCCACCC ACCCAGGGAT CCCCCACACT ACAGAGGAGC TCACCTCCTC CACCTCCATT    4440
CTCCCCAGCC AGGCCCTGGA GCAGCTGACG GGAGGGGCCT CAGATATTAC AGAAGGGACA    4500
```

```
CTGAGTGCGG TTTCACATGG CCCAGTTTGC AGCAAGGGCA GGAATCGAAC CTGGCGCCCT    4560

GGGGCACTTT CTAATTCATC CTACTGCCTG CATCCCACAG GCCAAGCAGA GTCTTCACCT    4620

TCACTGAGGG CCTGCGATCA GCTCAGCTCC GAGAGAACAG AGCAGTGGCT CAGTGGAGAG    4680

AGGTGGCAAA GTGGGCCCA GCCCTTCCCT TGCTGAGTGA CCTTGGGCAA GTCACAGCAC    4740

CTCTCTGAGC CATGGTTGCC TCATTGTCAG AAAAGGATGA TGATTTTTTG CCCTGCTTCT    4800

CCTCTAAGGC TGACAGACTC CTTGGGGCTC TAAAGCTGTT CTCCCTCATC CCTGCCTCCT    4860

CCCTCCCTCC GTTTTTACCC TGAGCTTCCT TCAGAGCTGG AGGGCACCCA CTATCCAGCC    4920

CCCTCCCCAC ATCTGATTCC AGGGAGGGGG CTCTGTGCAG GGACAGAGA ATGCGGGAGG    4980

GCCCGGACAT CTCCAGCATT TTCTTCCCTG TATCTCTCGA AGATCACCTC CCCCGTCTCC    5040

GGGATCAACG GCGACATTCG GGCGAAGAAG ATTGCCAGCA TCGCAGATGT GTGTGAGTCC    5100

ATGAAGGAGC AGCTGCTGGT TCTCGTTGAG TGGGCCAAGT ACATCCCAGC TTTCTGCGAG    5160

CTCCCCCTGG ACGACCAGGT GAGGATGGGC GTGGATGGTG GGCAGTAGTG GGCAGTGGGC    5220

GGGGCAGCCA GGGGGCTGCT GGCCCACCTG GGATATAGCC GTGGACTGGC TTGATTTTAT    5280

TTTATTTAAC AAAATATGTA GTGCACACAC GTGTCTGAAA CTTTAAATCA CCTTACAAAT    5340

ATTAACTCAG TTAGCTCCTC CAACAACTCT ATGAGGTAGG TACTAAGGTA CTATTATTAC    5400

TGCCATCTCA TAGGTGAGGA GATTGGGGCA CAGAGAGGTT AAGTAACCTG CTCAAGGTCA    5460

CATAGCTACT ATCCAGCATA GCTGGGATTT TTACAAAGCA CCCTTCATAA TTCTCCATAG    5520

CTGGTCCATG GGTGGGAATT TGGGACCCAC AGTTTTGGAA CTTTTTGGGA TCATAGACCT    5580

TTTTGAGAAT CTCAAAAAAG AAAAAAAAAG CACACAGAAT GTTGCTTACA GTTTCATCAG    5640

GCACACAGAA GAGGCCCAGC ACGAAGCAGT TTCTTGCCCA AGGACACAGC AGTTCAAGGA    5700

CAGAGTCAGC GCGAGGTCTC TCAGCTCTGA GCACATGTTC TTTCCCCTTC CAGGTTTCTA    5760

GTTTTATGGG TAGTAGTTTT ATGATGCCCA TTTCACAGTT CAGGCAGGTA GAGGCAGAGG    5820

GGAGCATTAA GCTGACTTGC CCAGCGTCAC TGAGTTGGCT ACGGGCAGCC TTCCCAAGGG    5880

TACAGATGGC AAACACTGTT CCTTCTCTCT TTCAGGTGGC CCTGCTCAGA GCCCATGCTG    5940

GCGAGCACCT GCTGCTCGGA GCCACCAAGA GATCCATGGT GTTCAAGGAC GTGCTGCTCC    6000

TAGGTGAGGC GGCTGCCTGC CCTGGCCAGG GCTCCAGGGA GGGTATGCCT AGCATGGCAC    6060

TCACCCAGGC AAGGAGATTC ACATGGTGGC ATGCAAGGGT GAGGGAGACT AGTCAGGAGT    6120

GGCCCTGTCC TCAGGCTTGC ATTGGAGGGC TCCAGGACTC AGTTTTCAAC TGGGTACCCC    6180

ACTCAGATGC AAGGAAATGT GGATGCAAGT CACCAAATTC CCAGCATTGA AGTCAGAGCA    6240

CGATCAGGGT TATCCCTGGA ATTACCTGTG CATCCTTTTT TCTTTTGACA GAGTCTTGCT    6300

CTGTCACTCA GGCTGGAGTG CAATGATGTG AGCAAACACT ACCTATTTTA ATATAACAAT    6360

GCTATGAGGG AGCTCGATTA TTTATCCTCA TCTTATAGAT AAGAAAACTG AGGCACAGAG    6420

AGGTTAAGTA ACTTATCCAA CTATAACCAG CTATCAGGGG CAGAGCCATT TAAGCAGGGC    6480

AGTGCAGTTC CAGAATCTGG TCCTTTAACC TTGATGCTTT GGTGCCTATC AGGTGACCTT    6540

TGAATGTCAT CGATCTTGTG AGTCATGTTG GTAAATGGAG CTTGGGTCAT GTGAAAGAGG    6600

TCCTAGAAAG CCAAGTTCCA AGCTCAGCCG GATGACTCAA GGCAGCTTAT CTTCTGAATC    6660

TGGGCCTCAG CTTCCTTACC TGTGAAATGG GAGTCACCAT CCCTGCAGGT CCTCCTCCCA    6720

CAGGCACCAG CTATCTTGCC AACTTAAAAG CCAAAACTAG AGGAGAGGGG TCAACCCAAG    6780

GTGACTTCCC ATCCTCCCTC CCTCCCAACC CTTCCAGGCA ATGACTACAT TGTCCCTCGG    6840

CACTGCCCGG AGCTGGCGGA GATGAGCCGG GTGTCCATAC GCATCCTTGA CGAGCTGGTG    6900
```

```
CTGCCCTTCC AGGAGCTGCA GATCGATGAC AATGAGTATG CCTACCTCAA AGCCATCATC    6960
TTCTTTGACC CAGGTACAGT GCACACCTCC TAAGCCATCC CTGACTCTCT CTCCAGAACG    7020
CTCTGCCAGA CTTCTCCTAT TGGGTTCTGT ACACTGAGTT CACAGCCTCA TCTCATGTTA    7080
ACGACAGCCA GGAGAGGCCG TTTTCATTTA ACAGATGAGG CAAGTCAAGA TTTGAAGAGA    7140
CAATATGGCC GGGCGCAGTG GCTCACACCT GTAATCCCAT CACTTTGGGA GGCTGAGGCG    7200
GGCGGATCAC CTGAGGTCAG GGGTCAAGAT GAGCCTGGCT AACATGGAGA AACCCCATCT    7260
CTACTTAAAA GTGGCTCTGC CAACAACTGG CTGTGCGACC CAGGACAAGT CCTATCTTTG    7320
CACTGTGTCT GGGTTTCCCC GTGTGTAAGA TGAGGCGGTT GCTAGGTGCT TATTGGATGC    7380
ATTCCTCAAG TCCCGCCCTC CATCTCCTAT TCCCCTCTCT TCTGGTTTAG TGCTTTAGGA    7440
AATGTGGCAG AAATCTTTTT CTGCCTGTGT CTAGGAAATC ATAATTCATG CTGGCGTACC    7500
CTGGTTGTTG AGGTCCCTGA ATCCTTGTGC CCACACTGCT GAAGACTCCT TGTGTGACAC    7560
AAGTCAGGGG ACATCTGGGT CTTGACTCCC CAGATGCTCC AGCTGGACCC TGCTGCCCTC    7620
CCTTGCCCAC CCTCTTCCAT TGTAGATGCC AAGGGGCTGA GCGATCCAGG GAAGATCAAG    7680
CGGCTGCGTT CCCAGGTGCA GGTGAGCTTG GAGGACTACA TCAACGACCG CCAGTATGAC    7740
TCGCGTGGCC GCTTTGGAGA GCTGCTGCTG CTGCTGCCCA CCTTGCAGAG CATCACCTGG    7800
CAGATGATCG AGCAGATCCA GTTCATCAAG CTCTTCGGCA TGGCCAAGAT TGACAACCTG    7860
TTGCAGGAGA TGCTGCTGGG AGGTCCGTGC CAAGCCCAGG AGGGGCGGGG TTGGAGTGGG    7920
GACTCCCCAG GAGACAGGCC TCACACAGTG AGCTCACCCC TCAGCTCCTT GGCTTCCCCA    7980
CTGTGCCGCT TTGGGCAAGT TGCTTAACCT GTCTGTGCCT CAGTTTCCTC ACCAGAAAAA    8040
TGGGAACAAG GCAATGGTCT ATTTGTTCAG GCACCGAGAA CCTAGCACGT GCCAGTCACT    8100
GTTCTAAGTG CTGGCAATTC AGCAAAGAAC AAGATCTTTG CCCTCGGGGA GGCTGTGTGT    8160
GTGTGAGTAT GTATGGATGC GTGGATATCT GTGTATATGC CCGTATGTGC GTGCATGTGT    8220
ATATAAAGCC TCACATTTTA TGATTTTGAA ATAAACAGGT AATATGAGGG ACACATAGAT    8280
GCTATAAGTA GGTCAGTTGG CTGCAGCAGA GATGTGGGGG ATGAGGCTGA AAGGTGAGGC    8340
GGGACCAAAT GGTTGAAGGA CTTGCACTCC AAGGAGCTTT GAGAGCCATT GATTACATCC    8400
ATTATGTTAC TATGTGACCA ATACATTACT CATTAGAACA TTTACGTGAT CTCAGAGCTT    8460
CCTTATATGC ACCTTGTTCC TTTCAACTCA CTTTTGTTCT CTTGGTTTTT TGGGGTCCTC    8520
TTAACACCCT CATGAAGTCT ATAGATGGGA ATGGTACACC CTAGTTTACT AACCCAGGAA    8580
TAGGTACCCA ACAGGCACTG CCAATATTGG ATGGGCTGGT TGATTGGCCA CGCCTGAGGA    8640
AGATGGCGTC CCAAGGCCTG AGGTCTGCAT CCCAGACTCT CCATCCTGAT CGACCTTCTC    8700
TACCTGCAGG GTCCCCCAGC GATGCACCCC ATGCCCACCA CCCCTGCAC CCTCACCTGA    8760
TGCAGGAACA TATGGGAACC AACGTCATCG TTGCCAACAC AATGCCCACT CACCTCAGCA    8820
ACGGACAGAT GTGTGAGTGG CCCCGACCCA GGGACAGGC AGGTGGGCAA ACTCTGGGAT    8880
TTTACCTTGC AAAGGGTGAG GATGGGGCTT AAGACAGGAG GCAGGAGAAA GTGGAGTCTA    8940
GAAGGTAGAA CCAGGATGCA ACAGTTTTCT GGGTTCCAGG GTAGGGAATA AAGGGCAAGA    9000
TTGTCCATTT GTTGAGGCTG TTTATTCAGT AAGGTGACTG ACAGCCTTTA CTGAATGAAG    9060
CCATTGTTGG GATGAGGCAA TCCACTGGAT GAGGTAACCC ATTGGGTGAA GATGTCTTGG    9120
GTGAGAATTC CATTAGTTGA CATTGTCCAT TAAGTAAAAG TGGTCATTGA AGTAAGGCTG    9180
CACAGTTGGG TAAGGCTATC CATTAGACAT TAGATGAGAC TACCCATTGG GTCAGGATGT    9240
CTGCTGGGCT ATTTGGGAGA AGCAGTCCAA GTCTGCATAT CAAATAAATG ATGGAGGAGA    9300
```

-continued

```
TGGGTGGTAG GACCTTCCAG ACCTCATAAA ACTTAGGCTT TATGATCTGG GACTCACAGA    9360

AGGTTGAGCA ATAAAAGACC TTAGGGATTA TCTGGCTTAA TTAATTCTCT CATTTTATAG    9420

AGGAAGAAAT TAAGTCAAGG TGGGGCAGGG TGGGAGGGGA GAACTTTCCC GGGGCTCTTC    9480

ATTTACTCCC ACAAAGGCTG GAATTTTGAG CAGCCCCTGT CTGTCTGTTT GTCCTTCCCC    9540

ACCCCTGAGA CCCCACAGCC CTCACCGCCA GGTGGCTCAG GGTCTGAGCC CTATAAGCTC    9600

CTGCCGGGAG CCGTCGCCAC AATCGTCAAG CCCCTCTCTG CCATCCCCCA GCCGACCATC    9660

ACCAAGCAGG AAGTTATCTA GCAAGCCGCT GGGGCTTGGG GGCTCCACTG GCTCCCCCCA    9720

GCCCCCTAAG AGAGCACCTG GTGATCACGT GGTCACGGCA AAGGAAGACG TGATGCCAGG    9780

ACCAGTCCCA GAGCAGGAAT GGGAAGGATG AAGGGCCCGA GAACATGGCC TAAGGCACAT    9840

CCCACTGCAC CCTGACGCCC TGCTCTGATA ACAAGACTTT GACTTGGGGA GACCCTCTAC    9900

TGCCTTGGAC AACTTTCTCA TGTTGAAGCC ACTGCCTTCA CCTTCACCTT CATCCATGTC    9960

CAACCCCCGA CTTCATCCCA AAGGACAGCC GCCTGGAGAT GACTTGAGCC TTAC         10014
```

(2) INFORMATION FOR SEQ ID NO:131:

(i) SEQUENCE CHARACTERISTICS:
        (A) LENGTH: 567 amino acids
        (B) TYPE: amino acid
        (C) STRANDEDNESS:
        (D) TOPOLOGY: linear (xi) SEQUENCE DESCRIPTION: SEQ ID NO:131:

```
Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Gly Pro Ser Ser His Cys Leu Thr Val
        35                  40                  45

Ala Leu Leu Gly Ala Trp His Ser Asp Met Met Ile Leu Leu Pro Leu
    50                  55                  60

Arg Leu Ala Arg Leu Arg His Pro Leu Arg His His Trp Ser Ile Ser
65                  70                  75                  80

Gly Gly Val Asp Ser Ser Pro Gln Gly Asp Thr Ser Pro Ser Glu Gly
                85                  90                  95

Thr Asn Leu Asn Ala Pro Asn Ser Leu Gly Val Ser Ala Leu Cys Ala
            100                 105                 110

Ile Cys Gly Asp Arg Ala Thr Gly Lys His Tyr Gly Ala Ser Ser Cys
        115                 120                 125

Asp Gly Cys Lys Gly Phe Phe Arg Arg Ser Val Arg Lys Asn His Met
    130                 135                 140

Tyr Ser Cys Arg Phe Ser Arg Gln Cys Val Val Asp Lys Asp Lys Arg
145                 150                 155                 160

Asn Gln Cys Arg Tyr Cys Arg Leu Lys Lys Cys Phe Arg Ala Gly Met
                165                 170                 175

Lys Lys Glu Ala Val Gln Asn Glu Arg Asp Arg Ile Ser Thr Arg Arg
            180                 185                 190

Ser Ser Tyr Glu Asp Ser Ser Leu Phe Ser Ile Asn Ala Leu Leu Gln
        195                 200                 205

Ala Glu Val Leu Ser Arg Gln Ile Thr Ser Pro Val Ser Gly Ile Asn
    210                 215                 220

Gly Asp Ile Arg Ala Lys Lys Ile Ala Ser Ile Ala Asp Val Cys Glu
225                 230                 235                 240
```

```
Ser Met Lys Glu Gln Leu Leu Val Leu Val Glu Trp Ala Lys Tyr Ile
                245                 250                 255

Pro Ala Phe Cys Glu Leu Pro Leu Asp Asp Gln Val Ala Leu Leu Arg
            260                 265                 270

Ala His Ala Gly Glu His Leu Leu Gly Ala Thr Lys Arg Ser Met
        275                 280                 285

Val Phe Lys Asp Val Leu Leu Gly Asn Asp Tyr Ile Val Pro Arg
    290                 295                 300

His Cys Pro Glu Leu Ala Glu Met Ser Arg Val Ser Ile Arg Ile Leu
305                 310                 315                 320

Asp Glu Leu Val Leu Pro Phe Gln Leu Gln Ile Asp Asp Asn Glu
                325                 330                 335

Tyr Ala Tyr Leu Lys Ala Ile Ile Phe Phe Asp Pro Asp Ala Lys Gly
            340                 345                 350

Leu Ser Asp Pro Gly Lys Ile Lys Arg Leu Arg Ser Gln Val Gln Val
                355                 360                 365

Ser Leu Glu Asp Tyr Ile Asn Asp Arg Gln Tyr Asp Ser Arg Gly Arg
    370                 375                 380

Phe Gly Glu Leu Leu Leu Leu Pro Thr Leu Glu Ser Ile Thr Trp
385                 390                 395                 400

Gln Met Ile Glu Gln Ile Gln Phe Ile Lys Leu Phe Gly Met Ala Lys
                405                 410                 415

Ile Asp Asn Leu Leu Gln Glu Met Leu Leu Gly Gly Pro Cys Gln
            420                 425                 430

Ala Gln Glu Gly Arg Gly Trp Ser Gly Asp Ser Pro Gly Asp Arg Pro
        435                 440                 445

His Thr Val Ser Ser Pro Leu Ser Ser Leu Ala Ser Pro Leu Cys Arg
    450                 455                 460

Phe Gly Gln Val Ala Gly Ser Pro Ser Asp Ala Pro His Ala His His
465                 470                 475                 480

Pro Leu His Pro His Leu Met Gln Glu His Met Gly Thr Asn Val Ile
                485                 490                 495

Val Ala Asn Thr Met Pro Thr His Leu Ser Asn Gly Gln Met Cys Glu
            500                 505                 510

Trp Pro Arg Pro Arg Gly Gln Ala Ala Thr Pro Glu Thr Pro Gln Pro
        515                 520                 525

Ser Pro Pro Gly Gly Ser Gly Ser Glu Pro Tyr Lys Leu Leu Pro Gly
    530                 535                 540

Ala Val Ala Thr Ile Val Lys Pro Leu Ser Ala Ile Pro Gln Pro Thr
545                 550                 555                 560

Ile Thr Lys Gln Glu Val Ile
                565
```

(2) INFORMATION FOR SEQ ID NO:132:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (xi) SEQUENCE DESCRIPTION: SEQ ID NO:132:

```
AAGTAAGCCT TGTTTTTCCA CACTCATTCT CCCAGGTTTT CTTTGGATAG GCTTACTTTT      60

CCATGCTGGA GGAGGGGCTA TCCCTTCATT TTGCCTCTCC CGCTTCCCTC CCTCTCCCCC     120

TCCCCCTGCT TTCTCTCCCT CTGCACTTTG TGAACTGCTG CTGCAGTGCT GAAGTCCAAA     180
```

| GTTCAGTAAC TTGCTAAGCA CACAGATAAA TATGAACCTT GGAGAATTTA CCAATGTAAA | 240 |
| CAGATAGCCA AGGGTCCCTT TATCAGCACT GGCTCAGGAC AGTCGTGGGG GGTCTGAAGT | 300 |
| GGCTCAATTT TGTATTTTGT TTTTTTTGGG GGGGTGTAAA GGCGGGAGGC TGCGCTGTGC | 360 |
| CCGCTGCTGA CAGTCGGGCG TGTTACCTCG GAACATGGT GTAGGGAAGC TGGAAGCAGG | 420 |
| ATAACGTGGA ACTCAACCCA AGAAACGCCA GCCTGAAGAC CATGGTCTCG | 470 |

(2) INFORMATION FOR SEQ ID NO:133:

(i) SEQUENCE CHARACTERISTICS:
        (A) LENGTH: 467 base pairs
        (B) TYPE: nucleic acid
        (C) STRANDEDNESS: single
        (D) TOPOLOGY: linear (xi) SEQUENCE DESCRIPTION: SEQ ID NO:133:

| TCACAGCTAT TAGCTCATCG CTGCCAAATT GCCCCTTTAC CTAGGCTTGT GTCACTTTCA | 60 |
| CCTTCTCATT CTCTTACTTT TACATTCTTC CTTGATATTT TGCTTTTTCA ACTTTTGGAA | 120 |
| ATTTCTTTCT CTCTTCTACC CCTCCTCATA TTCCTCTGCA CTCCCCCCTC TCTAACTCAT | 180 |
| GCACTTTGTG GGGTCCAAAG TTCAGTAACT TGCAAAGCAC AGGGATAAAG ATGAACCTTG | 240 |
| GAAGATTTAC TCTGCTCTGA TGTAAACAGA GAGTGACAAG GGTCCCTTAT CTATGTCTCA | 300 |
| GAGAAGCCTG TCCGGGGGT GACCACTTGC TGGTTGTGGC TGCACAGTGT GTTTTTTTGG | 360 |
| GGGGAGGAG GAAACAGAAG GTGGGTAGAG CATGGACTCC CGCCCGCTGA TCCGTGTTAC | 420 |
| AGCCGCAGAT GGTGAGGCAG TAGAAGGCAA CAGACAGGAT GGCGTCT | 467 |

(2) INFORMATION FOR SEQ ID NO:134:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (xi) SEQUENCE DESCRIPTION: SEQ ID NO:134:

| TTTCGGGGGT GGGACCCAAC GCTGCTCTCC TGATGGCCTC CCTGGCTCCC AGCACCTTCC | 60 |
| ATCCCAGCTG CTCAGGGCCC CTCACCTGCG CCTCCCCCAC CCTCCCCTCT GCCCACTCCC | 120 |
| ATCGCAGGCC ATAGCTCCCT GTCCCTCTCC GCTGCCATGA GGCCTGCACT TTGCAGGGCT | 180 |
| GAAGTCCAAA GTTCAGTCCC TTCGCTAAGC ACACGGATAA ATATGAACCT TGGAGAATTT | 240 |
| CCCCAGCTCC AATGTAAACA GAACAGGCAG GGGCCCTGAT TCACGGGCCG CTGGGGCCAG | 300 |
| GGTTGGGGGT TGGGGGTGCC CACAGGGCTT GGCTAGTGGG GTTTTGGGGG GCAGTGGGT | 360 |
| GCAAGGAGTT TGGTTTGTGT CTGCCGGCCG GCAGGCAAAC GCAACCCACG CGGTGGGGGA | 420 |
| GGCGGCTAGC GTGGTGGACC CGGGCCGCGT GGCCCTGTGG CAGCCGAGCC ATGGTTTCT | 479 |

(2) INFORMATION FOR SEQ ID NO:135:

(i) SEQUENCE CHARACTERISTICS:
        (A) LENGTH: 605 base pairs
        (B) TYPE: nucleic acid
        (C) STRANDEDNESS: single
        (D) TOPOLOGY: linear (xi) SEQUENCE DESCRIPTION: SEQ ID NO:135:

| TGGGGCCTGG GATTTAGGTT TCTAAATCGT GGGCCATGGG GCAGCCTTAT CTCTGCAAAA | 60 |
| GCATTGAGGG TAGAAGTCAA TGATTTGGGA AGTTATTGAA TTAGGGGATC TCGGAGGTAG | 120 |

```
GCTGTCAGTG CCTGATAGTA TCAGTTAGAA TGCCTGACTT GGGGTGACAA TGGCTTGGAG    180

GGGTGGGTGA GTCAAGGGTC AAATGAGTGC CCGTGAGTCA TGATGCCTGC CTTGTACAAT    240

TGATAACTGA ACATCGGTGA GTTAGGGCCC CAGCAGTTGT AATTAGCACC CCGGGTGTCA    300

GCCAGAAACC AACAAACAGC CAAATCCCTG CAGCCCCGCC CAGCCTATCC ACCGGCGGGG    360

GACCGATTAA CCATTAACCC CCACCCCTCC CCGGCAGAGC CTCCACCCCT TCACAGAGGC    420

TAGGCCAAGA CTCCCAGCAG ATCTTCCCAG AGGACGGTTT GAAAGGAAGG CAGAGAGGGC    480

ACTGGGAGGA GGCAGTGGGA GGGCGGAGGG CGGGGGCCTT CGGGGTGGGC GCCCAGGGTA    540

GGGCAGGTGG CCGCGGCGTG GAGGCAGGGA GAATGCGACT CTCCAAAACC CTCGTCGACG    600

ACATG                                                               605

(2) INFORMATION FOR SEQ ID NO:136:

(i) SEQUENCE CHARACTERISTICS:
        (A) LENGTH: 478 base pairs
        (B) TYPE: nucleic acid
        (C) STRANDEDNESS: single
        (D) TOPOLOGY: linear (xi) SEQUENCE DESCRIPTION: SEQ ID NO:136:

TCCTGGAGAG TGGGACCCAG CGCCGCACCC AGAGGCCTCC TGGCTCCTGC TGCCTCTAGC     60

CCTGCGCCCC TGGCCCCTCT CCACCTCCCC CACCCTCCCT TCTGCTCACT CCCAATTGCA    120

GGCCATGACT CCGGTCCGCG TCCCTCTCAC CCCCATGAGG CCTGCACTTG CAAGGCTGAA    180

GTCCAAAGTT CAGTCCCTTC GCTAAGCGCA CGGATAAATA TGAACCTTGG AGAATTTCCC    240

CAGCTCCAAT GTAAACAGAG CAGGCAGGGG CCCTGATTCA CTGGCCGCTG GGGCCAGGGT    300

TGGGGGCTGG GGGTGCCCAC AGAGCTTGAC TAGTGGGATT TGGGGGGGCA GTGGGTGCAG    360

CGAGCCCGGT CCGTTGACTG CCAGCCTGCC GGCAGGTAGA CACCGGCCGT GGGTGGGGGA    420

GGCGGCTAGC TCAGTGGCCT TGGGCCGCGT GGCTGGTGGC AGCGGAGCCA TGGTTTCT     478

(2) INFORMATION FOR SEQ ID NO:137:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (xi) SEQUENCE DESCRIPTION: SEQ ID NO:137:

TGGGCTTGGG TGTTAGGTTT CCAGTTCAAG CGACCCAGGA CAGCTTTATC TCAAATTGAG     60

GATAGAAGTC AATGATCTGG GACGTGATTG GCTTAGGGCT TCATAGTGGT AGGCTTGCCA    120

GTGTCTAAAC ATGTCAGCTG GGTTGTCCAC CTTGGTGAGA CTTGGGGGCT GCTGAGGCAA    180

GGGGTCCAAC CAATGCCAGT CCTGTTGGGT GCCTGCCTTG GAAGATTGGT AAGTGACTAT    240

TAATGAGCGG GAGGTGGGGG GGGGCAACA GTTGTAATTA GCACCCCAGG TGTCAGTCAG    300

AAACCAACAA ACAGCCAAAT CCTCGTGGCT CCACCCAGCC TACCCAGCAA CGGGGGTGAT    360

TAACCATTAA CTCCTACCCC TCCCCACAGA GCCTCCACCC TCTGCAGAGG CTAGGCCAGG    420

ACGCCAGGCT GAGTCTCCCA GAGGACAGTT TGAAAGAGAG GAAGGCAGAG AAGGGACCTG    480

GGAGGAGGCA GGAGGAGGGC GGGGACGGGG GGGGCTGGGG CTCAGCCCAG GGGCTTGGGT    540

GGCATCCTGG GCCGGGCAGG ACAGGGGGCT AAGGCGTGGG TAGGGAGAA TGCGACTCTC    600

TAAAACCCTT GCCGGCGATA TG                                           622
```

(2) INFORMATION FOR SEQ ID NO:138:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (xi) SEQUENCE DESCRIPTION: SEQ ID NO:138:

```
TCTTGGGCAG TGGGACCAGC GCTGCTCCCA GAGGCCTCCT GGCTCCTGGT GCCTCTCTCC      60
CTGCGCCCCT GGTTCCCGCT CCACCTCCCC CACCCGCCCT TCTGCTCACT CCCAATTGCA     120
AGCCATGGCT CCCGGTCCGG TCCCTCTCGC TGCTGTGAGG CCTGCACTTG CAAGGCTGAA     180
GTCCAAAGTT CAGTCCCTTC GCTAAGCACA CGGATAAATA TGAACCTTGG AGAATTTCCC     240
CAGCTCCAAT GTAAACAGAG CAGCAGGGGG CCCTGATTCA CTAGCCGCTG GGCCAGGGT      300
TGGGGGTTGG GGGTGCCCAC AGGGCTTGAC TAGTGGGATT TGGGGGAGCA GTGGGTGCAG     360
CGAGCCTGGT CCGTTGACTG CCAGCAGTAG ACACCGGCCG TGTGTGGGGG AGGCGGCTAG     420
CTCAGTGGCC TTGGGCCGCG TGGCCTGGCG GTAGAGGAGC CATGGTTTCT                470
```

(2) INFORMATION FOR SEQ ID NO:139:

(i) SEQUENCE CHARACTERISTICS:
        (A) LENGTH: 557 amino acids
        (B) TYPE: amino acid
        (C) STRANDEDNESS:
        (D) TOPOLOGY: linear (xi) SEQUENCE DESCRIPTION: SEQ ID NO:139:

```
Met Val Ser Lys Leu Thr Ser Leu Gln Gln Glu Leu Leu Ser Ala Leu
 1               5                  10                  15

Leu Ser Ser Gly Val Thr Lys Glu Val Leu Val Gln Ala Leu Glu Glu
                20                  25                  30

Leu Leu Pro Ser Pro Asn Phe Gly Val Lys Leu Glu Thr Leu Pro Leu
            35                  40                  45

Ser Pro Gly Ser Gly Ala Glu Pro Asp Thr Lys Pro Val Phe His Thr
        50                  55                  60

Leu Thr Asn Gly His Ala Lys Gly Arg Leu Ser Gly Asp Glu Gly Ser
65                  70                  75                  80

Glu Asp Gly Asp Asp Tyr Asp Thr Pro Pro Ile Leu Lys Glu Leu Gln
                85                  90                  95

Ala Leu Asn Thr Glu Glu Ala Ala Glu Gln Arg Ala Glu Val Asp Arg
                100                 105                 110

Met Leu Ser Glu Asp Pro Trp Arg Ala Ala Lys Met Ile Lys Gly Tyr
            115                 120                 125

Met Gln Gln His Asn Ile Pro Gln Arg Glu Val Val Asp Val Thr Gly
        130                 135                 140

Leu Asn Gln Ser His Leu Ser Gln His Leu Asn Lys Gly Thr Pro Met
145                 150                 155                 160

Lys Thr Gln Lys Arg Ala Ala Leu Tyr Thr Trp Tyr Val Arg Lys Gln
                165                 170                 175

Arg Glu Ile Leu Arg Gln Phe Asn Gln Thr Val Gln Ser Ser Gly Asn
            180                 185                 190

Met Thr Asp Lys Ser Ser Gln Asp Gln Leu Leu Phe Leu Phe Pro Glu
        195                 200                 205

Phe Ser Gln Gln Ser His Gly Pro Gly Gln Ser Asp Asp Ala Cys Ser
    210                 215                 220
```

```
Glu Pro Thr Asn Lys Lys Met Arg Arg Asn Arg Phe Lys Trp Gly Pro
225                 230                 235                 240

Ala Ser Gln Gln Ile Leu Tyr Gln Ala Tyr Asp Arg Gln Lys Asn Pro
            245                 250                 255

Ser Lys Glu Glu Arg Glu Ala Leu Val Glu Glu Cys Asn Arg Ala Glu
            260                 265                 270

Cys Leu Gln Arg Gly Val Ser Pro Ser Lys Ala His Gly Leu Gly Ser
            275                 280                 285

Asn Leu Val Thr Glu Val Arg Val Tyr Asn Trp Phe Ala Asn Arg Arg
            290                 295                 300

Lys Glu Glu Ala Phe Arg Gln Lys Leu Ala Met Asp Ala Tyr Ser Ser
305                 310                 315                 320

Asn Gln Thr His Ser Leu Asn Pro Leu Leu Ser His Gly Ser Pro His
                325                 330                 335

His Gln Pro Ser Ser Ser Pro Pro Asn Lys Leu Ser Gly Val Arg Tyr
            340                 345                 350

Ser Gln Gln Gly Asn Asn Glu Ile Thr Ser Ser Ser Thr Ile Ser His
            355                 360                 365

His Gly Asn Ser Ala Met Val Thr Ser Gln Ser Val Leu Gln Gln Val
            370                 375                 380

Ser Pro Ala Ser Leu Asp Pro Gly His Asn Leu Leu Ser Pro Asp Gly
385                 390                 395                 400

Lys Met Ile Ser Val Ser Gly Gly Leu Pro Pro Val Ser Thr Leu
            405                 410                 415

Thr Asn Ile His Ser Leu Ser His His Asn Pro Gln Gln Ser Gln Asn
            420                 425                 430

Leu Ile Met Thr Pro Leu Ser Gly Val Met Ala Ile Ala Gln Ser Leu
            435                 440                 445

Asn Thr Ser Gln Ala Gln Ser Val Pro Val Ile Asn Ser Val Ala Gly
            450                 455                 460

Ser Leu Ala Ala Leu Gln Pro Val Gln Phe Ser Gln Leu His Ser
465                 470                 475                 480

Pro His Gln Gln Pro Leu Met Gln Gln Ser Pro Gly Ser His Met Ala
            485                 490                 495

Gln Gln Pro Phe Met Ala Ala Val Thr Gln Leu Gln Asn Ser His Met
            500                 505                 510

Tyr Ala His Lys Gln Glu Pro Pro Gln Tyr Ser His Thr Ser Arg Phe
            515                 520                 525

Pro Ser Ala Met Val Val Thr Asp Thr Ser Ser Ile Ser Thr Leu Thr
530                 535                 540

Asn Met Ser Ser Ser Lys Gln Cys Pro Leu Gln Ala Trp
545                 550                 555

(2) INFORMATION FOR SEQ ID NO:140:

(i) SEQUENCE CHARACTERISTICS:
        (A) LENGTH: 516 amino acids
        (B) TYPE: amino acid
        (C) STRANDEDNESS:
        (D) TOPOLOGY: linear (xi) SEQUENCE DESCRIPTION: SEQ ID NO:140:

Met Asp Met Ala Asp Tyr Ser Ala Ala Leu Asp Pro Ala Tyr Thr Thr
1               5                   10                  15

Leu Glu Phe Glu Asn Val Gln Val Leu Thr Met Gly Asn Gly Pro Ser
            20                  25                  30
```

-continued

```
Ser Pro His Cys Leu Thr Val Ala Leu Leu Gly Ala Trp His Ser Asp
         35                  40                  45

Met Met Ile Leu Leu Pro Leu Arg Leu Ala Arg Leu Arg His Pro Leu
         50                  55                  60

Arg His His Trp Ser Ile Ser Gly Gly Val Asp Ser Ser Pro Gln Gly
65                  70                  75                  80

Asp Thr Ser Pro Ser Glu Gly Thr Asn Leu Asn Ala Pro Asn Ser Leu
                 85                  90                  95

Gly Val Ser Ala Leu Cys Ala Ile Cys Gly Asp Arg Ala Thr Gly Lys
                100                 105                 110

His Tyr Gly Ala Ser Ser Cys Asp Gly Cys Lys Gly Phe Phe Arg Arg
            115                 120                 125

Ser Val Arg Lys Asn His Met Tyr Ser Cys Arg Phe Ser Arg Gln Cys
        130                 135                 140

Val Val Asp Lys Asp Lys Arg Asn Gln Cys Arg Tyr Cys Arg Leu Lys
145                 150                 155                 160

Lys Cys Phe Arg Ala Gly Met Lys Lys Glu Ala Val Gln Asn Glu Arg
                165                 170                 175

Asp Arg Ile Ser Thr Arg Arg Ser Ser Tyr Glu Asp Ser Ser Leu Phe
                180                 185                 190

Ser Ile Asn Ala Leu Leu Gln Ala Glu Val Leu Ser Arg Gln Ile Thr
        195                 200                 205

Ser Pro Val Ser Gly Ile Asn Gly Asp Ile Arg Ala Lys Lys Ile Ala
    210                 215                 220

Ser Ile Ala Asp Val Cys Glu Ser Met Lys Glu Gln Leu Leu Val Leu
225                 230                 235                 240

Val Glu Trp Ala Lys Tyr Ile Pro Ala Phe Cys Glu Leu Pro Leu Asp
                245                 250                 255

Asp Gln Val Ala Leu Leu Arg Ala His Ala Gly Glu His Leu Leu Leu
                260                 265                 270

Gly Ala Thr Lys Arg Ser Met Val Phe Lys Asp Val Leu Leu Leu Gly
        275                 280                 285

Asn Asp Tyr Ile Val Pro Arg His Cys Pro Glu Leu Ala Glu Met Ser
    290                 295                 300

Arg Val Ser Ile Arg Ile Leu Asp Glu Leu Val Leu Pro Phe Gln Glu
305                 310                 315                 320

Leu Gln Ile Asp Asp Asn Glu Tyr Ala Tyr Leu Lys Ala Ile Ile Phe
                325                 330                 335

Phe Asp Pro Asp Ala Lys Gly Leu Ser Asp Pro Gly Lys Ile Lys Arg
                340                 345                 350

Leu Arg Ser Gln Val Gln Val Ser Leu Glu Asp Tyr Ile Asn Asp Arg
        355                 360                 365

Gln Tyr Asp Ser Arg Gly Arg Phe Gly Glu Leu Leu Leu Leu Leu Pro
    370                 375                 380

Thr Leu Glu Ser Ile Thr Trp Gln Met Ile Glu Gln Ile Gln Phe Ile
385                 390                 395                 400

Lys Leu Phe Gly Met Ala Lys Ile Asp Asn Leu Leu Gln Glu Met Leu
                405                 410                 415

Leu Gly Gly Ser Pro Ser Asp Ala Pro His Ala His His Pro Leu His
                420                 425                 430

Pro His Leu Met Gln Glu His Met Gly Thr Asn Val Ile Val Ala Asn
        435                 440                 445
```

```
Thr Met Pro Thr His Leu Ser Asn Gly Gln Met Cys Glu Trp Pro Arg
    450                 455                 460
Pro Arg Gly Gln Ala Ala Thr Pro Glu Thr Pro Gln Pro Ser Pro Pro
465                 470                 475                 480
Gly Gly Ser Gly Ser Glu Pro Tyr Lys Leu Leu Pro Gly Ala Val Ala
                485                 490                 495
Thr Ile Val Lys Pro Leu Ser Ala Ile Pro Gln Pro Thr Ile Thr Lys
            500                 505                 510
Gln Glu Val Ile
        515
```

(2) INFORMATION FOR SEQ ID NO:141:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:141:

GCGGGACCGG ATCAGCA                                        17

(2) INFORMATION FOR SEQ ID NO:142:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:142:

```
Arg Asp Arg Ile Ser
1               5
```

(2) INFORMATION FOR SEQ ID NO:143:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:143:

GCGGGACTGG ATCAGCA                                        17

(2) INFORMATION FOR SEQ ID NO:144:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:144:

```
Ala Glu Val Leu Ser Arg Gln
1               5
```

(2) INFORMATION FOR SEQ ID NO:145:

(i) SEQUENCE CHARACTERISTICS:
        (A) LENGTH: 30 base pairs
        (B) TYPE: nucleic acid
        (C) STRANDEDNESS: single
        (D) TOPOLOGY: linear -continued

```
    (ix) FEATURE:
         (A) NAME/KEY: modified_base
         (B) LOCATION: 16
         (D) OTHER INFORMATION: /note= "N = C or T"

(xi) SEQUENCE DESCRIPTION: SEQ ID NO:145:

GCGGAGGTCC TGTCCNGACA GGTACCGGGG                                       30

(2) INFORMATION FOR SEQ ID NO:146:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ix) FEATURE:
         (A) NAME/KEY: modified_base
         (B) LOCATION: 8
         (D) OTHER INFORMATION: /note= "N = C or T"

(xi) SEQUENCE DESCRIPTION: SEQ ID NO:146:

AAAGCAANGA GAGAT                                                       15

(2) INFORMATION FOR SEQ ID NO:147:

(i) SEQUENCE CHARACTERISTICS:
         (A) LENGTH: 4 amino acids
         (B) TYPE: amino acid
         (C) STRANDEDNESS:
         (D) TOPOLOGY: linear (ix) FEATURE:
         (A) NAME/KEY: Modified-site
         (B) LOCATION: 3
         (D) OTHER INFORMATION: /note= "X = R or any amino acid"

(xi) SEQUENCE DESCRIPTION: SEQ ID NO:147:

Lys Gln Xaa Glu
```